United States Patent [19]

Ladunga

[11] Patent Number: 5,987,390
[45] Date of Patent: Nov. 16, 1999

[54] METHODS AND SYSTEMS FOR IDENTIFICATION OF PROTEIN CLASSES

[75] Inventor: Istvan Ladunga, King of Prussia, Pa.

[73] Assignee: Smithkline Beecham Corporation, Philadelphia, Pa.

[21] Appl. No.: 08/959,640

[22] Filed: Oct. 28, 1997

[51] Int. Cl.$^6$ ............................ G06F 19/00; G06F 17/00; C07K 14/00; A61K 38/02
[52] U.S. Cl. ............................... 702/19; 702/19; 702/20; 530/350; 514/2
[58] Field of Search ..................................... 364/496, 497, 364/498, 499, 578, 528.01, 528.03; 514/2; 702/19, 27; 530/350, 300

[56] References Cited

U.S. PATENT DOCUMENTS

| | | | |
|---|---|---|---|
| 5,436,850 | 7/1995 | Eisenberg et al. ...................... | 364/496 |
| 5,536,637 | 7/1996 | Jacobs ......................................... | 435/6 |
| 5,632,041 | 5/1997 | Peterson et al. ......................... | 395/800 |
| 5,701,256 | 12/1997 | Marr et al. ................................ | 364/496 |

OTHER PUBLICATIONS

Suyama, M et al. Searching For Common Sequence Patterns Among Distantly Related Proteins. Protein Engineering, vol. 8, No. 11, pp. 1075–1080, 1995.
U. Hobohm and C. Sander, "A Sequence Property Approach to Searching Protein Databases", *J. Mol. Biol.*, vol. 251, pp. 390–399 (1995).
J. Lazović, "Selection of Amino Acid Parameters for Fourier Transform–based Analysis of Proteins", *Cabios Communication*, vol. 12, No. 6, pp. 553–562 (1996).
G. von Heijen, "Signal Sequences The Limits of Variation", *J. Mol. Biol.*, vol. 184, pp. 99–105 (1985).
Kaiser et al., "Many Random Sequences Functionally Replace the Secretion Signal Sequence of Yeast Invertase", *Science*, vol. 235, pp. 312–317 (1987).
Altschul et al., "Basic Local Alignment Search Tool", *J. Mol. Biol.*, vol. 215, pp. 403–410 (1990).
W. Pearson and D. Lipman, "Improved Tools for Biological Sequence Comparison", *Proc. Natl. Acad. Sci. U.S.A.*, vol. 85, pp. 2444–2448 (1988).
W. Pearson, "Rapid and Sensitive Sequence Comparison with FASTP and FASTA", *Methods Enzymol.*, vol. 183, pp. 63–98 (1989).
T. Smith and M. Waterman, "Identification of Common Molecular Subsequences", *J. Mol. Biol.*, vol. 147, pp. 195–197 (1981).
G. von Heijen, "A New Method for Predicting Signal Sequence Cleavage Sites", *Nucleic Acids Research*, vol. 14, pp. 4683–4691 (1986).
S. Pascarella and F. Bossa, "Cleavage: A Microcomputer Program for Predicting Signal Sequence Cleavage Sites", *Comput. Appl. Biosci.*, vol. 5, pp. 53–54 (1989).
R. Folz and J. Gordon, "Computer–Assisted Predictions of Signal Peptidase Processing Sites", *Biochem. Biophys. Res. Commun.*, vol. 146, pp. 870–877 (1987).

A. Popowicz and P. Dash, "SIGSEQ: A Computer Program for Predicting Signal Sequence Cleavage Sites", *Comp. Appl. Biosci.*, vol. 4, pp. 405–406 (1988).
Ladunga et al., "Improving Signal Peptide Prediction Accuracy by Simulated Neural Network", *Comp. Appl. Biosci.*, vol. 7, pp. 485–487 (1991).
M. Mézard and J. Nadal, "Learning in Feedforward Layered Networks: The Tiling Algorithm", *J. Phys. A: Math. Gen.*, vol. 22, pp. 2191–2203 (1989).
H. Nielsen et al., "Defining a Similarity Threshold for a Functional Protein Sequence Pattern: The Signal Peptide Cleavage Site", *Proteins*, vol. 24, pp. 165–177 (1996).
H. Nielsen et al., "Identification of Prokaryotic and Euraryotic Signal Peptides and Prediction of Their Cleavage Sites", *Prot. Engng.*, vol. 10, pp. 1–6 (1997).
K. Nakai and M. Kanehisa, "Expert System for Predicting Protein Localization Sites in Gram–Negative Bacteria", *Proteins*, vol. 11, pp. 95–110 (1991).
K. Nakai and M. Kanehisa, "A Knowledge Base for Predicting Protein Localization Sites in Eukaryotic Cells", *Genomics*, vol. 14, pp. 897–910 (1992).
P. Horton and K. Nakai, "A Probabilistic Classification System for Predicting the Cellular Localization Sites of Proteins", *Ismb.*, vol. 4, pp. 109–115 (1996).
Talmud et al., "Prediction of Signal Peptide Functional Properties: A Study of the Orientation and Angle of Insertion of Yeast Invertase Mutants and Human Apolipoprotein B Signal Peptide Variants", *Protein Eng.*, vol. 9, pp. 317–321 (1996).
Claros et al. "Prediction of N–terminal Protein Sorting Signals", *Curr. Opin. Struct. Biol.*, vol. 7, pp. 394–398 (1997).
I. Ladunga and R. Smith, "Amino Acid Substitutions Preserve Protein Folding by Conserving Steric and Hydrophobicity Properties", *Prot. Engng.*, vol. 10, pp. 187–196 (1997).
Nakai et al., "Cluster Analysis of Amino Acid Indices for Prediction of Protein Structure and Function", *Protein Engng.*, vol. 2, pp. 93–100 (1988).
K. Tomii and M. Kanehisa, "Analysis of Amino Acid Indices and Mutation Matrices for Sequence Comparison and Structure Prediction of Proteins", *Protein Engng.* vol. 9, pp. 27–36 (1996).
M. Kozak, "Interpreting cDNA Sequences: Some Insights from Studies on Translation", *Mammalian Genome*, vol. 7, pp. 563–574 (1996).
R. Gomory, "Outline of an Algorithm for Integer Solutions to Linear Programs", *Bull. Amer. Math. Soc.*, vol. 64, pp. 275–278 (1958).
Little et al., "An Algorithm for the Traveling Salesman Problem", *Operations Res.*, vol. 11, pp. 972–989 (1963).

(List continued on next page.)

*Primary Examiner*—Lila Feisee
*Assistant Examiner*—Nirmal S. Basi
*Attorney, Agent, or Firm*—Kirk Baumeister; William T. King

[57] ABSTRACT

Methods and computer systems for identifying protein classes from nucleic acid or amino acid sequence data are disclosed.

24 Claims, 1 Drawing Sheet

OTHER PUBLICATIONS

F. Beale and J. Tomlin, "An Integer Programming Approach to a Class of Combinatorial Problems", *Mathematical Programming,* vol. 3, pp. 339–344 (1972).

Beale et al., Integer Programming, pp. 409–448. in: Schittkowski, K. ed. *Computational Mathematical Programming,* Springer, Berlin (1985).

C. Barnhart, "Dual–Ascent Methods for Large–Scale Multicommodity Flow Problems", *Naval Research Logistics,* vol. 40, pp. 305–324 (1993).

K. Bennett and O. Mangasarian, "Robust Linear Programming Discrimination of Two Linearly Inseparable Sets", *Optimization Methods and Software,* vol. 1, pp. 23–34 (1992).

Bairoch, et al. "The PROSITE database, its Status in 1995", *Nucleic Acids Res.,* vol. 24, pp. 189–196 (1996).

B. Matthews, "Comparison of the Predicted and Observed Secondary Structure of T4 Phage Lysozyme", Biochem. Biophys. Acta, vol. 405, pp. 442–451 (1975).

_US 5,987,390_

METHODS AND SYSTEMS FOR IDENTIFICATION OF PROTEIN CLASSES

FIELD OF THE INVENTION

This invention relates to computer-based methods and systems for identification of protein classes, including secreted and non-secreted proteins, in protein or nucleic acid sequence data.

BACKGROUND OF THE INVENTION

Current large-scale sequencing techniques are elucidating numerous novel genes in various eukaryotic and prokaryotic genomes. It is generally recognized that these efforts will be beneficial to the advancement of medicine and biology. To achieve this benefit, identified novel genes must be classified and biological function determined.

Secreted and non-secreted proteins are important classes. Targeting protein drugs into body fluids or onto receptors located on the surface of the cellular membrane is much easier than transporting proteinaceous compounds into the cytosol or the organelles. The relative ease of targeting protein drugs explains why most approved protein drugs are secreted proteins, a trend that is likely to remain so in the foreseeable future. Known secreted proteins include all peptide hormones and their receptors, breast and colon cancer gene products, leptin and its receptor, serum albumin, superoxide dismutase, spliceosome proteins, 7-transmembrane proteins, immunoglobulins, deoxyribonuclease I and several families of serine proteinases.

Secreted proteins are synthesized by a host organism in the cytosol, and in eukaryotes, are exported cotranslationally into the endoplasmatic reticulum and subsequently secreted into the extracellular space or inserted into the membrane. Proteins are transported either across a translocation pore or in direct interaction with lipids.

The vehicles for protein transportation are the mostly amino-terminal signal peptides, extending to 12 to 50 residues in eukaryotes. Signal peptides are the most abundant functional domain in proteins. They consist of three short segments: a usually basic cytosolic part that generally starts with a methionine; a hydrophobic segment; and a cleavage site for the signal peptidase enzyme. In contrast to this sophisticated and effective mechanism, only sporadic natural pathways, such as pinocytosis and membrane punching by performs, exist for the transport in the opposite direction, i.e., from the extracellular space into the cytosol.

Traditional experimental methods for the identification of secreted proteins are labor and cost-intensive. Exemplary methods include peptide sequencing, immunoelectron microscopy and membrane ultracentrifugation.

A more recently developed experimental method for identifying secreted proteins is the DiscoverEase® protocol of Genetics Institute (U.S. Pat. No. 5,536,637). This protocol utilizes a yeast mutant strain defective in the invertase signal peptide and has been used to identify thousands of secreted proteins.

While experimental techniques are indispensable in finding novel types of secretory signals, screening hundreds of thousands of Expressed Sequence Tag (EST) assemblies generated by large-scale sequencing efforts to identify secreted proteins is feasible only by extremely fast computational tools that can predict secreted proteins for large amounts of sequences at a reasonable cost. However, signal peptides are a classic example of how an identical function is preserved across extremely variable sequences (1). In the hydrophobic segment, for instance, the order of leucine, valine, isoleucine and other hydrophobic residues seems to be irrelevant to function (2). As a result of this variation, signal peptides cannot be identified by the usual sequence analysis methods like BLAST (3), FASTA (4,5) or dynamic programming (6), all of which are based on the conservation of sequences.

Gunnar von Heijne (7) has created a profile-like method for the recognition of the cleavage site, the least variable segment of signal peptides, that works with an accuracy of about 70% on protein data. His method has been coded into computer programs by several authors, including Pascarella and Bossa (8), Folz and Gordon (9) and Popowicz and Dash (10). Attempts to improve the accuracy of this method by increasing the minimal score eliminates several false positives only at the expense of false rejection of bona fide signal peptides.

Neural networks are more accurate tools for the prediction of signal peptides. Ladunga et al. (11) applied the so-called tiling algorithm (12) for the amino-terminal 20 residues of signal peptides in combination with von Heijne's method. Nielsen et al. (13,14) used a standard feed-forward algorithm trained by the back-propagation algorithm (15). In the production system created by Nakai, Kanehisa and coworkers (16–18), decision rules are applied in the form of binary decision trees. A fundamentally different approach (19) predicts signal peptides by modeling the angle of insertion into the membrane and the orientation of the signal peptide in the yeast invertase system. For a recent review on computational methods to predict secreted proteins, see (20).

Despite the current efforts, a need exists to increase the precision of computational methods for identifying secreted proteins. Since large-scale sequencing efforts produce nucleotide rather than amino acid sequence data, the accuracy of predicting secreted proteins will depend upon the sequencing accuracy, the reading frame prediction accuracy and the accuracy of the prediction of the signal peptide/membrane anchor on the protein level. Taking into account the rate of sequencing errors in ESTs (including artificial frameshifts), and the uncertainty in finding the correct reading frame and translation initiation site, the identification of secreted proteins from EST data will require significantly more accurate computational predictions than the ones described above.

SUMMARY OF THE INVENTION

Accordingly, one aspect of the invention is a method for identifying protein classes from protein or nucleic acid sequence data comprising analyzing combinations of amino acid properties by mathematical programming.

Another aspect of the invention is a method for identifying protein classes from protein or nucleic acid sequence data comprising:

a) determining the average amino acid property values of non-overlapping oligopeptide windows in query sequence data and a protein reference set;

b) weighting the reference set values; and c) distinguishing between protein classes.

Another aspect of the invention is a method for identifying secreted and non-secreted proteins from protein or nucleic acid sequence data comprising:

a) determining the average amino acid property values of non-overlapping oligopeptide windows in reference sets of experimentally known secreted and non-secreted proteins;

b) determining weights of the determined property values;

c) identifying a putative amino terminus in query sequence data;

d) determining the average amino acid property values of non-overlapping oligopeptide windows in the putative amino terminus of the query sequence data; and e) distinguishing between secreted and non-secreted proteins.

Yet another aspect of the invention is computer systems for performing the methods of the invention.

DETAILED DESCRIPTION OF THE INVENTION

Figure 1:
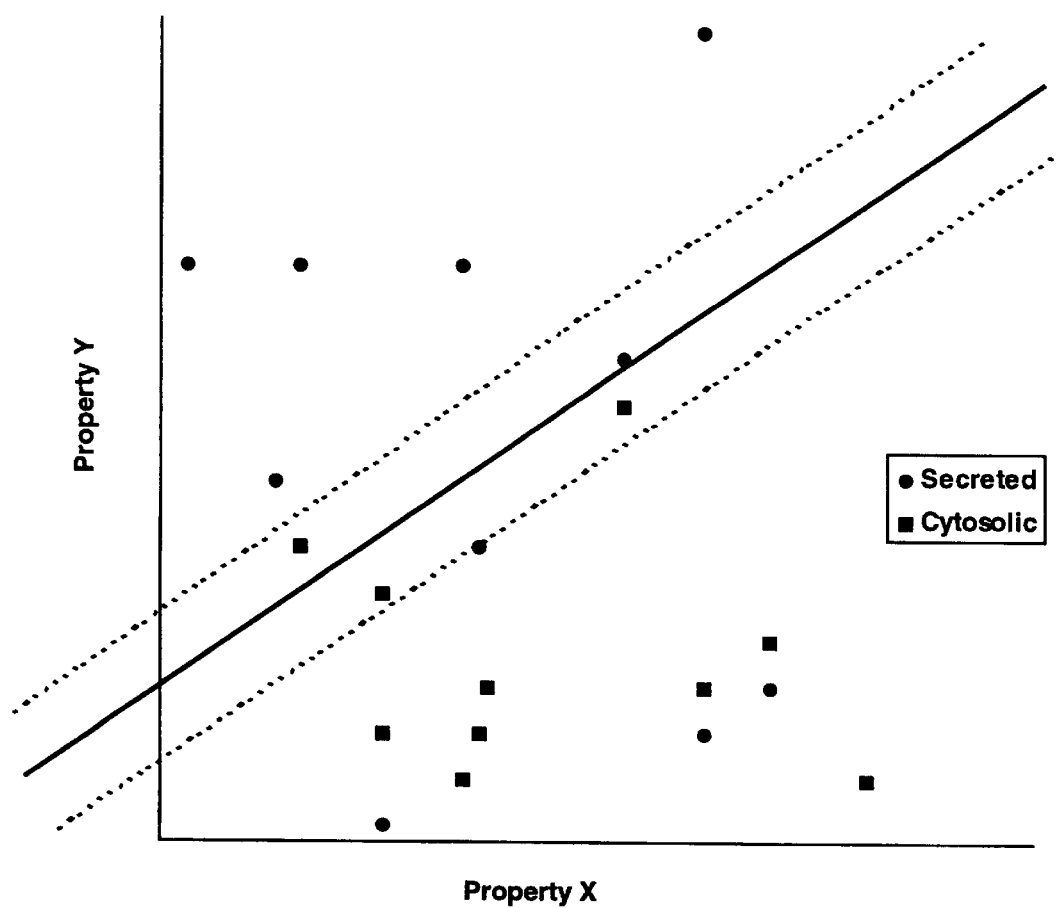
FIG. 1 is a demonstrative example of the linear separation of secreted and cytosolic proteins in weight optimization using two amino acid properties.

In the present invention, it has been observed that a properly weighted subset of a finite number of physicochemical, physical, chemical, biological, structural, steric, etc., properties of the amino acids can provide accurate distinction between different classes of proteins, such as secreted and non-secreted. Distinction between other protein classes such as chemokines, 7-transmembrane receptors, neuropeptides and the location of the cleavage site for the signal peptidase enzyme could also be achieved by the present invention.

Robust evolutionary conservation of amino acid properties that determine the fold of proteins (hydrophobicity measures, steric properties, etc.) has been observed at positions of multiple alignments of protein sequences in nine large multiple alignment databases (21). It has been shown that the best conserved properties are essential for the folding of the protein, i.e. the conservation of these properties conserves the fold of the protein. Conservation of these properties can be of diagnostic value even when the sequences themselves are not conserved. A classic example for that is signal peptides and membrane anchors: in spite of the tremendous variation in sequence, certain properties, such as those related to hydrophobicity, are well-conserved at certain positions of multiple alignments of these peptides. While the applicant does not intend to be bound by a particular theory, it is highly unlikely that these properties were conserved by chance alone in large samples. A more plausible explanation is the elimination of dysfunctional (improperly folded) mutants by natural selection. This implies that conservation of a property may indicate its functional and structural importance, i.e., more conserved properties are better indicators of a protein class, such as whether an unknown sequence contains a signal peptide or a membrane anchor or the amino-terminal segment of a cytosolic protein.

As used herein, the term "protein classes" refers to protein classifications such as secreted and non-secreted, chemokine, 7-transmembrane receptor, to protein domains such as signal peptidase cleavage site, and others.

As used herein, the term "secreted proteins" refers to proteins secreted into the extracellular space or into a cellular organelle (nucleus, mitochondrion, lysosome, chloroplast, etc.) or into a membrane, i.e., membrane-bound proteins. The term "non-secreted proteins" includes any proteins that are not translocated across biological membranes, such as cytosolic proteins.

As used herein, the term "nucleic acid sequence data" refers to a series of symbolic codes for deoxynucleotide or ribonucleotide bases. The term "protein sequence data" refers to a series of symbolic codes for amino acid residues. Both types of sequence data can be derived by automated or manual methods well known to those skilled in the art and can be stored in a database.

As used herein, the term "amino acid properties" refers to any of the different physical, chemical, physicochemical, biochemical, structural, steric and other properties (indices) of amino acids. The term "amino acid property values" refers to sets of 20 numerical values representing the different properties of amino acids. The amino acid properties include, but are not limited to, the 402 properties (indices) including propensities to form alpha-helices, beta-structures, composition, hydrophobicity, physicochemical and other properties that are listed together with their non-normalized values in the Amino Acid Index database (AAINDEX) available by Internet file transfer protocol from ftp.genome.ad.jp/db/genomenet/aaindex/. See also (22,23). AAINDEX entries are listed below after the Example section. In the method of the invention, comparison of amino acid properties with different units of measurement is facilitated by normalizing the values of each property to a range. Preferably, the range is −100 to +100.

The present invention provides for novel prediction methods of protein classes such as secreted proteins in nucleic acid or protein sequence data. The methods of the invention are computer-based. Despite an extreme sequence variation in the subdomains of signal peptides, there are characteristic patterns of amino acid properties for these subdomains. In the method of the present invention, it has been determined that analysis of combinations of amino acid property values by mathematical, i.e., linear, integer, mixed integer or quadratic, programming, allows selective and sensitive distinction between protein classes such as secreted and non-secreted proteins. The method provides a higher level of generalization as compared to direct sequence information.

Potential novel protein sequences can be identified by the method of the invention. The sequences identified by the method can be stored in a database and characterized for biological function. The nucleic acids and proteins represented by the sequence data are useful as potential drugs, targets for potential drugs, drug discovery reagents and/or biomedical research tools.

The method of the invention processes either protein or nucleic acid sequence data, the latter being translated in six reading frames. All segments having a putative amino terminus can be analyzed by the method of the invention. Putative amino termini are identified by location of a start site, i.e, a translation initiation codon or an initiating amino acid residue such as methionine in query sequence data. In the case of nucleic acid sequence data, segments having a translation initiation codon are analyzed provided that: (i) they do not contain STOP codons or ambiguous amino acid codons within a minimum of 30 codons; and (ii) their amino acid composition is within the compositional range of known signal peptides in the reference set or its subsets. Exemplary translation initiation codons are NTG, ATC or ATT. Optionally, Kozak's (24) rules can be enforced for identification of the translation initiation sites.

Inputs to the method of the invention are the query sequences (protein or nucleic acid), the normalized amino acid property values of the 20 amino acids, the weights of the selected properties, and the compositional ranges of the windows.

Output for both nucleic acid and protein sequence queries includes the position of the initiation codon, the distance ratio for the closest non-signal reference protein to the closest signal reference protein, the distance ratio for the second closest non-signal reference to the second closest signal reference and the amino acid sequence of the identified signal peptide. For nucleic acid data, the frame of translation is also included as output.

One embodiment of the present invention provides a method for identifying protein classes from protein or nucleic acid sequence data comprising analyzing combinations of amino acid properties by mathematical programming.

In another embodiment of the present invention, the average amino acid property values of non-overlapping oligopeptide windows in query sequence data and a protein reference set are determined, the reference set values are weighted and the values used to distinguish between protein classes.

In each of the above embodiments, exemplary protein classes are secreted and non-secreted, chemokine, 7-transmembrane receptor and signal peptidase cleavage site. Preferably, the protein classes are secreted and non-secreted. Also preferred is the method wherein the number of amino acid properties analyzed is about 17 to about 25.

In another embodiment of the present invention, secreted proteins are identified from protein or nucleic acid sequence data in a method comprising:
  a) determining the average amino acid property values of non-overlapping oligopeptide windows in reference sets of experimentally known secreted and non-secreted proteins;
  b) determining weights of the determined property values;
  c) identifying a putative amino terminus in query sequence data;
  d) determining the average amino acid property values of non-overlapping oligopeptide windows in the putative amino terminus of the query sequence data; and
  e) distinguishing between secreted and non-secreted proteins.

In the method of the invention, the amino acid properties of amino terminal segments of the reference sets of experimentally known secreted and non-secreted proteins and of the putative amino termini of query sequence data are determined. Preferably, the amino terminal segment length is 30 residues, as the typical length of an eukaryotic signal peptide is about 24 residues, and some additional amino-terminal residues of the passenger protein are also crucial in determining whether the protein can or cannot be transported (7). Each segment of peptide and translated nucleic acid sequence data is broken down into windows of non-overlapping oligopeptides. Preferably, the oligopeptides are pentapeptides. Each segment s is broken down into six windows w of nonoverlapping pentapeptides. Averages of each normalized amino acid property value k over the m resides (where m=5 for a pentapeptide) involved in oligopeptide window w are calculated by:

$$c(s, w, k) = \sum_{i=1}^{m} p(i, k) \quad (1)$$

where c(s,w,k) is the average value of property value k in window w of segment s; and p(i,k) is the value of property value k for window position i. For example, if a segment's third window contains amino acid residues LIAVM, the hydropathy of this window will be the average hydropathy of leucine, isoleucine, alanine, valine and methionine.

Distinguishing secreted proteins from non-secreted proteins using n properties requires separation of that property space into two respective parts. As secreted and cytosolic proteins are linearly inseparable in the property space used here, a distance method is used to distinguish these protein classes.

Distances d(q,s) between the query segment q and each signal peptide s (and cytosolic segment y) are calculated:

$$d(q, s) = \sum_{w=1}^{6} \sum_{k=1}^{N} u(w, k) \cdot |c(q, w, k) - c(s, w, k)| \quad (2)$$

where u(w,k) is the weight for property k in window w of segment s. To increase the speed of calculation, absolute value distances are preferred to Euclidean distances. These distances are compatible: if for the absolute value distances among any three points A, B and C, d(A,B)<d(A,C), then the same relation holds for the Euclidean distances as well.

Distances to the closest secreted protein and cytosolic protein, respectively, are selected and their ratio is computed. The query sequence is predicted either as a signal peptide or a membrane anchor, i.e., a secreted protein, provided that (i) the distance to the closest secreted protein does not exceed the largest distance between any pair of the known secreted proteins in the reference set; and (ii) the ratio of the distances to the closest nonsecreted versus the closest secreted protein exceeds a specified threshold. Preferably, the specified threshold is $\geq 1.0$. Most preferably, the specified threshold is $\geq 1.3$, as no cytosolic protein in the reference set was observed with a distance ratio of 1.29 or above during the cross-validation experiments (see Example 1, infra).

The value c(s,w,k) representing the average amino acid property value derived from the reference set is weighted to reflect its diagnostic value in distinguishing signal peptides or membrane anchors from cytosolic proteins. Proper weighting provides for maximization of the number of correctly predicted sequences (both secreted and cytosolic proteins). This is equivalent to the minimization of misclassifications. Property weights u(w, k) are calculated by (i) according evolutionary conservation of the property from which the importance in determining protein folds can be inferred; (ii) neural networks or genetic algorithm techniques; or (iii) by large-scale optimization using mathematical programming, which includes integer, mixed-integer, linear or quadratic programming. Preferably, mathematical programming is used.

In one embodiment of the invention, variation, or its inverse, conservation, is measured. Preferably, variation is measured. For each window w, property k and each signal peptide s in the reference set, p(s,w,k) is calculated (the arithmetic mean of the propensity values of the 5 residues in window w and sequence s). The variation of property k at window w is then defined as the R(secr,w,k) range of p(s,w,k) values over all signal peptides. The variations R(cyt,w,k) for windows and properties of non-secreted (cytosolic) proteins are calculated in an analogous manner.

The ratio $$q(w, k) = \frac{|\mu(\text{secr}, w, k) - \mu(cyt, w, k)|}{R(\text{secr}, w, k) - R(cyt, w, k)} \quad (3)$$

where $\mu(\text{secr}, w, k)$ and $\mu(cyt,w, k)$ are the average values of property k in window w and expresses the diagnostic value of property k in window w in distinguishing signal peptides or membrane anchors from cytosolic proteins. The u(w,k) weight of a property k at window w is given by:

$$u(w, k) = \frac{q(w, k)}{\sum_{k=1}^{N} q(w, k)} \quad (4)$$

The weights for all properties and windows are normalized to yield a sum of 10,000. As an example, Table 1 shows the 20 properties with the highest weight as calculated by evolutionary conservation (Eqs. 3–4) for pentapeptide No. 4 of the reference set (See Example 1, infra).

TABLE 1

Amino Acid Property Value Weights Calculated on the Basis of Evolutionary Conservation

| Property | Weight |
|---|---|
| Average relative fractional occurrence in AL(i) | 79 |
| Polarity | 66 |
| Parameter of charge transfer capability | 65 |
| Relative population of conformational state C | 53 |
| Normalized frequency of turn in all-alpha class | 53 |
| Hydration number | 53 |
| Boltzmann probability of backbone conformational states | 52 |
| Normalized relative frequency of extended structure | 45 |
| Normalized frequency of zeta R | 45 |
| Normalized frequency of extended structure | 45 |
| Information measure for extended without hydrogene bond | 44 |
| Polar requirement | 43 |
| Principal component IV | 42 |
| Normalized relative frequency of bend S | 42 |
| Weights for alpha-helix at the window position of −6 | 41 |
| Hydrophobicity | 41 |
| Weights for beta-sheet at the window position of −3 | 40 |
| Structural information content, mean | 39 |
| Retention factor of principal dinucleotides in high salt chromatography | 39 |
| Short and medium-range non-bonded energy per residue | 38 |

In another embodiment of the invention, property weights are determined by maximizing how secreted proteins can be discriminated from cytosolic proteins. Property weights are optimized by mathematical programming, simulated neural networks or genetic algorithms. A brute force optimization of N(dist) distances between all possible pairs of sequences for all windows:

$$N(dist) = N(w) \cdot \frac{N(seq)^2 - N(seq)}{2} \quad (5)$$

where N(w) is the number of windows and N(seq) is the number of sequences in the reference set, is practically impossible. In application to the refrence set below, the number of distances would be on the order of $10^7$. Taking into account that each distance can involve 402 or more dimensions, a problem of that size exceeds any currently available hardware capacity and CPU limitations.

Therefore, weights are instead optimized for a simplified model: the linear separation by an n−1 dimensional cutting plane (25). Determination of weights that provide optimal linear separation between secreted and cytosolic proteins were demonstrated in the cross-validation experiments in Example 1, infra, to provide even better separation for the more sensitive and selective distance method.

A fictitious example of a two-dimensional space with a one-dimensional cutting plane (straight line) is shown in FIG. 1. Secreted proteins above a defined dead zone (marked by dotted lines) surrounding the cutting plane (solid line) and non-secreted proteins below the dead zone are considered as correct classifications.

The set of secreted proteins may be concave, i.e., there may exist one or more lines connecting two secreted proteins that contain(s) non-secreted protein(s). In this case, the two classes cannot be separated by a cutting plane or a simple non-linear surface.

Preferably, weights for different properties in different windows are determined and optimized by mathematical programming (26) which results in maximization of the number of correct classifications in the reference set. Most preferred is the use of mixed-integer programming techniques (27–29). This sensitive and selective, highly CPU-intensive, branch of optimization finds the global maximum or minimum of a goal function through optimization of variables. Bounds and conditions should allow a solution, otherwise the model is not feasible. Once a linear or piecewise linear model can be formulated, linear programming can handle even millions of variables and conditions using powerful algorithms and software developed over the last five decades and known to those skilled in the art. See, e.g., Barnhart (30) who describes a large-scale multi-commodity flow problem. The mathematical programming model optimizes the weights (slopes) for each property as well as the vector product g=wx. The subset of the number of properties (dimensions) for each window that allows correct classification for the highest number of secreted and non-secreted proteins in the reference set is selected. Preferably, the subset is about 17 to about 25 properties.

A perfect cutting plane may not exist for a chosen reference set and properties, i.e., there may be no subsets of properties and their optimized weights that allow linear separation between secreted proteins s and cytosolic proteins y. In such cases, Robust Linear Programming (RLP) (31) can be used to minimize the sum of the distances of misclassified sequences from the cutting plane as follows:

$$\alpha(s) = \sum_{k=1}^{N(p)} u(w, k) \cdot r(w, k, s) - \gamma - 1 \geq 0 \quad (6)$$

$$\alpha(y) = \sum_{k=1}^{N(p)} u(w, k) \cdot r(w, k, s) - \gamma + 1 \leq 0 \quad (7)$$

where ideally, α(s) is positive for most secreted proteins s and α(y) is negative for most cytosolic proteins y; N(p) is the number of amino acid properties selected; u(w,k) is the weight for property k in window w; γ is the location of the cutting plane given by the vector product wx, and 1−(−1)=2 is the width of the dead zone where any protein is considered as misclassified. Due to the possible linear inseparability of the convex hulls, some proteins may end up on the wrong side of the cutting plane that separated most of the secreted proteins from most cytosolic proteins in the property space. In RLP, the (weighted) sum of the extents of violations (the negative α(s) and the positive α(y) values) are minimized.

RLP has a basic shortcoming. Errors in the reference sets (annotating some secreted proteins as "non-secreted" or vice versa) can produce large "violations" exceeding the effect of several real violations hence leading to the inappropriate allocation of the cutting plane. Therefore, in the method of the invention, the number of misclassifications, rather than the sum of the extents of violations, have been minimized by applying mixed integer programming or special ordered sets (27–29). We maximize the number of correct classifications: for each secreted protein s, C(s) was assigned 1 if α(s) was positive, otherwise 0; for each cytosolic protein y, C(y) was assigned 1 if α(y) was negative, otherwise 0:

$$\frac{1}{N(s)} \cdot \sum_{s=1}^{N(s)} C(s) + \frac{1}{N(y)} \sum_{y=1}^{N(y)} C(y) \qquad (8)$$

Variables to be optimized are the weights for each window and each property, the special ordered set or binary variables C(s) and C(y) indicating the correctness of the classification for each sequence and γ. The speed of optimization was greatly enhanced by specifying upper and lower bounds, solving priorities and by initializing values for most variables as well as by prescribing branching orders for the optimization of binary variables by declaring priorities in the mixed integer models (27). Weights for each selected property is assigned the absolute value of the weights u(w,k) in (Eqs. 5–6) by maximizing the goal function in Eq. 8 above. As a rule, about 20 properties were assigned non-zero weights. Their absolute values were taken and were subsequently normalized to produce a sum of 100. Examples of optimized weights for pentapeptide No. 4 of the reference set (see Example 1, infra) optimized by using special ordered sets are shown in Table 2. All other properties were assigned a weight of zero.

TABLE 2

Optimized Weights of Amino Acid Property Values

| Property | Weight |
|---|---|
| A parameter defined from the residuals obtained from the best correlation | 7.47 |
| A parameter of charge transfer donor capability | 1.31 |
| Free energy change of epsilon(i) to epsilon(ex) | 4.01 |
| Free energy change of epsilon(i) to alpha(Rh) | 1.21 |
| Flexibility parameter for two rigid neighbors | 1.53 |
| Average relative probability of beta-sheet | 18.95 |
| Free energy of solution in water | 9.19 |
| Hydrophobicity, Zimmerman | 0.10 |
| Number of bonds in the longest chain | 2.91 |
| Number of atoms in the side chain labelled 1 + 1 | 7.26 |
| Net charge | 2.26 |
| Dependence of partition coefficient on ionic strength | 4.53 |
| Weights for alpha-helix at the window position of 6, Qian and Sejnowski | 4.56 |
| Weights for alpha-helix at the window position of −1, Qian and Sejnowski | 1.77 |
| Weights for beta-sheet at the window position of 3, Qian and Sejnowski | 5.53 |
| Weights for beta-sheet at the window position of −3, Qian and Sejnowski | 8.26 |
| Spin-spin coupling constants 3JHalpha-NH | 8.26 |
| Chemical shift of the alpha-carbon 1H in random coils | 10.27 |
| Chemical shift of the alpha-carbon 1H in all secondary structures | 6.16 |
| Chemical shift of the amino 1H in alpha-helices | 0.35 |

Upon completion of the method of the invention, the identified sequences are stored in a database. The sequences may be further characterized on the basis of their sequence, structure, biological function or other related characteristics, which information can be linked to the sequences in the database.

One method of further characterizing protein or nucleic acid sequences is by homology to other known genes. Shared homology of a sequence with a known gene may indicate a similar biological role of function. In addition to this method, which can be automated, proteins identified by the method of the invention may also be characterized on the basis of expert commentary from relevant human specialists or by the results of biological experiments.

Another aspect of the invention is a computer system for identifying protein classes, such as secreted or non-secreted proteins, from nucleic acid or protein sequence data. A representative computer system includes a hardware environment on which the methods of the invention may be implemented. The hardware environment includes a central processing unit, a memory device, a display and a user interface device. Exemplary hardware environments are a Sun Microsystems Ultrasparc or Digital Equipment Corporation Alpha workstation, having a display and keyboard and/or mouse input devices.

In one embodiment, the computer system comprises means for analyzing combinations of amino acid properties by mathematical programming.

In another embodiment, the computer system comprises:
a) means for determining the average amino acid property values of non-overlapping oligopeptide windows in query sequence data and a protein reference set;
b) means for weighting the reference set values; and
c) means for distinguishing between protein classes.

In another embodiment, the computer system comprises:
a) means for determining the average amino acid property values of non-overlapping oligopeptide windows in reference sets of experimentally known secreted and non-secreted proteins;
b) means for determining weights of the determined property values;
c) means for identifying a putative amino terminus in query sequence data;
d) means for determining the average amino acid property values of non-overlapping oligopeptide windows in the putative amino terminus of the query sequence data; and
e) means for distinguishing between secreted and non-secreted proteins.

In another embodiment, the computer system comprises:
a) means for determining the average amino acid property values of non-overlapping oligopeptide windows in reference sets of experimentally known secreted and non-secreted proteins comprising:
  a1) means for determining amino acid property values in known signal peptides of secreted proteins and amino-termini of non-secreted proteins;
  a2) means for normalizing the values of each property to a range; and
  a3) means for selecting a subset of the most discriminative or conserved properties;
b) means for determining weights of the determined property values by mathematical programming;
c) means for identifying a putative amino terminus in query sequence data;
d) means for determining the average amino acid property values of non-overlapping oligopeptide windows in the putative amino terminus of the query sequence data;
e) means for calculating distance values between the average physicochemical property values determined by means a) and d);
f) means for identifying the secreted and non-secreted reference proteins having the closest distance to the query sequence; and
g) means for distinguishing between secreted and nonsecreted proteins comprising:
  g1) means for determining a ratio of the distances obtained by means e); and
  g2) means for predicting the query sequence as a secreted protein when the distance to the closest signal does not exceed the largest distance between any pair of the known signal peptides in the reference set and the ratio of the distances determined by means g1) is ≧1.0.

Preferably, in the systems of the invention, the oligopeptide windows are pentapeptides and the ratio of the distances is ≧1.3.

Preferably, in the systems of the invention, the protein classes are secreted and non-secreted, chemokine, 7-transmembrane receptor and signal peptidase cleavage site. Most preferably, the protein classes are secreted proteins and non-secreted proteins.

Any of the computer system embodiments can further comprise means for characterizing the potential gene or protein sequences.

In another embodiment, the computer system comprises a central processing unit executing a secreted protein identifying program stored in a memory device accessed by the central processing unit; a display on which the central processing unit displays screens of the secreted protein identifying program in response to user inputs; and a user interface device. As used herein, the term "secreted protein identifying program" refers to a program encoding any of the methods of the invention.

The present invention will now be described with reference to the following specific, non-limiting example.

EXAMPLE 1

Analysis of Protein Reference Set

Well-documented reference sets of secreted (including membrane-bound) and non-secreted (cytosolic) proteins were used to train the amino acid property distance method and test prediction accuracy. These sets were imported from Nielsen et al.'s (13,14) World Wide Web server (ftp://virus.cbs.dtu.dk/pub/signalp) and are herein incorporated by reference as though fully set forth. The proteins in the sets were selected from the SWISS-PROT Database of Protein Sequences (Version 29, (32)). Nielsen et al., supra, have discarded any signal peptide or membrane anchor identified by computer methods and entries with questionable evidence or alternative cleavage sites. Their eukaryotic sets include 2,282 eukaryotic signal peptides, 97 uncleaved membrane anchors and 854 cytosolic proteins, respectively.

In the reference sets of eukaryotic secreted and cytosolic proteins, averaged properties were calculated for 6 nonoverlapping pentapeptide windows (the amino-terminal 30 residues) of each sequence in accordance with Eq. 1. Optimization of weights by mathematical programming was performed on a SUN HP10000 workstation with 8 Gigabyte of memory using the CPLEX Package (33) under the AMPL (A Modeling Language for Mathematical Programming)(34) interface. Each pentapeptide window of each sequence was represented as a point in the high dimensional abstract space of the properties with non-zero weights.

The method was tested by random cross-validation (35). In each of 10 repetitions, three quarters of the sequences in the reference sets were selected by random number generator and declared as a training set, while the remaining one quarter was assigned as a test set. Only sequences in the training set were used for weight optimization for the amino acid property distance method and were used in the distance calculations. Predictions were performed on the test set and the results were compared to the experimental assessment of the cellular location of the sequences. Performance of the method was measured by a correlation coefficient r (36):

$$r = \frac{(TP \cdot TN) - (FN \cdot FP)}{\sqrt{(TN + FN)(TN + FP)(TP + FN)(TP + FP)}} \quad (9)$$

where TP and TN stand for true positives and negatives, FP and FN for false positives and negatives, respectively. Percentages of true/false positives and negatives, correlation coefficients for the cross-validation experiments on the subsets of eukaryotic secreted and cytosolic reference sets are shown in Table 3. On average, a correlation coefficient of 0.83 was achieved with over 93 percent correct predictions using a distance ratio of 1. The highest distance ratio for cytosolic proteins was 1.29. Thus, the probability of predicting a cytosolic protein as a secreted protein with distance ratios of 1.3 or higher is 1/3000. It is well known that cross-validation underestimates the accuracy of the method of the invention since all available sequences were not used for the training set. Depending on user requirements, the distance ratio threshold can be increased and will eliminate false positives (cytosolic proteins predicted as secreted) at the expense of increasing the number of false negatives (secreted proteins predicted as cytosolic).

TABLE 3

| Test set No. | No. of sequences | | | Correct | | Correl coeff. | Percent true | | Percent false | |
|---|---|---|---|---|---|---|---|---|---|---|
| | All | Secr. | Cyto. | # | % | | pos. | neg. | pos | neg. |
| 1 | 777 | 569 | 208 | 729 | 93.82 | 0.84 | 95.25 | 89.90 | 10.10 | 4.75 |
| 2 | 783 | 605 | 178 | 734 | 93.74 | 0.82 | 95.70 | 87.08 | 12.92 | 4.30 |
| 3 | 732 | 537 | 195 | 692 | 94.54 | 0.86 | 95.90 | 90.77 | 9.23 | 4.10 |
| 4 | 748 | 555 | 193 | 692 | 92.51 | 0.81 | 94.77 | 86.01 | 13.99 | 5.23 |
| 5 | 749 | 556 | 193 | 707 | 94.39 | 0.85 | 96.94 | 87.05 | 12.95 | 3.06 |
| 6 | 740 | 553 | 187 | 697 | 94.19 | 0.85 | 96.02 | 88.77 | 11.23 | 3.98 |
| 7 | 789 | 581 | 208 | 733 | 92.90 | 0.82 | 93.98 | 89.90 | 10.10 | 6.02 |
| 8 | 827 | 619 | 208 | 762 | 92.14 | 0.80 | 93.05 | 89.42 | 10.58 | 6.95 |
| 9 | 773 | 592 | 181 | 710 | 91.85 | 0.77 | 95.10 | 81.22 | 18.78 | 4.90 |
| 10 | 781 | 579 | 202 | 730 | 93.47 | 0.83 | 95.16 | 88.61 | 11.39 | 4.84 |
| Average | 770 | 575 | 195 | — | 93.36 | 0.83 | 95.19 | 87.87 | 12.13 | 4.81 |

All programs but the optimization were written in the C of PERL programming languages on UNIX platforms running on SUN Ultrasparc and DEC Alpha workstations.

REFERENCES

All publications from the scientific literature cited in this specification are herein incorporated by reference as though fully set forth.

1. von Heijne, G. *J. Mol. Biol.* 184: 99 (1985).
2. Kaiser, C. A., Preuss, D., Grisafi, P., Botstein, D. *Science* 235: 312 (1987).
3. Altschul, S. F., Gish, W., Miller, W., Myers, E. W., Lipman, D. J. *J. Mol. Biol.* 215: 403 (1990).
4. Pearson, W. R., Lipman, D. J. *Proc. Natl. Acad. Sci. U.S.A.* 85: 2444 (1988).
5. Pearson, W. R. *Methods Enzymol.* 183: 63 (1989).
6. Smith, T. F., Waterman, M. S. *J. Mol. Biol.* 13: 195 (1981).
7. von Heijne, G. *Nucleic Acids Res.* 14: 4683 (1986).
8. Pascarella, S., Bossa, F. *Comput. Appl. Biosci.* 5: 53 (1989).
9. Folz, R. J., Gordon, J. I. *Biochem. Biophys. Res. Commun.* 146: 870 (1987).
10. Popowicz, A. M., Dash, P. F. *Comp. Appl. Biosci.* 4: 405 (1988).
11. Ladunga, I., Czako, F., Csabai, I., Geszti, T. *Comp. Appl. BioSci.* 7: 485 (1991).
12. Mezard, M., Nadal, J. P. *J. Phys. A: Math. Gen.* 22: 2191 (1989).
13. Nielsen, H., Engelbrecht, J., von Heijne, G., Brunak, S. *Proteins* 24: 165 (1996).
14. Nielsen, H., Engelbrecht, J., Brunak, S., von Heijne, G. *Prot. Engng.* 10: 1 (1997).
15. Rumelhart, D. E., McClelland, J. L. *Parallel Distributed Processing*, MIT Press, Cambridge, Mass. (1988).
16. Nakai, K., Kanehisa, M. *Proteins* 11: 95 (1991).
17. Nakai, K., Kanehisa, M. *Genomics* 14: 897 (1992).
18. Horton, P., Nakai, K. *Ismb.* 4: 109 (1996).
19. Talmud, P., Lins, L., Brasseur, R. *Protein Eng.* 9: 317 (1996).
20. Claros, M. G., Brunak, S., von Heijne, G. *Curr. Opin. Struct. Biol.* 7: 394 (1997).
21. Ladunga, I., Smith, R. F. *Prot. Engng.* 10: 187 (1997).
22. Nakai, K., Kidera, A., Kanehisa, M. *Protein Engng.* 2: 93 (1988).
23. Tomii, K., Kanehisa, M. *Prot. Engng.* 9: 27 (1996).
24. Kozak, M. *Mammalian Genome* 7: 563 (1996).
25. Gomory, R. E. *Bull. Amer. Math. Soc.* 64: 275 (1958).
26. Chvatal, V. *Linear Programming*, p. 478. Freeman, New York. (1983).
27. Little, J. D. C., Murty, K. C., Sweeney, D. W., Karel, C. *Operations Res.* 11: 972 (1963).
28. Beale, E. M. L., Tomlin, J. A. *Mathematical Programming* 3: 339 (1972).
29. Beale, E. M. L. Integer programming. p. 409–448. in: Schittkowski, K. ed. *Computational Mathematical Programming*, Springer, Berlin (1985).
30. Barnhart, C. *Naval Research Logistics* 40: 305 (1993).
31. Bennett, K. P., Mangasarian, O. L. *Optimization Methods and Software* 1: 23 (1992).
32. Bairoch, A., Bucher, P., Hofmann, K. *Nucleic Acids Res.* 24: 189 (1996).
33. Ripley, B. D. *Pattern Recognition and Neural Networks*, Cambridge University Press, Cambridge (1996).
34. Fourer, R., Gay, D. M., Kernighan, B. W. *AMPL: A Modeling Language for Mathematical Programming*, p. 351, Boyd and Fraser, Danvers, Massachusetts (1993).
35. Stone, M. *Proc. Royal Soc. B* 36: 111 (1974).
36. Mathews, B. *Biochem. Biophys. Acta* 405: 442 (1975).

It will be apparent to those skilled in the art that various modifications can be made to the present method without departing from the scope or spirit of the invention, and it is intended that the present invention cover modifications and variations of the method provided they come within the scope of the appended claims and their equivalents.

I claim:

1. A computer-based method for identifying protein classes from protein or nucleic acid sequence data comprising:
    a) determining the average amino acid property values of non-overlapping oligopeptide windows in query sequence data and a protein reference set;
    b) weighting the reference set values; and
    c) distinguishing between protein classes.

2. The method of claim 1 wherein the protein classes are secreted and non-secreted, chemokine, 7-transmembrane receptor or signal peptidase cleavage site domain.

3. The method of claim 2 wherein the protein classes are secreted and non-secreted and the number of amino acid properties analyzed is about 17 to about 25.

4. A computer-based method for identifying secreted proteins from protein or nucleic acid sequence data comprising:
    a) determining the average amino acid property values of non-overlapping oligopeptide windows in reference sets of experimentally known secreted and non-secreted proteins;
    b) determining weights of the determined reference set property values;
    c) identifying a putative amino terminus in query sequence data;
    d) determining the average amino acid property values of non-overlapping oligopeptide windows in the putative amino terminus of the query sequence data; and
    e) distinguishing between secreted and non-secreted proteins.

5. The method of claim 4 wherein the step of distinguishing between secreted and non-secreted proteins comprises the step of separating secreted and non-secreted proteins with a cutting plane or a nonlinear surface.

6. The method of claim 4 wherein the step of distinguishing between secreted and non-secreted proteins comprises the steps of:
    e1) calculating distance values between the average physicochemical property values determined in steps a) and d);
    e2) identifying the secreted and non-secreted reference proteins having the closest distance to the query sequence;
    e3) determining a ratio of the distances obtained in e2); and
    e4) predicting the query sequence as a secreted protein when the distance to the closest secreted protein does not exceed the largest distance between any pair of the known secreted proteins in the reference set and the ratio of the distances determined in e3) is a specified threshold value.

7. The method of claim 6 wherein the specified threshold value is $\geq 1.0$.

8. The method of claim 6 wherein the specified threshold value is $\geq 1.3$.

9. The method of claim 4 wherein the number of amino acid properties analyzed is about 17 to about 25.

10. The method of claim 4 wherein the weights of the determined property values are determined according to their conservation or variation in secreted and non-secreted proteins.

11. The method of claim 4 wherein the weights of the determined property values are determined by mathematical programming.

12. The method of claim 4 wherein the determination of the average amino acid property values for the secreted and non-secreted protein reference set comprises the steps of:

a. determining physicochemical properties of amino acids in known signal peptides of secreted proteins and amino-termini of non-secreted proteins;

b. normalizing the values of each property to a range; and c. selecting a subset of the most discriminative or conserved properties.

13. The method of claim 4 wherein the oligopeptide windows are pentapeptides.

14. A computer-based method for identifying secreted proteins from protein or nucleic acid sequence data comprising:

a) determining the average amino acid property values of non-overlapping oligopeptide windows in reference sets of experimentally known secreted and non-secreted proteins by the steps of:

a1) determining physicochemical properties of amino acids in known signal peptides of secreted proteins and amino-termini of non-secreted proteins;

a2) normalizing the values of each property to a range; and a3) selecting a subset of the most discriminative or conserved properties;

b) determining weights of the determined property values by mathematical programming;

c) identifying a putative amino terminus in query sequence data;

d) determining the average amino acid property values of non-overlapping oligopeptide windows in the putative amino terminus of the query sequence data;

e) calculating distance values between the average physicochemical property values determined in steps a) and d);

f) identifying the secreted and non-secreted reference proteins having the closest distance to the query sequence; and g) distinguishing between secreted and nonsecreted proteins by the steps of:

g1) determining a ratio of the distances obtained in step e); and g2) predicting the query sequence as a secreted protein when the distance to the closest signal does not exceed the largest distance between any pair of the known signal peptides in the reference set and the ratio of the distances determined in step g1) is $\geq 1.0$.

15. The method of claim 14 wherein the oligopeptide windows are pentapeptides.

16. The method of claim 14 wherein the ratio of the distances is $\geq 1.3$.

17. The method of claim 14 wherein the subset of the most discriminative or conserved properties is about 17 to about 25 properties.

18. A computer system for identifying protein classes from protein or nucleic acid sequence data comprising:

a) means for determining the average amino acid property values of non-overlapping oligopeptide windows in query sequence data and a protein reference set;

b) means for weighting the reference set values; and c) means for distinguishing between protein classes.

19. A computer system for identifying secreted proteins from protein or nucleic acid sequence data comprising:

a) means for determining the average amino acid property values of non-overlapping oligopeptide windows in reference sets of experimentally known secreted and non-secreted proteins;

b) means for determining weights of the determined property values;

c) means for identifying a putative amino terminus in query sequence data;

d) means for determining the average amino acid property values of non-overlapping oligopeptide windows in the putative amino terminus of the query sequence data; and e) means for distinguishing between secreted and non-secreted proteins.

20. A computer system for identifying secreted proteins from protein or nucleic acid sequence data comprising:

a) means for determining the average amino acid property values of non-overlapping oligopeptide windows in reference sets of experimentally known secreted and non-secreted proteins comprising:

a1) means for determining amino acid property values in known signal peptides of secreted proteins and amino-termini of non-secreted proteins;

a2) means for normalizing the values of each property to a range; and a3) means for selecting a subset of the most discriminative or conserved properties;

b) means for determining weights of the determined property values by mathematical programming;

c) means for identifying a putative amino terminus in query sequence data;

d) means for determining the average amino acid property values of non-overlapping oligopeptide windows in the putative amino terminus of the query sequence data;

e) means for calculating distance values between the average physicochemical property values determined by means a) and d);

f) means for identifying the secreted and non-secreted reference proteins having the closest distance to the query sequence; and g) means for distinguishing between secreted and nonsecreted proteins comprising:

g1) means for determining a ratio of the distances obtained by means e); and g2) means for predicting the query sequence as a secreted protein when the distance to the closest signal does not exceed the largest distance between any pair of the known signal peptides in the reference set and the ratio of the distances determined by means g1) is $\geq 1.0$.

21. The computer system of claim 20 wherein the oligopeptide windows are pentapeptides.

22. The computer system of claim 20 wherein the ratio of the distances is $\geq 1.3$.

23. A computer system for identifying protein classes from protein or nucleic acid sequence data comprising:

(a) a central processing unit;

(b) a memory device having an executable secreted protein identifying program stored therein whereby the program determines average amino acid property values of non-overlapping oligopeptide windows in query sequence data and a protein reference set, weights the reference set values, and distinguishes between protein classes;

(c) a computer display on which the central processing unit displays screens of the secreted protein identifying program in response to user inputs; and (d) a user interface device.

24. The computer system of claims 18 or 23 wherein the protein classes are secreted and non-secreted, chemokine, 7-transmembrane receptor or signal peptidase cleavage site domain.

* * * * *

UNITED STATES PATENT AND TRADEMARK OFFICE
CERTIFICATE OF CORRECTION

PATENT NO. : 5,987,390
DATED : November 16, 1999
INVENTOR(S) : Ladunga

It is certified that error appears in the above-identified patent and that said Letters Patent is hereby corrected as shown below:

Pages 25 to 122 are missing from the specification and are enclosed herewith.

Signed and Sealed this

Twenty-ninth Day of August, 2000

Attest:

Q. TODD DICKINSON

Attesting Officer

Director of Patents and Trademarks

AAINDEX: Amino Acid Index Database

The AAindex1 section of the Amino Acid Index Database is a
collection of published indices together with the result of cluster
analysis using the correlation coefficient as the distance between
two indices. This section currently contains 402 indices.

References:

Nakai, K., Kidera, A., Kanehisa, M. Prot. Eng. 2: 93 (1988).

Tomii, K., Kanehisa, M. Prot. Eng. 9: 27 (1996).

(Data Format of AAindex1)
```
****************************************************************
*                                                              *
* Each entry has the following format.                         *
*                                                              *
* H Accession number                                           *
* D Data description                                           *
* R LITDB entry number                                         *
* A Author(s)                                                  *
* T Title of the article                                       *
* J Journal reference                                          *
* * Comment or missing                                         *
* C Accession numbers of similar entries with the correlation  *
*   coefficients of 0.8 (-0.8) or more (less).                 *
*   Notice: The correlation coefficient is calculated with zeros*
*   filled for missing values.                                 *
* I Amino acid index data in the following order               *
*   Ala   Arg   Asn   Asp   Cys   Gln   Glu   Gly   His   Ile *
*   Leu   Lys   Met   Phe   Pro   Ser   Thr   Trp   Tyr   Val *
* //                                                           *
****************************************************************
```

H ANDN920101
D alpha-CH chemical shifts (Andersen et al., 1992)
R 1810048b
A Andersen, N.H., Cao, B. and Chen, C.
T Peptide/protein structure analysis using the chemical shift index method:
  upfield alpha-CH values reveal dynamic helices and aL sites
J Biochem. and Biophys. Res. Comm. 184, 1008-1014 (1992)
C BUNA790102    0.949
I    A/L      R/K      N/M      D/F      C/P      Q/S      E/T      G/W      H/Y      I/V
     4.35     4.38     4.75     4.76     4.65     4.37     4.29     3.97     4.63     3.95
     4.17     4.36     4.52     4.66     4.44     4.50     4.35     4.70     4.60     3.95
//
H ARGP820101
D Hydrophobicity index (Argos et al., 1982)
R 0901079b
A Argos, P., Rao, J.K.M. and Hargrave, P.A.
T Structural prediction of membrane-bound proteins
J Eur. J. Biochem. 128, 565-575 (1982)
C JOND750101    1.000    SIMZ760101    0.967    GOLD730101    0.936
  MEEJ810101    0.891    CIDH920105    0.867    LEVM760106    0.865
  CIDH920102    0.862    MEEJ800102    0.855    MEEJ810102    0.853
  CIDH920103    0.827    PLIV810101    0.820    CIDH920104    0.819
  LEVM760107    0.806    NOZY710101    0.800    PARJ860101   -0.835
  WOLS870101   -0.838    BULH740101   -0.854
I    A/L      R/K      N/M      D/F      C/P      Q/S      E/T      G/W      H/Y      I/V
     0.61     0.60     0.06     0.46     1.07     0.       0.47     0.07     0.61     2.22
     1.53     1.15     1.18     2.02     1.95     0.05     0.05     2.65     1.88     1.32
//
H ARGP820102
D Signal sequence helical potential (Argos et al., 1982)
R 0901079b A Argos, P., Rao, J.K.M. and Hargrave, P.A.
T Structural prediction of membrane-bound proteins
J Eur. J. Biochem. 128, 565-575 (1982)
C ARGP820103    0.961  KYTJ820101    0.803
I   A/L    R/K    N/M    D/F    C/P    Q/S    E/T    G/W    H/Y    I/V
    1.18   0.20   0.23   0.05   1.89   0.72   0.11   0.49   0.31   1.45
    3.23   0.06   2.67   1.96   0.76   0.97   0.84   0.77   0.39   1.08
//
H ARGP820103
D Membrane-buried preference parameters (Argos et al., 1982)
R 0901079b
A Argos, P., Rao, J.K.M. and Hargrave, P.A.
T Structural prediction of membrane-bound proteins
J Eur. J. Biochem. 128, 565-575 (1982)
C ARGP820102    0.961  MIYS850101    0.822  NAKH900106    0.810
  EISD860103    0.810  KYTJ820101    0.806
I   A/L    R/K    N/M    D/F    C/P    Q/S    E/T    G/W    H/Y    I/V
    1.56   0.45   0.27   0.14   1.23   0.51   0.23   0.62   0.29   1.67
    2.93   0.15   2.96   2.03   0.76   0.81   0.91   1.08   0.68   1.14
//
H BEGF750101
D Conformational parameter of inner helix (Beghin-Dirkx, 1975)
R 1309065
A Beghin, F. and Dirkx, J.
T Une methode statistique simple de prediction des conformations
  proteiques
J Arch. Int. Physiol. Biochim. 83, 167-168 (1975)
C KANM800103    0.893  ROBB760103    0.852  CHOP780201    0.841
  QIAN880105    0.833  QIAN880107    0.815  PALJ810102    0.811
  CHOP780101   -0.803  CHOP780210   -0.804  CRAJ730103   -0.812
  ROBB760108   -0.819  ROBB760113   -0.826  CHAM830101   -0.854
  PALJ810106   -0.859
I   A/L    R/K    N/M    D/F    C/P    Q/S    E/T    G/W    H/Y    I/V
    1.     0.52   0.35   0.44   0.06   0.44   0.73   0.35   0.60   0.73
    1.     0.60   1.     0.60   0.06   0.35   0.44   0.73   0.44   0.82
//
H BEGF750102
D Conformational parameter of beta-structure (Beghin-Dirkx, 1975)
R 1309065
A Beghin, F. and Dirkx, J.
T Une methode statistique simple de prediction des conformations
  proteiques
J Arch. Int. Physiol. Biochim. 83, 167-168 (1975)
C PRAM900103    0.834  PALJ810110    0.834  LEVM780102    0.834
  NAGK730102    0.833  QIAN880120    0.829  QIAN880119    0.811
  ROBB760106    0.809  PTIO830102    0.807  LIFS790101    0.807
  MIYS850101    0.806  PONP800107    0.803  PALJ810104    0.801
  MEIH800101   -0.832  RACS770101   -0.840
I   A/L    R/K    N/M    D/F    C/P    Q/S    E/T    G/W    H/Y    I/V
    0.77   0.72   0.55   0.65   0.65   0.72   0.55   0.65   0.83   0.98
    0.83   0.55   0.98   0.98   0.55   0.55   0.83   0.77   0.83   0.98
//
H BEGF750103
D Conformational parameter of beta-turn (Beghin-Dirkx, 1975)
R 1309065
A Beghin, F. and Dirkx, J.
T Une methode statistique simple de prediction des conformations
  proteiques
J Arch. Int. Physiol. Biochim. 83, 167-168 (1975)
C ROBB760113    0.924  ROBB760108    0.922  ROBB760110    0.903
  CHOP780101    0.885  CRAJ730103    0.874  PALJ810106    0.859
  TANS770110    0.834
I   A/L    R/K    N/M    D/F    C/P    Q/S    E/T    G/W    H/Y    I/V
    0.37   0.84   0.97   0.97   0.84   0.64   0.53   0.97   0.75   0.37
    0.53   0.75   0.64   0.53   0.97   0.84   0.75   0.97   0.84   0.37
//
H BHAR880101
D Average flexibility indices (Bhaskaran-Ponnuswamy, 1988)

R 1414112
A Bhaskaran, R. and Ponnuswamy, P.K.
T Positional flexibilities of amino acid residues in globular proteins
J Int. J. Peptide Protein Res. 32, 241-255 (1988)
C KARP850102    0.806   WERD780101   -0.803   RICJ880111   -0.813
I   A/L     R/K     N/M     D/F     C/P     Q/S     E/T     G/W     H/Y     I/V
   0.357   0.529   0.463   0.511   0.346   0.493   0.497   0.544   0.323   0.462
   0.365   0.466   0.295   0.314   0.509   0.507   0.444   0.305   0.420   0.386
//
H BIGC670101
D Residue volume (Bigelow, 1967)
R 2004108b
A Bigelow, C.C.
T On the average hydrophobicity of proteins and the relation between it
  and protein structure
J J. Theor. Biol. 16, 187-211 (1967)
* (Asn Gln 5.0)
C GOLD730102    1.000   KRIW790103    0.993   CHOC750101    0.990
  GRAR740103    0.984   FAUJ880103    0.972   CHAM820101    0.966
  CHOC760101    0.960   FASG760101    0.919   LEVM760105    0.913
  ROSG850101    0.910   DAWD720101    0.903   LEVM760102    0.896
  LEVM760106    0.876   CHAM830106    0.870   LEVM760107    0.863
  FAUJ880106    0.860   RADA880106    0.856   MCMT640101    0.814
  RADA880103   -0.865   OOBM770105   -0.902   OOBM770104   -0.905
I   A/L     R/K     N/M     D/F     C/P     Q/S     E/T     G/W     H/Y     I/V
   52.6   109.1    75.7    68.4    68.3    89.7    84.7    36.3    91.9   102.0
  102.0   105.1    97.7   113.9    73.6    54.9    71.2   135.4   116.2    85.1
//
H BIOV880101
D Information value for accessibility; average fraction 35% (Biou et al., 1988)
R 1413106b
A Biou, V., Gibrat, J.F., Levin, J.M., Robson, B. and Garnier, J.
T Secondary structure prediction: combination of three different methods
J Protein Engineering 2, 185-191 (1988)
C ROSG850102    0.981   RADA880108    0.981   NISK860101    0.972
  BIOV880102    0.968   MIYS850101    0.960   WERD780101    0.951
  FAUJ830101    0.942   MEIH800103    0.934   CIDH920104    0.933
  PONP800103    0.926   PONP800102    0.926   NISK800101    0.920
  PONP800101    0.918   CIDH920105    0.912   PONP800108    0.907
  PLIV810101    0.899   MANP780101    0.899   ROBB790101    0.890
  CIDH920103    0.887   DESM900102    0.878   JANJ780102    0.875
  EISD860103    0.864   CIDH920102    0.864   MEEJ810101    0.855
  JANJ790102    0.848   CIDH920101    0.847   SWER830101    0.839
  KYTJ820101    0.829   EISD860101    0.828   JANJ790101    0.827
  MEEJ810102    0.824   CHOC760103    0.823   PONP800107    0.816
  EISD840101    0.811   DESM900101    0.807   KRIW710101   -0.813
  KARP850101   -0.825   JANJ780103   -0.829   WOEC730101   -0.829
  ROSM880101   -0.830   LEVM760101   -0.831   HOPT810101   -0.848
  ROSM880102   -0.854   WOLS870101   -0.854   RACS770103   -0.856
  OOBM770101   -0.858   KRIW790102   -0.869   KARP850102   -0.880
  PARJ860101   -0.889   RACS770101   -0.893   GRAR740102   -0.910
  KRIW790101   -0.910   OOBM770103   -0.920   GUYH850101   -0.929
  RACS770102   -0.937   MEIH800101   -0.949   MEIH800102   -0.956
I   A/L     R/K     N/M     D/F     C/P     Q/S     E/T     G/W     H/Y     I/V
    16.    -70.    -74.    -78.    168.    -73.   -106.    -13.     50.    151.
   145.   -141.    124.    189.    -20.    -70.    -38.    145.     53.    123.
//
H BIOV880102
D Information value for accessibility; average fraction 23% (Biou et al., 1988)
R 1413106b
A Biou, V., Gibrat, J.F., Levin, J.M., Robson, B. and Garnier, J.
T Secondary structure prediction: combination of three different methods
J Protein Engineering 2, 185-191 (1988)
C BIOV880101    0.968   ROSG850102    0.960   RADA880108    0.942
  NISK860101    0.939   MIYS850101    0.930   WERD780101    0.929
  MEIH800103    0.916   FAUJ830101    0.911   CIDH920104    0.890

```
       CIDH920105    0.882   PONP800103    0.879   DESM900102    0.876
       NISK800101    0.873   PONP800102    0.867   JANJ780102    0.862
       PONP800101    0.860   CIDH920103    0.860   PLIV810101    0.858
       JANJ790102    0.856   PONP800108    0.854   WARP780101    0.853
       MANP780101    0.847   EISD860103    0.845   CIDH920102    0.837
       EISD860101    0.832   NAKH900110    0.829   MEEJ810101    0.822
       ROBB790101    0.821   DESM900101    0.821   CIDH920101    0.819
       PONP800107    0.814   EISD840101    0.814   KARP850101   -0.804
       JANJ780101   -0.809   WOEC730101   -0.819   ROSM880101   -0.824
       ROSM880102   -0.837   WOLS870101   -0.842   LEVM760101   -0.847
       KARP850102   -0.859   JANJ780103   -0.860   HOPT810101   -0.864
       PARJ860101   -0.875   RACS770101   -0.875   KRIW790101   -0.876
       OOBM770101   -0.877   KRIW790102   -0.878   GRAR740102   -0.881
       GUYH850101   -0.885   RACS770103   -0.906   OOBM770103   -0.925
       RACS770102   -0.932   MEIH800101   -0.937   MEIH800102   -0.951
I      A/L      R/K      N/M      D/F      C/P      Q/S      E/T      G/W      H/Y      I/V
       44.     -68.     -72.     -91.      90.    -117.    -139.      -8.      47.     100.
      108.    -188.     121.     148.     -36.     -60.     -54.     163.      22.     117.
//
H BROC820101
D Retention coefficient in TFA (Browne et al., 1982)
R 0809229
A Browne, C.A., Bennett, H.P.J., and Solomon, S.
T The isolation of peptides by high-performance liquid chromatography
  using predicted elution positions
J Anal. Biochem. 124, 201-208 (1982)
C BROC820102    0.925   ZIMJ680105    0.896   MEEJ800102    0.877
  NAKH900110    0.830   NOZY710101    0.829   MEEJ810102    0.820
  RADA880102    0.811   BULH740101   -0.815   PARJ860101   -0.849
  WOLS870101   -0.871
I      A/L      R/K      N/M      D/F      C/P      Q/S      E/T      G/W      H/Y      I/V
       7.3     -3.6     -5.7     -2.9     -9.2     -0.3     -7.1     -1.2     -2.1      6.6
      20.0     -3.7      5.6     19.2      5.1     -4.1      0.8     16.3      5.9      3.5
//
H BROC820102
D Retention coefficient in HFBA (Browne et al., 1982)
R 0809229
A Browne, C.A., Bennett, H.P.J., and Solomon, S.
T The isolation of peptides by high-performance liquid chromatography
  using predicted elution positions
J Anal. Biochem. 124, 201-208 (1982)
C BROC820101    0.925   ZIMJ680105    0.865   MEEJ800102    0.857
  MEEJ800101    0.840
I      A/L      R/K      N/M      D/F      C/P      Q/S      E/T      G/W      H/Y      I/V
       3.9      3.2     -2.8     -2.8    -14.3      1.8     -7.5     -2.3      2.0     11.0
      15.0     -2.5      4.1     14.7      5.6     -3.5      1.1     17.8      3.8      2.1
//
H BULH740101
D Transfer free energy to surface (Bull-Breese, 1974)
R
A Bull, H.B. and Breese, K.
T Surface tension of amino acid solutions: A hydrophobicity scale of the
  amino acid residues
J Arch. Biochem. Biophys. 161, 665-670 (1974)
C WOLS870101    0.929   PARJ860101    0.909   GRAR740102    0.822
  ROBB790101   -0.813   BROC820101   -0.815   LEVM760106   -0.818
  CIDH920104   -0.829   FAUJ830101   -0.830   EISD860101   -0.833
  MIYS850101   -0.838   CIDH920103   -0.848   CIDH920102   -0.851
  JOND750101   -0.853   ARGP820101   -0.854   RADA880102   -0.856
  CIDH920105   -0.871   GOLD730101   -0.874   MEEJ800102   -0.875
  MEEJ810101   -0.876   ZIMJ680105   -0.879   MEEJ810102   -0.880
  NOZY710101   -0.892   SIMZ760101   -0.894   VENT840101   -0.907
  PLIV810101   -0.912   SWER830101   -0.923
I      A/L      R/K      N/M      D/F      C/P      Q/S      E/T      G/W      H/Y      I/V
      -0.20    -0.12     0.08    -0.20    -0.45     0.16    -0.30     0.00    -0.12    -2.26
      -2.46    -0.35    -1.47    -2.33    -0.98    -0.39    -0.52    -2.01    -2.24    -1.56
//
H BULH740102
```

D Apparent partial specific volume (Bull-Breese, 1974)
R
A Bull, H.B. and Breese, K.
T Surface tension of amino acid solutions: A hydrophobicity scale of the
  amino acid residues
J Arch. Biochem. Biophys. 161, 665-670 (1974)
* (Tyr !)
C COHE430101    0.923    ZIMJ680102    0.825    GOLD730101    0.825
  SIMZ760101    0.815
I   A/L     R/K     N/M     D/F     C/P     Q/S     E/T     G/W     H/Y     I/V
    0.691   0.728   0.596   0.558   0.624   0.649   0.632   0.592   0.646   0.809
    0.842   0.767   0.709   0.756   0.730   0.594   0.655   0.743   0.743   0.777
//
H BUNA790101
D alpha-NH chemical shifts (Bundi-Wuthrich, 1979)
R 0503064b
A Bundi, A. and Wuthrich, K.
T 1H-nmr parameters of the common amino acid residues measured in aqueous
  solutions of the linear tetrapeptides H-Gly-Gly-X-L-Ala-OH
J Biopolymers 18, 285-297 (1979)
* (Pro !)
C ROBB760104    0.823    FAUJ880113    0.818    CHOP780213    -0.822
  ISOY800104    -0.842   TANS770104    -0.867   FINA910102    -0.992
I   A/L     R/K     N/M     D/F     C/P     Q/S     E/T     G/W     H/Y     I/V
    8.249   8.274   8.747   8.410   8.312   8.411   8.368   8.391   8.415   8.195
    8.423   8.408   8.418   8.228   0.      8.380   8.236   8.094   8.183   8.436
//
H BUNA790102
D alpha-CH chemical shifts (Bundi-Wuthrich, 1979)
R 0503064b
A Bundi, A. and Wuthrich, K.
T 1H-nmr parameters of the common amino acid residues measured in aqueous
  solutions of the linear tetrapeptides H-Gly-Gly-X-L-Ala-OH
J Biopolymers 18, 285-297 (1979)
C ANDN920101    0.949
I   A/L     R/K     N/M     D/F     C/P     Q/S     E/T     G/W     H/Y     I/V
    4.349   4.396   4.755   4.765   4.686   4.373   4.295   3.972   4.630   4.224
    4.385   4.358   4.513   4.663   4.471   4.498   4.346   4.702   4.604   4.184
//
H BUNA790103
D Spin-spin coupling constants 3JHalpha-NH (Bundi-Wuthrich, 1979)
R 0503064b
A Bundi, A. and Wuthrich, K.
T 1H-nmr parameters of the common amino acid residues measured in aqueous
  solutions of the linear tetrapeptides H-Gly-Gly-X-L-Ala-OH
J Biopolymers 18, 285-297 (1979)
* (Met Pro Trp !)
C
I   A/L     R/K     N/M     D/F     C/P     Q/S     E/T     G/W     H/Y     I/V
    6.5     6.9     7.5     7.0     7.7     6.0     7.0     5.6     8.0     7.0
    6.5     6.5     0.      9.4     0.      6.5     6.9     0.      6.8     7.0
//
H BURA740101
D Normalized frequency of alpha-helix (Burgess et al., 1974)
R 2004075b
A Burgess, A.W., Ponnuswamy, P.K., and Scheraga, H.A.
T Analysis of conformations of amino acid residues and prediction of
  backbone topography in proteins
J Isr. J. Chem. 12, 239-286 (1974)
C TANS770101    0.917    CHOP780201    0.917    ROBB760101    0.912
  PALJ810102    0.900    CRAJ730101    0.900    NAGK730101    0.883
  GEIM800101    0.858    KANM800101    0.855    MAXF760101    0.852
  PALJ810101    0.850    ISOY800101    0.839    LEVM780104    0.833
  GEIM800104    0.819    KANM800103    0.810    RACS820108    0.809
  PRAM900102    0.805    LEVM780101    0.805    NAGK730103    -0.830
I   A/L     R/K     N/M     D/F     C/P     Q/S     E/T     G/W     H/Y     I/V
    0.486   0.262   0.193   0.288   0.200   0.418   0.538   0.120   0.400   0.370
    0.420   0.402   0.417   0.318   0.208   0.200   0.272   0.462   0.161   0.379

```
//
H BURA740102
D Normalized frequency of extended structure (Burgess et al., 1974)
R 2004075b
A Burgess, A.W., Ponnuswamy, P.K., and Scheraga, H.A.
T Analysis of conformations of amino acid residues and prediction of
  backbone topography in proteins
J Isr. J. Chem. 12, 239-286 (1974)
C ROBB760105    0.821
I  A/L    R/K    N/M    D/F    C/P    Q/S    E/T    G/W    H/Y    I/V
   0.288  0.362  0.229  0.271  0.533  0.327  0.262  0.312  0.200  0.411
   0.400  0.265  0.375  0.318  0.340  0.354  0.388  0.231  0.429  0.495
//
H CHAM810101
D Steric parameter (Charton, 1981)
R 2004112b
A Charton, M.
T Protein folding and the genetic code: An alternative quantitative
  model
J J. Theor. Biol. 91, 115-123 (1981)
* (Pro !)
C FAUJ880102    0.881  LEVM760104   -0.818
I  A/L    R/K    N/M    D/F    C/P    Q/S    E/T    G/W    H/Y    I/V
   0.52   0.68   0.76   0.76   0.62   0.68   0.68   0.00   0.70   1.02
   0.98   0.68   0.78   0.70   0.36   0.53   0.50   0.70   0.70   0.76
//
H CHAM820101
D Polarizability parameter (Charton-Charton, 1982)
R 0902079b
A Charton, M. and Charton, B.I.
T The structural dependence of amino acid hydrophobicity parameters
J J. Theor. Biol. 99, 629-644 (1982)
* (Pro 0.018)
C FAUJ880103    0.992  CHOC750101   0.982  GOLD730102   0.967
  CHOC760101    0.966  BIGC670101   0.966  KRIW790103   0.963
  FASG760101    0.962  GRAR740103   0.951  ROSG850101   0.917
  LEVM760105    0.915  LEVM760102   0.915  FAUJ880106   0.902
  CHAM830106    0.899  LEVM760107   0.891  MCMT640101   0.871
  DAWD720101    0.865  RADA880106   0.847  LEVM760106   0.818
  HUTJ700102    0.815  CHAM830105   0.809  SNEP660103   0.808
  RADA880103   -0.912  OOBM770105  -0.928  OOBM770104  -0.944
I  A/L    R/K    N/M    D/F    C/P    Q/S    E/T    G/W    H/Y    I/V
   0.046  0.291  0.134  0.105  0.128  0.180  0.151  0.000  0.230  0.186
   0.186  0.219  0.221  0.290  0.131  0.062  0.108  0.409  0.298  0.140
//
H CHAM820102
D Free energy of solution in water, kcal/mole (Charton-Charton, 1982)
R 0902079b
A Charton, M. and Charton, B.I.
T The structural dependence of amino acid hydrophobicity parameters
J J. Theor. Biol. 99, 629-644 (1982)
* (Asn His Lys Thr !)
C
I  A/L    R/K    N/M    D/F    C/P    Q/S    E/T    G/W    H/Y    I/V
  -0.368 -1.03   0.     2.06   4.53   0.731  1.77  -0.525  0.     0.791
   1.07   0.     0.656  1.06  -2.24  -0.524  0.     1.60   4.91   0.401
//
H CHAM830101
D The Chou-Fasman parameter of the coil conformation (Charton-Charton,
  1983)
R 0907093b
A Charton, M. and Charton, B.
T The dependence of the Chou-Fasman parameters on amino acid side chain
  structure
J J. Theor. Biol. 111, 447-450 (1983)
C CHOP780101    0.946  CHOP780216   0.942  PALJ810106   0.939
  GEIM800111    0.938  CHOP780203   0.931  QIAN880132   0.925
  TANS770110    0.917  GEIM800108   0.916  QIAN880133   0.913
```

```
   PRAM900104   0.909   LEVM780103   0.909   CHOP780210   0.905
   LEVM780106   0.900   ISOY800103   0.881   QIAN880131   0.860
   NAGK730103   0.857   ROBB760113   0.841   QIAN880134   0.841
   PALJ810105   0.826   CRAJ730103   0.821   QIAN880135   0.814
   ROBB760108   0.812   ROBB760110   0.804   QIAN880105  -0.803
   PALJ810102  -0.808   FAUJ880102  -0.809   ISOY800101  -0.815
   RICJ880109  -0.826   CHOP780201  -0.828   ROBB760101  -0.828
   PTIO830101  -0.841   BEGF750101  -0.854   QIAN880106  -0.856
   QIAN880107  -0.858   ROBB760103  -0.878   KANM800103  -0.889
   SUEM840101  -0.891
I    A/L    R/K    N/M    D/F    C/P    Q/S    E/T    G/W    H/Y    I/V
     0.71   1.06   1.37   1.21   1.19   0.87   0.84   1.52   1.07   0.66
     0.69   0.99   0.59   0.71   1.61   1.34   1.08   0.76   1.07   0.63
//
H CHAM830102
D A parameter defined from the residuals obtained from the best correlation
  of the Chou-Fasman parameter of beta-sheet (Charton-Charton, 1983)
R 0907093b
A Charton, M. and Charton, B.
T The dependence of the Chou-Fasman parameters on amino acid side chain
  structure
J J. Theor. Biol. 111, 447-450 (1983)
* (Pro !)
C
I    A/L    R/K    N/M    D/F    C/P    Q/S    E/T    G/W    H/Y    I/V
    -0.118  0.124  0.289  0.048  0.083 -0.105 -0.245  0.104  0.138  0.230
    -0.052  0.032 -0.258  0.015  0.     0.225  0.166  0.158  0.094  0.513
//
H CHAM830103
D The number of atoms in the side chain labelled 1+1 (Charton-Charton,
  1983)
R 0907093b
A Charton, M. and Charton, B.
T The dependence of the Chou-Fasman parameters on amino acid side chain
  structure
J J. Theor. Biol. 111, 447-450 (1983)
* (Pro !)
C
I    A/L    R/K    N/M    D/F    C/P    Q/S    E/T    G/W    H/Y    I/V
     0.     1.     1.     1.     1.     1.     1.     0.     1.     1.
     1.     1.     1.     1.     0.     1.     2.     1.     1.     2.
//
H CHAM830104
D The number of atoms in the side chain labelled 2+1 (Charton-Charton,
  1983)
R 0907093b
A Charton, M. and Charton, B.
T The dependence of the Chou-Fasman parameters on amino acid side chain
  structure
J J. Theor. Biol. 111, 447-450 (1983)
* (Pro !)
C
I    A/L    R/K    N/M    D/F    C/P    Q/S    E/T    G/W    H/Y    I/V
     0.     1.     1.     1.     0.     1.     1.     0.     1.     1.
     2.     1.     1.     1.     0.     0.     0.     1.     1.     0.
//
H CHAM830105
D The number of atoms in the side chain labelled 3+1 (Charton-Charton,
  1983)
R 0907093b
A Charton, M. and Charton, B.
T The dependence of the Chou-Fasman parameters on amino acid side chain
  structure
J J. Theor. Biol. 111, 447-450 (1983)
* (Pro !)
C CHAM830106   0.874   LEVM760102   0.843   FASG760101   0.839
  CHOC760101   0.833   LEVM760105   0.829   FAUJ880103   0.813
  CHAM820101   0.809   RADA880103  -0.808
```

```
I   A/L    R/K    N/M    D/F    C/P    Q/S    E/T    G/W    H/Y    I/V
    0.     1.     0.     0.     0.     1.     1.     0.     1.     0.
    0.     1.     1.     1.     0.     0.     0.     1.5    1.     0.
//
H CHAM830106
D The number of bonds in the longest chain (Charton-Charton, 1983)
R 0907093b
A Charton, M. and Charton, B.
T The dependence of the Chou-Fasman parameters on amino acid side chain
  structure
J J. Theor. Biol. 111, 447-450 (1983)
* (Pro !)
C LEVM760102     0.962    LEVM760105     0.958    FASG760101     0.943
  CHOC760101     0.937    FAUJ880103     0.927    RADA880106     0.922
  CHOC750101     0.906    CHAM820101     0.899    GRAR740103     0.890
  KRIW790103     0.876    CHAM830105     0.874    BIGC670101     0.870
  GOLD730102     0.869    OOBM770102     0.858    FAUJ880106     0.845
  FAUJ880104     0.817    OOBM770105    -0.835    RADA880103    -0.901
I   A/L    R/K    N/M    D/F    C/P    Q/S    E/T    G/W    H/Y    I/V
    0.     5.     2.     2.     1.     3.     3.     0.     3.     2.
    2.     4.     3.     4.     0.     1.     1.     5.     5.     1.
//
H CHAM830107
D A parameter of charge transfer capability (Charton-Charton, 1983)
R 0907093b
A Charton, M. and Charton, B.
T The dependence of the Chou-Fasman parameters on amino acid side chain
  structure
J J. Theor. Biol. 111, 447-450 (1983)
* (Pro !)
C
I   A/L    R/K    N/M    D/F    C/P    Q/S    E/T    G/W    H/Y    I/V
    0.     0.     1.     1.     0.     0.     1.     1.     0.     0.
    0.     0.     0.     0.     0.     0.     0.     0.     0.     0.
//
H CHAM830108
D A parameter of charge transfer donor capability (Charton-Charton, 1983)
R 0907093b
A Charton, M. and Charton, B.
T The dependence of the Chou-Fasman parameters on amino acid side chain
  structure
J J. Theor. Biol. 111, 447-450 (1983)
* (Pro !)
C
I   A/L    R/K    N/M    D/F    C/P    Q/S    E/T    G/W    H/Y    I/V
    0.     1.     1.     0.     1.     1.     0.     0.     1.     0.
    0.     1.     1.     1.     0.     0.     0.     1.     1.     0.
//
H CHOC750101
D Average volume of buried residue (Chothia, 1975)
R
A Chothia, C.
T Structural invariants in protein folding
J Nature 254, 304-308 (1975)
* (Arg missing)
C FAUJ880103     0.990    BIGC670101     0.990    GOLD730102     0.989
  KRIW790103     0.982    CHAM820101     0.982    CHOC760101     0.981
  GRAR740103     0.973    FASG760101     0.956    LEVM760105     0.939
  LEVM760102     0.933    ROSG850101     0.908    CHAM830106     0.906
  DAWD720101     0.901    FAUJ880106     0.888    RADA880106     0.867
  LEVM760107     0.858    LEVM760106     0.841    MCMT640101     0.822
  HUTJ700102     0.802    RADA880103    -0.892    OOBM770104    -0.922
  OOBM770105    -0.927
I   A/L    R/K    N/M    D/F    C/P    Q/S    E/T    G/W    H/Y    I/V
    91.5   202.0  135.2  124.5  117.7  161.1  155.1  66.4   167.3  168.8
    167.9  171.3  170.8  203.4  129.3  99.1   122.1  237.6  203.6  141.7
//
H CHOC760101
```

D Residue accessible surface area in tripeptide (Chothia, 1976)
R 2004094b
A Chothia, C.
T The nature of the accessible and buried surfaces in proteins
J J. Mol. Biol. 105, 1-14 (1976)
C FAUJ880103    0.985   CHOC750101   0.981   FASG760101   0.978
  LEVM760102    0.972   LEVM760105   0.968   CHAM820101   0.966
  GOLD730102    0.960   BIGC670101   0.960   KRIW790103   0.948
  GRAR740103    0.945   CHAM830106   0.937   DAWD720101   0.901
  FAUJ880106    0.898   RADA880106   0.875   WOLS870102   0.845
  ROSG850101    0.842   FAUJ880104   0.835   CHAM830105   0.833
  OOBM770102    0.824   HUTJ700102   0.819   MCMT640101   0.809
  LEVM760107    0.807   OOBM770104  -0.886   RADA880103  -0.924
  OOBM770105   -0.927
I   A/L     R/K     N/M     D/F    C/P    Q/S     E/T    G/W     H/Y    I/V
   115.    225.    160.    150.   135.   180.   190.    75.    195.   175.
   170.    200.    185.    210.   145.   115.   140.   255.    230.   155.
//
H CHOC760102
D Residue accessible surface area in folded protein (Chothia, 1976)
R 2004094b
A Chothia, C.
T The nature of the accessible and buried surfaces in proteins
J J. Mol. Biol. 105, 1-14 (1976)
C JANJ780101    0.973   JANJ780103   0.959   OOBM770101   0.925
  FAUJ880109    0.872   ROSM880102   0.845   MEIH800102   0.839
  PRAM900101    0.826   RACS770102   0.809   GUYH850101   0.807
  EISD860103   -0.802   MEIH800103  -0.802   JANJ790101  -0.809
  RADA880101   -0.814   ROSG850102  -0.819   DESM900102  -0.823
  RADA880104   -0.830   KYTJ820101  -0.838   WOLR810101  -0.840
  CHOC760104   -0.845   WARP780101  -0.849   EISD840101  -0.892
  CHOC760103   -0.912   RADA880107  -0.925   JANJ780102  -0.935
  JANJ790102   -0.969
I   A/L     R/K     N/M     D/F    C/P    Q/S     E/T    G/W     H/Y    I/V
    25.     90.     63.     50.    19.    71.    49.    23.     43.    18.
    23.     97.     31.     24.    50.    44.    47.    32.     60.    18.
//
H CHOC760103
D Proportion of residues 95% buried (Chothia, 1976)
R 2004094b
A Chothia, C.
T The nature of the accessible and buried surfaces in proteins
J J. Mol. Biol. 105, 1-14 (1976)
C KYTJ820101    0.964   JANJ780102   0.950   CHOC760104   0.907
  JANJ790102    0.905   EISD860103   0.892   JANJ790101   0.887
  EISD840101    0.885   DESM900102   0.877   WOLR810101   0.873
  RADA880107    0.870   MEIH800103   0.865   MANP780101   0.859
  RADA880101    0.853   ROSG850102   0.851   PONP800103   0.837
  PONP800102    0.836   RADA880108   0.830   PONP800101   0.830
  WARP780101    0.824   NAKH920108   0.824   BIOV880101   0.823
  RADA880104    0.821   PONP800107   0.813   MIYS850101   0.810
  LIFS790102    0.810   PONP800108   0.809   FAUJ880109  -0.806
  PRAM900101   -0.814   ROSM880101  -0.819   GUYH850101  -0.856
  ROSM880102   -0.869   RACS770102  -0.875   JANJ780103  -0.888
  JANJ780101   -0.892   MEIH800102  -0.894   OOBM770101  -0.902
  CHOC760102   -0.912
I   A/L     R/K     N/M     D/F    C/P    Q/S     E/T    G/W     H/Y    I/V
   0.38    0.01    0.12    0.15   0.45   0.07   0.18   0.36    0.17   0.60
   0.45    0.03    0.40    0.50   0.18   0.22   0.23   0.27    0.15   0.54
//
H CHOC760104
D Proportion of residues 100% buried (Chothia, 1976)
R 2004094b
A Chothia, C.
T The nature of the accessible and buried surfaces in proteins
J J. Mol. Biol. 105, 1-14 (1976)
* (normalized by the total number)
C CHOC760103    0.907   JANJ780102   0.903   KYTJ820101   0.889

```
    JANJ790101     0.886  WOLR810101    0.868  PONP800104    0.844
    JANJ790102     0.835  DESM900102    0.824  WARP780101    0.815
    CHOC760102    -0.845  JANJ780103   -0.851  JANJ780101   -0.854
    OOBM770101    -0.857
I   A/L    R/K    N/M    D/F    C/P    Q/S    E/T    G/W    H/Y    I/V
    0.20   0.00   0.03   0.04   0.22   0.01   0.03   0.18   0.02   0.19
    0.16   0.00   0.11   0.14   0.04   0.08   0.08   0.04   0.03   0.18
//
H CHOP780101
D Normalized frequency of beta-turn (Chou-Fasman, 1978a)
R 2004003a
A Chou, P.Y. and Fasman, G.D.
T Empirical predictions of protein conformation
J Ann. Rev. Biochem. 47, 251-276 (1978)
C PALJ810106     0.977  TANS770110    0.956  CHAM830101    0.946
  CHOP780203     0.940  CHOP780216    0.929  CHOP780210    0.921
  ROBB760113     0.907  GEIM800108    0.899  QIAN880133    0.897
  QIAN880132     0.896  LEVM780103    0.893  PRAM900104    0.891
  LEVM780106     0.890  ROBB760108    0.887  ISOY800103    0.885
  BEGF750103     0.885  CRAJ730103    0.882  GEIM800111    0.878
  PALJ810105     0.868  ROBB760110    0.863  NAGK730103    0.827
  QIAN880131     0.824  BEGF750101   -0.803  QIAN880107   -0.809
  KANM800103    -0.824  SUEM840101   -0.845
I   A/L    R/K    N/M    D/F    C/P    Q/S    E/T    G/W    H/Y    I/V
    0.66   0.95   1.56   1.46   1.19   0.98   0.74   1.56   0.95   0.47
    0.59   1.01   0.60   0.60   1.52   1.43   0.96   0.96   1.14   0.50
//
H CHOP780201
D Normalized frequency of alpha-helix (Chou-Fasman, 1978b)
R
A Chou, P.Y. and Fasman, G.D.
T Prediction of the secondary structure of proteins from their amino
  acid sequence
J Adv. Enzymol. 47, 45-148 (1978)
C PALJ810102     0.981  ROBB760101    0.969  ISOY800101    0.959
  MAXF760101     0.956  KANM800101    0.956  TANS770101    0.947
  BURA740101     0.917  KANM800103    0.912  GEIM800101    0.912
  NAGK730101     0.886  LEVM780104    0.886  PALJ810101    0.881
  QIAN880106     0.874  PRAM900102    0.873  LEVM780101    0.873
  RACS820108     0.868  GEIM800104    0.868  CRAJ730101    0.851
  QIAN880107     0.843  BEGF750101    0.841  QIAN880105    0.835
  PALJ810109     0.814  ROBB760103    0.806  CRAJ730103   -0.808
  ROBB760113    -0.811  CHAM830101   -0.828  NAGK730103   -0.837
I   A/L    R/K    N/M    D/F    C/P    Q/S    E/T    G/W    H/Y    I/V
    1.42   0.98   0.67   1.01   0.70   1.11   1.51   0.57   1.00   1.08
    1.21   1.16   1.45   1.13   0.57   0.77   0.83   1.08   0.69   1.06
//
H CHOP780202
D Normalized frequency of beta-sheet (Chou-Fasman, 1978b)
R
A Chou, P.Y. and Fasman, G.D.
T Prediction of the secondary structure of proteins from their amino
  acid sequence
J Adv. Enzymol. 47, 45-148 (1978)
C PALJ810104     0.970  LIFS790101    0.947  KANM800102    0.945
  PALJ810103     0.937  ROBB760106    0.931  LEVM780105    0.930
  GEIM800107     0.929  QIAN880120    0.915  PTIO830102    0.913
  QIAN880121     0.911  LIFS790103    0.908  GEIM800105    0.890
  ROBB760105     0.885  NAGK730102    0.858  QIAN880119    0.855
  CHOP780208     0.851  KANM800104    0.839  GEIM800106    0.839
  PRAM900103     0.833  LEVM780102    0.833  NISK860101    0.832
  SWER830101     0.823  CHOP780209    0.822  PALJ810112    0.815
  PONP800108     0.809  PALJ810110    0.808  VENT840101    0.805
  MANP780101     0.805  OOBM770103   -0.820  GEIM800110   -0.824
I   A/L    R/K    N/M    D/F    C/P    Q/S    E/T    G/W    H/Y    I/V
    0.83   0.93   0.89   0.54   1.19   1.10   0.37   0.75   0.87   1.60
    1.30   0.74   1.05   1.38   0.55   0.75   1.19   1.37   1.47   1.70
//
```

H CHOP780203
D Normalized frequency of beta-turn (Chou-Fasman, 1978b)
R
A Chou, P.Y. and Fasman, G.D.
T Prediction of the secondary structure of proteins from their amino
  acid sequence
J Adv. Enzymol. 47, 45-148 (1978)
C CHOP780216    0.979    TANS770110    0.940    CHOP780101    0.940
  LEVM780106    0.935    ISOY800103    0.933    GEIM800111    0.933
  CHAM830101    0.931    QIAN880132    0.928    PRAM900104    0.928
  LEVM780103    0.927    GEIM800108    0.925    CHOP780210    0.918
  QIAN880133    0.915    PALJ810106    0.907    PALJ810105    0.878
  QIAN880131    0.861    QIAN880134    0.838    RACS770101    0.827
  QIAN880135    0.811    QIAN880119   -0.814    PONP800107   -0.818
  SUEM840101   -0.892
I    A/L    R/K    N/M    D/F    C/P    Q/S    E/T    G/W    H/Y    I/V
     0.74   1.01   1.46   1.52   0.96   0.96   0.95   1.56   0.95   0.47
     0.50   1.19   0.60   0.66   1.56   1.43   0.98   0.60   1.14   0.59
//
H CHOP780204
D Normalized frequency of N-terminal helix (Chou-Fasman, 1978b)
R
A Chou, P.Y. and Fasman, G.D.
T Prediction of the secondary structure of proteins from their amino
  acid sequence
J Adv. Enzymol. 47, 45-148 (1978)
C ROBB760102    0.911
I    A/L    R/K    N/M    D/F    C/P    Q/S    E/T    G/W    H/Y    I/V
     1.29   0.44   0.81   2.02   0.66   1.22   2.44   0.76   0.73   0.67
     0.58   0.66   0.71   0.61   2.01   0.74   1.08   1.47   0.68   0.61
//
H CHOP780205
D Normalized frequency of C-terminal helix (Chou-Fasman, 1978b)
R
A Chou, P.Y. and Fasman, G.D.
T Prediction of the secondary structure of proteins from their amino
  acid sequence
J Adv. Enzymol. 47, 45-148 (1978)
C ROBB760104    0.841    QIAN880109    0.806
I    A/L    R/K    N/M    D/F    C/P    Q/S    E/T    G/W    H/Y    I/V
     1.20   1.25   0.59   0.61   1.11   1.22   1.24   0.42   1.77   0.98
     1.13   1.83   1.57   1.10   0.00   0.96   0.75   0.40   0.73   1.25
//
H CHOP780206
D Normalized frequency of N-terminal non helical region (Chou-Fasman,
1978b)
R
A Chou, P.Y. and Fasman, G.D.
T Prediction of the secondary structure of proteins from their amino
  acid sequence
J Adv. Enzymol. 47, 45-148 (1978)
C
I    A/L    R/K    N/M    D/F    C/P    Q/S    E/T    G/W    H/Y    I/V
     0.70   0.34   1.42   0.98   0.65   0.75   1.04   1.41   1.22   0.78
     0.85   1.01   0.83   0.93   1.10   1.55   1.09   0.62   0.99   0.75
//
H CHOP780207
D Normalized frequency of C-terminal non helical region (Chou-Fasman,
1978b)
R
A Chou, P.Y. and Fasman, G.D.
T Prediction of the secondary structure of proteins from their amino
  acid sequence
J Adv. Enzymol. 47, 45-148 (1978)
C
I    A/L    R/K    N/M    D/F    C/P    Q/S    E/T    G/W    H/Y    I/V
     0.52   1.24   1.64   1.06   0.94   0.70   0.59   1.64   1.86   0.87
     0.84   1.49   0.52   1.04   1.58   0.93   0.86   0.16   0.96   0.32

//
H CHOP780208
D Normalized frequency of N-terminal beta-sheet (Chou-Fasman, 1978b)
R
A Chou, P.Y. and Fasman, G.D.
T Prediction of the secondary structure of proteins from their amino
  acid sequence
J Adv. Enzymol. 47, 45-148 (1978)
C NAGK730102      0.860   CHOP780202    0.851   ROBB760106    0.846
  LIFS790101      0.820   QIAN880119    0.807   KANM800102    0.804
  QIAN880120      0.800
I   A/L    R/K    N/M    D/F    C/P    Q/S    E/T    G/W    H/Y    I/V
    0.86   0.90   0.66   0.38   0.87   1.65   0.35   0.63   0.54   1.94
    1.30   1.00   1.43   1.50   0.66   0.63   1.17   1.49   1.07   1.69
//
H CHOP780209
D Normalized frequency of C-terminal beta-sheet (Chou-Fasman, 1978b)
R
A Chou, P.Y. and Fasman, G.D.
T Prediction of the secondary structure of proteins from their amino
  acid sequence
J Adv. Enzymol. 47, 45-148 (1978)
C PALJ810104      0.849   CHOP780202    0.822   VENT840101    0.817
  PTIO830102      0.814   QIAN880121    0.809
I   A/L    R/K    N/M    D/F    C/P    Q/S    E/T    G/W    H/Y    I/V
    0.75   0.90   1.21   0.85   1.11   0.65   0.55   0.74   0.90   1.35
    1.27   0.74   0.95   1.50   0.40   0.79   0.75   1.19   1.96   1.79
//
H CHOP780210
D Normalized frequency of N-terminal non beta region (Chou-Fasman, 1978b)
R
A Chou, P.Y. and Fasman, G.D.
T Prediction of the secondary structure of proteins from their amino
  acid sequence
J Adv. Enzymol. 47, 45-148 (1978)
C CHOP780101      0.921   CHOP780203    0.918   PALJ810106    0.905
  CHAM830101      0.905   GEIM800108    0.896   CHOP780216    0.896
  GEIM800111      0.867   TANS770110    0.858   QIAN880132    0.852
  LEVM780103      0.852   PRAM900104    0.850   ISOY800103    0.829
  QIAN880131      0.826   QIAN880133    0.820   NAGK730103    0.814
  LEVM780106      0.812   PALJ810105    0.803   BEGF750101   -0.804
  RICJ880111     -0.804   RICJ880107   -0.818   PONP800107   -0.820
I   A/L    R/K    N/M    D/F    C/P    Q/S    E/T    G/W    H/Y    I/V
    0.67   0.89   1.86   1.39   1.34   1.09   0.92   1.46   0.78   0.59
    0.46   1.09   0.52   0.30   1.58   1.41   1.09   0.48   1.23   0.42
//
H CHOP780211
D Normalized frequency of C-terminal non beta region (Chou-Fasman, 1978b)
R
A Chou, P.Y. and Fasman, G.D.
T Prediction of the secondary structure of proteins from their amino
  acid sequence
J Adv. Enzymol. 47, 45-148 (1978)
C ROBB760112      0.841
I   A/L    R/K    N/M    D/F    C/P    Q/S    E/T    G/W    H/Y    I/V
    0.74   1.05   1.13   1.32   0.53   0.77   0.85   1.68   0.96   0.53
    0.59   0.82   0.85   0.44   1.69   1.49   1.16   1.59   1.01   0.59
//
H CHOP780212
D Frequency of the 1st residue in turn (Chou-Fasman, 1978b)
R
A Chou, P.Y. and Fasman, G.D.
T Prediction of the secondary structure of proteins from their amino
  acid sequence
J Adv. Enzymol. 47, 45-148 (1978)
C PALJ810106      0.801
I   A/L    R/K    N/M    D/F    C/P    Q/S    E/T    G/W    H/Y    I/V
    0.060  0.070  0.161  0.147  0.149  0.074  0.056  0.102  0.140  0.043

```
     0.061  0.055  0.068  0.059  0.102  0.120  0.086  0.077  0.082  0.062
//
H CHOP780213
D Frequency of the 2nd residue in turn (Chou-Fasman, 1978b)
R
A Chou, P.Y. and Fasman, G.D.
T Prediction of the secondary structure of proteins from their amino
  acid sequence
J Adv. Enzymol. 47, 45-148 (1978)
C TANS770104    0.954  ISOY800104    0.916  QIAN880134    0.870
  QIAN880135    0.851  FINA910102    0.832  BUNA790101   -0.822
  PTIO830101   -0.835
I   A/L    R/K    N/M    D/F    C/P    Q/S    E/T    G/W    H/Y    I/V
    0.076  0.106  0.083  0.110  0.053  0.098  0.060  0.085  0.047  0.034
    0.025  0.115  0.082  0.041  0.301  0.139  0.108  0.013  0.065  0.048
//
H CHOP780214
D Frequency of the 3rd residue in turn (Chou-Fasman, 1978b)
R
A Chou, P.Y. and Fasman, G.D.
T Prediction of the secondary structure of proteins from their amino
  acid sequence
J Adv. Enzymol. 47, 45-148 (1978)
C ISOY800105    0.923  TANS770105    0.862
I   A/L    R/K    N/M    D/F    C/P    Q/S    E/T    G/W    H/Y    I/V
    0.035  0.099  0.191  0.179  0.117  0.037  0.077  0.190  0.093  0.013
    0.036  0.072  0.014  0.065  0.034  0.125  0.065  0.064  0.114  0.028
//
H CHOP780215
D Frequency of the 4th residue in turn (Chou-Fasman, 1978b)
R
A Chou, P.Y. and Fasman, G.D.
T Prediction of the secondary structure of proteins from their amino
  acid sequence
J Adv. Enzymol. 47, 45-148 (1978)
C ROBB760111    0.825
I   A/L    R/K    N/M    D/F    C/P    Q/S    E/T    G/W    H/Y    I/V
    0.058  0.085  0.091  0.081  0.128  0.098  0.064  0.152  0.054  0.056
    0.070  0.095  0.055  0.065  0.068  0.106  0.079  0.167  0.125  0.053
//
H CHOP780216
D Normalized frequency of the 2nd and 3rd residues in turn (Chou-Fasman,
1978b)
R
A Chou, P.Y. and Fasman, G.D.
T Prediction of the secondary structure of proteins from their amino
  acid sequence
J Adv. Enzymol. 47, 45-148 (1978)
C CHOP780203    0.979  GEIM800111    0.955  LEVM780106    0.953
  LEVM780103    0.952  PRAM900104    0.951  GEIM800108    0.942
  CHAM830101    0.942  QIAN880133    0.939  QIAN880132    0.931
  TANS770110    0.930  CHOP780101    0.929  ISOY800103    0.921
  PALJ810106    0.904  QIAN880134    0.900  CHOP780210    0.896
  QIAN880135    0.884  PALJ810105    0.881  QIAN880131    0.873
  NAGK730103    0.819  QIAN880120   -0.800  FAUJ880102   -0.807
  KANM800103   -0.808  QIAN880107   -0.808  ROBB760103   -0.841
  PTIO830101   -0.855  SUEM840101   -0.874
I   A/L    R/K    N/M    D/F    C/P    Q/S    E/T    G/W    H/Y    I/V
    0.64   1.05   1.56   1.61   0.92   0.84   0.80   1.63   0.77   0.29
    0.36   1.13   0.51   0.62   2.04   1.52   0.98   0.48   1.08   0.43
//
H CIDH920101
D Normalized hydrophobicity scales for alpha-proteins (Cid et al., 1992)
R 1817105b
A Cid, H., Bunster, M., Canales, M. and Gazitua, F.
T Hydrophobicity and structural classes in proteins
J Protein Engineering 5, 373-375 (1992)
C CIDH920105    0.921  CIDH920102    0.921  NISK860101    0.882
```

```
    WERD780101    0.878  CIDH920103    0.872  RADA880108   0.858
    SWER830101    0.853  BIOV880101    0.847  ROBB790101   0.846
    PLIV810101    0.843  MIYS850101    0.843  CIDH920104   0.833
    ROSG850101    0.831  LEVM760106    0.826  BIOV880102   0.819
    PONP800101    0.805  OOBM770103   -0.818  KARP850102  -0.828
    RACS770101   -0.837  MEIH800101   -0.863  KARP850101  -0.864
    PARJ860101   -0.871
I   A/L    R/K     N/M     D/F    C/P    Q/S    E/T    G/W    H/Y    I/V
   -0.45  -0.24   -0.20   -1.52   0.79  -0.99  -0.80  -1.00   1.07   0.76
    1.29  -0.36    1.37    1.48  -0.12  -0.98  -0.70   1.38   1.49   1.26
//
H CIDH920102
D Normalized hydrophobicity scales for beta-proteins (Cid et al., 1992)
R 1817105b
A Cid, H., Bunster, M., Canales, M. and Gazitua, F.
T Hydrophobicity and structural classes in proteins
J Protein Engineering 5, 373-375 (1992)
C CIDH920105    0.969  CIDH920101    0.921  CIDH920103   0.911
  CIDH920104    0.904  NISK860101    0.897  ROBB790101   0.896
  NOZY710101    0.889  MEEJ810101    0.887  PLIV810101   0.877
  MIYS850101    0.873  LEVM760106    0.873  WERD780101   0.871
  SWER830101    0.870  ROSG850101    0.866  BIOV880101   0.864
  RADA880102    0.862  ARGP820101    0.862  JOND750101   0.861
  MEEJ800102    0.856  FAUJ830101    0.856  MEEJ810102   0.843
  BIOV880102    0.837  RADA880108    0.833  SIMZ760101   0.832
  GOLD730101    0.829  EISD860101    0.819  ZASB820101   0.809
  LIFS790101    0.808  RACS770101   -0.825  GRAR740102  -0.842
  BULH740101   -0.851  MEIH800101   -0.867  WOLS870101  -0.869
  KARP850101   -0.873  OOBM770103   -0.877  PARJ860101  -0.930
I   A/L    R/K     N/M     D/F    C/P    Q/S    E/T    G/W    H/Y    I/V
   -0.08  -0.09   -0.70   -0.71   0.76  -0.40  -1.31  -0.84   0.43   1.39
    1.24  -0.09    1.27    1.53  -0.01  -0.93  -0.59   2.25   1.53   1.09
//
H CIDH920103
D Normalized hydrophobicity scales for alpha+beta-proteins (Cid et al.,
1992)
R 1817105b
A Cid, H., Bunster, M., Canales, M. and Gazitua, F.
T Hydrophobicity and structural classes in proteins
J Protein Engineering 5, 373-375 (1992)
C CIDH920105    0.973  CIDH920104    0.955  CIDH920102   0.911
  NISK860101    0.909  MIYS850101    0.906  MANP780101   0.905
  PLIV810101    0.899  RADA880108    0.891  BIOV880101   0.887
  ROBB790101    0.884  WERD780101    0.881  PONP800101   0.876
  CIDH920101    0.872  FAUJ830101    0.868  SWER830101   0.865
  BIOV880102    0.860  NISK800101    0.855  PONP800102   0.849
  ROSG850102    0.846  PONP800108    0.841  MEEJ810101   0.837
  PONP800107    0.833  ARGP820101    0.827  JOND750101   0.826
  PONP800103    0.823  EISD860101    0.821  RADA880102   0.819
  LIFS790101    0.815  PTIO830102    0.807  MEIH800103   0.802
  KRIW790101   -0.819  MEIH800102   -0.825  RACS770102  -0.834
  BULH740101   -0.848  KARP850102   -0.852  OOBM770103  -0.863
  GRAR740102   -0.871  WOLS870101   -0.879  RACS770101  -0.881
  MEIH800101   -0.905  PARJ860101   -0.916
I   A/L    R/K     N/M     D/F    C/P    Q/S    E/T    G/W    H/Y    I/V
    0.36  -0.52   -0.90   -1.09   0.70  -1.05  -0.83  -0.82   0.16   2.17
    1.18  -0.56    1.21    1.01  -0.06  -0.60  -1.20   1.31   1.05   1.21
//
H CIDH920104
D Normalized hydrophobicity scales for alpha/beta-proteins (Cid et al.,
1992)
R 1817105b
A Cid, H., Bunster, M., Canales, M. and Gazitua, F.
T Hydrophobicity and structural classes in proteins
J Protein Engineering 5, 373-375 (1992)
C CIDH920105    0.970  CIDH920103    0.955  NISK860101   0.944
  BIOV880101    0.933  FAUJ830101    0.922  MANP780101   0.918
  MIYS850101    0.915  RADA880108    0.914  PONP800108   0.909
```

```
CIDH920102   0.904   ROBB790101   0.903   NISK800101   0.900
WERD780101   0.896   ROSG850102   0.896   PLIV810101   0.893
BIOV880102   0.890   PONP800101   0.888   PONP800102   0.880
MEEJ810101   0.878   PONP800103   0.863   SWER830101   0.862
MEIH800103   0.853   PTIO830102   0.842   MEEJ810102   0.837
EISD860103   0.834   CIDH920101   0.833   PONP800107   0.832
LIFS790101   0.832   KYTJ820101   0.824   ARGP820101   0.819
JOND750101   0.818   RADA880102   0.817   EISD860101   0.812
JANJ780102   0.803   DESM900102   0.802   KARP850101  -0.801
GUYH850101  -0.821   WOEC730101  -0.823   ROSM880101  -0.828
BULH740101  -0.829   ROSM880102  -0.831   KARP850102  -0.833
RACS770102  -0.854   RACS770101  -0.864   KRIW790101  -0.867
MEIH800102  -0.868   WOLS870101  -0.891   OOBM770103  -0.912
PARJ860101  -0.913   GRAR740102  -0.915   MEIH800101  -0.917
I    A/L     R/K     N/M     D/F     C/P     Q/S     E/T     G/W     H/Y     I/V
     0.17   -0.70   -0.90   -1.05    1.24   -1.20   -1.19   -0.57   -0.25    2.06
     0.96   -0.62    0.60    1.29   -0.21   -0.83   -0.62    1.51    0.66    1.21
//
H CIDH920105
D Normalized average hydrophobicity scales (Cid et al., 1992)
R 1817105b
A Cid, H., Bunster, M., Canales, M. and Gazitua, F.
T Hydrophobicity and structural classes in proteins
J Protein Engineering 5, 373-375 (1992)
C CIDH920103   0.973   CIDH920104   0.970   CIDH920102   0.969
  NISK860101   0.938   ROBB790101   0.921   CIDH920101   0.921
  MIYS850101   0.916   PLIV810101   0.914   BIOV880101   0.912
  WERD780101   0.905   RADA880108   0.898   FAUJ830101   0.893
  MEEJ810101   0.892   SWER830101   0.890   BIOV880102   0.882
  MANP780101   0.879   ARGP820101   0.867   JOND750101   0.866
  RADA880102   0.861   ROSG850102   0.858   NOZY710101   0.857
  PONP800101   0.856   NISK800101   0.854   MEEJ810102   0.844
  PONP800108   0.843   MEEJ800102   0.840   EISD860101   0.839
  SIMZ760101   0.837   PONP800102   0.831   LIFS790101   0.828
  LEVM760106   0.828   GOLD730101   0.820   PONP800107   0.818
  VENT840101   0.813   PTIO830102   0.813   PONP800103   0.807
  MEIH800103   0.804   WOEC730101  -0.800   KRIW790101  -0.816
  MEIH800102  -0.826   RACS770102  -0.830   KARP850102  -0.839
  KARP850101  -0.866   BULH740101  -0.871   GRAR740102  -0.884
  RACS770101  -0.887   WOLS870101  -0.899   OOBM770103  -0.904
  MEIH800101  -0.923   PARJ860101  -0.948
I    A/L     R/K     N/M     D/F     C/P     Q/S     E/T     G/W     H/Y     I/V
     0.02   -0.42   -0.77   -1.04    0.77   -1.10   -1.14   -0.80    0.26    1.81
     1.14   -0.41    1.00    1.35   -0.09   -0.97   -0.77    1.71    1.11    1.13
//
H COHE430101
D Partial specific volume (Cohn-Edsall, 1943)
R
A Cohn, E.J. and Edsall, J.T.
T
J "Protein, Amino Acid, and Peptides", Reinhold, New York (1943)
C BULH740102   0.923
I    A/L     R/K     N/M     D/F     C/P     Q/S     E/T     G/W     H/Y     I/V
     0.75    0.70    0.61    0.60    0.61    0.67    0.66    0.64    0.67    0.90
     0.90    0.82    0.75    0.77    0.76    0.68    0.70    0.74    0.71    0.86
//
H CRAJ730101
D Normalized frequency of middle helix (Crawford et al., 1973)
R
A Crawford, J.L., Lipscomb, W.N., and Schellman, C.G.
T The reverse turn as a polypeptide conformation in globular proteins
J Proc. Natl. Acad. Sci. USA 70, 538-542 (1973)
* Reported values normalized by the total percentage
C NAGK730101   0.925   BURA740101   0.900   PALJ810101   0.891
  PRAM900102   0.887   LEVM780101   0.887   ROBB760101   0.875
  PALJ810102   0.872   GEIM800101   0.870   LEVM780104   0.869
  CHOP780201   0.851   TANS770101   0.843   KANM800101   0.842
  ISOY800101   0.840   RACS820108   0.839   GEIM800104   0.838
```

```
     MAXF760101     0.826  PALJ810109     0.811  NAGK730103    -0.850
I    A/L    R/K    N/M    D/F    C/P    Q/S    E/T    G/W    H/Y    I/V
     1.33   0.79   0.72   0.97   0.93   1.42   1.66   0.58   1.49   0.99
     1.29   1.03   1.40   1.15   0.49   0.83   0.94   1.33   0.49   0.96
//
H CRAJ730102
D Normalized frequency of beta-sheet (Crawford et al., 1973)
R
A Crawford, J.L., Lipscomb, W.N., and Schellman, C.G.
T The reverse turn as a polypeptide conformation in globular proteins
J Proc. Natl. Acad. Sci. USA 70, 538-542 (1973)
* Reported values normalized by the total percentage
C ROBB760106     0.865  PTIO830102     0.820  PALJ810104     0.817
  NAGK730102     0.815
I    A/L    R/K    N/M    D/F    C/P    Q/S    E/T    G/W    H/Y    I/V
     1.00   0.74   0.75   0.89   0.99   0.87   0.37   0.56   0.36   1.75
     1.53   1.18   1.40   1.26   0.36   0.65   1.15   0.84   1.41   1.61
//
H CRAJ730103
D Normalized frequency of turn (Crawford et al., 1973)
R
A Crawford, J.L., Lipscomb, W.N., and Schellman, C.G.
T The reverse turn as a polypeptide conformation in globular proteins
J Proc. Natl. Acad. Sci. USA 70, 538-542 (1973)
* Reported values normalized by the total percentage
C ROBB760113     0.916  ROBB760108     0.912  ROBB760110     0.887
  PALJ810106     0.884  CHOP780101     0.882  BEGF750103     0.874
  TANS770110     0.859  CHAM830101     0.821  CHOP780201    -0.808
  PALJ810102    -0.809  BEGF750101    -0.812  QIAN880107    -0.840
I    A/L    R/K    N/M    D/F    C/P    Q/S    E/T    G/W    H/Y    I/V
     0.60   0.79   1.42   1.24   1.29   0.92   0.64   1.38   0.95   0.67
     0.70   1.10   0.67   1.05   1.47   1.26   1.05   1.23   1.35   0.48
//
H DAWD720101
D Size (Dawson, 1972)
R
A Dawson, D.M.
T
J In "The Biochemical Genetics of Man" (Brock, D.J.H. and Mayo, O.,
    eds.), Academic Press, New York, pp.1-38 (1972)
C GOLD730102     0.904  BIGC670101     0.903  CHOC760101     0.901
  CHOC750101     0.901  LEVM760105     0.898  KRIW790103     0.893
  FAUJ880103     0.880  LEVM760102     0.873  CHAM820101     0.865
  GRAR740103     0.853  FAUJ880106     0.853  FASG760101     0.833
I    A/L    R/K    N/M    D/F    C/P    Q/S    E/T    G/W    H/Y    I/V
     2.5    7.5    5.0    2.5    3.0    6.0    5.0    0.5    6.0    5.5
     5.5    7.0    6.0    6.5    5.5    3.0    5.0    7.0    7.0    5.0
//
H DAYM780101
D Amino acid composition (Dayhoff et al., 1978a)
R
A Dayhoff, M.O., Hunt, L.T., and Hurst-Calderone, S.
T Composition of proteins
J In "Atlas of Protein Sequence and Structure", Vol.5, Suppl.3 (Dayhoff,
    M.O., ed.), National Biomedical Research Foundation, Washington, D.C.,
    p.363 (1978)
C JUNJ780101     0.986  JUKT750101     0.975  JOND920101     0.954
  NAKH900101     0.940  NAKH900102     0.883  NAKH920101     0.882
  NAKH920107     0.861  NAKH920106     0.856  NAKH920103     0.851
  NAKH920104     0.819  NAKH920102     0.802
I    A/L    R/K    N/M    D/F    C/P    Q/S    E/T    G/W    H/Y    I/V
     8.6    4.9    4.3    5.5    2.9    3.9    6.0    8.4    2.0    4.5
     7.4    6.6    1.7    3.6    5.2    7.0    6.1    1.3    3.4    6.6
//
H DAYM780201
D Relative mutability (Dayhoff et al., 1978b)
R
A Dayhoff, M.O., Schwartz, R.M., and Orcutt, B.C.
```

T A model of evolutionary change in proteins
J In "Atlas of Protein Sequence and Structure", Vol.5, Suppl.3 (Dayhoff,
    M.O., ed.), National Biomedical Research Foundation, Washington, D.C.
    pp. 345-352 (1978)
C JOND920102    0.889
I   A/L     R/K     N/M     D/F     C/P     Q/S     E/T     G/W     H/Y     I/V
    100.    65.     134.    106.    20.     93.     102.    49.     66.     96.
    40.     56.     94.     41.     56.     120.    97.     18.     41.     74.
//
H DESM900101
D Membrane preference for cytochrome b: MPH89 (Degli Esposti et al., 1990)
R 1612111b
A Degli Esposti, M., Crimi, M. and Venturoli, G.
T A critical evaluation of the hydropathy profile of membrane proteins
J Eur. J. Biochem. 190, 207-219 (1990)
C DESM900102    0.955   PONP800103   0.887   PONP800102   0.871
  ROSG850102    0.866   WARP780101   0.864   MEIH800103   0.853
  JANJ780102    0.853   PONP800101   0.847   NISK800101   0.837
  KYTJ820101    0.837   BIOV880102   0.821   JANJ790102   0.818
  RADA880108    0.812   BIOV880101   0.807   RACS770102  -0.801
  KRIW710101   -0.807   MEIH800102  -0.822   KARP850102  -0.829
  GUYH850101   -0.831   KRIW790102  -0.835   RACS770103  -0.837
  JANJ780103   -0.838   KRIW790101  -0.847   OOBM770101  -0.894
I   A/L     R/K     N/M     D/F     C/P     Q/S     E/T     G/W     H/Y     I/V
    1.56    0.59    0.51    0.23    1.80    0.39    0.19    1.03    1.      1.27
    1.38    0.15    1.93    1.42    0.27    0.96    1.11    0.91    1.10    1.58
//
H DESM900102
D Average membrane preference: AMP07 (Degli Esposti et al., 1990)
R 1612111b
A Degli Esposti, M., Crimi, M. and Venturoli, G.
T A critical evaluation of the hydropathy profile of membrane proteins
J Eur. J. Biochem. 190, 207-219 (1990)
C DESM900101    0.955   JANJ780102   0.935   MEIH800103   0.924
  ROSG850102    0.914   KYTJ820101   0.898   JANJ790102   0.897
  PONP800103    0.896   WARP780101   0.882   RADA880108   0.881
  PONP800102    0.880   BIOV880101   0.878   CHOC760103   0.877
  BIOV880102    0.876   PONP800101   0.858   JANJ790101   0.855
  NISK800101    0.852   EISD860103   0.848   NISK860101   0.843
  PONP800108    0.833   MIYS850101   0.831   RADA880101   0.828
  EISD840101    0.828   CHOC760104   0.824   MANP780101   0.816
  FAUJ830101    0.816   WERD780101   0.814   CIDH920104   0.802
  MEIH800101   -0.804   ROSM880101  -0.812   KARP850102  -0.815
  ROSM880102   -0.816   CHOC760102  -0.823   WOEC730101  -0.847
  KRIW790102   -0.852   KRIW790101  -0.859   GRAR740101  -0.862
  RACS770102   -0.867   RACS770103  -0.868   JANJ780101  -0.878
  PRAM900101   -0.890   GUYH850101  -0.895   MEIH800102  -0.898
  JANJ780103   -0.908   OOBM770101  -0.950
I   A/L     R/K     N/M     D/F     C/P     Q/S     E/T     G/W     H/Y     I/V
    1.26    0.38    0.59    0.27    1.60    0.39    0.23    1.08    1.      1.44
    1.36    0.33    1.52    1.46    0.54    0.98    1.01    1.06    0.89    1.33
//
H EISD840101
D Consensus normalized hydrophobicity scale (Eisenberg, 1984)
R 2004004a
A Eisenberg, D.
T Three-dimensional structure of membrane and surface proteins
J Ann. Rev. Biochem. 53, 595-623 (1984)
* Original references:
* Eisenberg, D., Weiss, R.M., Terwilliger, T.C., and Wilcox, W.
* Faraday Symp. Chem. Soc. 17, 109-120 (1982)
* Eisenberg, D., Weiss, R.M., and Terwilliger, T.C.
* The hydrophobic moment detects periodicity in protein hydrophobicity
*,Proc. Natl. Acad. Sci. USA 81, 140-144 (1984)
C RADA880101    0.968   RADA880107   0.927   WOLR810101   0.914
  RADA880104    0.908   JANJ790102   0.900   CHOC760103   0.885
  EISD860101    0.884   KYTJ820101   0.878   FAUJ830101   0.875
  JANJ780102    0.874   NAKH900110   0.838   EISD860103   0.837

```
    DESM900102      0.828   RADA880108     0.817   BIOV880102     0.814
    BIOV880101      0.811   YUTK870101     0.809   ROSG850102     0.806
    WOLS870101     -0.820   GRAR740102    -0.823   MEIH800102    -0.829
    HOPT810101     -0.846   GUYH850101    -0.849   LEVM760101    -0.859
    OOBM770101     -0.878   JANJ780103    -0.881   FAUJ880109    -0.890
    CHOC760102     -0.892   JANJ780101    -0.907   VHEG790101    -0.924
    ROSM880102     -0.925   PRAM900101    -0.936   ROSM880101    -0.947
I    A/L     R/K     N/M     D/F     C/P     Q/S     E/T     G/W     H/Y     I/V
     0.25   -1.76   -0.64   -0.72    0.04   -0.69   -0.62    0.16   -0.40    0.73
     0.53   -1.10    0.26    0.61   -0.07   -0.26   -0.18    0.37    0.02    0.54
//
H EISD860101
D Solvation free energy (Eisenberg-McLachlan, 1986)
R 2004121b
A Eisenberg, D. and McLachlan, A.D.
T Solvation energy in protein folding and binding
J Nature 319, 199-203 (1986)
C  FAUJ830101      0.919   RADA880102     0.912   PLIV810101     0.904
   ZIMJ680105      0.900   RADA880101     0.891   MEEJ800102     0.890
   EISD840101      0.884   RADA880108     0.844   MIYS850101     0.842
   CIDH920105      0.839   BIOV880102     0.832   BIOV880101     0.828
   SWER830101      0.824   NOZY710101     0.822   CIDH920103     0.821
   NAKH900110      0.820   CIDH920102     0.819   NAKH900106     0.812
   NAKH900104      0.812   CIDH920104     0.812   MEEJ810102     0.808
   MEEJ810101      0.805   GUYH850101    -0.823   BULH740101    -0.833
   WOEC730101     -0.838   PRAM900101    -0.862   VHEG790101    -0.862
   ROSM880102     -0.868   GRAR740102    -0.871   PARJ860101    -0.876
   HOPT810101     -0.905   ROSM880101    -0.917   WOLS870101    -0.918
   LEVM760101     -0.921
I    A/L     R/K     N/M     D/F     C/P     Q/S     E/T     G/W     H/Y     I/V
     0.67   -2.1    -0.6    -1.2     0.38   -0.22   -0.76    0.      0.64    1.9
     1.9    -0.57    2.4     2.3     1.2     0.01    0.52    2.6     1.6     1.5
//
H EISD860102
D Atom-based hydrophobic moment (Eisenberg-McLachlan, 1986)
R 2004121b
A Eisenberg, D. and McLachlan, A.D.
T Solvation energy in protein folding and binding
J Nature 319, 199-203 (1986)
C  HUTJ700103      0.841   FAUJ880109     0.841   RADA880107    -0.837
   YUTK870103     -0.839   YUTK870104    -0.840
I    A/L     R/K     N/M     D/F     C/P     Q/S     E/T     G/W     H/Y     I/V
     0.     10.      1.3     1.9     0.17    1.9     3.      0.      0.99    1.2
     1.0     5.7     1.9     1.1     0.18    0.73    1.5    -1.6     1.8     0.48
//
H EISD860103
D Direction of hydrophobic moment (Eisenberg-McLachlan, 1986)
R 2004121b
A Eisenberg, D. and McLachlan, A.D.
T Solvation energy in protein folding and binding
J Nature 319, 199-203 (1986)
* (Gly Ala missing)
C  KYTJ820101      0.897   CHOC760103     0.892   JANJ780102     0.883
   FAUJ830101      0.876   RADA880108     0.873   MEIH800103     0.870
   BIOV880101      0.864   MIYS850101     0.858   PLIV810101     0.852
   RADA880101      0.850   DESM900102     0.848   ROSG850102     0.846
   BIOV880102      0.845   PONP800103     0.842   JANJ790102     0.838
   EISD840101      0.837   CIDH920104     0.834   JANJ790101     0.829
   MANP780101      0.826   WARP780101     0.820   PONP800102     0.814
   RADA880107      0.812   NISK860101     0.811   ARGP820103     0.810
   PONP800108      0.809   CHOC760102    -0.802   WOEC730101    -0.803
   JANJ780101     -0.808   MEIH800101    -0.810   FAUJ880110    -0.815
   JANJ780103     -0.819   PRAM900101    -0.831   GUYH850101    -0.832
   WOLS870101     -0.841   RACS770102    -0.858   GRAR740102    -0.871
   ROSM880101     -0.871   OOBM770101    -0.880   MEIH800102    -0.882
   ROSM880102     -0.943
I    A/L     R/K     N/M     D/F     C/P     Q/S     E/T     G/W     H/Y     I/V
     0.     -0.96   -0.86   -0.98    0.76   -1.0    -0.89    0.     -0.75    0.99
```

```
       0.89  -0.99   0.94   0.92   0.22  -0.67   0.09   0.67  -0.93   0.84
//
H FASG760101
D Molecular weight (Fasman, 1976)
R
A Fasman, G.D., ed.
T
J "Handbook of Biochemistry and Molecular Biology", 3rd ed., Proteins -
  Volume 1, CRC Press, Cleveland (1976)
C FAUJ880103     0.979   CHOC760101    0.978   LEVM760102    0.966
  CHAM820101     0.962   CHOC750101    0.956   LEVM760105    0.951
  CHAM830106     0.943   BIGC670101    0.919   GOLD730102    0.918
  KRIW790103     0.910   GRAR740103    0.908   FAUJ880106    0.899
  RADA880106     0.870   WOLS870102    0.866   MCMT640101    0.845
  CHAM830105     0.839   ROSG850101    0.838   DAWD720101    0.833
  FAUJ880104     0.825   OOBM770102    0.821   LEVM760107    0.815
  OOBM770104    -0.904   OOBM770105   -0.941   RADA880103   -0.954
I    A/L     R/K     N/M     D/F     C/P     Q/S     E/T     G/W     H/Y     I/V
    89.09  174.20  132.12  133.10  121.15  146.15  147.13   75.07  155.16  131.17
   131.17  146.19  149.21  165.19  115.13  105.09  119.12  204.24  181.19  117.15
//
H FASG760102
D Melting point (Fasman, 1976)
R
A Fasman, G.D., ed.
T
J "Handbook of Biochemistry and Molecular Biology", 3rd ed., Proteins -
  Volume 1, CRC Press, Cleveland (1976)
C
I    A/L     R/K     N/M     D/F     C/P     Q/S     E/T     G/W     H/Y     I/V
    297.    238.    236.    270.    178.    185.    249.    290.    277.    284.
    337.    224.    283.    284.    222.    228.    253.    282.    344.    293.
//
H FASG760103
D Optical rotation (Fasman, 1976)
R
A Fasman, G.D., ed.
T
J "Handbook of Biochemistry and Molecular Biology", 3rd ed., Proteins -
  Volume 1, CRC Press, Cleveland (1976)
C
I    A/L     R/K     N/M     D/F     C/P     Q/S     E/T     G/W     H/Y     I/V
    1.80   12.50   -5.60    5.05  -16.50    6.30   12.00    0.00  -38.50   12.40
  -11.00   14.60  -10.00  -34.50  -86.20   -7.50  -28.00  -33.70  -10.00    5.63
//
H FASG760104
D pK-N (Fasman, 1976)
R
A Fasman, G.D., ed.
T
J "Handbook of Biochemistry and Molecular Biology", 3rd ed., Proteins -
  Volume 1, CRC Press, Cleveland (1976)
C
I    A/L     R/K     N/M     D/F     C/P     Q/S     E/T     G/W     H/Y     I/V
    9.69    8.99    8.80    9.60    8.35    9.13    9.67    9.78    9.17    9.68
    9.60    9.18    9.21    9.18   10.64    9.21    9.10    9.44    9.11    9.62
//
H FASG760105
D pK-C (Fasman, 1976)
R
A Fasman, G.D., ed.
T
J "Handbook of Biochemistry and Molecular Biology", 3rd ed., Proteins -
  Volume 1, CRC Press, Cleveland (1976)
C JOND750102    0.833
I    A/L     R/K     N/M     D/F     C/P     Q/S     E/T     G/W     H/Y     I/V
    2.34    1.82    2.02    1.88    1.92    2.17    2.10    2.35    1.82    2.36
    2.36    2.16    2.28    2.16    1.95    2.19    2.09    2.43    2.20    2.32
```

//
H FAUJ830101
D Hydrophobic parameter pi (Fauchere-Pliska, 1983)
R 0912085
A Fauchere, J.L. and Pliska, V.
T Hydrophobic parameters pi of amino-acid side chains from the
  partitioning of N-acetyl-amino-acid amides
J Eur. J. Med. Chem. 18, 369-375 (1983)
C BIOV880101    0.942   RADA880108    0.932   PLIV810101    0.931
  CIDH920104    0.922   EISD860101    0.919   MIYS850101    0.914
  BIOV880102    0.911   NISK860101    0.906   ROSG850102    0.904
  MEEJ810101    0.902   CIDH920105    0.893   MEEJ810102    0.890
  EISD860103    0.876   PONP800108    0.875   EISD840101    0.875
  RADA880101    0.873   ROBB790101    0.868   CIDH920103    0.868
  PONP800103    0.863   WERD780101    0.862   MEEJ800102    0.858
  CIDH920102    0.856   NISK800101    0.849   MEIH800103    0.849
  RADA880102    0.846   MANP780101    0.843   PONP800102    0.841
  SWER830101    0.833   JANJ790102    0.826   JANJ780102    0.825
  PONP800101    0.822   ZIMJ680105    0.816   DESM900102    0.816
  KYTJ820101    0.811   NOZY710101    0.803   BULH740101   -0.830
  OOBM770101   -0.832   RACS770102   -0.843   PRAM900101   -0.853
  GUYH850101   -0.863   MEIH800101   -0.863   KRIW790101   -0.865
  MEIH800102   -0.875   WOEC730101   -0.880   OOBM770103   -0.899
  PARJ860101   -0.907   ROSM880101   -0.907   HOPT810101   -0.909
  LEVM760101   -0.919   ROSM880102   -0.927   WOLS870101   -0.928
  GRAR740102   -0.948
I    A/L     R/K     N/M     D/F     C/P     Q/S     E/T     G/W     H/Y     I/V
     0.31   -1.01   -0.60   -0.77    1.54   -0.22   -0.64    0.00    0.13    1.80
     1.70   -0.99    1.23    1.79    0.72   -0.04    0.26    2.25    0.96    1.22
//
H FAUJ880101
D Graph shape index (Fauchere et al., 1988)
R 1414114
A Fauchere, J.L., Charton, M., Kier, L.B., Verloop, A. and Pliska, V.
T Amino acid side chain parameters for correlation studies in biology
  and pharmacology
J Int. J. Peptide Protein Res. 32, 269-278 (1988)
* Original reference:
* Kier, L.B.
* Quant. Struct. Act. Relat. 6, 117-122 (1987)
C ZIMJ680102    0.888
I    A/L     R/K     N/M     D/F     C/P     Q/S     E/T     G/W     H/Y     I/V
     1.28    2.34    1.60    1.60    1.77    1.56    1.56    0.00    2.99    4.19
     2.59    1.89    2.35    2.94    2.67    1.31    3.03    3.21    2.94    3.67
//
H FAUJ880102
D Smoothed upsilon steric parameter (Fauchere et al., 1988)
R 1414114
A Fauchere, J.L., Charton, M., Kier, L.B., Verloop, A. and Pliska, V.
T Amino acid side chain parameters for correlation studies in biology
  and pharmacology
J Int. J. Peptide Protein Res. 32, 269-278 (1988)
* (Pro missing)
* Original reference of these two data:
* Fauchere, L.J.
* In "QSAR in Design of Bioactive Compounds", (Kuchar, M., ed.),
* Prous, Barcelona pp.135-144 (1984)
C CHAM810101    0.881   PTIO830101    0.832   CHOP780216   -0.807
  CHAM830101   -0.809   GEIM800108   -0.819   PRAM900104   -0.844
  LEVM780103   -0.846   QIAN880132   -0.849   QIAN880133   -0.851
  QIAN880134   -0.852   LEVM780106   -0.865   GEIM800111   -0.873
I    A/L     R/K     N/M     D/F     C/P     Q/S     E/T     G/W     H/Y     I/V
     0.53    0.69    0.58    0.59    0.66    0.71    0.72    0.00    0.64    0.96
     0.92    0.78    0.77    0.71    0.      0.55    0.63    0.84    0.71    0.89
//
H FAUJ880103
D Normalized van der Waals volume (Fauchere et al., 1988)
R 1414114

A Fauchere, J.L., Charton, M., Kier, L.B., Verloop, A. and Pliska, V.
T Amino acid side chain parameters for correlation studies in biology
  and pharmacology
J Int. J. Peptide Protein Res. 32, 269-278 (1988)
* (Pro !)
* Original reference of these two data:
* Fauchere, L.J.
* In "QSAR in Design of Bioactive Compounds", (Kuchar, M., ed.),
* Prous, Barcelona pp.135-144 (1984)
C CHAM820101    0.992   CHOC750101    0.990   CHOC760101    0.985
  FASG760101    0.979   GOLD730102    0.972   BIGC670101    0.972
  KRIW790103    0.965   GRAR740103    0.959   LEVM760102    0.947
  LEVM760105    0.945   CHAM830106    0.927   FAUJ880106    0.908
  ROSG850101    0.892   DAWD720101    0.880   LEVM760107    0.875
  RADA880106    0.869   MCMT640101    0.847   WOLS870102    0.814
  CHAM830105    0.813   HUTJ700102    0.807   FAUJ880104    0.804
  OOBM770102    0.801   RADA880103   -0.923   OOBM770104   -0.932
  OOBM770105   -0.936
I   A/L     R/K     N/M     D/F     C/P     Q/S     E/T     G/W     H/Y     I/V
    1.00    6.13    2.95    2.78    2.43    3.95    3.78    0.00    4.66    4.00
    4.00    4.77    4.43    5.89    2.72    1.60    2.60    8.08    6.47    3.00
//
H FAUJ880104
D STERIMOL length of the side chain (Fauchere et al., 1988)
R 1414114
A Fauchere, J.L., Charton, M., Kier, L.B., Verloop, A. and Pliska, V.
T Amino acid side chain parameters for correlation studies in biology
  and pharmacology
J Int. J. Peptide Protein Res. 32, 269-278 (1988)
* (Pro !)
* Original reference of these three data:
* Verloop, A.
* In "IUPAC, Pesticide Chemistry", Vol.1
* (Miyamoto, J. and Kearney, P.C., eds.),Pergamon, Oxford pp.339-334 (1983)
C LEVM760105    0.896   LEVM760102    0.867   HUTJ700103    0.839
  HUTJ700102    0.835   CHOC760101    0.835   FASG760101    0.825
  CHAM830106    0.817   FAUJ880103    0.804   RADA880103   -0.806
I   A/L     R/K     N/M     D/F     C/P     Q/S     E/T     G/W     H/Y     I/V
    2.87    7.82    4.58    4.74    4.47    6.11    5.97    2.06    5.23    4.92
    4.92    6.89    6.36    4.62    4.11    3.97    4.11    7.68    4.73    4.11
//
H FAUJ880105
D STERIMOL minimum width of the side chain (Fauchere et al., 1988)
R 1414114
A Fauchere, J.L., Charton, M., Kier, L.B., Verloop, A. and Pliska, V.
T Amino acid side chain parameters for correlation studies in biology
  and pharmacology
J Int. J. Peptide Protein Res. 32, 269-278 (1988)
* (Pro !)
* Original reference of these three data:
* Verloop, A.
* In "IUPAC, Pesticide Chemistry", Vol.1
* (Miyamoto, J. and Kearney, P.C., eds.),Pergamon, Oxford pp.339-334 (1983)
C
I   A/L     R/K     N/M     D/F     C/P     Q/S     E/T     G/W     H/Y     I/V
    1.52    1.52    1.52    1.52    1.52    1.52    1.52    1.00    1.52    1.90
    1.52    1.52    1.52    1.52    1.52    1.52    1.73    1.52    1.52    1.90
//
H FAUJ880106
D STERIMOL maximum width of the side chain (Fauchere et al., 1988)
R 1414114
A Fauchere, J.L., Charton, M., Kier, L.B., Verloop, A. and Pliska, V.
T Amino acid side chain parameters for correlation studies in biology
  and pharmacology
J Int. J. Peptide Protein Res. 32, 269-278 (1988)
* Original reference of these three data:
* Verloop, A.
* In "IUPAC, Pesticide Chemistry", Vol.1

```
 * (Miyamoto, J. and Kearney, P.C., eds.),Pergamon, Oxford pp.339-334 (1983)
C FAUJ880103    0.908  CHAM820101    0.902  LEVM760102    0.900
  FASG760101    0.899  CHOC760101    0.898  LEVM760105    0.889
  CHOC750101    0.888  WOLS870102    0.866  BIGC670101    0.860
  GOLD730102    0.857  DAWD720101    0.853  KRIW790103    0.845
  CHAM830106    0.845  GRAR740103    0.819  HUTJ700102    0.806
  OOBM770104   -0.814  RADA880103   -0.823  OOBM770105   -0.863
I    A/L    R/K    N/M    D/F    C/P    Q/S    E/T    G/W    H/Y    I/V
     2.04   6.24   4.37   3.78   3.41   3.53   3.31   1.00   5.66   3.49
     4.45   4.87   4.80   6.02   4.31   2.70   3.17   5.90   6.72   3.17
//
H FAUJ880107
D N.m.r. chemical shift of alpha-carbon (Fauchere et al., 1988)
R 1414114
A Fauchere, J.L., Charton, M., Kier, L.B., Verloop, A. and Pliska, V.
T Amino acid side chain parameters for correlation studies in biology
  and pharmacology
J Int. J. Peptide Protein Res. 32, 269-278 (1988)
* Original reference:
* Fauchere, J.L. and Lauterwein, J.
* Quant. Struct. Act. Rel. 4, 11-13 (1985)
C
I    A/L    R/K    N/M    D/F    C/P    Q/S    E/T    G/W    H/Y    I/V
     7.3   11.1    8.0    9.2   14.4   10.6   11.4    0.0   10.2   16.1
    10.1   10.9   10.4   13.9   17.8   13.1   16.7   13.2   13.9   17.2
//
H FAUJ880108
D Localized electrical effect (Fauchere et al., 1988)
R 1414114
A Fauchere, J.L., Charton, M., Kier, L.B., Verloop, A. and Pliska, V.
T Amino acid side chain parameters for correlation studies in biology
  and pharmacology
J Int. J. Peptide Protein Res. 32, 269-278 (1988)
* (Pro missing)
* Original reference:
* Charton, M. and Charton, B.I.
* J. Theor. Biol. 102, 121-134 (1983)
C
I    A/L    R/K    N/M    D/F    C/P    Q/S    E/T    G/W    H/Y    I/V
    -0.01   0.04   0.06   0.15   0.12   0.05   0.07   0.00   0.08  -0.01
    -0.01   0.00   0.04   0.03   0.     0.11   0.04   0.00   0.03   0.01
//
H FAUJ880109
D Number of hydrogen bond donors (Fauchere et al., 1988)
R 1414114
A Fauchere, J.L., Charton, M., Kier, L.B., Verloop, A. and Pliska, V.
T Amino acid side chain parameters for correlation studies in biology
  and pharmacology
J Int. J. Peptide Protein Res. 32, 269-278 (1988)
* Original reference of these two data:
* IUPAC-IUB Joint Commission on Biochemical Nomenclature
* Eur. J. Biochem. 138, 9-37 (1984)
C CHOC760102    0.872  JANJ780101    0.850  ROSM880101    0.846
  EISD860102    0.841  ROSM880102    0.824  PRAM900101    0.815
  CHOC760103   -0.806  JANJ790102   -0.822  RADA880101   -0.873
  RADA880105   -0.889  EISD840101   -0.890  WOLR810101   -0.904
  RADA880104   -0.926  RADA880107   -0.957
I    A/L    R/K    N/M    D/F    C/P    Q/S    E/T    G/W    H/Y    I/V
     0.     4.     2.     1.     0.     2.     1.     0.     1.     0.
     0.     2.     0.     0.     0.     1.     1.     1.     1.     0.
//
H FAUJ880110
D Number of full nonbonding orbitals (Fauchere et al., 1988)
R 1414114
A Fauchere, J.L., Charton, M., Kier, L.B., Verloop, A. and Pliska, V.
T Amino acid side chain parameters for correlation studies in biology
  and pharmacology
J Int. J. Peptide Protein Res. 32, 269-278 (1988)
```

* Original reference of these two data:
* IUPAC-IUB Joint Commission on Biochemical Nomenclature
* Eur. J. Biochem. 138, 9-37 (1984)
C ROSM880101    0.888    WOEC730101    0.812    SNEP660102    -0.804
  EISD860103   -0.815    RADA880101   -0.838
I    A/L     R/K     N/M     D/F     C/P     Q/S     E/T     G/W     H/Y     I/V
     0.      3.      3.      4.      0.      3.      4.      0.      1.      0.
     0.      1.      0.      0.      0.      2.      2.      0.      2.      0.
//
H FAUJ880111
D Positive charge (Fauchere et al., 1988)
R 1414114
A Fauchere, J.L., Charton, M., Kier, L.B., Verloop, A. and Pliska, V.
T Amino acid side chain parameters for correlation studies in biology
  and pharmacology
J Int. J. Peptide Protein Res. 32, 269-278 (1988)
C ZIMJ680104    0.813
I    A/L     R/K     N/M     D/F     C/P     Q/S     E/T     G/W     H/Y     I/V
     0.      1.      0.      0.      0.      0.      0.      0.      1.      0.
     0.      1.      0.      0.      0.      0.      0.      0.      0.      0.
//
H FAUJ880112
D Negative charge (Fauchere et al., 1988)
R 1414114
A Fauchere, J.L., Charton, M., Kier, L.B., Verloop, A. and Pliska, V.
T Amino acid side chain parameters for correlation studies in biology
  and pharmacology
J Int. J. Peptide Protein Res. 32, 269-278 (1988)
C RICJ880106    0.849
I    A/L     R/K     N/M     D/F     C/P     Q/S     E/T     G/W     H/Y     I/V
     0.      0.      0.      1.      0.      0.      1.      0.      0.      0.
     0.      0.      0.      0.      0.      0.      0.      0.      0.      0.
//
H FAUJ880113
D pK-a(RCOOH) (Fauchere et al., 1988)
R 1414114
A Fauchere, J.L., Charton, M., Kier, L.B., Verloop, A. and Pliska, V.
T Amino acid side chain parameters for correlation studies in biology
  and pharmacology
J Int. J. Peptide Protein Res. 32, 269-278 (1988)
* (Pro missing)
C BUNA790101    0.818    ROBB760103    0.802
I    A/L     R/K     N/M     D/F     C/P     Q/S     E/T     G/W     H/Y     I/V
     4.76    4.30    3.64    5.69    3.67    4.54    5.48    3.77    2.84    4.81
     4.79    4.27    4.25    4.31    0.      3.83    3.87    4.75    4.30    4.86
//
H FINA770101
D Helix-coil equilibrium constant (Finkelstein-Ptitsyn, 1977)
R 2004052b
A Finkelstein, A.V. and Ptitsyn, O.B.
T Theory of protein molecule self-organization. II. A comparison of
  calculated thermodynamic parameters of local secondary structures with
  experiments
J Biopolymers 16, 497-524 (1977)
* (Pro 0.096)
C SUEM840101    0.883    PTIO830101    0.826    KANM800103    0.823
  QIAN880107    0.814    QIAN880106    0.810    MAXF760101    0.810
I    A/L     R/K     N/M     D/F     C/P     Q/S     E/T     G/W     H/Y     I/V
     1.08    1.05    0.85    0.85    0.95    0.95    1.15    0.55    1.00    1.05
     1.25    1.15    1.15    1.10    0.71    0.75    0.75    1.10    1.10    0.95
//
H FINA910101
D Helix initiation parameter at posision i-1 (Finkelstein et al., 1991)
R d716158b
A Finkelstein, A.V., Badretdinov, A.Y. and Ptitsyn, O.B.
T Physical reasons for secondary structure stability: alpha-helices in
  short
  peptides

```
J PROTEINS 10, 287-299 (1991)
* In these four data, each of Arg, Asp, Glu, His and Lys has two value.
* See comment lines.
* Arg pH < 12       ( 1    when pH > 12    )
* Asp pH >  4       ( 1.7  when pH <  4    )
* Glu pH >  4.3     ( 1    when pH <  4.3  )
* His pH >  6.3     ( 0.7  when pH <  6.3  )
* Lys pH < 10.5     ( 1    when pH > 10.5  )
C
I   A/L    R/K    N/M    D/F    C/P    Q/S    E/T    G/W    H/Y    I/V
    1.     0.70   1.70   3.20   1.     1.     1.70   1.     1.     0.60
    1.     0.70   1.     1.     1.     1.70   1.70   1.     1.     0.60
//
H FINA910102
D Helix initiation parameter at posision i,i+1,i+2 (Finkelstein et al.,
1991)
R 1716158b
A Finkelstein, A.V., Badretdinov, A.Y. and Ptitsyn, O.B.
T Physical reasons for secondary structure stability: alpha-helices in
short
   peptides
J PROTEINS 10, 287-299 (1991)
* In these four data, each of Arg, Asp, Glu, His and Lys has two value.
* See comment lines.
* Arg pH < 12       ( 1    when pH > 12    )
* Asp pH >  4       ( 1    when pH <  4    )
* Glu pH >  4.3     ( 1    when pH <  4.3  )
* His pH >  6.3     ( 0.7  when pH <  6.3  )
* Lys pH < 10.5     ( 1    when pH > 10.5  )
* (Pro !)
C TANS770104    0.876    ISOY800104    0.844    CHOP780213    0.832
  ROBB760104   -0.844    BUNA790101   -0.992
I   A/L    R/K    N/M    D/F    C/P    Q/S    E/T    G/W    H/Y    I/V
    1.     0.70   1.     1.70   1.     1.     1.70   1.30   1.     1.
    1.     0.70   1.     1.     13.    1.     1.     1.     1.     1.
//
H FINA910103
D Helix termination parameter at posision j-2,j-1,j (Finkelstein et al.,
1991)
R 1716158b
A Finkelstein, A.V., Badretdinov, A.Y. and Ptitsyn, O.B.
T Physical reasons for secondary structure stability: alpha-helices in
short
   peptides
J PROTEINS 10, 287-299 (1991)
* In these four data, each of Arg, Asp, Glu, His and Lys has two value.
* See comment lines.
* Arg pH < 12       ( 1    when pH > 12    )
* Asp pH >  4       ( 1    when pH <  4    )
* Glu pH >  4.3     ( 1    when pH <  4.3  )
* His pH >  6.3     ( 1.7  when pH <  6.3  )
* Lys pH < 10.5     ( 1    when pH > 10.5  )
C ZIMJ680104    0.805
I   A/L    R/K    N/M    D/F    C/P    Q/S    E/T    G/W    H/Y    I/V
    1.20   1.70   1.20   0.70   1.     1.     0.70   0.80   1.20   0.80
    1.     1.70   1.     1.     1.     1.50   1.     1.     1.     0.80
//
H FINA910104
D Helix termination parameter at posision j+1 (Finkelstein et al., 1991)
R 1716158b
A Finkelstein, A.V., Badretdinov, A.Y. and Ptitsyn, O.B.
T Physical reasons for secondary structure stability: alpha-helices in
short
   peptides
J PROTEINS 10, 287-299 (1991)
* In these four data, each of Arg, Asp, Glu, His and Lys has two value.
* See comment lines.
* Arg pH < 12       ( 1    when pH > 12    )
```

```
* Asp pH >  4      ( 1    when pH <  4    )
* Glu pH >  4.3    ( 1    when pH <  4.3  )
* His pH >  6.3    ( 1.7  when pH <  6.3  )
* Lys pH < 10.5    ( 1    when pH > 10.5  )
C
I   A/L    R/K    N/M    D/F    C/P    Q/S    E/T    G/W    H/Y    I/V
    1.     1.70   1.     0.70   1.     1.     0.70   1.50   1.     1.
    1.     1.70   1.     1.     0.10   1.     1.     1.     1.     1.
//
H GARJ730101
D Partition coefficient (Garel et al., 1973)
R 2004092b
A Garel, J.P., Filliol, D., and Mandel, P.
T Coefficients de partage d'aminoacides, nucleobases, nucleosides et
  nucleotides dans un systeme solvant salin
J J. Chromatogr. 78, 381-391 (1973)
C LEVM760107    0.860   NOZY710101   0.821   OOBM770104   -0.815
  OOBM850102   -0.877   WEBA780101  -0.924
I   A/L    R/K    N/M    D/F    C/P    Q/S    E/T    G/W    H/Y    I/V
    0.28   0.10   0.25   0.21   0.28   0.35   0.33   0.17   0.21   0.82
    1.00   0.09   0.74   2.18   0.39   0.12   0.21   5.70   1.26   0.60
//
H GEIM800101
D Alpha-helix indices (Geisow-Roberts, 1980)
R 0701087b
A Geisow, M.J. and Roberts, R.D.B.
T Amino acid preferences for secondary structure vary with protein class
J Int. J. Biol. Macromol. 2, 387-389 (1980)
C PALJ810101    0.951   LEVM780104   0.950   KANM800101    0.942
  TANS770101    0.918   PRAM900102   0.912   NAGK730101    0.912
  LEVM780101    0.912   CHOP780201   0.912   PALJ810102    0.910
  ISOY800101    0.903   GEIM800104   0.903   ROBB760101    0.897
  MAXF760101    0.895   KANM800103   0.881   RACS820108    0.880
  CRAJ730101    0.870   BURA740101   0.858   PALJ810109    0.816
I   A/L    R/K    N/M    D/F    C/P    Q/S    E/T    G/W    H/Y    I/V
    1.29   1.     0.81   1.10   0.79   1.07   1.49   0.63   1.33   1.05
    1.31   1.33   1.54   1.13   0.63   0.78   0.77   1.18   0.71   0.81
//
H GEIM800102
D Alpha-helix indices for alpha-proteins (Geisow-Roberts, 1980)
R 0701087b
A Geisow, M.J. and Roberts, R.D.B.
T Amino acid preferences for secondary structure vary with protein class
J Int. J. Biol. Macromol. 2, 387-389 (1980)
C PALJ810107    0.919   GEIM800109  -0.993
I   A/L    R/K    N/M    D/F    C/P    Q/S    E/T    G/W    H/Y    I/V
    1.13   1.09   1.06   0.94   1.32   0.93   1.20   0.83   1.09   1.05
    1.13   1.08   1.23   1.01   0.82   1.01   1.17   1.32   0.88   1.13
//
H GEIM800103
D Alpha-helix indices for beta-proteins (Geisow-Roberts, 1980)
R 0701087b
A Geisow, M.J. and Roberts, R.D.B.
T Amino acid preferences for secondary structure vary with protein class
J Int. J. Biol. Macromol. 2, 387-389 (1980)
C
I   A/L    R/K    N/M    D/F    C/P    Q/S    E/T    G/W    H/Y    I/V
    1.55   0.20   1.20   1.55   1.44   1.13   1.67   0.59   1.21   1.27
    1.25   1.20   1.37   0.40   0.21   1.01   0.55   1.86   1.08   0.64
//
H GEIM800104
D Alpha-helix indices for alpha/beta-proteins (Geisow-Roberts, 1980)
R 0701087b
A Geisow, M.J. and Roberts, R.D.B.
T Amino acid preferences for secondary structure vary with protein class
J Int. J. Biol. Macromol. 2, 387-389 (1980)
C PALJ810109    0.937   KANM800101   0.916   PRAM900102    0.907
  LEVM780101    0.907   GEIM800101   0.903   MAXF760101    0.897
```

```
    ISOY800101   0.891   PALJ810102   0.886   LEVM780104   0.872
    CHOP780201   0.868   ROBB760101   0.855   RACS820108   0.851
    TANS770101   0.841   PALJ810101   0.841   CRAJ730101   0.838
    NAGK730101   0.828   BURA740101   0.819
I   A/L    R/K    N/M    D/F    C/P    Q/S    E/T    G/W    H/Y    I/V
    1.19   1.     0.94   1.07   0.95   1.32   1.64   0.60   1.03   1.12
    1.18   1.27   1.49   1.02   0.68   0.81   0.85   1.18   0.77   0.74
//
H GEIM800105
D Beta-strand indices (Geisow-Roberts, 1980)
R 0701087b
A Geisow, M.J. and Roberts, R.D.B.
T Amino acid preferences for secondary structure vary with protein class
J Int. J. Biol. Macromol. 2, 387-389 (1980)
C PALJ810103   0.945   LEVM780105   0.926   KANM800102   0.916
  GEIM800107   0.901   CHOP780202   0.890   ROBB760105   0.877
  KANM800104   0.861   ROBB760106   0.856   PALJ810104   0.856
  LIFS790101   0.855   TANS770103   0.850   ISOY800102   0.843
  LIFS790103   0.832   PALJ810112   0.830   QIAN880119   0.829
  QIAN880120   0.822   MAXF760102   0.819   QIAN880121   0.811
  QIAN880118   0.810   PTIO830102   0.810
I   A/L    R/K    N/M    D/F    C/P    Q/S    E/T    G/W    H/Y    I/V
    0.84   1.04   0.66   0.59   1.27   1.02   0.57   0.94   0.81   1.29
    1.10   0.86   0.88   1.15   0.80   1.05   1.20   1.15   1.39   1.56
//
H GEIM800106
D Beta-strand indices for beta-proteins (Geisow-Roberts, 1980)
R 0701087b
A Geisow, M.J. and Roberts, R.D.B.
T Amino acid preferences for secondary structure vary with protein class
J Int. J. Biol. Macromol. 2, 387-389 (1980)
C GEIM800107   0.878   PALJ810110   0.851   CHOP780202   0.839
  ROBB760106   0.838   QIAN880120   0.825   KANM800102   0.821
  LIFS790103   0.814   GEIM800110  -0.929
I   A/L    R/K    N/M    D/F    C/P    Q/S    E/T    G/W    H/Y    I/V
    0.86   1.15   0.60   0.66   0.91   1.11   0.37   0.86   1.07   1.17
    1.28   1.01   1.15   1.34   0.61   0.91   1.14   1.13   1.37   1.31
//
H GEIM800107
D Beta-strand indices for alpha/beta-proteins (Geisow-Roberts, 1980)
R 0701087b
A Geisow, M.J. and Roberts, R.D.B.
T Amino acid preferences for secondary structure vary with protein class
J Int. J. Biol. Macromol. 2, 387-389 (1980)
C KANM800102   0.955   CHOP780202   0.929   PALJ810104   0.928
  PALJ810112   0.905   GEIM800105   0.901   ROBB760106   0.899
  PALJ810103   0.890   LIFS790101   0.888   LEVM780105   0.884
  GEIM800106   0.878   KANM800104   0.876   QIAN880121   0.875
  PTIO830102   0.850   QIAN880120   0.843   PRAM900103   0.842
  LEVM780102   0.842   ROBB760105   0.836   NAGK730102   0.830
  PALJ810110   0.826   LIFS790103   0.823   PONP800108   0.817
  NISK860101   0.813   QIAN880119   0.807   GEIM800110  -0.815
I   A/L    R/K    N/M    D/F    C/P    Q/S    E/T    G/W    H/Y    I/V
    0.91   0.99   0.72   0.74   1.12   0.90   0.41   0.91   1.01   1.29
    1.23   0.86   0.96   1.26   0.65   0.93   1.05   1.15   1.21   1.58
//
H GEIM800108
D Aperiodic indices (Geisow-Roberts, 1980)
R 0701087b
A Geisow, M.J. and Roberts, R.D.B.
T Amino acid preferences for secondary structure vary with protein class
J Int. J. Biol. Macromol. 2, 387-389 (1980)
C GEIM800111   0.967   CHOP780216   0.942   LEVM780106   0.932
  PRAM900104   0.931   LEVM780103   0.931   QIAN880133   0.930
  ISOY800103   0.930   CHOP780203   0.925   CHAM830101   0.916
  QIAN880132   0.906   CHOP780101   0.899   CHOP780210   0.896
  TANS770110   0.886   QIAN880134   0.884   QIAN880135   0.877
  PALJ810105   0.873   GEIM800110   0.870   PALJ810106   0.862
```

```
  QIAN880131    0.860  ROBB760103   -0.802  QIAN880120   -0.804
  QIAN880119   -0.810  FAUJ880102   -0.819  PTIO830101   -0.840
  SUEM840101   -0.875
I  A/L    R/K    N/M    D/F    C/P    Q/S    E/T    G/W    H/Y    I/V
   0.91   1.     1.64   1.40   0.93   0.94   0.97   1.51   0.90   0.65
   0.59   0.82   0.58   0.72   1.66   1.23   1.04   0.67   0.92   0.60
//
H GEIM800109
D Aperiodic indices for alpha-proteins (Geisow-Roberts, 1980)
R 0701087b
A Geisow, M.J. and Roberts, R.D.B.
T Amino acid preferences for secondary structure vary with protein class
J Int. J. Biol. Macromol. 2, 387-389 (1980)
C PALJ810107   -0.909  GEIM800102   -0.993
I  A/L    R/K    N/M    D/F    C/P    Q/S    E/T    G/W    H/Y    I/V
   0.80   0.96   1.10   1.60   0.     1.60   0.40   2.     0.96   0.85
   0.80   0.94   0.39   1.20   2.10   1.30   0.60   0.     1.80   0.80
//
H GEIM800110
D Aperiodic indices for beta-proteins (Geisow-Roberts, 1980)
R 0701087b
A Geisow, M.J. and Roberts, R.D.B.
T Amino acid preferences for secondary structure vary with protein class
J Int. J. Biol. Macromol. 2, 387-389 (1980)
C GEIM800108    0.870  GEIM800111    0.857  QIAN880134    0.853
  QIAN880135    0.842  QIAN880133    0.822  LEVM780106    0.809
  QIAN880121   -0.806  KANM800102   -0.814  GEIM800107   -0.815
  ROBB760106   -0.819  CHOP780202   -0.824  PALJ810110   -0.840
  QIAN880119   -0.853  LIFS790101   -0.862  LIFS790103   -0.889
  QIAN880120   -0.898  GEIM800106   -0.929
I  A/L    R/K    N/M    D/F    C/P    Q/S    E/T    G/W    H/Y    I/V
   1.10   0.93   1.57   1.41   1.05   0.81   1.40   1.30   0.85   0.67
   0.52   0.94   0.69   0.60   1.77   1.13   0.88   0.62   0.41   0.58
//
H GEIM800111
D Aperiodic indices for alpha/beta-proteins (Geisow-Roberts, 1980)
R 0701087b
A Geisow, M.J. and Roberts, R.D.B.
T Amino acid preferences for secondary structure vary with protein class
J Int. J. Biol. Macromol. 2, 387-389 (1980)
C GEIM800108    0.967  CHOP780216    0.955  PRAM900104    0.954
  LEVM780103    0.952  LEVM780106    0.951  QIAN880133    0.943
  CHAM830101    0.938  CHOP780203    0.933  QIAN880132    0.929
  ISOY800103    0.929  QIAN880134    0.919  QIAN880135    0.895
  TANS770110    0.883  CHOP780101    0.878  CHOP780210    0.867
  QIAN880131    0.857  GEIM800110    0.857  PALJ810105    0.855
  PALJ810106    0.844  LIFS790101   -0.801  KANM800103   -0.812
  QIAN880120   -0.816  ROBB760103   -0.843  FAUJ880102   -0.873
  PTIO830101   -0.876  SUEM840101   -0.885
I  A/L    R/K    N/M    D/F    C/P    Q/S    E/T    G/W    H/Y    I/V
   0.93   1.01   1.36   1.22   0.92   0.83   1.05   1.45   0.96   0.58
   0.59   0.91   0.60   0.71   1.67   1.25   1.08   0.68   0.98   0.62
//
H GOLD730101
D Hydrophobicity factor (Goldsack-Chalifoux, 1973)
R 2004110b
A Goldsack, D.E. and Chalifoux, R.C.
T Contribution of the free energy of mixing of hydrophobic side chains
  to the stability of the tertiary structure
J J. Theor. Biol. 39, 645-651 (1973)
* (Asn Gln !)
C SIMZ760101    0.939  ARGP820101    0.936  JOND750101    0.935
  MEEJ800102    0.866  LAWE840101    0.829  CIDH920102    0.829
  LEVM760106    0.827  BULH740102    0.825  MEEJ810101    0.824
  ZIMJ680105    0.820  CIDH680105    0.820  ZIMJ680102    0.818
  MEEJ800101    0.808  MEEJ810102    0.806  VENT840101    0.802
  PARJ860101   -0.827  WOLS870101   -0.854  BULH740101   -0.874
I  A/L    R/K    N/M    D/F    C/P    Q/S    E/T    G/W    H/Y    I/V
```

```
         0.75   0.75   0.69   0.00   1.00   0.59   0.00   0.00   0.00   2.95
         2.40   1.50   1.30   2.65   2.60   0.00   0.45   3.00   2.85   1.70
//
H GOLD730102
D Residue volume (Goldsack-Chalifoux, 1973)
R 2004110b
A Goldsack, D.E. and Chalifoux, R.C.
T Contribution of the free energy of mixing of hydrophobic side chains
  to the stability of the tertiary structure
J J. Theor. Biol. 39, 645-651 (1973)
* (Asn Gln 8.8)
C BIGC670101    1.000  KRIW790103    0.994  CHOC750101    0.989
  GRAR740103    0.984  FAUJ880103    0.972  CHAM820101    0.967
  CHOC760101    0.960  FASG760101    0.918  LEVM760105    0.911
  ROSG850101    0.909  DAWD720101    0.904  LEVM760102    0.893
  LEVM760106    0.875  CHAM830106    0.869  LEVM760107    0.865
  FAUJ880106    0.857  RADA880106    0.854  MCMT640101    0.814
  RADA880103   -0.864  OOBM770105   -0.901  OOBM770104   -0.905
I    A/L    R/K    N/M    D/F    C/P    Q/S    E/T    G/W    H/Y    I/V
     88.3  181.2  125.1  110.8  112.4  148.7  140.5   60.0  152.6  168.5
    168.5  175.6  162.2  189.0  122.2   88.7  118.2  227.0  193.0  141.4
//
H GRAR740101
D Composition (Grantham, 1974)
R 2004143b
A Grantham, R.
T Amino acid difference formula to help explain protein evolution
J Science 185, 862-864 (1974)
* (Atomic weight ratio of noncarbons to carbons in the side chain)
C
I    A/L    R/K    N/M    D/F    C/P    Q/S    E/T    G/W    H/Y    I/V
     0.00   0.65   1.33   1.38   2.75   0.89   0.92   0.74   0.58   0.00
     0.00   0.33   0.00   0.00   0.39   1.42   0.71   0.13   0.20   0.00
//
H GRAR740102
D Polarity (Grantham, 1974)
R 2004143b
A Grantham, R.
T Amino acid difference formula to help explain protein evolution
J Science 185, 862-864 (1974)
C WOEC730101    0.960  WOLS870101    0.910  OOBM770103    0.896
  PARJ860101    0.891  ROSM880101    0.887  HOPT810101    0.874
  ROSM880102    0.870  LEVM760101    0.865  PRAM900101    0.855
  KRIW790101    0.847  OOBM770101    0.841  MEIH800102    0.836
  MEIH800101    0.824  BULH740101    0.822  GUYH850101    0.818
  JANJ780102   -0.809  MEEJ810102   -0.811  EISD840101   -0.823
  WERD780101   -0.826  ROBB790101   -0.832  MEEJ810101   -0.839
  CIDH920102   -0.842  PONP800101   -0.849  KYTJ820101   -0.859
  RADA880101   -0.861  DESM900102   -0.862  MEIH800103   -0.866
  MANP780101   -0.868  CIDH920103   -0.871  EISD860101   -0.871
  EISD860103   -0.871  PONP800102   -0.871  NISK800101   -0.879
  ROSG850102   -0.880  BIOV880102   -0.881  CIDH920105   -0.884
  PLIV810101   -0.888  MIYS850101   -0.895  SWER830101   -0.896
  PONP800103   -0.897  RADA880108   -0.899  NISK860101   -0.900
  PONP800108   -0.907  BIOV880101   -0.910  CIDH920104   -0.915
  FAUJ830101   -0.948
I    A/L    R/K    N/M    D/F    C/P    Q/S    E/T    G/W    H/Y    I/V
      8.1   10.5   11.6   13.0    5.5   10.5   12.3    9.0   10.4    5.2
      4.9   11.3    5.7    5.2    8.0    9.2    8.6    5.4    6.2    5.9
//
H GRAR740103
D Volume (Grantham, 1974)
R 2004143b
A Grantham, R.
T Amino acid difference formula to help explain protein evolution
J Science 185, 862-864 (1974)
C KRIW790103    0.989  GOLD730102    0.984  BIGC670101    0.984
  CHOC750101    0.973  FAUJ880103    0.959  CHAM820101    0.951
```

```
  CHOC760101    0.945  ROSG850101    0.922  RADA880106    0.920
  FASG760101    0.908  LEVM760105    0.900  CHAM830106    0.890
  LEVM760102    0.885  DAWD720101    0.853  LEVM760106    0.846
  LEVM760107    0.841  FAUJ880106    0.819  MCMT640101    0.817
  RADA880103   -0.881  OOBM770105   -0.887  OOBM770104   -0.900
I   A/L    R/K    N/M    D/F    C/P    Q/S    E/T    G/W    H/Y    I/V
    31.   124.    56.    54.    55.    85.    83.     3.    96.   111.
   111.   119.   105.   132.   32.5    32.    61.   170.   136.    84.
//
H GUYH850101
D Partition energy (Guy, 1985)
R 2004051b
A Guy, H.R.
T Amino acid side-chain partition energies and distribution of residues
  in soluble proteins
J Biophys. J. 47, 61-70 (1985)
C RACS770102    0.934  MEIH800102    0.934  MEIH800101    0.893
  KRIW790101    0.885  KRIW790102    0.864  RACS770101    0.853
  OOBM770101    0.848  KARP850102    0.840  ROSM880102    0.837
  KRIW710101    0.831  JANJ780103    0.829  JANJ780101    0.821
  PRAM900101    0.820  GRAR740102    0.818  RACS770103    0.816
  CHOC760102    0.807  ROSM880101    0.803  HOPT810101    0.802
  NISK800101   -0.811  YUTK870101   -0.813  RADA880101   -0.815
  CIDH920104   -0.821  EISD860101   -0.823  PONP800106   -0.826
  DESM900101   -0.831  EISD860103   -0.832  PLIV810101   -0.836
  MANP780101   -0.838  KYTJ820101   -0.843  EISD840101   -0.849
  CHOC760103   -0.856  FAUJ830101   -0.863  JANJ790102   -0.865
  WERD780101   -0.871  JANJ780102   -0.872  NISK860101   -0.877
  PONP800101   -0.877  MEIH800103   -0.880  PONP800102   -0.883
  BIOV880102   -0.885  PONP800103   -0.887  DESM900102   -0.895
  MIYS850101   -0.909  BIOV880101   -0.929  ROSG850102   -0.929
  RADA880108   -0.948
I   A/L    R/K    N/M    D/F    C/P    Q/S    E/T    G/W    H/Y    I/V
    0.10   1.91   0.48   0.78  -1.42   0.95   0.83   0.33  -0.50  -1.13
   -1.18   1.40  -1.59  -2.12   0.73   0.52   0.07  -0.51  -0.21  -1.27
//
H HOPA770101
D Hydration number (Hopfinger, 1971), Cited by Charton-Charton (1982)
R
A Hopfinger, A.J.
T
J "Intermolecular Interactions and Biomolecular Organizations", Wiley,
  New York (1977)
* Cited by Charton-Charton (1982)
* (Cys !)
C WOEC730101    0.876  ZIMJ680103    0.815
I   A/L    R/K    N/M    D/F    C/P    Q/S    E/T    G/W    H/Y    I/V
    1.0    2.3    2.2    6.5    0.1    2.1    6.2    1.1    2.8    0.8
    0.8    5.3    0.7    1.4    0.9    1.7    1.5    1.9    2.1    0.9
//
H HOPT810101
D Hydrophilicity value (Hopp-Woods, 1981)
R 0707598
A Hopp, T.P. and Woods, K.R.
T Prediction of protein antigenic determinants from amino acid sequecces
J Proc. Natl. Acad. Sci. USA 78, 3824-3828 (1981)
C LEVM760101    0.985  WOEC730101    0.886  PRAM900101    0.881
  GRAR740102    0.874  VHEG790101    0.849  ROSM880101    0.848
  OOBM770103    0.833  WOLS870101    0.830  PARJ860101    0.819
  GUYH850101    0.802  MIYS850101   -0.800  NAKH900110   -0.812
  ZIMJ680105   -0.816  NISK860101   -0.822  ROSG850102   -0.825
  MEEJ800102   -0.826  RADA880101   -0.829  RADA880108   -0.831
  EISD840101   -0.846  BIOV880101   -0.848  RADA880102   -0.859
  BIOV880102   -0.864  EISD860101   -0.905  FAUJ830101   -0.909
I   A/L    R/K    N/M    D/F    C/P    Q/S    E/T    G/W    H/Y    I/V
   -0.5    3.0    0.2    3.0   -1.0    0.2    3.0    0.0   -0.5   -1.8
   -1.8    3.0   -1.3   -2.5    0.0    0.3   -0.4   -3.4   -2.3   -1.5
//
```

```
H HUTJ700101
D Heat capacity (Hutchens, 1970)
R
A Hutchens, J.O.
T Heat capacities, absolute entropies, and entropies of formation of
  amino acids and related compounds
J In "Handbook of Biochemistry", 2nd ed. (Sober, H.A., ed.), Chemical
  Rubber Co., Cleveland, Ohio, pp. B60-B61 (1970)
C
I    A/L    R/K    N/M    D/F    C/P    Q/S    E/T    G/W    H/Y    I/V
    29.22  26.37  38.30  37.09  50.70  44.02  41.84  23.71  59.64  45.00
    48.03  57.10  69.32  48.52  36.13  32.40  35.20  56.92  51.73  40.35
//
H HUTJ700102
D Absolute entropy (Hutchens, 1970)
R
A Hutchens, J.O.
T Heat capacities, absolute entropies, and entropies of formation of
  amino acids and related compounds
J In "Handbook of Biochemistry", 2nd ed. (Sober, H.A., ed.), Chemical
  Rubber Co., Cleveland, Ohio, pp. B60-B61 (1970)
C HUTJ700103    0.867  LEVM760105    0.864  LEVM760102    0.835
  FAUJ880104    0.835  CHOC760101    0.819  CHAM820101    0.815
  FAUJ880103    0.807  FAUJ880106    0.806  CHOC750101    0.802
  RADA880103   -0.812
I    A/L    R/K    N/M    D/F    C/P    Q/S    E/T    G/W    H/Y    I/V
    30.88  68.43  41.70  40.66  53.83  46.62  44.98  24.74  65.99  49.71
    50.62  63.21  55.32  51.06  39.21  35.65  36.50  60.00  51.15  42.75
//
H HUTJ700103
D Entropy of formation (Hutchens, 1970)
R
A Hutchens, J.O.
T Heat capacities, absolute entropies, and entropies of formation of
  amino acids and related compounds
J In "Handbook of Biochemistry", 2nd ed. (Sober, H.A., ed.), Chemical
  Rubber Co., Cleveland, Ohio, pp. B60-B61 (1970)
C HUTJ700102    0.867  EISD860102    0.841  FAUJ880104    0.839
  LEVM760105    0.834
I    A/L    R/K    N/M    D/F    C/P    Q/S    E/T    G/W    H/Y    I/V
   154.33 341.01 207.90 194.91 219.79 235.51 223.16 127.90 242.54 233.21
   232.30 300.46 202.65 204.74 179.93 174.06 205.80 237.01 229.15 207.60
//
H ISOY800101
D Normalized relative frequency of alpha-helix (Isogai et al., 1980)
R 2004053b
A Isogai, Y., Nemethy, G., Rackovsky, S., Leach, S.J., and Scheraga,H.A
T Characterization of multiple bends in proteins
J Biopolymers 19, 1183-1210 (1980)
* Recalculated by Kidera using a different set of proteins
C MAXF760101    0.982  PALJ810102    0.965  KANM800101    0.963
  CHOP780201    0.959  ROBB760101    0.957  KANM800103    0.931
  PRAM900102    0.929  LEVM780101    0.929  TANS770101    0.906
  RACS820108    0.904  LEVM780104    0.904  QIAN880106    0.903
  GEIM800101    0.903  GEIM800104    0.891  QIAN880107    0.887
  PALJ810101    0.882  PALJ810109    0.874  NAGK730101    0.862
  ROBB760103    0.841  CRAJ730101    0.840  BURA740101    0.839
  QIAN880105    0.828  CHAM830101   -0.815  NAGK730103   -0.821
I    A/L    R/K    N/M    D/F    C/P    Q/S    E/T    G/W    H/Y    I/V
     1.53   1.17   0.60   1.00   0.89   1.27   1.63   0.44   1.03   1.07
     1.32   1.26   1.66   1.22   0.25   0.65   0.86   1.05   0.70   0.93
//
H ISOY800102
D Normalized relative frequency of extended structure (Isogai et al., 1980)
R 2004053b
A Isogai, Y., Nemethy, G., Rackovsky, S., Leach, S.J., and Scheraga,H.A
T Characterization of multiple bends in proteins
J Biopolymers 19, 1183-1210 (1980)
```

\* Recalculated by Kidera using a different set of proteins
C MAXF760102    0.931  TANS770103    0.929  ROBB760105    0.847
  GEIM800105    0.843  PALJ810103    0.807  WOEC730101   -0.803
I  A/L   R/K   N/M   D/F   C/P   Q/S   E/T   G/W   H/Y   I/V
   0.86  0.98  0.74  0.69  1.39  0.89  0.66  0.70  1.06  1.31
   1.01  0.77  1.06  1.16  1.16  1.09  1.24  1.17  1.28  1.40
//
H ISOY800103
D Normalized relative frequency of bend (Isogai et al., 1980)
R 2004053b
A Isogai, Y., Nemethy, G., Rackovsky, S., Leach, S.J., and Scheraga,H.A
T Characterization of multiple bends in proteins
J Biopolymers 19, 1183-1210 (1980)
\* Recalculated by Kidera using a different set of proteins
C LEVM780106    0.941  PRAM900104    0.934  CHOP780203    0.933
  LEVM780103    0.932  GEIM800108    0.930  GEIM800111    0.929
  PALJ810105    0.928  CHOP780216    0.921  QIAN880133    0.908
  TANS770110    0.897  QIAN880132    0.892  CHOP780101    0.885
  CHAM830101    0.881  CHOP780210    0.829  QIAN880134    0.828
  PALJ810116    0.814  PALJ810114    0.809  ROBB760112    0.807
  PALJ810106    0.807  SUEM840101   -0.850
I  A/L   R/K   N/M   D/F   C/P   Q/S   E/T   G/W   H/Y   I/V
   0.78  1.06  1.56  1.50  0.60  0.78  0.97  1.73  0.83  0.40
   0.57  1.01  0.30  0.67  1.55  1.19  1.09  0.74  1.14  0.44
//
H ISOY800104
D Normalized relative frequency of bend R (Isogai et al., 1980)
R 2004053b
A Isogai, Y., Nemethy, G., Rackovsky, S., Leach, S.J., and Scheraga,H.A
T Characterization of multiple bends in proteins
J Biopolymers 19, 1183-1210 (1980)
\* Recalculated by Kidera using a different set of proteins
C TANS770104    0.918  CHOP780213    0.916  QIAN880134    0.893
  FINA910102    0.844  QIAN880135    0.837  ROBB760104   -0.817
  ROBB760103   -0.830  PTIO830101   -0.832  BUNA790101   -0.842
  QIAN880108   -0.847
I  A/L   R/K   N/M   D/F   C/P   Q/S   E/T   G/W   H/Y   I/V
   1.09  0.97  1.14  0.77  0.50  0.83  0.92  1.25  0.67  0.66
   0.44  1.25  0.45  0.50  2.96  1.21  1.33  0.62  0.94  0.56
//
H ISOY800105
D Normalized relative frequency of bend S (Isogai et al., 1980)
R 2004053b
A Isogai, Y., Nemethy, G., Rackovsky, S., Leach, S.J., and Scheraga,H.A
T Characterization of multiple bends in proteins
J Biopolymers 19, 1183-1210 (1980)
\* Recalculated by Kidera using a different set of proteins
C CHOP780214    0.923  TANS770105    0.836  ISOY800108    0.812
I  A/L   R/K   N/M   D/F   C/P   Q/S   E/T   G/W   H/Y   I/V
   0.35  0.75  2.12  2.16  0.50  0.73  0.65  2.40  1.19  0.12
   0.58  0.83  0.22  0.89  0.43  1.24  0.85  0.62  1.44  0.43
//
H ISOY800106
D Normalized relative frequency of helix end (Isogai et al., 1980)
R 2004053b
A Isogai, Y., Nemethy, G., Rackovsky, S., Leach, S.J., and Scheraga,H.A
T Characterization of multiple bends in proteins
J Biopolymers 19, 1183-1210 (1980)
\* Recalculated by Kidera using a different set of proteins
C MAXF760106    0.849
I  A/L   R/K   N/M   D/F   C/P   Q/S   E/T   G/W   H/Y   I/V
   1.09  1.07  0.88  1.24  1.04  1.09  1.14  0.27  1.07  0.97
   1.30  1.20  0.55  0.80  1.78  1.20  0.99  1.03  0.69  0.77
//
H ISOY800107
D Normalized relative frequency of double bend (Isogai et al., 1980)
R 2004053b
A Isogai, Y., Nemethy, G., Rackovsky, S., Leach, S.J., and Scheraga,H.A

```
T Characterization of multiple bends in proteins
J Biopolymers 19, 1183-1210 (1980)
* Recalculated by Kidera using a different set of proteins
C
I    A/L    R/K    N/M    D/F    C/P    Q/S    E/T    G/W    H/Y    I/V
     1.34   2.78   0.92   1.77   1.44   0.79   2.54   0.95   0.00   0.52
     1.05   0.79   0.00   0.43   0.37   0.87   1.14   1.79   0.73   0.00
//
H ISOY800108
D Normalized relative frequency of coil (Isogai et al., 1980)
R 2004053b
A Isogai, Y., Nemethy, G., Rackovsky, S., Leach, S.J., and Scheraga,H.A
T Characterization of multiple bends in proteins
J Biopolymers 19, 1183-1210 (1980)
* Recalculated by Kidera using a different set of proteins
C MAXF760104    0.945  RICJ880115    0.889  RACS820109    0.848
  RACS820106    0.831  TANS770107    0.827  TANS770109    0.816
  ISOY800105    0.812  MAXF760105    0.810
I    A/L    R/K    N/M    D/F    C/P    Q/S    E/T    G/W    H/Y    I/V
     0.47   0.52   2.16   1.15   0.41   0.95   0.64   3.03   0.89   0.62
     0.53   0.98   0.68   0.61   0.63   1.03   0.39   0.63   0.83   0.76
//
H JANJ780101
D Average accessible surface area (Janin et al., 1978)
R 0502087
A Janin, J., Wodak, S., Levitt, M., and Maigret, B.
T Conformation of amino acid side-chains in proteins
J J. Mol. Biol. 125, 357-386 (1978)
C JANJ780103    0.985  CHOC760102    0.973  OOBM770101    0.953
  PRAM900101    0.901  ROSM880102    0.853  FAUJ880109    0.850
  MEIH800102    0.843  ROSM880101    0.822  GUYH850101    0.821
  EISD860103   -0.808  BIOV880102   -0.809  MEIH800103   -0.811
  JANJ790101   -0.824  RADA880104   -0.825  ROSG850102   -0.836
  RADA880101   -0.844  KYTJ820101   -0.852  CHOC760101   -0.854
  WOLR810101   -0.864  WARP780101   -0.869  DESM900102   -0.878
  CHOC760103   -0.892  EISD840101   -0.907  RADA880107   -0.917
  JANJ780102   -0.949  JANJ790102   -0.989
I    A/L    R/K    N/M    D/F    C/P    Q/S    E/T    G/W    H/Y    I/V
     27.8   94.7   60.1   60.6   15.5   68.7   68.2   24.5   50.7   22.8
     27.6  103.0   33.5   25.5   51.5   42.0   45.0   34.7   55.2   23.7
//
H JANJ780102
D Percentage of buried residues (Janin et al., 1978)
R 0502087
A Janin, J., Wodak, S., Levitt, M., and Maigret, B.
T Conformation of amino acid side-chains in proteins
J J. Mol. Biol. 125, 357-386 (1978)
C JANJ790102    0.966  CHOC760103    0.950  JANJ790101    0.941
  DESM900102    0.935  KYTJ820101    0.922  ROSG850102    0.909
  CHOC760104    0.903  MEIH800103    0.897  EISD860103    0.883
  PONP800103    0.882  WARP780101    0.878  PONP800102    0.875
  BIOV880101    0.875  EISD840101    0.874  RADA880108    0.869
  PONP800108    0.863  BIOV880102    0.862  RADA880107    0.856
  RADA880101    0.855  NISK800101    0.853  DESM900101    0.853
  WOLR810101    0.851  PONP800101    0.851  MANP780101    0.842
  FAUJ830101    0.825  NISK860101    0.813  MIYS850101    0.806
  CIDH920104    0.803  GRAR740102   -0.809  KRIW790102   -0.818
  RACS770103   -0.828  ROSM880101   -0.835  KRIW790101   -0.837
  PRAM900101   -0.860  RACS770102   -0.869  ROSM880102   -0.870
  GUYH850101   -0.872  MEIH800102   -0.907  CHOC760102   -0.935
  JANJ780101   -0.949  JANJ780103   -0.957  OOBM770101   -0.968
I    A/L    R/K    N/M    D/F    C/P    Q/S    E/T    G/W    H/Y    I/V
     51.    5.     22.    19.    74.    16.    16.    52.    34.    66.
     60.    3.     52.    58.    25.    35.    30.    49.    24.    64.
//
H JANJ780103
D Percentage of exposed residues (Janin et al., 1978)
R 0502087
```

A Janin, J., Wodak, S., Levitt, M., and Maigret, B.
T Conformation of amino acid side-chains in proteins
J J. Mol. Biol. 125, 357-386 (1978)
C JANJ780101    0.985   OOBM770101   0.965   CHOC760102   0.959
  PRAM900101    0.884   MEIH800101   0.873   KRIW790102   0.848
  RACS770103    0.847   ROSM880102   0.838   GUYH850101   0.829
  RACS770102    0.823   ROSM880101   0.810   KRIW790101   0.805
  RADA880108   -0.805   PONP800103  -0.812   RADA880101  -0.817
  EISD860103   -0.819   WOLR810101  -0.822   BIOV880101  -0.829
  JANJ790101   -0.832   DESM900101  -0.838   KYTJ820101  -0.845
  CHOC760104   -0.851   RADA880107  -0.856   BIOV880102  -0.860
  MEIH800103   -0.866   ROSG850102  -0.879   EISD840101  -0.881
  CHOC760103   -0.888   WARP780101  -0.890   DESM900102  -0.908
  JANJ780102   -0.957   JANJ790102  -0.980
I   A/L    R/K    N/M    D/F    C/P    Q/S    E/T    G/W    H/Y    I/V
    15.    67.    49.    50.    5.     56.    55.    10.    34.    13.
    16.    85.    20.    10.    45.    32.    32.    17.    41.    14.
//
H JANJ790101
D Ratio of buried and accessible molar fractions (Janin, 1979)
R 2004120b
A Janin, J.
T Surface and inside volumes in globular proteins
J Nature 277, 491-492 (1979)
C JANJ780102    0.941   PONP800102   0.897   CHOC760103   0.887
  PONP800103    0.886   CHOC760104   0.886   PONP800108   0.881
  NISK800101    0.875   KYTJ820101   0.867   PONP800101   0.866
  JANJ790102    0.860   ROSG850102   0.857   DESM900102   0.855
  MANP780101    0.842   MEIH800103   0.838   EISD860103   0.829
  BIOV880101    0.827   RADA880108   0.824   CHOC760102  -0.809
  KRIW790101   -0.810   KRIW710101  -0.815   MEIH800102  -0.821
  JANJ780101   -0.824   JANJ780103  -0.832   OOBM770101  -0.871
I   A/L    R/K    N/M    D/F    C/P    Q/S    E/T    G/W    H/Y    I/V
    1.7    0.1    0.4    0.4    4.6    0.3    0.3    1.8    0.8    3.1
    2.4    0.05   1.9    2.2    0.6    0.8    0.7    1.6    0.5    2.9
//
H JANJ790102
D Transfer free energy (Janin, 1979)
R 2004120b
A Janin, J.
T Surface and inside volumes in globular proteins
J Nature 277, 491-492 (1979)
C JANJ780102    0.966   RADA880107   0.906   CHOC760103   0.905
  EISD840101    0.900   DESM900102   0.897   ROSG850102   0.892
  WARP780101    0.877   KYTJ820101   0.866   JANJ790101   0.860
  BIOV880102    0.856   RADA880108   0.853   MEIH800103   0.853
  BIOV880101    0.848   PONP800103   0.844   RADA880101   0.839
  EISD860103    0.838   CHOC760104   0.835   WOLR810101   0.828
  FAUJ830101    0.826   PONP800102   0.822   DESM900101   0.818
  PONP800108    0.802   FAUJ880109  -0.822   ROSM880101  -0.824
  KRIW790101   -0.825   RACS770103  -0.834   KRIW790102  -0.847
  RACS770102   -0.851   GUYH850101  -0.865   ROSM880102  -0.866
  PRAM900101   -0.890   MEIH800102  -0.894   OOBM770101  -0.963
  CHOC760102   -0.969   JANJ780103  -0.980   JANJ780101  -0.989
I   A/L    R/K    N/M    D/F    C/P    Q/S    E/T    G/W    H/Y    I/V
    0.3   -1.4   -0.5   -0.6    0.9   -0.7   -0.7    0.3   -0.1    0.7
    0.5   -1.8    0.4    0.5   -0.3   -0.1   -0.2    0.3   -0.4    0.6
//
H JOND750101
D Hydrophobicity (Jones, 1975)
R
A Jones, D.D.
T Amino acid properties and side-chain orientation in proteins: A cross correlation approach
J J. Theor. Biol. 50, 167-183 (1975)
C ARGP820101    1.000   SIMZ760101   0.966   GOLD730101   0.935
  MEEJ810101    0.891   CIDH920105   0.866   LEVM760106   0.864
  CIDH920102    0.861   MEEJ800102   0.855   MEEJ810102   0.852

```
  CIDH920103     0.826   PLIV810101    0.819   CIDH920104    0.818
  LEVM760107     0.806   PARJ860101   -0.834   WOLS870101   -0.837
  BULH740101    -0.853
I   A/L    R/K    N/M    D/F    C/P    Q/S    E/T    G/W    H/Y    I/V
    0.87   0.85   0.09   0.66   1.52   0.00   0.67   0.10   0.87   3.15
    2.17   1.64   1.67   2.87   2.77   0.07   0.07   3.77   2.67   1.87
//
H JOND750102
D pK (-COOH) (Jones, 1975)
R
A Jones, D.D.
T Amino acid properties and side-chain orientation in proteins: A cross
  correlation approach
J J. Theor. Biol. 50, 167-183 (1975)
* Original reference of this data:
* McMeekin, T.L., Groves, M.L., and Hipp, N.J.
* In "Amino Acids and Serum Proteins" (Stekol, J.A., ed.), American
* Chemical Society, Washington, D.C., p. 54 (1964)
C FASG760105     0.833
I   A/L    R/K    N/M    D/F    C/P    Q/S    E/T    G/W    H/Y    I/V
    2.34   1.18   2.02   2.01   1.65   2.17   2.19   2.34   1.82   2.36
    2.36   2.18   2.28   1.83   1.99   2.21   2.10   2.38   2.20   2.32
//
H JOND920101
D Relative frequency of occurrence (Jones et al., 1992)
R 1814076
A Jones, D.T., Taylor, W.R. and Thornton, J.M.
T The rapid generation of mutation data matrices from protein sequences
J CABIOS 8, 275-282 (1992)
C NAKH900101     0.993   DAYM780101    0.954   JUKT750101    0.953
  JUNJ780101     0.932   NAKH920101    0.900   NAKH920107    0.893
  NAKH920106     0.889   NAKH920104    0.887   NAKH920103    0.881
  NAKH900109     0.878   NAKH900102    0.846
I   A/L    R/K    N/M    D/F    C/P    Q/S    E/T    G/W    H/Y    I/V
    0.077  0.051  0.043  0.052  0.020  0.041  0.062  0.074  0.023  0.053
    0.091  0.059  0.024  0.040  0.051  0.069  0.059  0.014  0.032  0.066
//
H JOND920102
D Relative mutability (Jones et al., 1992)
R 1814076
A Jones, D.T., Taylor, W.R. and Thornton, J.M.
T The rapid generation of mutation data matrices from protein sequences
J CABIOS 8, 275-282 (1992)
C DAYM780201     0.889
I   A/L    R/K    N/M    D/F    C/P    Q/S    E/T    G/W    H/Y    I/V
    100.   83.    104.   86.    44.    84.    77.    50.    91.    103.
    54.    72.    93.    51.    58.    117.   107.   25.    50.    98.
//
H JUKT750101
D Amino acid distribution (Jukes et al., 1975)
R
A Jukes, T.H., Holmquist, R., and Moise, H.
T Amino acid composition of proteins: Selection against the genetic code
J Science 189, 50-51 (1975)
C JUNJ780101     0.980   DAYM780101    0.975   JOND920101    0.953
  NAKH900101     0.941   NAKH920107    0.862   NAKH920101    0.849
  NAKH920103     0.837   NAKH920106    0.831   NAKH920104    0.827
  NAKH900109     0.815
I   A/L    R/K    N/M    D/F    C/P    Q/S    E/T    G/W    H/Y    I/V
    5.3    2.6    3.0    3.6    1.3    2.4    3.3    4.8    1.4    3.1
    4.7    4.1    1.1    2.3    2.5    4.5    3.7    0.8    2.3    4.2
//
H JUNJ780101
D Sequence frequency (Jungck, 1978)
R 2004107b
A Jungck, J.R.
T The genetic code as a periodic table
J J. Mol. Evol. 11, 211-224 (1978)
```

```
C DAYM780101    0.986  JUKT750101    0.980  JOND920101    0.932
  NAKH900101    0.918  NAKH920107    0.856  NAKH900102    0.853
  NAKH920106    0.829  NAKH920101    0.826  NAKH920103    0.820
  NAKH920104    0.807
I   A/L    R/K    N/M    D/F    C/P    Q/S    E/T    G/W    H/Y    I/V
   685.   382.   397.   400.   241.   313.   427.   707.   155.   394.
   581.   575.   132.   303.   366.   593.   490.    99.   292.   553.
//
H KANM800101
D Average relative probability of helix (Kanehisa-Tsong, 1980)
R 0611060
A Kanehisa, M.I. and Tsong, T.Y.
T Local hydrophobicity stabilizes secondary structures in proteins
J Biopolymers 19, 1617-1628 (1980)
C ISOY800101    0.963  PALJ810102    0.962  LEVM780104    0.958
  CHOP780201    0.956  MAXF760101    0.950  ROBB760101    0.945
  PRAM900102    0.942  LEVM780101    0.942  GEIM800101    0.942
  PALJ810101    0.928  TANS770101    0.927  GEIM800104    0.916
  RACS820108    0.914  KANM800103    0.912  NAGK730101    0.883
  BURA740101    0.855  QIAN880107    0.854  QIAN880106    0.854
  PALJ810109    0.849  CRAJ730101    0.842  QIAN880105    0.827
I   A/L    R/K    N/M    D/F    C/P    Q/S    E/T    G/W    H/Y    I/V
   1.36   1.00   0.89   1.04   0.82   1.14   1.48   0.63   1.11   1.08
   1.21   1.22   1.45   1.05   0.52   0.74   0.81   0.97   0.79   0.94
//
H KANM800102
D Average relative probability of beta-sheet (Kanehisa-Tsong, 1980)
R 0611060
A Kanehisa, M.I. and Tsong, T.Y.
T Local hydrophobicity stabilizes secondary structures in proteins
J Biopolymers 19, 1617-1628 (1980)
C GEIM800107    0.955  PALJ810104    0.948  CHOP780202    0.945
  LIFS790101    0.940  ROBB760106    0.938  LEVM780105    0.938
  PALJ810103    0.932  KANM800104    0.928  PTIO830102    0.917
  GEIM800105    0.916  QIAN880121    0.900  ROBB760105    0.898
  QIAN880120    0.896  QIAN880119    0.888  NAGK730102    0.878
  PALJ810112    0.869  LIFS790103    0.863  PRAM900103    0.856
  LEVM780102    0.856  PONP800108    0.849  PALJ810110    0.836
  MANP780101    0.833  PONP800101    0.829  GEIM800106    0.821
  NISK860101    0.819  PONP800102    0.815  NISK800101    0.809
  CHOP780208    0.804  PONP800103    0.803  QIAN880118    0.801
  LIFS790102    0.801  OOBM770103   -0.812  GEIM800110   -0.814
I   A/L    R/K    N/M    D/F    C/P    Q/S    E/T    G/W    H/Y    I/V
   0.81   0.85   0.62   0.71   1.17   0.98   0.53   0.88   0.92   1.48
   1.24   0.77   1.05   1.20   0.61   0.92   1.18   1.18   1.23   1.66
//
H KANM800103
D Average relative probability of inner helix (Kanehisa-Tsong, 1980)
R 0611060
A Kanehisa, M.I. and Tsong, T.Y.
T Local hydrophobicity stabilizes secondary structures in proteins
J Biopolymers 19, 1617-1628 (1980)
C ISOY800101    0.931  PALJ810102    0.916  KANM800101    0.912
  CHOP780201    0.912  QIAN880107    0.908  MAXF760101    0.901
  BEGF750101    0.893  QIAN880106    0.889  ROBB760103    0.887
  ROBB760101    0.886  GEIM800101    0.881  LEVM780104    0.859
  RACS820108    0.858  PRAM900102    0.850  LEVM780101    0.850
  TANS770101    0.843  PALJ810101    0.836  RICJ880109    0.829
  QIAN880108    0.829  QIAN880109    0.824  FINA770101    0.823
  SUEM840101    0.820  QIAN880110    0.820  QIAN880105    0.820
  BURA740101    0.810  CHOP780216   -0.808  GEIM800111   -0.812
  PRAM900104   -0.814  LEVM780103   -0.816  CHOP780101   -0.824
  PALJ810106   -0.840  NAGK730103   -0.847  CHAM830101   -0.889
I   A/L    R/K    N/M    D/F    C/P    Q/S    E/T    G/W    H/Y    I/V
   1.45   1.15   0.64   0.91   0.70   1.14   1.29   0.53   1.13   1.23
   1.56  -1.27   1.83   1.20   0.21   0.48   0.77   1.17   0.74   1.10
//
H KANM800104
```

D Average relative probability of inner beta-sheet (Kanehisa-Tsong, 1980)
R 0611060
A Kanehisa, M.I. and Tsong, T.Y.
T Local hydrophobicity stabilizes secondary structures in proteins
J Biopolymers 19, 1617-1628 (1980)
C KANM800102    0.928   ROBB760105   0.885   ROBB760106   0.877
  GEIM800107    0.876   GEIM800105   0.861   PTIO830102   0.858
  PALJ810104    0.851   PONP800108   0.849   QIAN880119   0.841
  LEVM780105    0.841   CHOP780202   0.839   LIFS790101   0.834
  QIAN880121    0.829   MANP780101   0.827   KYTJ820101   0.824
  PONP800101    0.823   PALJ810103   0.823   PONP800102   0.813
  PALJ810112    0.813   LIFS790102   0.809   QIAN880120   0.803
I   A/L    R/K    N/M    D/F    C/P    Q/S    E/T    G/W    H/Y    I/V
    0.75   0.79   0.33   0.31   1.46   0.75   0.46   0.83   0.83   1.87
    1.56   0.66   0.86   1.37   0.52   0.82   1.36   0.79   1.08   2.00
//
H KARP850101
D Flexibility parameter for no rigid neighbors (Karplus-Schulz, 1985)
R 1110994
A Karplus, P.A. and Schulz, G.E.
T Prediction of chain flexibility in proteins
J Naturwiss. 72, 212-213 (1985)
C RACS770101    0.837   MEIH800101   0.832   CIDH920104   -0.801
  BIOV880102   -0.804   RADA880108  -0.804   ROSG850101   -0.807
  MIYS850101   -0.811   MEEJ810101  -0.818   BIOV880101   -0.825
  NISK860101   -0.828   WERD780101  -0.842   CIDH920101   -0.864
  CIDH920105   -0.866   CIDH920102  -0.873
I   A/L    R/K    N/M    D/F    C/P    Q/S    E/T    G/W    H/Y    I/V
    1.041  1.038  1.117  1.033  0.960  1.165  1.094  1.142  0.982  1.002
    0.967  1.093  0.947  0.930  1.055  1.169  1.073  0.925  0.961  0.982
//
H KARP850102
D Flexibility parameter for one rigid neighbor (Karplus-Schulz, 1985)
R 1110994
A Karplus, P.A. and Schulz, G.E.
T Prediction of chain flexibility in proteins
J Naturwiss. 72, 212-213 (1985)
C KRIW790101    0.917   MEIH800101   0.884   RACS770101   0.869
  KRIW710101    0.855   RACS770102   0.852   KRIW790102   0.843
  GUYH850101    0.840   MEIH800102   0.837   OOBM770103   0.820
  BHAR880101    0.806   DESM900102  -0.815   PONP800106  -0.820
  CIDH920101   -0.828   DESM900101  -0.829   CIDH920104  -0.833
  CIDH920105   -0.839   CIDH920103  -0.852   BIOV880102  -0.859
  MANP780101   -0.863   PONP800103  -0.870   MIYS850101  -0.878
  RADA880108   -0.879   BIOV880101  -0.880   NISK800101  -0.885
  PONP800102   -0.887   PONP800101  -0.889   ROSG850102  -0.897
  NISK860101   -0.901   WERD780101  -0.909
I   A/L    R/K    N/M    D/F    C/P    Q/S    E/T    G/W    H/Y    I/V
    0.946  1.028  1.006  1.089  0.878  1.025  1.036  1.042  0.952  0.892
    0.961  1.082  0.862  0.912  1.085  1.048  1.051  0.917  0.930  0.927
//
H KARP850103
D Flexibility parameter for two rigid neighbors (Karplus-Schulz, 1985)
R 1110994
A Karplus, P.A. and Schulz, G.E.
T Prediction of chain flexibility in proteins
J Naturwiss. 72, 212-213 (1985)
C
I   A/L    R/K    N/M    D/F    C/P    Q/S    E/T    G/W    H/Y    I/V
    0.892  0.901  0.930  0.932  0.925  0.885  0.933  0.923  0.894  0.872
    0.921  1.057  0.804  0.914  0.932  0.923  0.934  0.803  0.837  0.913
//
H KHAG800101
D The Kerr-constant increments (Khanarian-Moore, 1980)
R 0611050b
A Khanarian, G. and Moore, W.J.
T The Kerr effect of amino acids in water
J Aust. J. Chem. 33, 1727-1741 (1980)

```
 * (Cys Lys Tyr.!).
C
I   A/L    R/K     N/M    D/F    C/P    Q/S    E/T    G/W    H/Y    I/V
    49.1   133.    -3.6   0.     0.     20.    0.     64.6   75.7   18.9
    15.6   0.      6.8    54.7   43.8   44.4   31.0   70.5   0.     29.5
//
H KLEP840101
D Net charge (Klein et al., 1984)
R 1008055
A Klein, P., Kanehisa, M., and DeLisi, C.
T Prediction of protein function from sequence properties: Discriminant
  analysis of a data base
J Biochim. Biophys. Acta 787, 221-226 (1984)
C ZIMJ680104    0.941
I   A/L    R/K     N/M    D/F    C/P    Q/S    E/T    G/W    H/Y    I/V
    0.     1.      0.     -1.    0.     0.     -1.    0.     0.     0.
    0.     1.      0.     0.     0.     0.     0.     0.     0.     0.
//
H KRIW710101
D Side chain interaction parameter (Krigbaum-Rubin, 1971)
R 2004046b
A Krigbaum, W.R. and Rubin, B.H.
T Local interactions as structure determinant for globular proteins
J Biochim. Biophys. Acta 229, 368-383 (1971)
C KRIW790101    0.908    KARP850102   0.855    KRIW790102    0.839
  GUYH850101    0.831    DESM900101  -0.807    BIOV880101   -0.813
  JANJ790101   -0.815    WERD780101  -0.819    NISK800101   -0.831
  PONP800106   -0.841    RADA880108  -0.847    PONP800101   -0.850
  ROSG850102   -0.852    PONP800102  -0.887    PONP800103   -0.890
I   A/L    R/K     N/M    D/F    C/P    Q/S    E/T    G/W    H/Y    I/V
    4.60   6.50    5.90   5.70   -1.00  6.10   5.60   7.60   4.50   2.60
    3.25   7.90    1.40   3.20   7.00   5.25   4.80   4.00   4.35   3.40
//
H KRIW790101
D Side chain interaction parameter (Krigbaum-Komoriya, 1979)
R 0502056
A Krigbaum, W.R. and Komoriya, A.
T Local interactions as a structure determinant for protein molecules:
  II
J Biochim. Biophys. Acta 576, 204-228 (1979)
C KARP850102    0.917    KRIW790102   0.914    KRIW710101    0.908
  GUYH850101    0.885    MEIH800102   0.876    RACS770102    0.871
  MEIH800101    0.869    OOBM770103   0.865    GRAR740102    0.847
  RACS770101    0.828    OOBM770101   0.816    JANJ780103    0.805
  PTIO830102   -0.801    QIAN880121  -0.803    KYTJ820101   -0.805
  JANJ790101   -0.810    CIDH920105  -0.816    CIDH920103   -0.819
  JANJ790102   -0.825    JANJ780102  -0.837    DESM900101   -0.847
  MEIH800103   -0.850    DESM900102  -0.859    PONP800108   -0.860
  FAUJ830101   -0.865    CIDH920104  -0.867    MANP780101   -0.870
  BIOV880102   -0.876    PONP800101  -0.888    NISK800101   -0.896
  RADA880108   -0.897    WERD780101  -0.899    NISK860101   -0.907
  BIOV880101   -0.910    MIYS850101  -0.910    PONP800102   -0.915
  PONP800103   -0.930    ROSG850102  -0.935
I   A/L    R/K     N/M    D/F    C/P    Q/S    E/T    G/W    H/Y    I/V
    4.32   6.55    6.24   6.04   1.73   6.13   6.17   6.09   5.66   2.31
    3.93   7.92    2.44   2.59   7.19   5.37   5.16   2.78   3.58   3.31
//
H KRIW790102
D Fraction of site occupied by water (Krigbaum-Komoriya, 1979)
R 0502056
A Krigbaum, W.R. and Komoriya, A.
T Local interactions as a structure determinant for protein molecules:
  II
J Biochim. Biophys. Acta 576, 204-228 (1979)
C KRIW790101    0.914    MEIH800102   0.898    RACS770102    0.895
  RACS770103    0.889    GUYH850101   0.864    JANJ780103    0.848
  KARP850102    0.843    KRIW710101   0.839    MEIH800101    0.835
  OOBM770103    0.824    OOBM770101   0.822    RACS770101    0.814
```

```
    PONP800101   -0.804   JANJ780102   -0.818   PONP800102   -0.830
    DESM900101   -0.835   JANJ790102   -0.847   DESM900102   -0.852
    PONP800103   -0.853   NISK860101   -0.855   RADA880108   -0.856
    BIOV880101   -0.869   MIYS850101   -0.869   WERD780101   -0.875
    BIOV880102   -0.878   MEIH800103   -0.885   ROSG850102   -0.922
I    A/L    R/K    N/M    D/F    C/P    Q/S    E/T    G/W    H/Y    I/V
     0.28   0.34   0.31   0.33   0.11   0.39   0.37   0.28   0.23   0.12
     0.16   0.59   0.08   0.10   0.46   0.27   0.26   0.15   0.25   0.22
//
H KRIW790103
D Side chain volume (Krigbaum-Komoriya, 1979)
R 0502056
A Krigbaum, W.R. and Komoriya, A.
T Local interactions as a structure determinant for protein molecules:
  II
J Biochim. Biophys. Acta 576, 204-228 (1979)
* (Gly Pro 7.8)
C GOLD730102    0.994   BIGC670101    0.993   GRAR740103    0.989
  CHOC750101    0.982   FAUJ880103    0.965   CHAM820101    0.963
  CHOC760101    0.948   ROSG850101    0.920   FASG760101    0.910
  LEVM760105    0.900   DAWD720101    0.893   LEVM760102    0.884
  RADA880106    0.883   CHAM830106    0.876   LEVM760106    0.862
  LEVM760107    0.860   FAUJ880106    0.845   MCMT640101    0.810
  RADA880103   -0.871   OOBM770105   -0.892   OOBM770104   -0.904
I    A/L    R/K    N/M    D/F    C/P    Q/S    E/T    G/W    H/Y    I/V
     27.5   105.0  58.7   40.0   44.6   80.7   62.0   0.0    79.0   93.5
     93.5   100.0  94.1   115.5  41.9   29.3   51.3   145.5  117.3  71.5
//
H KYTJ820101
D Hydropathy index (Kyte-Doolittle, 1982)
R 0807099
A Kyte, J. and Doolittle, R.F.
T A simple method for displaying the hydropathic character of a protein
J J. Mol. Biol. 157, 105-132 (1982)
C CHOC760103    0.964   JANJ780102    0.922   DESM900102    0.898
  EISD860103    0.897   CHOC760104    0.889   WOLR810101    0.885
  RADA880101    0.884   MANP780101    0.881   EISD840101    0.878
  PONP800103    0.870   NAKH920108    0.868   JANJ790101    0.867
  JANJ790102    0.866   PONP800102    0.861   MEIH800103    0.856
  PONP800101    0.851   PONP800108    0.850   WARP780101    0.845
  RADA880108    0.842   ROSG850102    0.841   DESM900101    0.837
  BIOV880101    0.829   RADA880107    0.828   LIFS790102    0.824
  KANM800104    0.824   CIDH920104    0.824   MIYS850101    0.821
  RADA880104    0.819   NAKH900111    0.817   NISK800101    0.812
  FAUJ830101    0.811   ARGP820103    0.806   NAKH920105    0.803
  ARGP820102    0.803   KRIW790101   -0.805   CHOC760102   -0.838
  GUYH850101   -0.843   RACS770102   -0.844   JANJ780103   -0.845
  ROSM880101   -0.845   PRAM900101   -0.850   JANJ780101   -0.852
  GRAR740102   -0.859   MEIH800102   -0.871   ROSM880102   -0.878
  OOBM770101   -0.899
I    A/L    R/K    N/M    D/F    C/P    Q/S    E/T    G/W    H/Y    I/V
     1.8    -4.5   -3.5   -3.5   2.5    -3.5   -3.5   -0.4   -3.2   4.5
     3.8    -3.9   1.9    2.8    -1.6   -0.8   -0.7   -0.9   -1.3   4.2
//
H LAWE840101
D Transfer free energy, CHP/water (Lawson et al., 1984)
R 1004126
A Lawson, E.Q., Sadler, A.J., Harmatz, D., Brandau, D.T., Micanovic, R.
  MacElroy, R.D., and Middaught, C.R.
T A simple experimental model for hydrophobic interactions in proteins
J J. Biol. Chem. 259, 2910-2912 (1984)
C GOLD730101    0.829   SIMZ760101    0.815   ZIMJ680105    0.809
I    A/L    R/K    N/M    D/F    C/P    Q/S    E/T    G/W    H/Y    I/V
    -0.48  -0.06  -0.87  -0.75  -0.32  -0.32  -0.71  0.00   -0.51  0.81
     1.02  -0.09  0.81   1.03   2.03   0.05   -0.35  0.66   1.24   0.56
//
H LEVM760101
D Hydrophobic parameter (Levitt, 1976)
```

R 2004093b
A Levitt, M.
T A simplified representation of protein conformations for rapid
  simulation of protein folfing
J J. Mol. Biol. 104, 59-107 (1976)
C HOPT810101    0.985  PRAM900101   0.881  ROSM880101   0.876
  WOEC730101    0.872  GRAR740102   0.865  WOLS870101   0.845
  VHEG790101    0.825  ROSM880102   0.823  PARJ860101   0.806
  OOBM770103    0.805  PLIV810101  -0.801  RADA880108  -0.824
  BIOV880101   -0.831  RADA880101  -0.838  RADA880102  -0.838
  ZIMJ680105   -0.844  BIOV880102  -0.847  MEEJ800102  -0.855
  EISD840101   -0.859  FAUJ830101  -0.919  EISD860101  -0.921
I   A/L    R/K    N/M    D/F    C/P    Q/S    E/T    G/W    H/Y    I/V
   -0.5    3.0    0.2    2.5   -1.0    0.2    2.5    0.0   -0.5   -1.8
   -1.8    3.0   -1.3   -2.5   -1.4    0.3   -0.4   -3.4   -2.3   -1.5
//
H LEVM760102
D Distance between C-alpha and centroid of side chain (Levitt, 1976)
R 2004093b
A Levitt, M.
T A simplified representation of protein conformations for rapid
  simulation of protein folfing
J J. Mol. Biol. 104, 59-107 (1976)
C LEVM760105    0.987  CHOC760101   0.972  FASG760101   0.966
  CHAM830106    0.962  FAUJ880103   0.947  CHOC750101   0.933
  CHAM820101    0.915  FAUJ880106   0.900  BIGC670101   0.896
  GOLD730102    0.893  GRAR740103   0.885  KRIW790103   0.884
  WOLS870102    0.881  DAWD720101   0.873  RADA880106   0.871
  OOBM770102    0.869  FAUJ880104   0.867  CHAM830105   0.843
  HUTJ700102    0.835  OOBM770105  -0.880  RADA880103  -0.913
I   A/L    R/K    N/M    D/F    C/P    Q/S    E/T    G/W    H/Y    I/V
   0.77   3.72   1.98   1.99   1.38   2.58   2.63   0.00   2.76   1.83
   2.08   2.94   2.34   2.97   1.42   1.28   1.43   3.58   3.36   1.49
//
H LEVM760103
D Side chain angle theta(AAR) (Levitt, 1976)
R 2004093b
A Levitt, M.
T A simplified representation of protein conformations for rapid
  simulation of protein folfing
J J. Mol. Biol. 104, 59-107 (1976)
* (Gly missing)
C RICJ880115   -0.829  LEVM760104  -0.840
I   A/L    R/K    N/M    D/F    C/P    Q/S    E/T    G/W    H/Y    I/V
  121.9  121.4  117.5  121.2  113.7  118.0  118.2    0.   118.2  118.9
  118.1  122.0  113.1  118.2   81.9  117.9  117.1  118.4  110.0  121.7
//
H LEVM760104
D Side chain torsion angle phi(AAAR) (Levitt, 1976)
R 2004093b
A Levitt, M.
T A simplified representation of protein conformations for rapid
  simulation of protein folfing
J J. Mol. Biol. 104, 59-107 (1976)
C PRAM820102    0.812  CHAM810101  -0.818  LEVM760103  -0.840
I   A/L    R/K    N/M    D/F    C/P    Q/S    E/T    G/W    H/Y    I/V
  243.2  206.6  207.1  215.0  209.4  205.4  213.6  300.0  219.9  217.9
  205.6  210.9  204.0  203.7  237.4  232.0  226.7  203.7  195.6  220.3
//
H LEVM760105
D Radius of gyration of side chain (Levitt, 1976)
R 2004093b
A Levitt, M.
T A simplified representation of protein conformations for rapid
  simulation of protein folfing
J J. Mol. Biol. 104, 59-107 (1976)
* (Gly 0.089)
C LEVM760102    0.987  CHOC760101   0.968  CHAM830106   0.958

```
    FASG760101   0.951   FAUJ880103   0.945   CHOC750101   0.939
    CHAM820101   0.915   BIGC670101   0.913   GOLD730102   0.911
    KRIW790103   0.900   GRAR740103   0.900   DAWD720101   0.898
    FAUJ880104   0.896   FAUJ880106   0.889   RADA880106   0.871
    OOBM770102   0.868   HUTJ700102   0.864   WOLS870102   0.836
    HUTJ700103   0.834   CHAM830105   0.829   OOBM770105  -0.844
    RADA880103  -0.893
I   A/L    R/K    N/M    D/F    C/P    Q/S    E/T    G/W    H/Y    I/V
    0.77   2.38   1.45   1.43   1.22   1.75   1.77   0.58   1.78   1.56
    1.54   2.08   1.80   1.90   1.25   1.08   1.24   2.21   2.13   1.29
//
H LEVM760106
D van der Waals parameter R0 (Levitt, 1976)
R 2004093b
A Levitt, M.
T A simplified representation of protein conformations for rapid
  simulation of protein folfing
J J. Mol. Biol. 104, 59-107 (1976)
C ROSG850101   0.896   BIGC670101   0.876   GOLD730102   0.875
  ZIMJ680102   0.873   CIDH920102   0.873   ARGP820101   0.865
  JOND750101   0.864   KRIW790103   0.862   SIMZ760101   0.848
  GRAR740103   0.846   CHOC750101   0.841   PLIV810101   0.830
  CIDH920105   0.828   MEEJ810101   0.827   GOLD730101   0.827
  CIDH920101   0.826   CHAM820101   0.818   ROBB790101   0.804
  LEVM760107   0.804   BULH740101  -0.818   OOBM770104  -0.829
  PARJ860101  -0.832
I   A/L    R/K    N/M    D/F    C/P    Q/S    E/T    G/W    H/Y    I/V
    5.2    6.0    5.0    5.0    6.1    6.0    6.0    4.2    6.0    7.0
    7.0    6.0    6.8    7.1    6.2    4.9    5.0    7.6    7.1    6.4
//
H LEVM760107
D van der Waals parameter epsilon (Levitt, 1976)
R 2004093b
A Levitt, M.
T A simplified representation of protein conformations for rapid
  simulation of protein folfing
J J. Mol. Biol. 104, 59-107 (1976)
C CHAM820101   0.891   FAUJ880103   0.875   GOLD730102   0.865
  BIGC670101   0.863   KRIW790103   0.860   GARJ730101   0.860
  CHOC750101   0.858   ROSG850101   0.852   NOZY710101   0.845
  GRAR740103   0.841   SNEP660103   0.818   FASG760101   0.815
  CHOC760101   0.807   JOND750101   0.806   ARGP820101   0.806
  LEVM760106   0.804   OOBM770105  -0.825   OOBM770104  -0.915
  WEBA780101  -0.923
I   A/L    R/K    N/M    D/F    C/P    Q/S    E/T    G/W    H/Y    I/V
    0.025  0.20   0.10   0.10   0.10   0.10   0.10   0.025  0.10   0.19
    0.19   0.20   0.19   0.39   0.17   0.025  0.10   0.56   0.39   0.15
//
H LEVM780101
D Normalized frequency of alpha-helix, with weights (Levitt, 1978)
R 0411042
A Levitt, M.
T Conformational preferences of amino acids in globular proteins
J Biochemistry 17, 4277-4285 (1978)
C PRAM900102   1.000   LEVM780104   0.964   PALJ810101   0.943
  KANM800101   0.942   ISOY800101   0.929   MAXF760101   0.924
  ROBB760101   0.916   GEIM800101   0.912   GEIM800104   0.907
  RACS820108   0.904   PALJ810102   0.902   PALJ810109   0.898
  NAGK730101   0.894   CRAJ730101   0.887   CHOP780201   0.873
  TANS770101   0.854   KANM800103   0.850   QIAN880107   0.829
  QIAN880106   0.827   BURA740101   0.805   NAGK730103  -0.809
I   A/L    R/K    N/M    D/F    C/P    Q/S    E/T    G/W    H/Y    I/V
    1.29   0.96   0.90   1.04   1.11   1.27   1.44   0.56   1.22   0.97
    1.30   1.23   1.47   1.07   0.52   0.82   0.82   0.99   0.72   0.91
//
H LEVM780102
D Normalized frequency of beta-sheet, with weights (Levitt, 1978)
R 0411042
```

```
A Levitt, M.
T Conformational preferences of amino acids in globular proteins
J Biochemistry 17, 4277-4285 (1978)
C PRAM900103    1.000    PALJ810112    0.913    LEVM780105    0.899
  PALJ810104    0.868    PTIO830102    0.865    LIFS790101    0.864
  QIAN880120    0.858    KANM800103    0.856    PALJ810103    0.846
  GEIM800107    0.842    QIAN880119    0.834    BEGF750102    0.834
  CHOP780202    0.833    QIAN880121    0.805
I    A/L    R/K    N/M    D/F    C/P    Q/S    E/T    G/W    H/Y    I/V
     0.90   0.99   0.76   0.72   0.74   0.80   0.75   0.92   1.08   1.45
     1.02   0.77   0.97   1.32   0.64   0.95   1.21   1.14   1.25   1.49
//
H LEVM780103
D Normalized frequency of reverse turn, with weights (Levitt, 1978)
R 0411042
A Levitt, M.
T Conformational preferences of amino acids in globular proteins
J Biochemistry 17, 4277-4285 (1978)
C PRAM900104    1.000    LEVM780106    0.984    GEIM800111    0.952
  CHOP780216    0.952    QIAN880133    0.948    QIAN880134    0.935
  ISOY800103    0.932    QIAN880132    0.931    GEIM800108    0.931
  CHOP780203    0.927    PALJ810105    0.909    CHAM830101    0.909
  QIAN880135    0.906    CHOP780101    0.893    TANS770110    0.875
  CHOP780210    0.852    PALJ810106    0.848    RACS770101    0.808
  KANM800103   -0.816    QIAN880108   -0.820    QIAN880107   -0.834
  ROBB760103   -0.843    FAUJ880102   -0.846    QIAN880109   -0.848
  PTIO830101   -0.860    SUEM840101   -0.864
I    A/L    R/K    N/M    D/F    C/P    Q/S    E/T    G/W    H/Y    I/V
     0.77   0.88   1.28   1.41   0.81   0.98   0.99   1.64   0.68   0.51
     0.58   0.96   0.41   0.59   1.91   1.32   1.04   0.76   1.05   0.47
//
H LEVM780104
D Normalized frequency of alpha-helix, unweighted (Levitt, 1978)
R 0411042
A Levitt, M.
T Conformational preferences of amino acids in globular proteins
J Biochemistry 17, 4277-4285 (1978)
C PALJ810101    0.988    PRAM900102    0.964    LEVM780101    0.964
  KANM800101    0.958    GEIM800101    0.950    NAGK730101    0.918
  ROBB760101    0.911    TANS770101    0.908    PALJ810102    0.906
  MAXF760101    0.904    ISOY800101    0.904    RACS820108    0.889
  CHOP780201    0.886    GEIM800104    0.872    CRAJ730101    0.869
  KANM800103    0.859    BURA740101    0.833    QIAN880107    0.822
  PALJ810109    0.819    QIAN880106    0.804
I    A/L    R/K    N/M    D/F    C/P    Q/S    E/T    G/W    H/Y    I/V
     1.32   0.98   0.95   1.03   0.92   1.10   1.44   0.61   1.31   0.93
     1.31   1.25   1.39   1.02   0.58   0.76   0.79   0.97   0.73   0.93
//
H LEVM780105
D Normalized frequency of beta-sheet, unweighted (Levitt, 1978)
R 0411042
A Levitt, M.
T Conformational preferences of amino acids in globular proteins
J Biochemistry 17, 4277-4285 (1978)
C PALJ810103    0.980    KANM800102    0.938    CHOP780202    0.930
  LIFS790101    0.928    GEIM800105    0.926    PALJ810104    0.921
  QIAN880120    0.913    QIAN880119    0.903    PRAM900103    0.899
  LEVM780102    0.899    LIFS790103    0.897    PTIO830102    0.894
  GEIM800107    0.884    QIAN880121    0.876    PALJ810112    0.870
  ROBB760106    0.869    ROBB760105    0.842    KANM800104    0.841
  QIAN880118    0.819
I    A/L    R/K    N/M    D/F    C/P    Q/S    E/T    G/W    H/Y    I/V
     0.86   0.97   0.73   0.69   1.04   1.00   0.66   0.89   0.85   1.47
     1.04   0.77   0.93   1.21   0.68   1.02   1.27   1.26   1.31   1.43
//
H LEVM780106
D Normalized frequency of reverse turn, unweighted (Levitt, 1978)
R 0411042
```

A Levitt, M.
T Conformational preferences of amino acids in globular proteins
J Biochemistry 17, 4277-4285 (1978)
C LEVM780103   0.984   PRAM900104   0.983   QIAN880133   0.971
  CHOP780216   0.953   GEIM800111   0.951   QIAN880132   0.943
  ISOY800103   0.941   CHOP780203   0.935   QIAN880134   0.932
  GEIM800108   0.932   QIAN880135   0.902   PALJ810105   0.902
  CHAM830101   0.900   TANS770110   0.892   CHOP780101   0.890
  PALJ810106   0.850   CHOP780210   0.812   GEIM800110   0.809
  LIFS790101  -0.806   QIAN880119  -0.810   QIAN880107  -0.813
  QIAN880109  -0.815   QIAN880120  -0.831   PTIO830101  -0.854
  FAUJ880102  -0.865   SUEM840101  -0.878
I   A/L    R/K    N/M    D/F    C/P    Q/S    E/T    G/W    H/Y    I/V
    0.79   0.90   1.25   1.47   0.79   0.92   1.02   1.67   0.81   0.50
    0.57   0.99   0.51   0.77   1.78   1.30   0.97   0.79   0.93   0.46
//
H LEWP710101
D Frequency of occurrence in beta-bends (Lewis et al., 1971)
R
A Lewis, P. N., Momany, F.A., and Scheraga, H.A.
T Folding of polypeptide chains in proteins: A proposed mechanism for folding
J Proc. Natl. Acad. Sci. USA 68, 2293-2297 (1971)
C
I   A/L    R/K    N/M    D/F    C/P    Q/S    E/T    G/W    H/Y    I/V
    0.22   0.28   0.42   0.73   0.20   0.26   0.08   0.58   0.14   0.22
    0.19   0.27   0.38   0.08   0.46   0.55   0.49   0.43   0.46   0.08
//
H LIFS790101
D Conformational preference for all beta-strands (Lifson-Sander, 1979)
R 0512128
A Lifson, S., and Sander, C.
T Antiparallel and parallel beta-strands differ in amino acid residue preference
J Nature 282, 109-111 (1979)
C QIAN880120   0.969   CHOP780202   0.947   LIFS790103   0.944
  PTIO830102   0.941   KANM800102   0.940   QIAN880121   0.930
  QIAN880119   0.929   PALJ810104   0.929   LEVM780105   0.928
  PALJ810103   0.912   ROBB760106   0.906   GEIM800107   0.888
  ROBB760105   0.867   PRAM900103   0.864   LEVM780102   0.864
  NISK860101   0.859   MANP780101   0.859   GEIM800105   0.855
  PALJ810112   0.845   KANM800104   0.834   CIDH920104   0.832
  PONP800108   0.828   CIDH920105   0.828   NISK800101   0.827
  PONP800101   0.823   CHOP780208   0.820   PALJ810110   0.817
  SWER830101   0.815   CIDH920103   0.815   VENT840101   0.814
  CIDH920102   0.808   BEGF750102   0.807   LIFS790102   0.803
  PONP800107   0.801   GEIM800111  -0.801   QIAN880134  -0.804
  LEVM780106  -0.806   QIAN880132  -0.806   MEIH800101  -0.809
  QIAN880133  -0.848   OOBM770103  -0.855   GEIM800110  -0.862
I   A/L    R/K    N/M    D/F    C/P    Q/S    E/T    G/W    H/Y    I/V
    0.92   0.93   0.60   0.48   1.16   0.95   0.61   0.61   0.93   1.81
    1.30   0.70   1.19   1.25   0.40   0.82   1.12   1.54   1.53   1.81
//
H LIFS790102
D Conformational preference for parallel beta-strands (Lifson-Sander, 1979)
R 0512128
A Lifson, S. and Sander, C.
T Antiparallel and parallel beta-strands differ in amino acid residue preference
J Nature 282, 109-111 (1979)
C PTIO830102   0.874   MANP780101   0.870   PONP800107   0.849
  KYTJ820101   0.824   CHOC760103   0.810   KANM800104   0.809
  PONP800101   0.804   LIFS790101   0.803   KANM800102   0.801
I   A/L    R/K    N/M    D/F    C/P    Q/S    E/T    G/W    H/Y    I/V
    1.00   0.68   0.54   0.50   0.91   0.28   0.59   0.79   0.38   2.60
    1.42  -0.59   1.49   1.30   0.35   0.70   0.59   0.89   1.08   2.63
//
H LIFS790103

D Conformational preference for antiparallel beta-strands (Lifson-Sander, 1979)
R 0512128
A Lifson, S. and Sander, C.
T Antiparallel and parallel beta-strands differ in amino acid residue preference
J Nature 282, 109-111 (1979)
C LIFS790101    0.944    QIAN880120    0.939    CHOP780202    0.908
  LEVM780105    0.897    QIAN880121    0.882    QIAN880119    0.877
  PALJ810103    0.877    KANM800102    0.863    PALJ810104    0.860
  GEIM800105    0.832    ROBB760106    0.827    GEIM800107    0.823
  PTIO830102    0.822    GEIM800106    0.814    OOBM770103   -0.807
  GEIM800110   -0.889
I   A/L     R/K     N/M     D/F     C/P     Q/S     E/T     G/W     H/Y     I/V
    0.90    1.02    0.62    0.47    1.24    1.18    0.62    0.56    1.12    1.54
    1.26    0.74    1.09    1.23    0.42    0.87    1.30    1.75    1.68    1.53
//
H MANP780101
D Average surrounding hydrophobicity (Manavalan-Ponnuswamy, 1978)
R 0411088
A Manavalan, P. and Ponnuswamy, P.K.
T Hydrophobic character of amino acid residues in globular proteins
J Nature 275, 673-674 (1978)
C PONP800101    0.963    PONP800102    0.945    NISK800101    0.940
  PONP800108    0.935    NISK860101    0.930    CIDH920104    0.918
  PONP800103    0.913    MIYS850101    0.909    CIDH920103    0.905
  ROSG850102    0.903    RADA880108    0.900    BIOV880101    0.899
  KYTJ820101    0.881    CIDH920105    0.879    PONP800107    0.871
  LIFS790102    0.870    PTIO830102    0.861    LIFS790101    0.859
  CHOC760103    0.859    PLIV810101    0.856    WERD780101    0.853
  BIOV880102    0.847    FAUJ830101    0.843    JANJ790101    0.842
  JANJ780102    0.842    MEIH800103    0.839    ROBB790101    0.834
  KANM800102    0.833    KANM800104    0.827    EISD860103    0.826
  ROBB760106    0.824    SWER830101    0.821    DESM900102    0.816
  PONP800106    0.813    QIAN880120    0.806    ROBB760105    0.805
  PALJ810104    0.805    CHOP780202    0.805    QIAN880121    0.802
  OOBM770101   -0.806    WOLS870101   -0.809    GUYH850101   -0.838
  PARJ860101   -0.841    OOBM770103   -0.859    KARP850102   -0.863
  MEIH800102   -0.865    RACS770102   -0.865    GRAR740102   -0.868
  KRIW790101   -0.870    RACS770101   -0.878    MEIH800101   -0.897
I   A/L     R/K     N/M     D/F     C/P     Q/S     E/T     G/W     H/Y     I/V
   12.97   11.72   11.42   10.85   14.63   11.76   11.89   12.43   12.16   15.67
   14.90   11.36   14.39   14.00   11.37   11.23   11.69   13.93   13.42   15.71
//
H MAXF760101
D Normalized frequency of alpha-helix (Maxfield-Scheraga, 1976)
R 2004036b
A Maxfield, F.R. and Scheraga, H.A.
T Status of empirical methods for the prediction of protein backbone topography
J Biochemistry 15, 5138-5153 (1976)
* Recalculated by Kidera using a different set of proteins
* Reported values normalized by the total number
C ISOY800101    0.982    PALJ810102    0.959    ROBB760101    0.956
  CHOP780201    0.956    KANM800101    0.950    TANS770101    0.930
  PRAM900102    0.924    LEVM780101    0.924    LEVM780104    0.904
  KANM800103    0.901    GEIM800104    0.897    GEIM800101    0.895
  PALJ810101    0.889    QIAN880107    0.885    QIAN880106    0.881
  NAGK730101    0.877    PALJ810109    0.876    RACS820108    0.860
  BURA740101    0.852    CRAJ730101    0.826    QIAN880105    0.811
  FINA770101    0.810    NAGK730103   -0.801
I   A/L     R/K     N/M     D/F     C/P     Q/S     E/T     G/W     H/Y     I/V
    1.43    1.18    0.64    0.92    0.94    1.22    1.67    0.46    0.98    1.04
    1.36    1.27    1.53    1.19    0.49    0.70    0.78    1.01    0.69    0.98
//
H MAXF760102
D Normalized frequency of extended structure (Maxfield-Scheraga, 1976)
R 2004036b A Maxfield, F.R. and Scheraga, H.A.
T Status of empirical methods for the prediction of protein backbone topography
J Biochemistry 15, 5138-5153 (1976)
* Recalculated by Kidera using a different set of proteins
* Reported values normalized by the total number
C ISOY800102    0.931   TANS770103   0.881   GEIM800105   0.819
  RACS820111    0.815   WOEC730101   0.842
I   A/L    R/K    N/M    D/F    C/P    Q/S    E/T    G/W    H/Y    I/V
    0.86   0.94   0.74   0.72   1.17   0.89   0.62   0.97   1.06   1.24
    0.98   0.79   1.08   1.16   1.22   1.04   1.18   1.07   1.25   1.33
//
H MAXF760103
D Normalized frequency of zeta R (Maxfield-Scheraga, 1976)
R 2004036b
A Maxfield, F.R. and Scheraga, H.A.
T Status of empirical methods for the prediction of protein backbone topography
J Biochemistry 15, 5138-5153 (1976)
* Recalculated by Kidera using a different set of proteins
* Reported values normalized by the total number
C
I   A/L    R/K    N/M    D/F    C/P    Q/S    E/T    G/W    H/Y    I/V
    0.64   0.62   3.14   1.92   0.32   0.80   1.01   0.63   2.05   0.92
    0.37   0.89   1.07   0.86   0.50   1.01   0.92   1.00   1.31   0.87
//
H MAXF760104
D Normalized frequency of left-handed alpha-helix (Maxfield-Scheraga, 1976)
R 2004036b
A Maxfield, F.R. and Scheraga, H.A.
T Status of empirical methods for the prediction of protein backbone topography
J Biochemistry 15, 5138-5153 (1976)
* Recalculated by Kidera using a different set of proteins
* Reported values normalized by the total number
C ISOY800108    0.945   RICJ880115   0.919   TANS770107   0.913
  MAXF760105    0.850   RACS820109   0.844   TANS770109   0.821
I   A/L    R/K    N/M    D/F    C/P    Q/S    E/T    G/W    H/Y    I/V
    0.17   0.76   2.62   1.08   0.95   0.91   0.28   5.02   0.57   0.26
    0.21   1.17   0.00   0.28   0.12   0.57   0.23   0.00   0.97   0.24
//
H MAXF760105
D Normalized frequency of zeta L (Maxfield-Scheraga, 1976)
R 2004036b
A Maxfield, F.R. and Scheraga, H.A.
T Status of empirical methods for the prediction of protein backbone topography
J Biochemistry 15, 5138-5153 (1976)
* Recalculated by Kidera using a different set of proteins
* Reported values normalized by the total number
C TANS770109    0.878   MAXF760104   0.850   ISOY800108   0.810
  RICJ880115    0.802
I   A/L    R/K    N/M    D/F    C/P    Q/S    E/T    G/W    H/Y    I/V
    1.13   0.48   1.11   1.18   0.38   0.41   1.02   3.84   0.30   0.40
    0.65   1.13   0.00   0.45   0.00   0.81   0.71   0.93   0.38   0.48
//
H MAXF760106
D Normalized frequency of alpha region (Maxfield-Scheraga, 1976)
R 2004036b
A Maxfield, F.R. and Scheraga, H.A.
T Status of empirical methods for the prediction of protein backbone topography
J Biochemistry 15, 5138-5153 (1976)
* Recalculated by Kidera using a different set of proteins
* Reported values normalized by the total number
C ISOY800106    0.849
I   A/L    R/K    N/M    D/F    C/P    Q/S    E/T    G/W    H/Y    I/V
    1.00   1.18   0.87   1.39   1.09   1.13   1.04   0.46   0.71   0.68

```
     1.01   1.05   0.36   0.65   1.95   1.56   1.23   1.10   0.87   0.58
//
H MCMT640101
D Refractivity (McMeekin et al., 1964), Cited by Jones (1975)
R
A McMeekin, T.L., Groves, M.L., and Hipp, N.J.
T
J In "Amino Acids and Serum Proteins" (Stekol, J.A., ed.), American
  Chemical Society, Washington, D.C., p. 54 (1964)
C CHAM820101    0.871   ROSG850101    0.857   FAUJ880103    0.847
  FASG760101    0.845   CHOC750101    0.822   GRAR740103    0.817
  GOLD730102    0.814   BIGC670101    0.814   KRIW790103    0.810
  CHOC760101    0.809   RADA880103   -0.833   OOBM770104   -0.835
I    A/L     R/K     N/M     D/F     C/P     Q/S     E/T     G/W     H/Y     I/V
     4.34   26.66   13.28   12.00   35.77   17.56   17.26    0.00   21.81   19.06
    18.78   21.29   21.64   29.40   10.93    6.35   11.01   42.53   31.53   13.92
//
H MEEJ800101
D Retention coefficient in HPLC, pH7.4 (Meek, 1980)
R 0604247
A Meek, J.L.
T Prediction of peptide retention times in high-pressure liquid
  chromatography on the basis of amino acid composition
J Proc. Natl. Acad. Sci. USA 77, 1632-1636 (1980)
C MEEJ800102    0.886   ZIMJ680105    0.842   BROC820102    0.840
  GOLD730101    0.808   PARJ860101   -0.806   WOLS870101   -0.823
I    A/L     R/K     N/M     D/F     C/P     Q/S     E/T     G/W     H/Y     I/V
     0.5     0.8     0.8    -8.2    -6.8    -4.8   -16.9     0.0    -3.5    13.9
     8.8     0.1     4.8    13.2     6.1     1.2     2.7    14.9     6.1     2.7
//
H MEEJ800102
D Retention coefficient in HPLC, pH2.1 (Meek, 1980)
R 0604247
A Meek, J.L.
T Prediction of peptide retention times in high-pressure liquid
  chromatography on the basis of amino acid composition
J Proc. Natl. Acad. Sci. USA 77, 1632-1636 (1980)
C ZIMJ680105    0.921   RADA880102    0.900   NOZY710101    0.895
  EISD860101    0.890   MEEJ800101    0.886   MEEJ810101    0.881
  BROC820101    0.877   MEEJ810101    0.871   PLIV810101    0.867
  GOLD730101    0.866   SIMZ760101    0.861   FAUJ830101    0.858
  BROC820102    0.857   CIDH920102    0.856   JOND750101    0.855
  ARGP820101    0.855   CIDH920105    0.840   ROBB790101    0.807
  WEBA780101   -0.808   HOPT810101   -0.826   LEVM760101   -0.855
  BULH740101   -0.875   PARJ860101   -0.902   WOLS870101   -0.925
I    A/L     R/K     N/M     D/F     C/P     Q/S     E/T     G/W     H/Y     I/V
    -0.1    -4.5    -1.6    -2.8    -2.2    -2.5    -7.5    -0.5     0.8    11.8
    10.0    -3.2     7.1    13.9     8.0    -3.7     1.5    18.1     8.2     3.3
//
H MEEJ810101
D Retention coefficient in NaClO4 (Meek-Rossetti, 1981)
R 0708201
A Meek, J.L. and Rossetti, Z.L.
T Factors affecting retention and resolution of peptides in
  high-performance liquid chromatography
J J. Chromatogr. 211, 15-28 (1981)
C MEEJ810102    0.987   PLIV810101    0.914   FAUJ830101    0.902
  CIDH920105    0.892   JOND750101    0.891   ARGP820101    0.891
  CIDH920102    0.887   NOZY710101    0.882   CIDH920104    0.878
  MEEJ800102    0.871   MIYS850101    0.863   ROBB790101    0.861
  BIOV880101    0.855   NISK860101    0.848   CIDH920103    0.837
  SIMZ760101    0.836   LEVM760106    0.827   WERD780101    0.825
  GOLD730101    0.824   BIOV880102    0.822   VENT840101    0.813
  SWER830101    0.806   EISD860101    0.805   RADA880108    0.804
  MEIH800101   -0.809   KARP850101   -0.818   WEBA780101   -0.831
  GRAR740102   -0.839   OOBM770103   -0.861   BULH740101   -0.876
  WOLS870101   -0.906   PARJ860101   -0.920
I    A/L     R/K     N/M     D/F     C/P     Q/S     E/T     G/W     H/Y     I/V
```

```
         1.1     0.4    -4.2   -1.6    7.1   -2.9    0.7   -0.2   -0.7    8.5
        11.0    -1.9    5.4   13.4    4.4   -3.2   -1.7   17.1    7.4    5.9
//
H MEEJ810102
D Retention coefficient in NaH2PO4 (Meek-Rossetti, 1981)
R 0708201
A Meek, J.L. and Rossetti, Z.L.
T Factors affecting retention and resolution of peptides in
  high-performance liquid chromatography
J J. Chromatogr. 211, 15-28 (1981)
C MEEJ810101     0.987    NOZY710101    0.899    PLIV810101    0.898
  FAUJ830101     0.890    MEEJ800102    0.881    ARGP820101    0.853
  JOND750101     0.852    MIYS850101    0.844    CIDH920105    0.844
  CIDH920102     0.843    CIDH920104    0.837    VENT840101    0.831
  BIOV880101     0.824    ROBB790101    0.821    BROC820101    0.820
  RADA880102     0.813    NISK860101    0.810    SIMZ760101    0.808
  EISD860101     0.808    GOLD730101    0.806    GRAR740102   -0.811
  OOBM770103    -0.831    WEBA780101   -0.854    BULH740101   -0.880
  PARJ860101    -0.897    WOLS870101   -0.905
I A/L     R/K     N/M     D/F     C/P     Q/S     E/T     G/W     H/Y     I/V
  1.0    -2.0    -3.0    -0.5    4.6    -2.0    1.1     0.2    -2.2    7.0
  9.6    -3.0    4.0    12.6    3.1    -2.9   -0.6    15.1     6.7    4.6
//
H MEIH800101
D Average reduced distance for C-alpha (Meirovitch et al., 1980)
R 0702089
A Meirovitch, H., Rackovsky, S., and Scheraga, H.A.
T Empirical studies of hydrophobicity. 1. Effect of protein size on the
  hydrophobic behavior of amino acids
J Macromolecules 13, 1398-1405 (1980)
* Database taken from group C
C RACS770101     0.973    RACS770102    0.963    MEIH800102    0.952
  PARJ860101     0.905    OOBM770103    0.897    GUYH850101    0.893
  KARP850102     0.884    KRIW790101    0.869    WOLS870101    0.852
  RACS770103     0.837    KRIW790102    0.835    KARP850101    0.832
  GRAR740102     0.824    RICJ880111   -0.802    DESM900101   -0.804
  LIFS790101    -0.809    MEEJ810101   -0.809    EISD860103   -0.810
  RADA880102    -0.816    PONP800108   -0.825    PTIO830102   -0.828
  SWER830101    -0.830    BEGF750102   -0.832    NISK800101   -0.852
  PONP800103    -0.856    CIDH920101   -0.863    FAUJ830101   -0.863
  CIDH920102    -0.867    ROBB790101   -0.868    PONP800102   -0.870
  MEIH800103    -0.875    PONP800101   -0.888    PLIV810101   -0.896
  MANP780101    -0.897    CIDH920103   -0.905    PONP800107   -0.909
  CIDH920104    -0.917    CIDH920105   -0.923    ROSG850102   -0.930
  BIOV880102    -0.937    RADA880108   -0.940    WERD780101   -0.943
  BIOV880101    -0.949    MIYS850101   -0.957    NISK860101   -0.960
I A/L     R/K     N/M     D/F     C/P     Q/S     E/T     G/W     H/Y     I/V
  0.93   0.98    0.98    1.01    0.88   1.02    1.02    1.01    0.89    0.79
  0.85   1.05    0.84    0.78    1.00   1.02    0.99    0.83    0.93    0.81
//
H MEIH800102
D Average reduced distance for side chain (Meirovitch et al., 1980)
R 0702089
A Meirovitch, H., Rackovsky, S., and Scheraga, H.A.
T Empirical studies of hydrophobicity. 1. Effect of protein size on the
  hydrophobic behavior of amino acids
J Macromolecules 13, 1398-1405 (1980)
* Database taken from group C
* (Gly 0.067)
C RACS770102     0.987    MEIH800101    0.952    GUYH850101    0.934
  RACS770101     0.905    RACS770103    0.903    KRIW790102    0.898
  OOBM770101     0.881    KRIW790101    0.876    JANJ780103    0.873
  ROSM880102     0.859    OOBM770103    0.859    JANJ780101    0.843
  CHOC760102     0.839    KARP850102    0.837    GRAR740102    0.836
  PARJ860101     0.831    WOLS870101    0.813    NAKH900110   -0.802
  JANJ790101    -0.821    DESM900101   -0.822    CIDH920103   -0.825
  CIDH920105    -0.826    WARP780101   -0.826    EISD840101   -0.829
  PONP800108    -0.836    NISK800101   -0.844    PLIV810101   -0.849
```

```
         PONP800107     -0.858   MANP780101    -0.865   CIDH920104    -0.868
         KYTJ820101     -0.871   FAUJ830101    -0.875   PONP800101    -0.877
         EISD860103     -0.882   PONP800102    -0.883   PONP800103    -0.891
         CHOC760103     -0.894   JANJ790102    -0.894   DESM900102    -0.898
         WERD780101     -0.903   JANJ780102    -0.907   NISK860101    -0.920
         MIYS850101     -0.934   MEIH800103    -0.941   BIOV880102    -0.951
         RADA880108     -0.953   BIOV880101    -0.956   ROSG850102    -0.959
    I     A/L      R/K      N/M      D/F      C/P      Q/S      E/T      G/W      H/Y      I/V
         0.94     1.09     1.04     1.08     0.84     1.11     1.12     1.01     0.92     0.76
         0.82     1.23     0.83     0.73     1.04     1.04     1.02     0.87     1.03     0.81
    //
    H MEIH800103
    D Average side chain orientation angle (Meirovitch et al., 1980)
    R 0702089
    A Meirovitch, H., Rackovsky, S., and Scheraga, H.A.
    T Empirical studies of hydrophobicity. 1. Effect of protein size on the
      hydrophobic behavior of amino acids
    J Macromolecules 13, 1398-1405 (1980)
    * Database taken from group C
    * (Gly 7.4)
    C ROSG850102      0.948   BIOV880101     0.934   DESM900102     0.924
      RADA880108      0.916   BIOV880102     0.916   NISK860101     0.909
      MIYS850101      0.908   JANJ780102     0.897   WERD780101     0.895
      PONP800103      0.895   PONP800102     0.885   NISK800101     0.871
      EISD860103      0.870   PONP800101     0.869   CHOC760103     0.865
      PONP800108      0.862   KYTJ820101     0.856   JANJ790102     0.853
      DESM900101      0.853   CIDH920104     0.853   FAUJ830101     0.849
      MANP780101      0.839   JANJ790101     0.838   WARP780101     0.835
      PLIV810101      0.811   CIDH920105     0.804   CIDH920103     0.802
      ROBB790101      0.801   CHOC760102    -0.802   WOEC730101    -0.802
      PARJ860101     -0.808   JANJ780101    -0.811   ROSM880102    -0.829
      RACS770101     -0.845   KRIW790101    -0.850   GRAR740102    -0.866
      JANJ780103     -0.866   OOBM770103    -0.866   MEIH800101    -0.875
      GUYH850101     -0.880   KRIW790102    -0.885   OOBM770101    -0.896
      RACS770102     -0.918   RACS770103    -0.919   MEIH800102    -0.941
    I    A/L      R/K      N/M      D/F      C/P      Q/S      E/T      G/W      H/Y      I/V
         87.      81.      70.      71.      104.     66.      72.      90.      90.      105.
         104.     65.      100.     108.     78.      83.      83.      94.      83.      94.
    //
    H MIYS850101
    D Effective partition energy (Miyazawa-Jernigan, 1985)
    R 2004114b
    A Miyazawa, S. and Jernigan, R.L.
    T Estimation of effective interresidue contact energies from protein
      crystal structures: Quasi-chemical approximation
    J Macromolecules 18, 534-552 (1985)
    C NISK860101      0.960   BIOV880101     0.960   RADA880108     0.950
      PLIV810101      0.944   ROSG850102     0.937   WERD780101     0.934
      BIOV880102      0.930   CIDH920105     0.916   CIDH920104     0.915
      FAUJ830101      0.914   MANP780101     0.909   MEIH800103     0.908
      CIDH920103      0.906   PONP800103     0.898   ROBB790101     0.895
      PONP800101      0.892   PONP800102     0.891   SWER830101     0.889
      PONP800107      0.884   CIDH920102     0.873   NISK800101     0.864
      MEEJ810101      0.863   EISD860103     0.858   PONP800108     0.847
      MEEJ810102      0.844   CIDH920101     0.843   EISD860101     0.842
      DESM900102      0.831   RADA880108     0.824   ARGP820103     0.822
      KYTJ820101      0.821   PONP800106     0.812   NOZY710101     0.810
      CHOC760103      0.810   PTIO830102     0.807   JANJ780102     0.806
      BEGF750102      0.806   NAKH900110     0.804   HOPT810101    -0.800
      KARP850101     -0.811   RACS770103    -0.818   ROSM880102    -0.825
      BULH740101     -0.838   KRIW790102    -0.869   KARP850102    -0.878
      GRAR740102     -0.895   WOLS870101    -0.899   GUYH850101    -0.909
      KRIW790101     -0.910   OOBM770103    -0.910   PARJ860101    -0.929
      MEIH800102     -0.934   RACS770101    -0.940   RACS770102    -0.943
      MEIH800101     -0.957
    I    A/L      R/K      N/M      D/F      C/P      Q/S      E/T      G/W      H/Y      I/V
         2.36     1.92     1.70     1.67     3.36     1.75     1.74     2.06     2.41     2.17
         3.93     1.23     4.22     4.37     1.89     1.81     2.04     3.82     2.91     3.49
```

```
//
H NAGK730101
D Normalized frequency of alpha-helix (Nagano, 1973)
R
A Nagano, K.
T Local analysis of the mechanism of protein folding. I. Prediction of
  helices, loops, and beta-structures from primary structure
J J. Mol. Biol. 75, 401-420 (1973)
C PALJ810101    0.953   TANS770101   0.925   CRAJ730101   0.925
  LEVM780104    0.918   GEIM800101   0.912   ROBB760101   0.910
  PRAM900102    0.894   LEVM780101   0.894   CHOP780201   0.886
  KANM800101    0.883   BURA740101   0.883   MAXF760101   0.877
  PALJ810102    0.876   ISOY800101   0.862   GEIM800104   0.828
  RACS820108    0.820   NAGK730103  -0.870
I    A/L    R/K    N/M    D/F    C/P    Q/S    E/T    G/W    H/Y    I/V
     1.29   0.83   0.77   1.00   0.94   1.10   1.54   0.72   1.29   0.94
     1.23   1.23   1.23   1.23   0.70   0.78   0.87   1.06   0.63   0.97
//
H NAGK730102
D Normalized frequency of bata-structure (Nagano, 1973)
R
A Nagano, K.
T Local analysis of the mechanism of protein folding. I. Prediction of
  helices, loops, and beta-structures from primary structure
J J. Mol. Biol. 75, 401-420 (1973)
C ROBB760106    0.887   KANM800102   0.878   PALJ810104   0.867
  CHOP780208    0.860   CHOP780202   0.858   BEGF750102   0.833
  GEIM800107    0.830   ROBB760105   0.815   CRAJ730102   0.815
  PTIO830102    0.811
I    A/L    R/K    N/M    D/F    C/P    Q/S    E/T    G/W    H/Y    I/V
     0.96   0.67   0.72   0.90   1.13   1.18   0.33   0.90   0.87   1.54
     1.26   0.81   1.29   1.37   0.75   0.77   1.23   1.13   1.07   1.41
//
H NAGK730103
D Normalized frequency of coil (Nagano, 1973)
R
A Nagano, K.
T Local analysis of the mechanism of protein folding. I. Prediction of
  helices, loops, and beta-structures from primary structure
J J. Mol. Biol. 75, 401-420 (1973)
C CHAM830101    0.857   CHOP780101   0.827   CHOP780216   0.819
  CHOP780210    0.814   ROBB760113   0.811   PALJ810105   0.804
  TANS770101   -0.800   MAXF760101  -0.801   PALJ810101  -0.808
  LEVM780101   -0.809   PRAM900102  -0.809   PALJ810102  -0.818
  ISOY800101   -0.821   BURA740101  -0.830   CHOP780201  -0.837
  KANM800103   -0.847   CRAJ730101  -0.850   ROBB760101  -0.861
  NAGK730101   -0.870
I    A/L    R/K    N/M    D/F    C/P    Q/S    E/T    G/W    H/Y    I/V
     0.72   1.33   1.38   1.04   1.01   0.81   0.75   1.35   0.76   0.80
     0.63   0.84   0.62   0.58   1.43   1.34   1.03   0.87   1.35   0.83
//
H NAKH900101
D AA composition of total proteins (Nakashima et al., 1990)
R 2004138b
A Nakashima, H., Nishikawa, K., and Ooi, T.
T Distinct character in hydrophobicity of amino acid composition of
  mitochondrial proteins
J PROTEINS 8, 173-178 (1990)
C JOND920101    0.993   JUKT750101   0.941   DAYM780101   0.940
  JUNJ780101    0.918   NAKH920101   0.907   NAKH920106   0.900
  NAKH900109    0.866   NAKH920107   0.863   NAKH900102   0.858
  NAKH920104    0.857   NAKH920103   0.854
I    A/L    R/K    N/M    D/F    C/P    Q/S    E/T    G/W    H/Y    I/V
     7.99   5.86   4.33   5.14   1.81   3.98   6.10   6.91   2.17   5.48
     9.16   6.01   2.50   3.83   4.95   6.84   5.77   1.34   3.15   6.65
//
H NAKH900102
D SD of AA composition of total proteins (Nakashima et al., 1990)
```

R 2004138b
A Nakashima, H., Nishikawa, K., and Ooi, T.
T Distinct character in hydrophobicity of amino acid composition of
  mitochondrial proteins
J PROTEINS 8, 173-178 (1990)
C DAYM780101    0.883   NAKH920106   0.872   NAKH900101   0.858
  NAKH920101    0.854   JUNJ780101   0.853   JOND920101   0.846
  RACS820105   -0.839
I   A/L    R/K    N/M    D/F    C/P    Q/S    E/T    G/W    H/Y    I/V
    3.73   3.34   2.33   2.23   2.30   2.36   3.     3.36   1.55   2.52
    3.40   3.36   1.37   1.94   3.18   2.83   2.63   1.15   1.76   2.53
//
H NAKH900103
D AA composition of mt-proteins (Nakashima et al., 1990)
R 2004138b
A Nakashima, H., Nishikawa, K., and Ooi, T.
T Distinct character in hydrophobicity of amino acid composition of
  mitochondrial proteins
J PROTEINS 8, 173-178 (1990)
C NAKH900105    0.992   NAKH900112   0.966   NAKH900107   0.927
  NAKH900111    0.832   NAKH920105   0.829   NAKH920108   0.826
I   A/L    R/K    N/M    D/F    C/P    Q/S    E/T    G/W    H/Y    I/V
    5.74   1.92   5.25   2.11   1.03   2.30   2.63   5.66   2.30   9.12
   15.36   3.20   5.30   6.51   4.79   7.55   7.51   2.51   4.08   5.12
//
H NAKH900104
D Normalized composition of mt-proteins (Nakashima et al., 1990)
R 2004138b
A Nakashima, H., Nishikawa, K., and Ooi, T.
T Distinct character in hydrophobicity of amino acid composition of
  mitochondrial proteins
J PROTEINS 8, 173-178 (1990)
C NAKH900106    0.986   NAKH900108   0.849   EISD860101   0.812
I   A/L    R/K    N/M    D/F    C/P    Q/S    E/T    G/W    H/Y    I/V
   -0.60  -1.18   0.39  -1.36  -0.34  -0.71  -1.16  -0.37   0.08   1.44
    1.82  -0.84   2.04   1.38  -0.05   0.25  -0.66   1.02   0.53  -0.60
//
H NAKH900105
D AA composition of mt-proteins from animal (Nakashima et al., 1990)
R 2004138b
A Nakashima, H., Nishikawa, K., and Ooi, T.
T Distinct character in hydrophobicity of amino acid composition of
  mitochondrial proteins
J PROTEINS 8, 173-178 (1990)
C NAKH900103    0.992   NAKH900112   0.974   NAKH900107   0.870
  NAKH900111    0.815   NAKH920105   0.806   NAKH920108   0.801
I   A/L    R/K    N/M    D/F    C/P    Q/S    E/T    G/W    H/Y    I/V
    5.88   1.54   4.38   1.70   1.11   2.30   2.60   5.29   2.33   8.78
   16.52   2.58   6.00   6.58   5.29   7.68   8.38   2.89   3.51   4.66
//
H NAKH900106
D Normalized composition from animal (Nakashima et al., 1990)
R 2004138b
A Nakashima, H., Nishikawa, K., and Ooi, T.
T Distinct character in hydrophobicity of amino acid composition of
  mitochondrial proteins
J PROTEINS 8, 173-178 (1990)
C NAKH900104    0.986   EISD860101   0.812   ARGP820103   0.810
I   A/L    R/K    N/M    D/F    C/P    Q/S    E/T    G/W    H/Y    I/V
   -0.57  -1.29   0.02  -1.54  -0.30  -0.71  -1.17  -0.48   0.10   1.31
    2.16  -1.02   2.55   1.42   0.11   0.30   0.99   1.35   0.20  -0.79
//
H NAKH900107
D AA composition of mt-proteins from fungi and plant (Nakashima et al.,
  1990)
R 2004138b
A Nakashima, H., Nishikawa, K., and Ooi, T.
T Distinct character in hydrophobicity of amino acid composition of

```
    mitochondrial proteins
J PROTEINS 8, 173-178 (1990)
C NAKH900103      0.927   NAKH900105     0.870   NAKH900112     0.850
  NAKH920108      0.816   NAKH920105     0.814
I   A/L     R/K     N/M     D/F     C/P     Q/S     E/T     G/W     H/Y     I/V
    5.39    2.81    7.31    3.07    0.86    2.31    2.70    6.52    2.23    9.94
   12.64    4.67    3.68    6.34    3.62    7.24    5.44    1.64    5.42    6.18
//
H NAKH900108
D Normalized composition from fungi and plant (Nakashima et al., 1990)
R 2004138b
A Nakashima, H., Nishikawa, K., and Ooi, T.
T Distinct character in hydrophobicity of amino acid composition of
  mitochondrial proteins
J PROTEINS 8, 173-178 (1990)
C NAKH900104      0.849
I   A/L     R/K     N/M     D/F     C/P     Q/S     E/T     G/W     H/Y     I/V
   -0.70   -0.91    1.28   -0.93   -0.41   -0.71   -1.13   -0.12    0.04    1.77
    1.02   -0.40    0.86    1.29   -0.42    0.14   -0.13    0.26    1.29   -0.19
//
H NAKH900109
D AA composition of membrane proteins (Nakashima et al., 1990)
R 2004138b
A Nakashima, H., Nishikawa, K., and Ooi, T.
T Distinct character in hydrophobicity of amino acid composition of
  mitochondrial proteins
J PROTEINS 8, 173-178 (1990)
C NAKH900111      0.890   JOND920101     0.878   NAKH900101     0.866
  NAKH920105      0.823   JUKT750101     0.815   NAKH920108     0.811
I   A/L     R/K     N/M     D/F     C/P     Q/S     E/T     G/W     H/Y     I/V
    9.25    3.96    3.71    3.89    1.07    3.17    4.80    8.51    1.88    6.47
   10.94    3.50    3.14    6.36    4.36    6.26    5.66    2.22    3.28    7.55
//
H NAKH900110
D Normalized composition of membrane proteins (Nakashima et al., 1990)
R 2004138b
A Nakashima, H., Nishikawa, K., and Ooi, T.
T Distinct character in hydrophobicity of amino acid composition of
  mitochondrial proteins
J PROTEINS 8, 173-178 (1990)
C EISD840101      0.838   BROC820101     0.830   BIOV880102     0.829
  EISD860101      0.820   MIYS850101     0.804   MEIH800102    -0.802
  PARJ860101     -0.808   HOPT810101    -0.812   ROSM880101    -0.812
  WOLS870101     -0.832   VHEG790101    -0.848
I   A/L     R/K     N/M     D/F     C/P     Q/S     E/T     G/W     H/Y     I/V
    0.34   -0.57   -0.27   -0.56   -0.32   -0.34   -0.43    0.48   -0.19    0.39
    0.52   -0.75    0.47    1.30   -0.19   -0.20   -0.04    0.77    0.07    0.36
//
H NAKH900111
D Transmembrane regions of non-mt-proteins (Nakashima et al., 1990)
R 2004138b
A Nakashima, H., Nishikawa, K., and Ooi, T.
T Distinct character in hydrophobicity of amino acid composition of
  mitochondrial proteins
J PROTEINS 8, 173-178 (1990)
C NAKH920108      0.975   NAKH920105     0.958   NAKH900109     0.890
  NAKH900112      0.878   NAKH900103     0.832   KYTJ820101     0.817
  NAKH900105      0.815
I   A/L     R/K     N/M     D/F     C/P     Q/S     E/T     G/W     H/Y     I/V
   10.17    1.21    1.36    1.18    1.48    1.57    1.15    8.87    1.07   10.91
   16.22    1.04    4.12    9.60    2.24    5.38    5.61    2.67    2.68   11.44
//
H NAKH900112
D Transmembrane regions of mt-proteins (Nakashima et al., 1990)
R 2004138b
A Nakashima, H., Nishikawa, K., and Ooi, T.
T Distinct character in hydrophobicity of amino acid composition of
  mitochondrial proteins
```

```
J PROTEINS 8, 173-178 (1990)
C NAKH900105    0.974  NAKH900103    0.966  NAKH920105    0.881
  NAKH920108    0.879  NAKH900111    0.878  NAKH900107    0.850
I   A/L    R/K    N/M    D/F    C/P    Q/S    E/T    G/W    H/Y    I/V
    6.61   0.41   1.84   0.59   0.83   1.20   1.63   4.88   1.14  12.91
   21.66   1.15   7.17   7.76   3.51   6.84   8.89   2.11   2.57   6.30
//
H NAKH900113
D Ratio of average and computed composition (Nakashima et al., 1990)
R 2004138b
A Nakashima, H., Nishikawa, K., and Ooi, T.
T Distinct character in hydrophobicity of amino acid composition of
  mitochondrial proteins
J PROTEINS 8, 173-178 (1990)
C
I   A/L    R/K    N/M    D/F    C/P    Q/S    E/T    G/W    H/Y    I/V
    1.61   0.40   0.73   0.75   0.37   0.61   1.50   3.12   0.46   1.61
    1.37   0.62   1.59   1.24   0.67   0.68   0.92   1.63   0.67   1.30
//
H NAKH920101
D AA composition of CYT of single-spanning proteins (Nakashima-Nishikawa,
  1992)
R 1811095b
A Nakashima, H. and Nishikawa, K.
T The amino acid composition is different between the cytoplasmic and
  extracellular sides in membrane proteins
J FEBS Lett. 303, 141-146 (1992)
C NAKH920106    0.929  NAKH920102    0.929  NAKH900101    0.907
  JOND920101    0.900  DAYM780101    0.882  NAKH900102    0.854
  JUKT750101    0.849  JUNJ780101    0.826  NAKH920104    0.822
  NAKH920103    0.811
I   A/L    R/K    N/M    D/F    C/P    Q/S    E/T    G/W    H/Y    I/V
    8.63   6.75   4.18   6.24   1.03   4.76   7.82   6.80   2.70   3.48
    8.44   6.25   2.14   2.73   6.28   8.53   4.43   0.80   2.54   5.44
//
H NAKH920102
D AA composition of CYT2 of single-spanning proteins (Nakashima-Nishikawa,
  1992)
R 1811095b
A Nakashima, H. and Nishikawa, K.
T The amino acid composition is different between the cytoplasmic and
  extracellular sides in membrane proteins
J FEBS Lett. 303, 141-146 (1992)
C NAKH920101    0.929  NAKH920106    0.832  DAYM780101    0.802
I   A/L    R/K    N/M    D/F    C/P    Q/S    E/T    G/W    H/Y    I/V
   10.88   6.01   5.75   6.13   0.69   4.68   9.34   7.72   2.15   1.80
    8.03   6.11   3.79   2.93   7.21   7.25   3.51   0.47   1.01   4.57
//
H NAKH920103
D AA composition of EXT of single-spanning proteins (Nakashima-Nishikawa,
  1992)
R 1811095b
A Nakashima, H. and Nishikawa, K.
T The amino acid composition is different between the cytoplasmic and
  extracellular sides in membrane proteins
J FEBS Lett. 303, 141-146 (1992)
C NAKH920104    0.904  NAKH920107    0.882  JOND920101    0.881
  NAKH900101    0.854  DAYM780101    0.851  JUKT750101    0.837
  JUNJ780101    0.820  NAKH920101    0.811  NAKH920106    0.809
I   A/L    R/K    N/M    D/F    C/P    Q/S    E/T    G/W    H/Y    I/V
    5.15   4.38   4.81   5.75   3.24   4.45   7.05   6.38   2.69   4.40
    8.11   5.25   1.60   3.52   5.65   8.04   7.41   1.68   3.42   7.00
//
H NAKH920104
D AA composition of EXT2 of single-spanning proteins (Nakashima-Nishikawa,
  1992)
R 1811095b
A Nakashima, H. and Nishikawa, K.
```

T The amino acid composition is different between the cytoplasmic and
  extracellular sides in membrane proteins
J FEBS Lett. 303, 141-146 (1992)
C NAKH920103    0.904   NAKH920107    0.889   JOND920101    0.887
  NAKH900101    0.857   NAKH920106    0.829   JUKT750101    0.827
  NAKH920101    0.822   DAYM780101    0.819   JUNJ780101    0.807
I   A/L    R/K    N/M    D/F    C/P    Q/S    E/T    G/W    H/Y    I/V
   5.04   3.73   5.94   5.26   2.20   4.50   6.07   7.09   2.99   4.32
   9.88   6.31   1.85   3.72   6.22   8.05   5.20   2.10   3.32   6.19
//
H NAKH920105
D AA composition of MEM of single-spanning proteins (Nakashima-Nishikawa, 1992)
R 1811095b
A Nakashima, H. and Nishikawa, K.
T The amino acid composition is different between the cytoplasmic and
  extracellular sides in membrane proteins
J FEBS Lett. 303, 141-146 (1992)
C NAKH920108    0.959   NAKH900111    0.958   NAKH900112    0.881
  NAKH900103    0.829   NAKH900109    0.823   NAKH900107    0.814
  NAKH900105    0.806   KYTJ820101    0.803
I   A/L    R/K    N/M    D/F    C/P    Q/S    E/T    G/W    H/Y    I/V
   9.90   0.09   0.94   0.35   2.55   0.87   0.08   8.14   0.20  15.25
  22.28   0.16   1.85   6.47   2.38   4.17   4.33   2.21   3.42  14.34
//
H NAKH920106
D AA composition of CYT of multi-spanning proteins (Nakashima-Nishikawa, 1992)
R 1811095b
A Nakashima, H. and Nishikawa, K.
T The amino acid composition is different between the cytoplasmic and
  extracellular sides in membrane proteins
J FEBS Lett. 303, 141-146 (1992)
C NAKH920101    0.929   NAKH900101    0.900   JOND920101    0.889
  NAKH900102    0.872   DAYM780101    0.856   NAKH920102    0.832
  JUKT750101    0.831   NAKH920104    0.829   JUNJ780101    0.829
  NAKH920103    0.809
I   A/L    R/K    N/M    D/F    C/P    Q/S    E/T    G/W    H/Y    I/V
   6.69   6.65   4.49   4.97   1.70   5.39   7.76   6.32   2.11   4.51
   8.23   8.36   2.46   3.59   5.20   7.40   5.18   1.06   2.75   5.27
//
H NAKH920107
D AA composition of EXT of multi-spanning proteins (Nakashima-Nishikawa, 1992)
R 1811095b
A Nakashima, H. and Nishikawa, K.
T The amino acid composition is different between the cytoplasmic and
  extracellular sides in membrane proteins
J FEBS Lett. 303, 141-146 (1992)
C JOND920101    0.893   NAKH920104    0.889   NAKH920103    0.882
  NAKH900101    0.863   JUKT750101    0.862   DAYM780101    0.861
  JUNJ780101    0.856
I   A/L    R/K    N/M    D/F    C/P    Q/S    E/T    G/W    H/Y    I/V
   5.08   4.75   5.75   5.96   2.95   4.24   6.04   8.20   2.10   4.95
   8.03   4.93   2.61   4.36   4.84   6.41   5.87   2.31   4.55   6.07
//
H NAKH920108
D AA composition of MEM of multi-spanning proteins (Nakashima-Nishikawa, 1992)
R 1811095b
A Nakashima, H. and Nishikawa, K.
T The amino acid composition is different between the cytoplasmic and
  extracellular sides in membrane proteins
J FEBS Lett. 303, 141-146 (1992)
C NAKH900111    0.975   NAKH920105    0.959   NAKH900112    0.879
  KYTJ820101    0.868   NAKH900103    0.826   CHOC760103    0.824
  NAKH900107    0.816   NAKH900109    0.811   NAKH900105    0.801
I   A/L    R/K    N/M    D/F    C/P    Q/S    E/T    G/W    H/Y    I/V

```
       9.36    0.27    2.31    0.94    2.56    1.14    0.94    6.17    0.47   13.73
      16.64    0.58    3.93   10.99    1.96    5.58    4.68    2.20    3.13   12.43
//
H NISK800101
D 8 A contact number (Nishikawa-Ooi, 1980)
R 2004068b
A Nishikawa, K. and Ooi, T.
T Prediction of the surface-interior diagram of globular proteins by an
  empirical method
J Int. J. Peptide Protein Res. 16, 19-32 (1980)
C PONP800108    0.976  PONP800102    0.965  PONP800101    0.960
  NISK860101    0.943  ROSG850102    0.942  PONP800103    0.941
  MANP780101    0.940  BIOV880101    0.920  RADA880108    0.902
  CIDH920104    0.900  WERD780101    0.891  JANJ790101    0.875
  BIOV880102    0.873  MEIH800103    0.871  MIYS850101    0.864
  CIDH920103    0.855  CIDH920105    0.854  JANJ780102    0.853
  DESM900102    0.852  FAUJ830101    0.849  DESM900101    0.837
  ROBB790101    0.830  LIFS790101    0.827  QIAN880121    0.818
  KYTJ820101    0.812  KANM800102    0.809  QIAN880122    0.808
  RACS770101   -0.805  GUYH850101   -0.811  RACS770102   -0.818
  KRIW710101   -0.831  MEIH800102   -0.844  OOBM770101   -0.845
  MEIH800101   -0.852  GRAR740102   -0.879  KARP850102   -0.885
  OOBM770103   -0.894  KRIW790101   -0.896
I    A/L      R/K      N/M      D/F      C/P      Q/S      E/T      G/W      H/Y      I/V
     0.23    -0.26    -0.94    -1.13    1.78    -0.57    -0.75    -0.07    0.11    1.19
     1.03    -1.05     0.65     0.48   -0.76    -0.67    -0.36     0.90    0.59    1.24
//
H NISK860101
D 14 A contact number (Nishikawa-Ooi, 1986)
R 1211490
A Nishikawa, K. and Ooi, T.
T Radial locations of amino acid residues in a globular protein:
  Correlation with the sequence
J J. Biochem. 100, 1043-1047 (1986)
* Values supplied by the author
C BIOV880101    0.972  WERD780101    0.966  ROSG850102    0.962
  MIYS850101    0.960  RADA880108    0.950  CIDH920104    0.944
  NISK800101    0.943  BIOV880102    0.939  CIDH920105    0.938
  PONP800101    0.930  MANP780101    0.930  PONP800102    0.924
  PONP800108    0.921  ROBB790101    0.912  PONP800103    0.910
  MEIH800103    0.909  CIDH920103    0.909  FAUJ830101    0.906
  CIDH920102    0.897  PLIV810101    0.892  CIDH920101    0.882
  SWER830101    0.865  LIFS790101    0.859  MEEJ810101    0.848
  PONP800107    0.847  DESM900102    0.843  QIAN880120    0.837
  CHOP780202    0.832  QIAN880121    0.829  PTIO830102    0.825
  KANM800102    0.819  JANJ780102    0.813  GEIM800107    0.813
  EISD860103    0.811  ROBB760106    0.810  MEEJ810102    0.810
  PALJ810104    0.809  HOPT810101   -0.822  WOEC730101   -0.822
  KARP850101   -0.828  RACS770103   -0.837  WOLS870101   -0.848
  KRIW790102   -0.855  GUYH850101   -0.877  GRAR740102   -0.900
  KARP850102   -0.901  KRIW790101   -0.907  RACS770102   -0.913
  PARJ860101   -0.916  MEIH800102   -0.920  RACS770101   -0.923
  OOBM770103   -0.949  MEIH800101   -0.960
I    A/L      R/K      N/M      D/F      C/P      Q/S      E/T      G/W      H/Y      I/V
    -0.22   -0.93    -2.65    -4.12    4.66    -2.76    -3.64    -1.62    1.28    5.58
     5.01   -4.18     3.51     5.27   -3.03    -2.84    -1.20     5.20    2.15    4.45
//
H NOZY710101
D Transfer energy, organic solvent/water (Nozaki-Tanford, 1971)
R
A Nozaki, Y. and Tanford, C.
T The solubility of amino acids and two glycine peptides in aqueous
  ethanol and dioxane solutions
J J. Biol. Chem. 246, 2211-2217 (1971)
* Missing values filled with zeros
C RADA880102    0.917  MEEJ810102    0.899  VENT840101    0.897
  MEEJ800102    0.895  CIDH920102    0.889  MEEJ810101    0.882
  CIDH920105    0.857  LEVM760107    0.845  PLIV810101    0.839
```

```
     ZIMJ680105    0.837   SWER830101    0.836   ROSG850101    0.834
     BROC820101    0.829   EISD860101    0.822   GARJ730101    0.821
     MIYS850101    0.810   SIMZ760101    0.807   FAUJ830101    0.803
     ARGP820101    0.800   OOBM770104   -0.826   OOBM770103   -0.828
     WOLS870101   -0.874   WEBA780101   -0.890   BULH740101   -0.892
     PARJ860101   -0.900
I    A/L    R/K    N/M    D/F    C/P    Q/S    E/T    G/W    H/Y    I/V
     0.5    0.0    0.0    0.0    0.0    0.0    0.0    0.0    0.5    1.8
     1.8    0.0    1.3    2.5    0.0    0.0    0.4    3.4    2.3    1.5
//
H OOBM770101
D Average non-bonded energy per atom (Oobatake-Ooi, 1977)
R 2004111b
A Oobatake, M. and Ooi, T.
T An analysis of non-bonded energy of proteins
J J. Theor. Biol. 67, 567-584 (1977)
* Last two calcualted by Kidera; multiplied by the number of heavy atoms
C JANJ780103    0.965   JANJ780101    0.953   CHOC760102    0.925
  PRAM900101    0.907   MEIH800102    0.881   RACS770103    0.871
  ROSM880102    0.867   ROSM880101    0.854   GUYH850101    0.848
  GRAR740102    0.841   RACS770102    0.838   KRIW790102    0.822
  KRIW790101    0.816   WOEC730101    0.804   MANP780101   -0.806
  FAUJ830101   -0.832   PONP800101   -0.835   NISK800101   -0.845
  WOLR810101   -0.847   PONP800108   -0.851   RADA880107   -0.854
  CHOC760104   -0.857   BIOV880101   -0.858   PONP800102   -0.862
  RADA880101   -0.863   RADA880108   -0.864   JANJ790101   -0.871
  BIOV880102   -0.877   EISD840101   -0.878   EISD860103   -0.880
  PONP800103   -0.880   DESM900101   -0.894   MEIH800103   -0.896
  KYTJ820101   -0.899   CHOC760103   -0.902   ROSG850102   -0.903
  WARP780101   -0.937   DESM900102   -0.950   JANJ790102   -0.963
  JANJ780102   -0.968
I    A/L    R/K    N/M    D/F    C/P    Q/S    E/T    G/W    H/Y    I/V
    -1.895 -1.475 -1.560 -1.518 -2.035 -1.521 -1.535 -1.898 -1.755 -1.951
    -1.966 -1.374 -1.963 -1.864 -1.699 -1.753 -1.767 -1.869 -1.686 -1.981
//
H OOBM770102
D Short and medium range non-bonded energy per atom (Oobatake-Ooi, 1977)
R 2004111b
A Oobatake, M. and Ooi, T.
T An analysis of non-bonded energy of proteins
J J. Theor. Biol. 67, 567-584 (1977)
* Last two calcualted by Kidera; multiplied by the number of heavy atoms
C LEVM760102    0.869   LEVM760105    0.868   CHAM830106    0.858
  CHOC760101    0.824   FASG760101    0.821   FAUJ880103    0.801
I    A/L    R/K    N/M    D/F    C/P    Q/S    E/T    G/W    H/Y    I/V
    -1.404 -0.921 -1.178 -1.162 -1.365 -1.116 -1.163 -1.364 -1.215 -1.189
    -1.315 -1.074 -1.303 -1.135 -1.236 -1.297 -1.252 -1.030 -1.030 -1.254
//
H OOBM770103
D Long range non-bonded energy per atom (Oobatake-Ooi, 1977)
R 2004111b
A Oobatake, M. and Ooi, T.
T An analysis of non-bonded energy of proteins
J J. Theor. Biol. 67, 567-584 (1977)
* Last two calcualted by Kidera; multiplied by the number of heavy atoms
C MEIH800101    0.897   GRAR740102    0.896   PARJ860101    0.891
  KRIW790101    0.865   MEIH800102    0.859   WOLS870101    0.852
  WOEC730101    0.835   RACS770101    0.835   HOPT810101    0.833
  RACS770102    0.828   KRIW790102    0.824   RACS770103    0.823
  KARP850102    0.820   LEVM760101    0.805   PTIO830102   -0.801
  LIFS790103   -0.807   KANM800102   -0.812   CIDH920101   -0.818
  PONP800107   -0.819   CHOP780202   -0.820   QIAN880120   -0.824
  NOZY710101   -0.828   MEEJ810102   -0.831   SWER830101   -0.833
  PONP800101   -0.848   PLIV810101   -0.852   PONP800102   -0.854
  LIFS790101   -0.855   MANP780101   -0.859   MEEJ810101   -0.861
  CIDH920103   -0.863   PONP800103   -0.865   MEIH800103   -0.866
  CIDH920102   -0.877   RADA880108   -0.878   NISK800101   -0.894
  PONP800108   -0.896   FAUJ830101   -0.899   CIDH920105   -0.904
```

```
    WERD780101   -0.906  ROBB790101  -0.909  MIYS850101  -0.910
    CIDH920104   -0.912  ROSG850102  -0.916  BIOV880101  -0.920
    BIOV880102   -0.925  NISK860101  -0.949
I   A/L     R/K     N/M     D/F     C/P     Q/S     E/T     G/W     H/Y     I/V
   -0.491  -0.554  -0.382  -0.356  -0.670  -0.405  -0.371  -0.534  -0.540  -0.762
   -0.650  -0.300  -0.659  -0.729  -0.463  -0.455  -0.515  -0.839  -0.656  -0.728
//
H OOBM770104
D Average non-bonded energy per residue (Oobatake-Ooi, 1977)
R 2004111b
A Oobatake, M. and Ooi, T.
T An analysis of non-bonded energy of proteins
J J. Theor. Biol. 67, 567-584 (1977)
* Last two calcualted by Kidera; multiplied by the number of heavy atoms
C OOBM770105    0.952  WEBA780101   0.901  RADA880103   0.873
  FAUJ880106   -0.814  GARJ730101  -0.815  NOZY710101  -0.826
  LEVM760106   -0.829  SNEP660103  -0.830  MCMT640101  -0.835
  CHOC760101   -0.886  GRAR740103  -0.900  FASG760101  -0.904
  KRIW790103   -0.904  BIGC670101  -0.905  GOLD730102  -0.905
  LEVM760107   -0.915  CHOC750101  -0.922  FAUJ880103  -0.932
  CHAM820101   -0.944  ROSG850101  -0.945
I   A/L     R/K     N/M     D/F     C/P     Q/S     E/T     G/W     H/Y     I/V
   -9.475 -16.225 -12.480 -12.144 -12.210 -13.689 -13.815  -7.592 -17.550 -15.608
  -15.728 -12.366 -15.704 -20.504 -11.893 -10.518 -12.369 -26.166 -20.232 -13.867
//
H OOBM770105
D Short and medium range non-bonded energy per residue (Oobatake-Ooi, 1977)
R 2004111b
A Oobatake, M. and Ooi, T.
T An analysis of non-bonded energy of proteins
J J. Theor. Biol. 67, 567-584 (1977)
* Last two calcualted by Kidera; multiplied by the number of heavy atoms
C OOBM770104    0.952  RADA880103   0.912  WOLS870102  -0.804
  LEVM760107   -0.825  CHAM830106  -0.835  LEVM760105  -0.844
  FAUJ880106   -0.863  ROSG850101  -0.871  LEVM760102  -0.880
  GRAR740103   -0.887  KRIW790103  -0.892  GOLD730102  -0.901
  BIGC670101   -0.902  CHOC750101  -0.927  CHOC760101  -0.927
  CHAM820101   -0.928  FAUJ880103  -0.936  FASG760101  -0.941
I   A/L     R/K     N/M     D/F     C/P     Q/S     E/T     G/W     H/Y     I/V
   -7.020 -10.131  -9.424  -9.296  -8.190 -10.044 -10.467  -5.456 -12.150  -9.512
  -10.520  -9.666 -10.424 -12.485  -8.652  -7.782  -8.764 -14.420 -12.360  -8.778
//
H OOBM850101
D Optimized beta-structure-coil equilibrium constant (Oobatake et al.,
1985)
R 1207075b
A Oobatake, M., Kubota, Y. and Ooi, T.
T Optimization of amino acid parameters for correspondence of sequence to
  tertiary structures of proteuins
J Bull. Inst. Chem. Res., Kyoto Univ. 63, 82-94 (1985)
C QIAN880119    0.825
I   A/L     R/K     N/M     D/F     C/P     Q/S     E/T     G/W     H/Y     I/V
    2.01    0.84    0.03   -2.05    1.98    1.02    0.93    0.12   -0.14    3.70
    2.73    2.55    1.75    2.68    0.41    1.47    2.39    2.49    2.23    3.50
//
H OOBM850102
D Optimized propensity to form reverse turn (Oobatake et al., 1985)
R 1207075b
A Oobatake, M., Kubota, Y. and Ooi, T.
T Optimization of amino acid parameters for correspondence of sequence to
  tertiary structures of proteuins
J Bull. Inst. Chem. Res., Kyoto Univ. 63, 82-94 (1985)
C ZASB820101   -0.853  GARJ730101  -0.877
I   A/L     R/K     N/M     D/F     C/P     Q/S     E/T     G/W     H/Y     I/V
    1.34    0.95    2.49    3.32    1.07    1.49    2.20    2.07    1.27    0.66
    0.54   -0.61    0.70    0.80    2.12    0.94    1.09   -4.65   -0.17    1.32
//
H OOBM850103
```

```
D Optimized transfer energy parameter (Oobatake et al., 1985)
R 1207075b
A Oobatake, M., Kubota, Y. and Ooi, T.
T Optimization of amino acid parameters for correspondence of sequence to
  tertiary structures of proteuins
J Bull. Inst. Chem. Res., Kyoto Univ. 63, 82-94 (1985)
C
I    A/L     R/K     N/M     D/F     C/P     Q/S     E/T     G/W     H/Y     I/V
     0.46   -1.54    1.31   -0.33    0.20   -1.12    0.48    0.64   -1.31    3.28
     0.43   -1.71    0.15    0.52   -0.58   -0.83   -1.52    1.25   -2.21    0.54
//
H OOBM850104
D Optimized average non-bonded energy per atom (Oobatake et al., 1985)
R 1207075b
A Oobatake, M., Kubota, Y. and Ooi, T.
T Optimization of amino acid parameters for correspondence of sequence to
  tertiary structures of proteuins
J Bull. Inst. Chem. Res., Kyoto Univ. 63, 82-94 (1985)
C
I    A/L     R/K     N/M     D/F     C/P     Q/S     E/T     G/W     H/Y     I/V
    -2.49    2.55    2.27    8.86   -3.13    1.79    4.04   -0.56    4.22  -10.87
    -7.16   -9.97   -4.96   -6.64    5.19   -1.60   -4.75  -17.84    9.25   -3.97
//
H OOBM850105
D Optimized side chain interaction parameter (Oobatake et al., 1985)
R 1207075b
A Oobatake, M., Kubota, Y. and Ooi, T.
T Optimization of amino acid parameters for correspondence of sequence to
  tertiary structures of proteuins
J Bull. Inst. Chem. Res., Kyoto Univ. 63, 82-94 (1985)
C QIAN880127   -0.813
I    A/L     R/K     N/M     D/F     C/P     Q/S     E/T     G/W     H/Y     I/V
     4.55    5.97    5.56    2.85   -0.78    4.15    5.16    9.14    4.48    2.10
     3.24   10.68    2.18    4.37    5.14    6.78    8.60    1.97    2.40    3.81
//
H PALJ810101
D Normalized frequency of alpha-helix from LG (Palau et al., 1981)
R 0805095
A Palau, J., Argos, P. and Puigdomenech, P.
T Protein secondary structure
J Int. J. Peptide Protein Res. 19, 394-401 (1981)
* LG :a set of protein samples formed by 44 proteins.
* CF :a set of protein samples formed by 33 proteins.
C LEVM780104    0.988   NAGK730101    0.953   GEIM800101    0.951
  PRAM900102    0.943   LEVM780101    0.943   KANM800101    0.928
  TANS770101    0.918   ROBB760101    0.914   CRAJ730101    0.891
  PALJ810102    0.889   MAXF760101    0.889   ISOY800101    0.882
  CHOP780201    0.881   RACS820108    0.872   BURA740101    0.850
  GEIM800104    0.841   KANM800103    0.836   NAGK730103   -0.808
I    A/L     R/K     N/M     D/F     C/P     Q/S     E/T     G/W     H/Y     I/V
     1.30    0.93    0.90    1.02    0.92    1.04    1.43    0.63    1.33    0.87
     1.30    1.23    1.32    1.09    0.63    0.78    0.80    1.03    0.71    0.95
//
H PALJ810102
D Normalized frequency of alpha-helix from CF (Palau et al., 1981)
R 0805095
A Palau, J., Argos, P. and Puigdomenech, P.
T Protein secondary structure
J Int. J. Peptide Protein Res. 19, 394-401 (1981)
* LG :a set of protein samples formed by 44 proteins.
* CF :a set of protein samples formed by 33 proteins.
C CHOP780201    0.981   ISOY800101    0.965   KANM800101    0.962
  MAXF760101    0.959   ROBB760101    0.946   TANS770101    0.923
  KANM800103    0.916   GEIM800101    0.910   LEVM780104    0.906
  PRAM900102    0.902   LEVM780101    0.902   BURA740101    0.900
  PALJ810101    0.889   GEIM800104    0.886   RACS820108    0.881
  NAGK730101    0.876   CRAJ730101    0.872   QIAN880106    0.871
  PALJ810109    0.864   QIAN880107    0.856   BEGF750101    0.811
```

```
         CHAM830101  -0.808  CRAJ730103  -0.809  NAGK730103  -0.818
I    A/L     R/K     N/M     D/F     C/P     Q/S     E/T     G/W     H/Y     I/V
     1.32    1.04    0.74    0.97    0.70    1.25    1.48    0.59    1.06    1.01
     1.22    1.13    1.47    1.10    0.57    0.77    0.86    1.02    0.72    1.05
//
H PALJ810103
D Normalized frequency of beta-sheet from LG (Palau et al., 1981)
R 0805095
A Palau, J., Argos, P. and Puigdomenech, P.
T Protein secondary structure
J Int. J. Peptide Protein Res. 19, 394-401 (1981)
* LG :a set of protein samples formed by 44 proteins.
* CF :a set of protein samples formed by 33 proteins.
C LEVM780105    0.980  GEIM800105   0.945  CHOP780202   0.937
  KANM800102    0.932  LIFS790101   0.912  PALJ810104   0.907
  GEIM800107    0.890  ROBB760106   0.886  QIAN880120   0.886
  LIFS790103    0.877  QIAN880121   0.875  ROBB760105   0.869
  PTIO830102    0.867  QIAN880119   0.861  PRAM900103   0.846
  LEVM780102    0.846  QIAN880118   0.845  PALJ810112   0.841
  TANS770103    0.824  KANM800104   0.823  ISOY800102   0.807
I    A/L     R/K     N/M     D/F     C/P     Q/S     E/T     G/W     H/Y     I/V
     0.81    1.03    0.81    0.71    1.12    1.03    0.59    0.94    0.85    1.47
     1.03    0.77    0.96    1.13    0.75    1.02    1.19    1.24    1.35    1.44
//
H PALJ810104
D Normalized frequency of beta-sheet from CF (Palau et al., 1981)
R 0805095
A Palau, J., Argos, P. and Puigdomenech, P.
T Protein secondary structure
J Int. J. Peptide Protein Res. 19, 394-401 (1981)
* LG :a set of protein samples formed by 44 proteins.
* CF :a set of protein samples formed by 33 proteins.
C CHOP780202    0.970  KANM800102   0.948  PTIO830102   0.937
  LIFS790101    0.929  GEIM800107   0.928  LEVM780105   0.921
  QIAN880121    0.910  PALJ810103   0.907  ROBB760106   0.894
  QIAN880120    0.886  PRAM900103   0.868  LEVM780102   0.868
  NAGK730102    0.867  LIFS790103   0.860  GEIM800105   0.856
  KANM800104    0.851  PALJ810112   0.849  CHOP780209   0.849
  ROBB760105    0.835  VENT840101   0.831  QIAN880119   0.822
  CRAJ730102    0.817  SWER830101   0.809  NISK860101   0.809
  MANP780101    0.805  BEGF750102   0.801
I    A/L     R/K     N/M     D/F     C/P     Q/S     E/T     G/W     H/Y     I/V
     0.90    0.75    0.82    0.75    1.12    0.95    0.44    0.83    0.86    1.59
     1.24    0.75    0.94    1.41    0.46    0.70    1.20    1.28    1.45    1.73
//
H PALJ810105
D Normalized frequency of turn from LG (Palau et al., 1981)
R 0805095
A Palau, J., Argos, P. and Puigdomenech, P.
T Protein secondary structure
J Int. J. Peptide Protein Res. 19, 394-401 (1981)
* LG :a set of protein samples formed by 44 proteins.
* CF :a set of protein samples formed by 33 proteins.
C ISOY800103    0.928  LEVM780103   0.909  PRAM900104   0.906
  LEVM780106    0.902  PALJ810116   0.891  CHOP780216   0.881
  CHOP780203    0.878  GEIM800108   0.873  CHOP780101   0.868
  TANS770110    0.860  GEIM800111   0.855  QIAN880133   0.843
  QIAN880132    0.830  CHAM830101   0.826  PALJ810106   0.809
  NAGK730103    0.804  CHOP780210   0.803
I    A/L     R/K     N/M     D/F     C/P     Q/S     E/T     G/W     H/Y     I/V
     0.84    0.91    1.48    1.28    0.69    1.      0.78    1.76    0.53    0.55
     0.49    0.95    0.52    0.88    1.47    1.29    1.05    0.88    1.28    0.51
//
H PALJ810106
D Normalized frequency of turn from CF (Palau et al., 1981)
R 0805095
A Palau, J., Argos, P. and Puigdomenech, P.
T Protein secondary structure
```

J Int. J. Peptide Protein Res. 19, 394-401 (1981)
* LG :a set of protein samples formed by 44 proteins.
* CF :a set of protein samples formed by 33 proteins.
C CHOP780101    0.977   CHAM830101   0.939   TANS770110   0.925
  CHOP780203    0.907   CHOP780210   0.905   CHOP780216   0.904
  ROBB760113    0.895   CRAJ730103   0.884   ROBB760108   0.882
  ROBB760110    0.864   GEIM800108   0.862   QIAN880133   0.860
  QIAN880132    0.859   BEGF750103   0.859   LEVM780106   0.850
  LEVM780103    0.848   PRAM900104   0.844   GEIM800111   0.844
  QIAN880131    0.809   PALJ810105   0.809   ISOY800103   0.807
  CHOP780212    0.801   QIAN880107  -0.821   SUEM840101  -0.832
  KANM800103   -0.840   BEGF750101  -0.859
I   A/L   R/K   N/M   D/F   C/P   Q/S   E/T   G/W   H/Y   I/V
    0.65  0.93  1.45  1.47  1.43  0.94  0.75  1.53  0.96  0.57
    0.56  0.95  0.71  0.72  1.51  1.46  0.96  0.90  1.12  0.55
//
H PALJ810107
D Normalized frequency of alpha-helix in all-alpha class (Palau et al., 1981)
R 0805095
A Palau, J., Argos, P. and Puigdomenech, P.
T Protein secondary structure
J Int. J. Peptide Protein Res. 19, 394-401 (1981)
* LG :a set of protein samples formed by 44 proteins.
* CF :a set of protein samples formed by 33 proteins.
C GEIM800102    0.919   GEIM800109  -0.909
I   A/L   R/K   N/M   D/F   C/P   Q/S   E/T   G/W   H/Y   I/V
    1.08  0.93  1.05  0.86  1.22  0.95  1.09  0.85  1.02  0.98
    1.04  1.01  1.11  0.96  0.91  0.95  1.15  1.17  0.80  1.03
//
H PALJ810108
D Normalized frequency of alpha-helix in alpha+beta class (Palau et al., 1981)
R 0805095
A Palau, J., Argos, P. and Puigdomenech, P.
T Protein secondary structure
J Int. J. Peptide Protein Res. 19, 394-401 (1981)
* LG :a set of protein samples formed by 44 proteins.
* CF :a set of protein samples formed by 33 proteins.
C
I   A/L   R/K   N/M   D/F   C/P   Q/S   E/T   G/W   H/Y   I/V
    1.34  0.91  0.83  1.06  1.27  1.13  1.69  0.47  1.11  0.84
    1.39  1.08  0.90  1.02  0.48  1.05  0.74  0.64  0.73  1.18
//
H PALJ810109
D Normalized frequency of alpha-helix in alpha/beta class (Palau et al., 1981)
R 0805095
A Palau, J., Argos, P. and Puigdomenech, P.
T Protein secondary structure
J Int. J. Peptide Protein Res. 19, 394-401 (1981)
* LG :a set of protein samples formed by 44 proteins.
* CF :a set of protein samples formed by 33 proteins.
C GEIM800104    0.937   PRAM900102   0.898   LEVM780101   0.898
  MAXF760101    0.876   ISOY800101   0.874   PALJ810102   0.864
  KANM800101    0.849   LEVM780104   0.819   GEIM800101   0.816
  CHOP780201    0.814   CRAJ730101   0.811   ROBB760101   0.805
I   A/L   R/K   N/M   D/F   C/P   Q/S   E/T   G/W   H/Y   I/V
    1.15  1.06  0.87  1.    1.03  1.43  1.37  0.64  0.95  0.99
    1.22  1.20  1.45  0.92  0.72  0.84  0.97  1.11  0.72  0.82
//
H PALJ810110
D Normalized frequency of beta-sheet in all-beta class (Palau et al., 1981)
R 0805095
A Palau, J., Argos, P. and Puigdomenech, P.
T Protein secondary structure
J Int. J. Peptide Protein Res. 19, 394-401 (1981)
* LG :a set of protein samples formed by 44 proteins.

```
* CF :a set of protein samples formed by 33 proteins.
C GEIM800106     0.851  ROBB760106     0.836  KANM800102     0.836
  BEGF750102     0.834  GEIM800107     0.826  QIAN880120     0.824
  QIAN880119     0.824  LIFS790101     0.817  CHOP780202     0.808
  ROBB760105     0.804  GEIM800110    -0.840
I    A/L    R/K    N/M    D/F    C/P    Q/S    E/T    G/W    H/Y    I/V
     0.89   1.06   0.67   0.71   1.04   1.06   0.72   0.87   1.04   1.14
     1.02   1.     1.41   1.32   0.69   0.86   1.15   1.06   1.35   1.66
//
H PALJ810111
D Normalized frequency of beta-sheet in alpha+beta class (Palau et al.,
1981)
R 0805095
A Palau, J., Argos, P. and Puigdomenech, P.
T Protein secondary structure
J Int. J. Peptide Protein Res. 19, 394-401 (1981)
* LG :a set of protein samples formed by 44 proteins.
* CF :a set of protein samples formed by 33 proteins.
C
I    A/L    R/K    N/M    D/F    C/P    Q/S    E/T    G/W    H/Y    I/V
     0.82   0.99   1.27   0.98   0.71   1.01   0.54   0.94   1.26   1.67
     0.94   0.73   1.30   1.56   0.69   0.65   0.98   1.25   1.26   1.22
//
H PALJ810112
D Normalized frequency of beta-sheet in alpha/beta class (Palau et al.,
1981)
R 0805095
A Palau, J., Argos, P. and Puigdomenech, P.
T Protein secondary structure
J Int. J. Peptide Protein Res. 19, 394-401 (1981)
* LG :a set of protein samples formed by 44 proteins.
* CF :a set of protein samples formed by 33 proteins.
C PRAM900103     0.913  LEVM780102     0.913  GEIM800107     0.905
  LEVM780105     0.870  KANM800102     0.869  PALJ810104     0.849
  LIFS790101     0.845  PALJ810103     0.841  GEIM800105     0.830
  CHOP780202     0.815  KANM800104     0.813  QIAN880121     0.812
  PTIO830102     0.811
I    A/L    R/K    N/M    D/F    C/P    Q/S    E/T    G/W    H/Y    I/V
     0.98   1.03   0.66   0.74   1.01   0.63   0.59   0.90   1.17   1.38
     1.05   0.83   0.82   1.23   0.73   0.98   1.20   1.26   1.23   1.62
//
H PALJ810113
D Normalized frequency of turn in all-alpha class (Palau et al., 1981)
R 0805095
A Palau, J., Argos, P. and Puigdomenech, P.
T Protein secondary structure
J Int. J. Peptide Protein Res. 19, 394-401 (1981)
* LG :a set of protein samples formed by 44 proteins.
* CF :a set of protein samples formed by 33 proteins.
* (Arg Cys Leu Trp missing)
C
I    A/L    R/K    N/M    D/F    C/P    Q/S    E/T    G/W    H/Y    I/V
     0.69   0.     1.52   2.42   0.     1.44   0.63   2.64   0.22   0.43
     0.     1.18   0.88   2.20   1.34   1.43   0.28   0.     1.53   0.14
//
H PALJ810114
D Normalized frequency of turn in all-beta class (Palau et al., 1981)
R 0805095
A Palau, J., Argos, P. and Puigdomenech, P.
T Protein secondary structure
J Int. J. Peptide Protein Res. 19, 394-401 (1981)
* LG :a set of protein samples formed by 44 proteins.
* CF :a set of protein samples formed by 33 proteins.
* (Met missing)
C ISOY800103     0.809
I    A/L    R/K    N/M    D/F    C/P    Q/S    E/T    G/W    H/Y    I/V
     0.87   1.30   1.36   1.24   0.83   1.06   0.91   1.69   0.91   0.27
     0.67   0.66   0.     0.47   1.54   1.08   1.12   1.24   0.54   0.69
```

```
//
H PALJ810105
D Normalized frequency of turn in alpha+beta class (Palau et al., 1981)
R 0805095
A Palau, J., Argos, P. and Puigdomenech, P.
T Protein secondary structure
J Int. J. Peptide Protein Res. 19, 394-401 (1981)
* LG :a set of protein samples formed by 44 proteins.
* CF :a set of protein samples formed by 33 proteins.
C ROBB760112    0.885   QIAN880132    0.804
I    A/L    R/K    N/M    D/F    C/P    Q/S    E/T    G/W    H/Y    I/V
     0.91   0.77   1.32   0.90   0.50   1.06   0.53   1.61   1.08   0.36
     0.77   1.27   0.76   0.37   1.62   1.34   0.87   1.10   1.24   0.52
//
H PALJ810116
D Normalized frequency of turn in alpha/beta class (Palau et al., 1981)
R 0805095
A Palau, J., Argos, P. and Puigdomenech, P.
T Protein secondary structure
J Int. J. Peptide Protein Res. 19, 394-401 (1981)
* LG :a set of protein samples formed by 44 proteins.
* CF :a set of protein samples formed by 33 proteins.
C PALJ810105    0.891   ISOY800103    0.814
I    A/L    R/K    N/M    D/F    C/P    Q/S    E/T    G/W    H/Y    I/V
     0.92   0.90   1.57   1.22   0.62   0.66   0.92   1.61   0.39   0.79
     0.50   0.86   0.50   0.96   1.30   1.40   1.11   0.57   1.78   0.50
//
H PARJ860101
D HPLC parameter (Parker et al., 1986)
R 1211071
A Parker, J.M.R., Guo, D., and Hodges, R.S.
T New hydrophilicity scale derived from high-performance liquid
  chromatography peptide retention data: Correlation of predicted
  surface residues with antigencity and x-ray-derived accessible sites
J Biochemistry 25, 5425-5432 (1986)
C WOLS870101    0.964   BULH740101    0.909   MEIH800101    0.905
  OOBM770103    0.891   GRAR740102    0.891   RACS770101    0.871
  RACS770102    0.834   MEIH800102    0.831   WOEC730101    0.821
  HOPT810101    0.819   LEVM760101    0.806   ROSM880101    0.803
  ROSM880102    0.801   MEEJ800101   -0.806   MEIH800103   -0.808
  NAKH900110   -0.808   ROSG850102   -0.823   SIMZ760101   -0.825
  GOLD730101   -0.827   LEVM760106   -0.832   JOND750101   -0.834
  ARGP820101   -0.835   MANP780101   -0.841   VENT840101   -0.846
  BROC820101   -0.849   RADA880108   -0.865   PONP800107   -0.868
  WERD780101   -0.869   CIDH920101   -0.871   BIOV880102   -0.875
  EISD860101   -0.876   RADA880102   -0.883   ZIMJ680105   -0.886
  BIOV880101   -0.889   ROBB790101   -0.893   SWER830101   -0.893
  MEEJ810102   -0.897   NOZY710101   -0.900   MEEJ800102   -0.902
  FAUJ830101   -0.907   CIDH920104   -0.913   CIDH920103   -0.916
  NISK860101   -0.916   MEEJ810101   -0.920   MIYS850101   -0.929
  CIDH920102   -0.930   CIDH920105   -0.948   PLIV810101   -0.958
I    A/L    R/K    N/M    D/F    C/P    Q/S    E/T    G/W    H/Y    I/V
     2.1    4.2    7.0   10.0    1.4    6.0    7.8    5.7    2.1   -8.0
    -9.2    5.7   -4.2   -9.2    2.1    6.5    5.2  -10.0   -1.9   -3.7
//
H PLIV810101
D Partition coefficient (Pliska et al., 1981)
R 0712223
A Pliska, V., Schmidt, M., and Fauchere, J.L.
T Partition coefficients of amino acids and hydrophobic parameters pi of
  their side-chains as measured by thin-layer chromatography
J J. Chromatogr. 216, 79-92 (1981)
* (Arg 0.25)
C MIYS850101    0.944   FAUJ830101    0.931   MEEJ810101    0.914
  CIDH920105    0.914   RADA880108    0.906   EISD860101    0.904
  CIDH920103    0.899   BIOV880101    0.899   MEEJ810102    0.898
  CIDH920104    0.893   NISK860101    0.892   CIDH920102    0.877
  ZIMJ680105    0.875   SWER830101    0.875   ROBB790101    0.875
```

```
      MEEJ800102    0.867   PONP800107    0.866   BIOV880102    0.858
      MANP780101    0.856   EISD860103    0.852   RADA880102    0.845
      CIDH920101    0.843   WERD780101    0.841   ROSG850102    0.841
      NOZY710101    0.839   LEVM760106    0.830   ARGP820101    0.820
      JOND750101    0.819   MEIH800103    0.811   PONP800101    0.806
      SIMZ760101    0.805   PONP800103    0.802   LEVM760101   -0.801
      ROSM880101   -0.834   GUYH850101   -0.836   MEIH800102   -0.849
      OOBM770103   -0.852   RACS770102   -0.859   ROSM880102   -0.864
      RACS770101   -0.868   GRAR740102   -0.888   MEIH800101   -0.896
      BULH740101   -0.912   PARJ860101   -0.958   WOLS870101   -0.963
I     A/L      R/K      N/M      D/F      C/P      Q/S      E/T      G/W      H/Y      I/V
     -2.89    -3.30    -3.41    -3.38    -2.49    -3.15    -2.94    -3.25    -2.84    -1.72
     -1.61    -3.31    -1.84    -1.63    -2.50    -3.30    -2.91    -1.75    -2.42    -2.08
//
H PONP800101
D Surrounding hydrophobicity in folded form (Ponnuswamy et al., 1980)
R 0608056
A Ponnuswamy, P.K., Prabhakaran, M., and Manavalan, P.
T Hydrophobic packing and spatial arrangement of amino acid residues in
  globular proteins
J Biochim. Biophys. Acta 623, 301-316 (1980)
C PONP800102    0.990   MANP780101    0.963   NISK800101    0.960
  PONP800103    0.957   ROSG850102    0.938   PONP800108    0.938
  RADA880108    0.934   NISK860101    0.930   BIOV880101    0.918
  MIYS850101    0.892   CIDH920104    0.888   WERD780101    0.880
  CIDH920103    0.876   PONP800106    0.871   MEIH800103    0.869
  JANJ790101    0.866   BIOV880102    0.860   DESM900102    0.858
  CIDH920105    0.856   KYTJ820101    0.851   JANJ780102    0.851
  DESM900101    0.847   CHOC760103    0.830   ROBB760106    0.829
  KANM800102    0.829   ROBB760105    0.823   LIFS790101    0.823
  KANM800104    0.823   ROBB790101    0.822   FAUJ830101    0.822
  PTIO830102    0.819   QIAN880121    0.815   PLIV810101    0.806
  CIDH920101    0.805   LIFS790102    0.804   QIAN880122    0.801
  KRIW790102   -0.804   OOBM770101   -0.835   OOBM770103   -0.848
  GRAR740102   -0.849   KRIW710101   -0.850   RACS770101   -0.863
  RACS770102   -0.870   GUYH850101   -0.877   MEIH800102   -0.877
  KRIW790101   -0.888   MEIH800101   -0.888   KARP850102   -0.889
I     A/L      R/K      N/M      D/F      C/P      Q/S      E/T      G/W      H/Y      I/V
     12.28    11.49    11.00    10.97    14.93    11.28    11.19    12.01    12.84    14.77
     14.10    10.80    14.33    13.43    11.19    11.26    11.65    12.95    13.29    15.07
//
H PONP800102
D Average gain in surrounding hydrophobicity (Ponnuswamy et al., 1980)
R 0608056
A Ponnuswamy, P.K., Prabhakaran, M., and Manavalan, P.
T Hydrophobic packing and spatial arrangement of amino acid residues in
  globular proteins
J Biochim. Biophys. Acta 623, 301-316 (1980)
C PONP800101    0.990   PONP800103    0.986   NISK800101    0.965
  ROSG850102    0.949   PONP800108    0.948   MANP780101    0.945
  RADA880108    0.938   BIOV880101    0.926   NISK860101    0.924
  JANJ790101    0.897   MIYS850101    0.891   MEIH800103    0.885
  WERD780101    0.883   PONP800106    0.883   DESM900102    0.880
  CIDH920104    0.880   JANJ780102    0.875   DESM900101    0.871
  BIOV880102    0.867   KYTJ820101    0.861   CIDH920103    0.849
  FAUJ830101    0.841   CHOC760103    0.836   CIDH920105    0.831
  ROBB760105    0.828   ROBB760106    0.822   JANJ790102    0.822
  KANM800102    0.815   EISD860103    0.814   KANM800104    0.813
  ROBB790101    0.807   RACS770103   -0.809   RACS770101   -0.827
  KRIW790102   -0.830   OOBM770103   -0.854   OOBM770101   -0.862
  RACS770102   -0.864   MEIH800101   -0.870   GRAR740102   -0.871
  GUYH850101   -0.883   MEIH800102   -0.883   KARP850102   -0.887
  KRIW710101   -0.887   KRIW790101   -0.915
I     A/L      R/K      N/M      D/F      C/P      Q/S      E/T      G/W      H/Y      I/V
      7.62     6.81     6.17     6.18    10.93     6.67     6.38     7.31     7.85     9.99
      9.37    -5.72     9.83     8.99     6.64     6.93     7.08     8.41     8.53    10.38
//
H PONP800103
```

```
D Average gain ratio in surrounding hydrophobicity (Ponnuswamy et al.,
  1980)
R 0608056
A Ponnuswamy, P.K., Prabhakaran, M., and Manavalan, P.
T Hydrophobic packing and spatial arrangement of amino acid residues in
  globular proteins
J Biochim. Biophys. Acta 623, 301-316 (1980)
C PONP800102    0.986  PONP800101    0.957  ROSG850102    0.947
  NISK800101    0.941  RADA880108    0.934  PONP800108    0.931
  BIOV880101    0.926  MANP780101    0.913  NISK860101    0.910
  MIYS850101    0.898  DESM900102    0.896  MEIH800103    0.895
  DESM900101    0.887  JANJ790101    0.886  PONP800106    0.883
  JANJ780102    0.882  BIOV880102    0.879  WERD780101    0.876
  KYTJ820101    0.870  FAUJ830101    0.863  CIDH920104    0.863
  JANJ790102    0.844  EISD860103    0.842  CHOC760103    0.837
  ROBB760105    0.823  CIDH920103    0.823  ROBB760106    0.812
  CIDH920105    0.807  KANM800102    0.803  PLIV810101    0.802
  JANJ780103   -0.812  RACS770103   -0.819  WOEC730101   -0.823
  KRIW790102   -0.853  MEIH800101   -0.856  RACS770102   -0.860
  OOBM770103   -0.865  KARP850102   -0.870  OOBM770101   -0.880
  GUYH850101   -0.887  KRIW710101   -0.890  MEIH800102   -0.891
  GRAR740102   -0.897  KRIW790101   -0.930
I     A/L    R/K    N/M    D/F    C/P    Q/S    E/T    G/W    H/Y    I/V
     2.63   2.45   2.27   2.29   3.36   2.45   2.31   2.55   2.57   3.08
     2.98   2.12   3.18   3.02   2.46   2.60   2.55   2.85   2.79   3.21
//
H PONP800104
D Surrounding hydrophobicity in alpha-helix (Ponnuswamy et al., 1980)
R 0608056
A Ponnuswamy, P.K., Prabhakaran, M., and Manavalan, P.
T Hydrophobic packing and spatial arrangement of amino acid residues in
  globular proteins
J Biochim. Biophys. Acta 623, 301-316 (1980)
C CHOC760104    0.844
I     A/L    R/K    N/M    D/F    C/P    Q/S    E/T    G/W    H/Y    I/V
    13.65  11.28  12.24  10.98  14.49  11.30  12.55  15.36  11.59  14.63
    14.01  11.96  13.40  14.08  11.51  11.26  13.00  12.06  12.64  12.88
//
H PONP800105
D Surrounding hydrophobicity in beta-sheet (Ponnuswamy et al., 1980)
R 0608056
A Ponnuswamy, P.K., Prabhakaran, M., and Manavalan, P.
T Hydrophobic packing and spatial arrangement of amino acid residues in
  globular proteins
J Biochim. Biophys. Acta 623, 301-316 (1980)
C
I     A/L    R/K    N/M    D/F    C/P    Q/S    E/T    G/W    H/Y    I/V
    14.60  13.24  11.79  13.78  15.90  12.02  13.59  14.18  15.35  14.10
    16.49  13.28  16.23  14.18  14.10  13.36  14.50  13.90  14.76  16.30
//
H PONP800106
D Surrounding hydrophobicity in turn (Ponnuswamy et al., 1980)
R 0608056
A Ponnuswamy, P.K., Prabhakaran, M., and Manavalan, P.
T Hydrophobic packing and spatial arrangement of amino acid residues in
  globular proteins
J Biochim. Biophys. Acta 623, 301-316 (1980)
C PONP800103    0.883  PONP800102    0.883  PONP800101    0.871
  RADA880108    0.835  MANP780101    0.813  MIYS850101    0.812
  ROSG850102    0.807  KARP850102   -0.820  GUYH850101   -0.826
  KRIW710101   -0.841
I     A/L    R/K    N/M    D/F    C/P    Q/S    E/T    G/W    H/Y    I/V
    10.67  11.05  10.85  10.21  14.15  11.71  11.71  10.95  12.07  12.95
    13.07   9.93  15.00  13.27  10.62  11.18  10.53  11.41  11.52  13.86
//
H PONP800107
D Accessibility reduction ratio (Ponnuswamy et al., 1980)
R 0608056
```

```
A Ponnuswamy, P.K., Prabhakaran, M., and Manavalan, P.
T Hydrophobic packing and spatial arrangement of amino acid residues in
  globular proteins
J Biochim. Biophys. Acta 623, 301-316 (1980)
C MIYS850101    0.884   MANP780101    0.871   PLIV810101    0.866
  LIFS790102    0.849   NISK860101    0.847   PTIO830102    0.837
  CIDH920103    0.833   CIDH920104    0.832   CIDH920105    0.818
  BIOV880101    0.816   BIOV880102    0.814   CHOC760103    0.813
  VENT840101    0.805   ROSG850102    0.803   BEGF750102    0.803
  LIFS790101    0.801   RADA880108    0.800   CHOP780203   -0.818
  OOBM770103   -0.819   CHOP780210   -0.820   WOLS870101   -0.852
  MEIH800102   -0.858   PARJ860101   -0.868   RACS770102   -0.878
  RACS770101   -0.905   MEIH800101   -0.909
I   A/L    R/K    N/M    D/F    C/P    Q/S    E/T    G/W    H/Y    I/V
    3.70   2.53   2.12   2.60   3.03   2.70   3.30   3.13   3.57   7.69
    5.88   1.79   5.21   6.60   2.12   2.43   2.60   6.25   3.03   7.14
//
H PONP800108
D Average number of surrounding residues (Ponnuswamy et al., 1980)
R 0608056
A Ponnuswamy, P.K., Prabhakaran, M., and Manavalan, P.
T Hydrophobic packing and spatial arrangement of amino acid residues in
  globular proteins
J Biochim. Biophys. Acta 623, 301-316 (1980)
C NISK800101    0.976   PONP800102    0.948   PONP800101    0.938
  MANP780101    0.935   PONP800103    0.931   NISK860101    0.921
  ROSG850102    0.919   CIDH920104    0.909   BIOV880101    0.907
  RADA880108    0.889   JANJ790101    0.881   FAUJ830101    0.875
  JANJ780102    0.863   MEIH800103    0.862   BIOV880102    0.854
  KYTJ820101    0.850   KANM800104    0.849   KANM800102    0.849
  MIYS850101    0.847   WERD780101    0.843   CIDH920105    0.843
  CIDH920103    0.841   DESM900102    0.833   ROBB790101    0.831
  LIFS790101    0.828   ROBB760105    0.820   GEIM800107    0.817
  QIAN880122    0.811   EISD860103    0.809   CHOP780202    0.809
  CHOC760103    0.809   ROBB760106    0.808   QIAN880121    0.802
  JANJ790102    0.802   MEIH800101   -0.825   WOEC730101   -0.831
  MEIH800102   -0.836   OOBM770101   -0.851   KRIW790101   -0.860
  OOBM770103   -0.896   GRAR740102   -0.907
I   A/L    R/K    N/M    D/F    C/P    Q/S    E/T    G/W    H/Y    I/V
    6.05   5.70   5.04   4.95   7.86   5.45   5.10   6.16   5.80   7.51
    7.37   4.88   6.39   6.62   5.65   5.53   5.81   6.98   6.73   7.62
//
H PRAM820101
D Intercept in regression analysis (Prabhakaran-Ponnuswamy, 1982)
R 2004113b
A Prabhakaran, M. and Ponnuswamy, P.K.
T Shape and surface features of globular proteins
J Macromolecules 15, 314-320 (1982)
* Regression analysis of solvent contact area and spatial position
C
I   A/L     R/K     N/M     D/F     C/P     Q/S     E/T     G/W     H/Y     I/V
    0.305   0.227   0.322   0.335   0.339   0.306   0.282   0.352   0.215   0.278
    0.262   0.391   0.280   0.195   0.346   0.326   0.251   0.291   0.293   0.291
//
H PRAM820102
D Slope in regression analysis x 1.0E1 (Prabhakaran-Ponnuswamy, 1982)
R 2004113b
A Prabhakaran, M. and Ponnuswamy, P.K.
T Shape and surface features of globular proteins
J Macromolecules 15, 314-320 (1982)
* Regression analysis of solvent contact area and spatial position
C LEVM760104    0.812   PRAM820103    0.802
I   A/L     R/K     N/M     D/F     C/P     Q/S     E/T     G/W     H/Y     I/V
    0.175   0.083   0.090   0.140   0.074   0.093   0.135   0.201   0.125   0.100
    0.104   0.058   0.054   0.104   0.136   0.155   0.152   0.092   0.081   0.096
//
H PRAM820103
```

D Correlation coefficient in regression analysis (Prabhakaran-Ponnuswamy, 1982)
R 2004113b
A Prabhakaran, M. and Ponnuswamy, P.K.
T Shape and surface features of globular proteins
J Macromolecules 15, 314-320 (1982)
* Regression analysis of solvent contact area and spatial position
C PRAM820102    0.802
I   A/L     R/K     N/M     D/F     C/P     Q/S     E/T     G/W     H/Y     I/V
    0.687   0.590   0.489   0.632   0.263   0.527   0.669   0.670   0.594   0.564
    0.541   0.407   0.328   0.577   0.600   0.692   0.713   0.632   0.495   0.529
//
H PRAM900101
D Hydrophobicity (Prabhakaran, 1990)
R 1614053b
A Prabhakaran, M.
T The distribution of physical, chemical and conformational properties in signal
  and nascent peptides
J Biochem. J. 269, 691-696 (1990)
* Original references:
* Engelman, D.M., Steitz, T.A. and Terwilliger, T.C.
* Annu. Rev. Biophys. Chem. 15, 321-353 (1986)
C ROSM880101    0.917   VHEG790101    0.909   OOBM770101    0.907
  JANJ780101    0.901   ROSM880102    0.892   JANJ780103    0.884
  LEVM760101    0.881   HOPT810101    0.881   WOEC730101    0.871
  GRAR740102    0.855   ZIMJ680103    0.854   CHOC760102    0.826
  GUYH850101    0.820   FAUJ880109    0.815   RADA880104   -0.803
  CHOC760103   -0.814   WARP780101   -0.827   EISD860103   -0.831
  KYTJ820101   -0.850   FAUJ830101   -0.853   JANJ780102   -0.860
  EISD860101   -0.862   RADA880107   -0.865   WOLR810101   -0.887
  DESM900102   -0.890   JANJ790102   -0.890   RADA880101   -0.932
  EISD840101   -0.936
I   A/L     R/K     N/M     D/F     C/P     Q/S     E/T     G/W     H/Y     I/V
   -6.70   51.50   20.10   38.50   -8.40   17.20   34.30   -4.20   12.60  -13.
  -11.70   36.80  -14.20  -15.50    0.80   -2.50   -5.     -7.90    2.90  -10.90
//
H PRAM900102
D Relative frequency in alpha-helix (Prabhakaran, 1990)
R 1614053b
A Prabhakaran, M.
T The distribution of physical, chemical and conformational properties in signal
  and nascent peptides
J Biochem. J. 269, 691-696 (1990)
* Original reference of these three data:
* Creighton, T.E.
* In "Protein Structure and Melecular Properties", (Freeman, W.H., ed.),
* San Francisco P.235 (1983)
C LEVM780101    1.000   LEVM780104    0.964   PALJ810101    0.943
  KANM800101    0.942   ISOY800101    0.929   MAXF760101    0.924
  ROBB760101    0.916   GEIM800101    0.912   GEIM800104    0.907
  RACS820108    0.904   PALJ810102    0.902   PALJ810109    0.898
  NAGK730101    0.894   CRAJ730101    0.887   CHOP780201    0.873
  TANS770101    0.854   KANM800103    0.850   QIAN880107    0.829
  QIAN880106    0.827   BURA740101    0.805   NAGK730103   -0.809
I   A/L     R/K     N/M     D/F     C/P     Q/S     E/T     G/W     H/Y     I/V
    1.29    0.96    0.90    1.04    1.11    1.27    1.44    0.56    1.22    0.97
    1.30    1.23    1.47    1.07    0.52    0.82    0.82    0.99    0.72    0.91
//
H PRAM900103
D Relative frequency in beta-sheet (Prabhakaran, 1990)
R 1614053b
A Prabhakaran, M.
T The distribution of physical, chemical and conformational properties in signal
  and nascent peptides
J Biochem. J. 269, 691-696 (1990)

```
* Original reference of these three data:
* Creighton, T.E.
* In "Protein Structure and Melecular Properties", (Freeman, W.H., ed.),
* San Francisco P.235 (1983)
C LEVM780102    1.000   PALJ810112    0.913   LEVM780105    0.899
  PALJ810104    0.868   PTIO830102    0.865   LIFS790101    0.864
  QIAN880120    0.858   KANM800102    0.856   PALJ810103    0.846
  GEIM800107    0.842   QIAN880119    0.834   BEGF750102    0.834
  CHOP780202    0.833   QIAN880121    0.805
I   A/L    R/K    N/M    D/F    C/P    Q/S    E/T    G/W    H/Y    I/V
    0.90   0.99   0.76   0.72   0.74   0.80   0.75   0.92   1.08   1.45
    1.02   0.77   0.97   1.32   0.64   0.95   1.21   1.14   1.25   1.49
//
H PRAM900104
D Relative frequency in reverse-turn (Prabhakaran, 1990)
R 1614053b
A Prabhakaran, M.
T The distribution of physical, chemical and conformational properties in signal
  and nascent peptides
J Biochem. J. 269, 691-696 (1990)
* Original reference of these three data:
* Creighton, T.E.
* In "Protein Structure and Molecular Properties", (Freeman, W.H., ed.),
* San Francisco P.235 (1983)
C LEVM780103    1.000   LEVM780106    0.983   GEIM800111    0.954
  CHOP780216    0.951   QIAN880133    0.947   QIAN880134    0.934
  ISOY800103    0.934   QIAN880132    0.932   GEIM800108    0.931
  CHOP780203    0.928   CHAM830101    0.909   PALJ810105    0.906
  QIAN880135    0.903   CHOP780101    0.891   TANS770110    0.873
  CHOP780210    0.850   PALJ810106    0.850   RACS770101    0.809
  KANM800103   -0.814   QIAN880108   -0.819   QIAN880107   -0.829
  ROBB760103   -0.840   FAUJ880102   -0.844   QIAN880109   -0.846
  PTIO830101   -0.858   SUEM840101   -0.865
I   A/L    R/K    N/M    D/F    C/P    Q/S    E/T    G/W    H/Y    I/V
    0.78   0.88   1.28   1.41   0.80   0.97   1.     1.64   0.69   0.51
    0.59   0.96   0.39   0.58   1.91   1.33   1.03   0.75   1.05   0.47
//
H PTIO830101
D Helix-coil equilibrium constant (Ptitsyn-Finkelstein, 1983)
R 0904057
A Ptitsyn, O.B. and Finkelstein, A.V.
T Theory of protein secondary structure and algorithm of its prediction
J Biopolymers 22, 15-25 (1983)
* Charged state for Arg, His, Lys, Asp, and Glu
C ROBB760103    0.903   QIAN880109    0.886   QIAN880108    0.884
  SUEM840101    0.877   QIAN880111    0.857   QIAN880107    0.846
  QIAN880110    0.835   FAUJ880102    0.832   FINA770101    0.826
  ROBB760104    0.817   QIAN880131   -0.826   ISOY800104   -0.832
  QIAN880132   -0.833   CHOP780213   -0.835   GEIM800108   -0.840
  CHAM830101   -0.841   LEVM780106   -0.854   CHOP780216   -0.855
  PRAM900104   -0.858   LEVM780103   -0.860   QIAN880133   -0.864
  GEIM800111   -0.876   QIAN880135   -0.899   QIAN880134   -0.920
I   A/L    R/K    N/M    D/F    C/P    Q/S    E/T    G/W    H/Y    I/V
    1.10   0.95   0.80   0.65   0.95   1.00   1.00   0.60   0.85   1.10
    1.25   1.00   1.15   1.10   0.10   0.75   0.75   1.10   1.10   0.95
//
H PTIO830102
D Beta-coil equilibrium constant (Ptitsyn-Finkelstein, 1983)
R 0904057
A Ptitsyn, O.B. and Finkelstein, A.V.
T Theory of protein secondary structure and algorithm of its prediction
J Biopolymers 22, 15-25 (1983)
* Charged state for Arg, His, Lys, Asp, and Glu
C LIFS790101    0.941   PALJ810104    0.937   KANM800102    0.917
  CHOP780202    0.913   QIAN880120    0.908   LEVM780105    0.894
  ROBB760106    0.882   QIAN880121    0.880   ROBB760105    0.878
  LIFS790102    0.874   PALJ810103    0.867   QIAN880119    0.865
```

```
   PRAM900103    0.865   LEVM780102    0.865   MANP780101    0.861
   KANM800101    0.858   SWER830101    0.856   GEIM800107    0.850
   VENT840101    0.842   CIDH920104    0.842   PONP800107    0.837
   NISK860101    0.825   LIFS790103    0.822   CRAJ730102    0.820
   PONP800101    0.819   CHOP780209    0.814   CIDH920105    0.813
   PALJ810112    0.811   NAGK730102    0.811   GEIM800105    0.810
   MIYS850101    0.807   CIDH920103    0.807   BEGF750102    0.807
   KRIW790101   -0.801   OOBM770103   -0.801   MEIH800101   -0.828
I   A/L    R/K     N/M    D/F    C/P    Q/S    E/T    G/W    H/Y    I/V
    1.00   0.70    0.60   0.50   1.90   1.00   0.70   0.30   0.80   4.00
    2.00   0.70    1.90   3.10   0.20   0.90   1.70   2.20   2.80   4.00
//
H QIAN880101
D Weights for alpha-helix at the window position of -6 (Qian-Sejnowski,
1988)
R 1411084
A Qian, N. and Sejnowski, T.J.
T Predicting the secondary structure of globular proteins using neural
  network models
J J. Mol. Biol. 202, 865-884 (1988)
C
I   A/L    R/K     N/M    D/F    C/P    Q/S    E/T    G/W    H/Y    I/V
    0.12   0.04   -0.10   0.01  -0.25  -0.03  -0.02  -0.02  -0.06  -0.07
    0.05   0.26    0.00   0.05  -0.19  -0.19  -0.04  -0.06  -0.14  -0.03
//
H QIAN880102
D Weights for alpha-helix at the window position of -5 (Qian-Sejnowski,
1988)
R 1411084
A Qian, N. and Sejnowski, T.J.
T Predicting the secondary structure of globular proteins using neural
  network models
J J. Mol. Biol. 202, 865-884 (1988)
C
I   A/L    R/K     N/M    D/F    C/P    Q/S    E/T    G/W    H/Y    I/V
    0.26  -0.14   -0.03   0.15  -0.15  -0.13   0.21  -0.37   0.10  -0.03
   -0.02   0.12    0.00   0.12  -0.08   0.01  -0.34  -0.01  -0.29   0.02
//
H QIAN880103
D Weights for alpha-helix at the window position of -4 (Qian-Sejnowski,
1988)
R 1411084
A Qian, N. and Sejnowski, T.J.
T Predicting the secondary structure of globular proteins using neural
  network models
J J. Mol. Biol. 202, 865-884 (1988)
C
I   A/L    R/K     N/M    D/F    C/P    Q/S    E/T    G/W    H/Y    I/V
    0.64  -0.10    0.09   0.33   0.03  -0.23   0.51  -0.09  -0.23  -0.22
    0.41  -0.17    0.13  -0.03  -0.43  -0.10  -0.07  -0.02  -0.38  -0.01
//
H QIAN880104
D Weights for alpha-helix at the window position of -3 (Qian-Sejnowski,
1988)
R 1411084
A Qian, N. and Sejnowski, T.J.
T Predicting the secondary structure of globular proteins using neural
  network models
J J. Mol. Biol. 202, 865-884 (1988)
C QIAN880106    0.851   QIAN880105    0.824
I   A/L    R/K     N/M    D/F    C/P    Q/S    E/T    G/W    H/Y    I/V
    0.29  -0.03   -0.04   0.11  -0.05   0.26   0.28  -0.67  -0.26   0.00
    0.47  -0.19    0.27   0.24  -0.34  -0.17  -0.20   0.25  -0.30  -0.01
//
H QIAN880105
D Weights for alpha-helix at the window position of -2 (Qian-Sejnowski,
1988)
R 1411084
```

A Qian, N. and Sejnowski, T.J.
T Predicting the secondary structure of globular proteins using neural network models
J J. Mol. Biol. 202, 865-884 (1988)
C ROBB760101    0.874   QIAN880106   0.846   CHOP780201   0.835
  BEGF750101    0.833   QIAN880107   0.829   ISOY800101   0.828
  KANM800101    0.827   QIAN880104   0.824   RACS820108   0.820
  KANM800103    0.820   ROBB760103   0.811   MAXF760101   0.811
  CHAM830101   -0.803
I   A/L     R/K     N/M     D/F     C/P     Q/S     E/T     G/W     H/Y     I/V
    0.68   -0.22   -0.09   -0.02   -0.15   -0.15    0.44   -0.73   -0.14   -0.08
    0.61    0.03    0.39    0.06   -0.76   -0.26   -0.10    0.20   -0.04    0.12
//
H QIAN880106
D Weights for alpha-helix at the window position of -1 (Qian-Sejnowski, 1988)
R 1411084
A Qian, N. and Sejnowski, T.J.
T Predicting the secondary structure of globular proteins using neural network models
J J. Mol. Biol. 202, 865-884 (1988)
C ROBB760101    0.904   ISOY800101   0.903   QIAN880107   0.896
  KANM800103    0.889   MAXF760101   0.881   CHOP780201   0.874
  PALJ810102    0.871   RACS820108   0.866   ROBB760103   0.854
  KANM800101    0.854   QIAN880104   0.851   QIAN880105   0.846
  RICJ880109    0.834   PRAM900102   0.827   LEVM780101   0.827
  TANS770101    0.819   FINA770101   0.810   LEVM780104   0.804
  QIAN880132   -0.813   CHAM830101  -0.856
I   A/L     R/K     N/M     D/F     C/P     Q/S     E/T     G/W     H/Y     I/V
    0.34    0.22   -0.33    0.06   -0.18    0.01    0.20   -0.88   -0.09   -0.03
    0.20   -0.11    0.43    0.15   -0.81   -0.35   -0.37    0.07   -0.31    0.13
//
H QIAN880107
D Weights for alpha-helix at the window position of 0 (Qian-Sejnowski, 1988)
R 1411084
A Qian, N. and Sejnowski, T.J.
T Predicting the secondary structure of globular proteins using neural network models
J J. Mol. Biol. 202, 865-884 (1988)
C KANM800103    0.908   QIAN880106   0.896   ROBB760103   0.889
  ISOY800101    0.887   MAXF760101   0.885   QIAN880108   0.872
  ROBB760101    0.867   QIAN880109   0.865   PALJ810102   0.856
  KANM800101    0.854   QIAN880110   0.853   PTIO830101   0.846
  CHOP780201    0.843   RACS820108   0.831   QIAN880105   0.829
  PRAM900102    0.829   LEVM780101   0.829   LEVM780104   0.822
  BEGF750101    0.815   FINA770101   0.814   TANS770101   0.804
  SUEM840101    0.803   CHOP780216  -0.808   CHOP780101  -0.809
  QIAN880133   -0.809   LEVM780106  -0.813   PALJ810106  -0.821
  PRAM900104   -0.829   LEVM780103  -0.834   CRAJ730103  -0.840
  CHAM830101   -0.858
I   A/L     R/K     N/M     D/F     C/P     Q/S     E/T     G/W     H/Y     I/V
    0.57    0.23   -0.36   -0.46   -0.15    0.15    0.26   -0.71   -0.05    0.00
    0.48    0.16    0.41    0.03   -1.12   -0.47   -0.54   -0.10   -0.35    0.31
//
H QIAN880108
D Weights for alpha-helix at the window position of 1 (Qian-Sejnowski, 1988)
R 1411084
A Qian, N. and Sejnowski, T.J.
T Predicting the secondary structure of globular proteins using neural network models
J J. Mol. Biol. 202, 865-884 (1988)
C QIAN880109    0.951   ROBB760103   0.914   QIAN880110   0.901
  PTIO830101    0.884   ROBB760104   0.879   QIAN880107   0.872
  KANM800103    0.829   RACS820108   0.820   QIAN880111   0.819
  PRAM900104   -0.819   LEVM780103  -0.820   QIAN880135  -0.836
  QIAN880136   -0.843   QIAN880134  -0.845   ISOY800104  -0.847

```
I   A/L     R/K     N/M     D/F     C/P     Q/S     E/T     G/W     H/Y     I/V
    0.33    0.10   -0.19   -0.44   -0.03    0.19    0.21   -0.46    0.27   -0.33
    0.57    0.23    0.79   -0.48   -1.86   -0.23   -0.33    0.15   -0.19    0.24
//
H QIAN880109
D Weights for alpha-helix at the window position of 2 (Qian-Sejnowski,
  1988)
R 1411084
A Qian, N. and Sejnowski, T.J.
T Predicting the secondary structure of globular proteins using neural
  network models
J J. Mol. Biol. 202, 865-884 (1988)
C QIAN880110    0.953   QIAN880108    0.951   QIAN880111    0.912
  PTIO830101    0.886   ROBB760104    0.871   ROBB760103    0.868
  QIAN880107    0.865   QIAN880112    0.824   KANM800103    0.824
  CHOP780205    0.806   LEVM780106   -0.815   QIAN880134   -0.841
  PRAM900104   -0.846   LEVM780103   -0.848   QIAN880135   -0.884
  QIAN880136   -0.927
I   A/L     R/K     N/M     D/F     C/P     Q/S     E/T     G/W     H/Y     I/V
    0.13    0.08   -0.07   -0.71   -0.09    0.12    0.13   -0.39    0.32    0.00
    0.50    0.37    0.63    0.15   -1.40   -0.28   -0.21    0.02   -0.10    0.17
//
H QIAN880110
D Weights for alpha-helix at the window position of 3 (Qian-Sejnowski,
  1988)
R 1411084
A Qian, N. and Sejnowski, T.J.
T Predicting the secondary structure of globular proteins using neural
  network models
J J. Mol. Biol. 202, 865-884 (1988)
C QIAN880109    0.953   QIAN880111    0.922   QIAN880108    0.901
  QIAN880107    0.853   PTIO830101    0.835   QIAN880112    0.828
  KANM800103    0.820   ROBB760103    0.807   ROBB760104    0.806
  QIAN880136   -0.890
I   A/L     R/K     N/M     D/F     C/P     Q/S     E/T     G/W     H/Y     I/V
    0.31    0.18   -0.10   -0.81   -0.26    0.41   -0.06   -0.42    0.51   -0.15
    0.56    0.47    0.58    0.10   -1.33   -0.49   -0.44    0.14   -0.08   -0.01
//
H QIAN880111
D Weights for alpha-helix at the window position of 4 (Qian-Sejnowski,
  1988)
R 1411084
A Qian, N. and Sejnowski, T.J.
T Predicting the secondary structure of globular proteins using neural
  network models
J J. Mol. Biol. 202, 865-884 (1988)
C QIAN880110    0.922   QIAN880109    0.912   QIAN880112    0.861
  PTIO830101    0.857   QIAN880108    0.819   QIAN880135   -0.878
  QIAN880136   -0.900
I   A/L     R/K     N/M     D/F     C/P     Q/S     E/T     G/W     H/Y     I/V
    0.21    0.07   -0.04   -0.58   -0.12    0.13   -0.23   -0.15    0.37    0.31
    0.70    0.28    0.61   -0.06   -1.03   -0.28   -0.25    0.21    0.16    0.00
//
H QIAN880112
D Weights for alpha-helix at the window position of 5 (Qian-Sejnowski,
  1988)
R 1411084
A Qian, N. and Sejnowski, T.J.
T Predicting the secondary structure of globular proteins using neural
  network models
J J. Mol. Biol. 202, 865-884 (1988)
C QIAN880111    0.861   QIAN880113    0.859   QIAN880110    0.828
  QIAN880109    0.824   QIAN880136   -0.812
I   A/L     R/K     N/M     D/F     C/P     Q/S     E/T     G/W     H/Y     I/V
    0.18    0.21   -0.03   -0.32   -0.29   -0.27   -0.25   -0.40    0.28   -0.03
    0.62   -0.41    0.21    0.05   -0.84   -0.05   -0.16    0.32    0.11    0.06
//
H QIAN880113
```

D Weights for alpha-helix at the window position of 6 (Qian-Sejnowski, 1988)
R 1411084
A Qian, N. and Sejnowski, T.J.
T Predicting the secondary structure of globular proteins using neural network models
J J. Mol. Biol. 202, 865-884 (1988)
C QIAN880112    0.859
I    A/L    R/K    N/M    D/F    C/P    Q/S    E/T    G/W    H/Y    I/V
    -0.08   0.05  -0.08  -0.24  -0.25  -0.28  -0.19  -0.10   0.29  -0.01
     0.28   0.45   0.11   0.00  -0.42   0.07  -0.33   0.36   0.00  -0.13
//
H QIAN880114
D Weights for beta-sheet at the window position of -6 (Qian-Sejnowski, 1988)
R 1411084
A Qian, N. and Sejnowski, T.J.
T Predicting the secondary structure of globular proteins using neural network models
J J. Mol. Biol. 202, 865-884 (1988)
C QIAN880115    0.832
I    A/L    R/K    N/M    D/F    C/P    Q/S    E/T    G/W    H/Y    I/V
    -0.18  -0.13   0.28   0.05  -0.26   0.21  -0.06   0.23   0.24  -0.42
    -0.23   0.03  -0.42  -0.18  -0.13   0.41   0.33  -0.10  -0.10  -0.07
//
H QIAN880115
D Weights for beta-sheet at the window position of -5 (Qian-Sejnowski, 1988)
R 1411084
A Qian, N. and Sejnowski, T.J.
T Predicting the secondary structure of globular proteins using neural network models
J J. Mol. Biol. 202, 865-884 (1988)
C QIAN880114    0.832
I    A/L    R/K    N/M    D/F    C/P    Q/S    E/T    G/W    H/Y    I/V
    -0.01   0.02   0.41  -0.09  -0.27   0.01   0.09   0.13   0.22  -0.27
    -0.25   0.08  -0.57  -0.12   0.26   0.44   0.35  -0.15   0.15  -0.09
//
H QIAN880116
D Weights for beta-sheet at the window position of -4 (Qian-Sejnowski, 1988)
R 1411084
A Qian, N. and Sejnowski, T.J.
T Predicting the secondary structure of globular proteins using neural network models
J J. Mol. Biol. 202, 865-884 (1988)
C QIAN880126    0.823
I    A/L    R/K    N/M    D/F    C/P    Q/S    E/T    G/W    H/Y    I/V
    -0.19   0.03   0.02  -0.06  -0.29   0.02  -0.10   0.19  -0.16  -0.08
    -0.42  -0.09  -0.38  -0.32   0.05   0.25   0.22  -0.19   0.05  -0.15
//
H QIAN880117
D Weights for beta-sheet at the window position of -3 (Qian-Sejnowski, 1988)
R 1411084
A Qian, N. and Sejnowski, T.J.
T Predicting the secondary structure of globular proteins using neural network models
J J. Mol. Biol. 202, 865-884 (1988)
C
I    A/L    R/K    N/M    D/F    C/P    Q/S    E/T    G/W    H/Y    I/V
    -0.14   0.14  -0.27  -0.10  -0.64  -0.11  -0.39   0.46  -0.04   0.16
    -0.57   0.04   0.24   0.08   0.02  -0.12   0.00  -0.10   0.18   0.29
//
H QIAN880118
D Weights for beta-sheet at the window position of -2 (Qian-Sejnowski, 1988)
R 1411084

A Qian, N. and Sejnowski, T.J.
T Predicting the secondary structure of globular proteins using neural network models
J J. Mol. Biol. 202, 865-884 (1988)
C PALJ810103    0.845    LEVM780105    0.819    QIAN880119    0.812
  GEIM800105    0.810    KANM800102    0.801
I   A/L     R/K     N/M     D/F     C/P     Q/S     E/T     G/W     H/Y     I/V
   -0.31    0.25   -0.53   -0.54   -0.06    0.07   -0.52    0.37   -0.32    0.57
    0.09   -0.29    0.29    0.24   -0.31    0.11    0.03    0.15    0.29    0.48
//
H QIAN880119
D Weights for beta-sheet at the window position of -1 (Qian-Sejnowski, 1988)
R 1411084
A Qian, N. and Sejnowski, T.J.
T Predicting the secondary structure of globular proteins using neural network models
J J. Mol. Biol. 202, 865-884 (1988)
C QIAN880120    0.959    LIFS790101    0.929    LEVM780105    0.903
  ROBB760106    0.897    KANM800102    0.888    LIFS790103    0.877
  PTIO830102    0.865    QIAN880121    0.862    PALJ810103    0.861
  ROBB760105    0.859    CHOP780202    0.855    KANM800104    0.841
  PRAM900103    0.834    LEVM780102    0.834    GEIM800105    0.829
  OOBM850101    0.825    PALJ810110    0.824    PALJ810104    0.822
  QIAN880118    0.812    BEGF750102    0.811    GEIM800107    0.807
  CHOP780208    0.807    GEIM800108   -0.810    LEVM780106   -0.810
  CHOP780203   -0.814    QIAN880131   -0.830    QIAN880133   -0.849
  GEIM800110   -0.853    QIAN880132   -0.858
I   A/L     R/K     N/M     D/F     C/P     Q/S     E/T     G/W     H/Y     I/V
   -0.10    0.19   -0.89   -0.89    0.13   -0.04   -0.34   -0.45   -0.34    0.95
    0.32   -0.46    0.43    0.36   -0.91   -0.12    0.49    0.34    0.42    0.76
//
H QIAN880120
D Weights for beta-sheet at the window position of 0 (Qian-Sejnowski, 1988)
R 1411084
A Qian, N. and Sejnowski, T.J.
T Predicting the secondary structure of globular proteins using neural network models
J J. Mol. Biol. 202, 865-884 (1988)
C LIFS790101    0.969    QIAN880119    0.959    LIFS790103    0.939
  QIAN880121    0.935    CHOP780202    0.915    LEVM780105    0.913
  ROBB760106    0.908    PTIO830102    0.908    KANM800102    0.896
  PALJ810104    0.886    PALJ810103    0.886    ROBB760105    0.860
  PRAM900103    0.858    LEVM780102    0.858    GEIM800107    0.843
  NISK860101    0.837    BEGF750102    0.829    SWER830101    0.825
  GEIM800106    0.825    PALJ810110    0.824    GEIM800105    0.822
  MANP780101    0.806    KANM800104    0.803    CHOP780208    0.800
  CHOP780216   -0.800    QIAN880131   -0.801    GEIM800108   -0.804
  GEIM800111   -0.816    OOBM770103   -0.824    LEVM780106   -0.831
  QIAN880132   -0.839    QIAN880134   -0.842    QIAN880133   -0.863
  GEIM800110   -0.898
I   A/L     R/K     N/M     D/F     C/P     Q/S     E/T     G/W     H/Y     I/V
   -0.25   -0.02   -0.77   -1.01    0.13   -0.12   -0.62   -0.72   -0.16    1.10
    0.23   -0.59    0.32    0.48   -1.24   -0.31    0.17    0.45    0.77    0.69
//
H QIAN880121
D Weights for beta-sheet at the window position of 1 (Qian-Sejnowski, 1988)
R 1411084
A Qian, N. and Sejnowski, T.J.
T Predicting the secondary structure of globular proteins using neural network models
J J. Mol. Biol. 202, 865-884 (1988)
C QIAN880120    0.935    LIFS790101    0.930    CHOP780202    0.911
  PALJ810104    0.910    ROBB760106    0.907    KANM800102    0.900
  LIFS790103    0.882    PTIO830102    0.880    LEVM780105    0.876
  PALJ810103    0.875    GEIM800107    0.875    QIAN880119    0.862
  QIAN880122    0.838    ROBB760105    0.834    NISK860101    0.829
  KANM800104    0.829    NISK800101    0.818    PONP800101    0.815

```
            PALJ810102     0.812  GEIM800105     0.811  CHOP780209     0.809
            PRAM900103     0.805  LEVM780102     0.805  PONP800108     0.802
            MANP780101     0.802  QIAN880133    -0.802  KRIW790101    -0.803
            GEIM800110    -0.806  QIAN880134    -0.838
I     A/L      R/K      N/M      D/F      C/P      Q/S      E/T      G/W      H/Y      I/V
     -0.26    -0.09    -0.34    -0.55     0.47    -0.33    -0.75    -0.56    -0.04     0.94
      0.25    -0.55    -0.05     0.20    -1.28    -0.28     0.08     0.22     0.53     0.67
//
H QIAN880122
D Weights for beta-sheet at the window position of 2 (Qian-Sejnowski, 1988)
R 1411084
A Qian, N. and Sejnowski, T.J.
T Predicting the secondary structure of globular proteins using neural
  network models
J J. Mol. Biol. 202, 865-884 (1988)
C QIAN880121     0.838  PONP800108     0.811  NISK800101     0.808
  PONP800101     0.801
I     A/L      R/K      N/M      D/F      C/P      Q/S      E/T      G/W      H/Y      I/V
      0.05    -0.11    -0.40    -0.11     0.36    -0.67    -0.35     0.14     0.02     0.47
      0.32    -0.51    -0.10     0.20    -0.79     0.03    -0.15     0.09     0.34     0.58
//
H QIAN880123
D Weights for beta-sheet at the window position of 3 (Qian-Sejnowski, 1988)
R 1411084
A Qian, N. and Sejnowski, T.J.
T Predicting the secondary structure of globular proteins using neural
  network models
J J. Mol. Biol. 202, 865-884 (1988)
C
I     A/L      R/K      N/M      D/F      C/P      Q/S      E/T      G/W      H/Y      I/V
     -0.44    -0.13     0.05    -0.20     0.13    -0.58    -0.28     0.08     0.09    -0.04
     -0.12    -0.33    -0.21    -0.13    -0.48     0.27     0.47    -0.22    -0.11     0.06
//
H QIAN880124
D Weights for beta-sheet at the window position of 4 (Qian-Sejnowski, 1988)
R 1411084
A Qian, N. and Sejnowski, T.J.
T Predicting the secondary structure of globular proteins using neural
  network models
J J. Mol. Biol. 202, 865-884 (1988)
C
I     A/L      R/K      N/M      D/F      C/P      Q/S      E/T      G/W      H/Y      I/V
     -0.31    -0.10     0.06     0.13    -0.11    -0.47    -0.05     0.45    -0.06    -0.25
     -0.44    -0.44    -0.28    -0.04    -0.29     0.34     0.27    -0.08     0.06     0.11
//
H QIAN880125
D Weights for beta-sheet at the window position of 5 (Qian-Sejnowski, 1988)
R 1411084
A Qian, N. and Sejnowski, T.J.
T Predicting the secondary structure of globular proteins using neural
  network models
J J. Mol. Biol. 202, 865-884 (1988)
C
I     A/L      R/K      N/M      D/F      C/P      Q/S      E/T      G/W      H/Y      I/V
     -0.02     0.04     0.03     0.11    -0.02    -0.17     0.10     0.38    -0.09    -0.48
     -0.26    -0.39    -0.14    -0.03    -0.04     0.41     0.36    -0.01    -0.08    -0.18
//
H QIAN880126
D Weights for beta-sheet at the window position of 6 (Qian-Sejnowski, 1988)
R 1411084
A Qian, N. and Sejnowski, T.J.
T Predicting the secondary structure of globular proteins using neural
  network models
J J. Mol. Biol. 202, 865-884 (1988)
C QIAN880116     0.823
I     A/L      R/K      N/M      D/F      C/P      Q/S      E/T      G/W      H/Y      I/V
     -0.06     0.02     0.10     0.24    -0.19    -0.04    -0.04     0.17     0.19    -0.20
     -0.46    -0.43    -0.52    -0.33     0.37     0.43     0.50    -0.32     0.35     0.09
```

```
//
H QIAN880127
D Weights for coil at the window position of -6 (Qian-Sejnowski, 1988)
R 1411084
A Qian, N. and Sejnowski, T.J.
T Predicting the secondary structure of globular proteins using neural
  network models
J J. Mol. Biol. 202, 865-884 (1988)
C OOBM850105   -0.813
I   A/L    R/K    N/M    D/F    C/P    Q/S    E/T    G/W    H/Y    I/V
   -0.05   0.06   0.00   0.15   0.30  -0.08  -0.02  -0.14  -0.07   0.26
    0.04  -0.42   0.25   0.09   0.31  -0.11  -0.06   0.19   0.33   0.04
//
H QIAN880128
D Weights for coil at the window position of -5 (Qian-Sejnowski, 1988)
R 1411084
A Qian, N. and Sejnowski, T.J.
T Predicting the secondary structure of globular proteins using neural
  network models
J J. Mol. Biol. 202, 865-884 (1988)
C
I   A/L    R/K    N/M    D/F    C/P    Q/S    E/T    G/W    H/Y    I/V
   -0.19   0.17  -0.38   0.09   0.41   0.04  -0.20   0.28  -0.19  -0.06
    0.34  -0.20   0.45   0.07   0.04  -0.23  -0.02   0.16   0.22   0.05
//
H QIAN880129
D Weights for coil at the window position of -4 (Qian-Sejnowski, 1988)
R 1411084
A Qian, N. and Sejnowski, T.J.
T Predicting the secondary structure of globular proteins using neural
  network models
J J. Mol. Biol. 202, 865-884 (1988)
C
I   A/L    R/K    N/M    D/F    C/P    Q/S    E/T    G/W    H/Y    I/V
   -0.43   0.06   0.00  -0.31   0.19   0.14  -0.41  -0.21   0.21   0.29
   -0.10   0.33  -0.01   0.25   0.28  -0.23  -0.26   0.15   0.09  -0.10
//
H QIAN880130
D Weights for coil at the window position of -3 (Qian-Sejnowski, 1988)
R 1411084
A Qian, N. and Sejnowski, T.J.
T Predicting the secondary structure of globular proteins using neural
  network models
J J. Mol. Biol. 202, 865-884 (1988)
C
I   A/L    R/K    N/M    D/F    C/P    Q/S    E/T    G/W    H/Y    I/V
   -0.19  -0.07   0.17  -0.27   0.42  -0.29  -0.22   0.17   0.17  -0.34
   -0.22   0.00  -0.53  -0.31   0.14   0.22   0.10  -0.15  -0.02  -0.33
//
H QIAN880131
D Weights for coil at the window position of -2 (Qian-Sejnowski, 1988)
R 1411084
A Qian, N. and Sejnowski, T.J.
T Predicting the secondary structure of globular proteins using neural
  network models
J J. Mol. Biol. 202, 865-884 (1988)
C TANS770110    0.873  CHOP780216    0.873  QIAN880133    0.871
  CHOP780203    0.861  GEIM800108    0.860  CHAM830101    0.860
  GEIM800111    0.857  QIAN880132    0.847  QIAN880135    0.844
  QIAN880134    0.832  CHOP780210    0.826  CHOP780101    0.824
  PALJ810106    0.809  QIAN880120   -0.801  SUEM840101   -0.823
  PTIO830101   -0.826  QIAN880119   -0.830
I   A/L    R/K    N/M    D/F    C/P    Q/S    E/T    G/W    H/Y    I/V
   -0.25   0.12   0.61   0.60   0.18   0.09  -0.12   0.09   0.42  -0.54
   -0.55   0.14  -0.47  -0.29   0.89   0.24   0.16  -0.44  -0.19  -0.45
//
H QIAN880132
D Weights for coil at the window position of -1 (Qian-Sejnowski, 1988)
```

```
R 1411084
A Qian, N. and Sejnowski, T.J.
T Predicting the secondary structure of globular proteins using neural
  network models
J J. Mol. Biol. 202, 865-884 (1988)
C QIAN880133     0.957  LEVM780106     0.943  PRAM900104     0.932
  LEVM780103     0.931  CHOP780216     0.931  GEIM800111     0.929
  CHOP780203     0.928  CHAM830101     0.925  QIAN880134     0.909
  GEIM800108     0.906  TANS770110     0.903  CHOP780101     0.896
  ISOY800103     0.892  PALJ810106     0.859  CHOP780210     0.852
  QIAN880131     0.847  PALJ810105     0.830  QIAN880135     0.824
  PALJ810115     0.804  ROBB760112     0.800  LIFS790101    -0.806
  QIAN880106    -0.813  ROBB760103    -0.827  PTIO830101    -0.833
  QIAN880120    -0.839  FAUJ880102    -0.849  QIAN880119    -0.858
  SUEM840101    -0.880
I    A/L    R/K    N/M    D/F    C/P    Q/S    E/T    G/W    H/Y    I/V
    -0.27  -0.40   0.71   0.54   0.00  -0.08  -0.12   1.14   0.18  -0.74
    -0.54   0.45  -0.76  -0.47   1.40   0.40  -0.10  -0.46  -0.05  -0.86
//
H QIAN880133
D Weights for coil at the window position of 0 (Qian-Sejnowski, 1988)
R 1411084
A Qian, N. and Sejnowski, T.J.
T Predicting the secondary structure of globular proteins using neural
  network models
J J. Mol. Biol. 202, 865-884 (1988)
C LEVM780106     0.971  QIAN880132     0.957  LEVM780103     0.948
  PRAM900104     0.947  GEIM800111     0.943  CHOP780216     0.939
  QIAN880134     0.938  GEIM800108     0.930  TANS770110     0.920
  CHOP780203     0.915  CHAM830101     0.913  ISOY800103     0.908
  QIAN880135     0.907  CHOP780101     0.897  QIAN880131     0.871
  PALJ810106     0.860  PALJ810105     0.843  GEIM800110     0.822
  CHOP780210     0.820  ROBB760112     0.814  QIAN880121    -0.802
  ROBB760103    -0.807  QIAN880107    -0.809  LIFS790101    -0.848
  QIAN880119    -0.849  FAUJ880102    -0.851  QIAN880120    -0.863
  PTIO830101    -0.864  SUEM840101    -0.879
I    A/L    R/K    N/M    D/F    C/P    Q/S    E/T    G/W    H/Y    I/V
    -0.42  -0.23   0.81   0.95  -0.18  -0.01  -0.09   1.24   0.05   1.17
    -0.69   0.09  -0.86  -0.39   1.77   0.63   0.29  -0.37  -0.41  -1.32
//
H QIAN880134
D Weights for coil at the window position of 1 (Qian-Sejnowski, 1988)
R 1411084
A Qian, N. and Sejnowski, T.J.
T Predicting the secondary structure of globular proteins using neural
  network models
J J. Mol. Biol. 202, 865-884 (1988)
C QIAN880135     0.961  QIAN880133     0.938  LEVM780103     0.935
  PRAM900104     0.934  LEVM780106     0.932  GEIM800111     0.919
  QIAN880132     0.909  CHOP780216     0.900  ISOY800103     0.893
  GEIM800108     0.884  CHOP780213     0.870  GEIM800110     0.853
  CHAM830101     0.841  CHOP780203     0.838  TANS770104     0.837
  QIAN880131     0.832  ISOY800103     0.828  ROBB760104    -0.802
  LIFS790101    -0.804  QIAN880121    -0.838  QIAN880109    -0.841
  QIAN880120    -0.842  QIAN880108    -0.845  FAUJ880102    -0.852
  ROBB760103    -0.855  PTIO830101    -0.920
I    A/L    R/K    N/M    D/F    C/P    Q/S    E/T    G/W    H/Y    I/V
    -0.24  -0.04   0.45   0.65  -0.38   0.01   0.07   0.85  -0.21  -0.65
    -0.80   0.17  -0.71  -0.61   2.27   0.33   0.13  -0.44  -0.49  -0.99
//
H QIAN880135
D Weights for coil at the window position of 2 (Qian-Sejnowski, 1988)
R 1411084
A Qian, N. and Sejnowski, T.J.
T Predicting the secondary structure of globular proteins using neural
  network models
J J. Mol. Biol. 202, 865-884 (1988)
* (Gin !)
```

```
C QIAN880134    0.961  QIAN880133   0.907  LEVM780103   0.906
  PRAM900104    0.903  LEVM780106   0.902  GEIM800111   0.895
  CHOP780216    0.884  GEIM800108   0.877  CHOP780213   0.851
  QIAN880131    0.844  GEIM800110   0.842  QIAN880136   0.838
  ISOY800104    0.837  QIAN880132   0.824  CHAM830101   0.814
  CHOP780203    0.811  ROBB760103  -0.834  QIAN880108  -0.836
  QIAN880111   -0.878  QIAN880109  -0.884  PTIO830101  -0.899
I    A/L    R/K    N/M    D/F    C/P    Q/S    E/T    G/W    H/Y    I/V
    -0.14   0.21   0.35   0.66  -0.09   0.11   0.06   0.36  -0.31  -0.51
    -0.80  -0.14  -0.56  -0.25   1.59   0.32   0.21  -0.17  -0.35  -0.70
//
H QIAN880136
D Weights for coil at the window position of 3 (Qian-Sejnowski, 1988)
R 1411084
A Qian, N. and Sejnowski, T.J.
T Predicting the secondary structure of globular proteins using neural
  network models
J J. Mol. Biol. 202, 865-884 (1988)
C QIAN880135    0.838  QIAN880112  -0.812  QIAN880108  -0.843
  QIAN880110   -0.890  QIAN880111  -0.900  QIAN880109  -0.927
I    A/L    R/K    N/M    D/F    C/P    Q/S    E/T    G/W    H/Y    I/V
     0.01  -0.13  -0.11   0.78  -0.31  -0.13   0.09   0.14  -0.56  -0.09
    -0.81  -0.43  -0.49  -0.20   1.14   0.13  -0.02  -0.20   0.10  -0.11
//
H QIAN880137
D Weights for coil at the window position of 4 (Qian-Sejnowski, 1988)
R 1411084
A Qian, N. and Sejnowski, T.J.
T Predicting the secondary structure of globular proteins using neural
  network models
J J. Mol. Biol. 202, 865-884 (1988)
C
I    A/L    R/K    N/M    D/F    C/P    Q/S    E/T    G/W    H/Y    I/V
    -0.30  -0.09  -0.12   0.44   0.03   0.24   0.18  -0.12  -0.20  -0.07
    -0.18   0.06  -0.44   0.11   0.77  -0.09  -0.27  -0.09  -0.25  -0.06
//
H QIAN880138
D Weights for coil at the window position of 5 (Qian-Sejnowski, 1988)
R 1411084
A Qian, N. and Sejnowski, T.J.
T Predicting the secondary structure of globular proteins using neural
  network models
J J. Mol. Biol. 202, 865-884 (1988)
C
I    A/L    R/K    N/M    D/F    C/P    Q/S    E/T    G/W    H/Y    I/V
    -0.23  -0.20   0.06   0.34   0.19   0.47   0.28   0.14  -0.22   0.42
    -0.36  -0.15  -0.19  -0.02   0.78  -0.29  -0.30  -0.18   0.07   0.29
//
H QIAN880139
D Weights for coil at the window position of 6 (Qian-Sejnowski, 1988)
R 1411084
A Qian, N. and Sejnowski, T.J.
T Predicting the secondary structure of globular proteins using neural
  network models
J J. Mol. Biol. 202, 865-884 (1988)
C
I    A/L    R/K    N/M    D/F    C/P    Q/S    E/T    G/W    H/Y    I/V
     0.08  -0.01  -0.06   0.04   0.37   0.48   0.36  -0.02  -0.45   0.09
     0.24  -0.27   0.16   0.34   0.16  -0.35  -0.04  -0.06  -0.20   0.18
//
H RACS770101
D Average reduced distance for C-alpha (Rackovsky-Scheraga, 1977)
R 2004126b
A Rackovsky, S. and Scheraga, H.A.
T Hydrophobicity, hydrophilicity, and the radial and orientational
  distributions of residues in native proteins
J Proc. Natl. Acad. Sci. USA 74, 5248-5251 (1977)
C MEIH800101    0.973  RACS770102   0.946  MEIH800102   0.905
```

|                |        |            |        |            |        |
|----------------|--------|------------|--------|------------|--------|
| PARJ860101     | 0.871  | KARP850102 | 0.869  | GUYH850101 | 0.853  |
| KARP850101     | 0.837  | OOBM770103 | 0.835  | KRIW790101 | 0.828  |
| CHOP780203     | 0.827  | KRIW790102 | 0.814  | PRAM900104 | 0.809  |
| LEVM780103     | 0.808  | RACS770103 | 0.801  | SWER830101 | -0.803 |
| NISK800101     | -0.805 | CIDH920102 | -0.825 | PONP800102 | -0.827 |
| CIDH920101     | -0.837 | ROBB790101 | -0.839 | BEGF750102 | -0.840 |
| MEIH800103     | -0.845 | RICJ880111 | -0.846 | PONP800101 | -0.863 |
| CIDH920104     | -0.864 | PLIV810101 | -0.868 | BIOV880102 | -0.875 |
| MANP780101     | -0.878 | ROSG850102 | -0.880 | CIDH920103 | -0.881 |
| CIDH920105     | -0.887 | RADA880108 | -0.887 | BIOV880101 | -0.893 |
| PONP800107     | -0.905 | WERD780101 | -0.912 | NISK860101 | -0.923 |
| MIYS850101     | -0.940 |            |        |            |        |

I  A/L    R/K    N/M    D/F    C/P    Q/S    E/T    G/W    H/Y    I/V
   0.934  0.962  0.986  0.994  0.900  1.047  0.986  1.015  0.882  0.766
   0.825  1.040  0.804  0.773  1.047  1.056  1.008  0.848  0.931  0.825
//
H RACS770102
D Average reduced distance for side chain (Rackovsky-Scheraga, 1977)
R 2004126b
A Rackovsky, S. and Scheraga, H.A.
T Hydrophobicity, hydrophilicity, and the radial and orientational
  distributions of residues in native proteins
J Proc. Natl. Acad. Sci. USA 74, 5248-5251 (1977)
* (Gly 0.080)

|            |        |            |        |            |        |
|------------|--------|------------|--------|------------|--------|
| C MEIH800102 | 0.987 | MEIH800101 | 0.963  | RACS770101 | 0.946  |
| GUYH850101 | 0.934  | KRIW790102 | 0.895  | RACS770103 | 0.889  |
| KRIW790101 | 0.871  | KARP850102 | 0.852  | OOBM770101 | 0.838  |
| PARJ860101 | 0.834  | OOBM770103 | 0.828  | ROSM880102 | 0.824  |
| JANJ780103 | 0.823  | CHOC760102 | 0.809  | WOLS870101 | 0.802  |
| DESM900101 | -0.801 | NISK800101 | -0.818 | CIDH920105 | -0.830 |
| CIDH920103 | -0.834 | FAUJ830101 | -0.843 | KYTJ820101 | -0.844 |
| JANJ790102 | -0.851 | CIDH920104 | -0.854 | EISD860103 | -0.858 |
| PLIV810101 | -0.859 | PONP800103 | -0.860 | PONP800102 | -0.864 |
| MANP780101 | -0.865 | DESM900102 | -0.867 | JANJ780102 | -0.869 |
| PONP800101 | -0.870 | CHOC760103 | -0.875 | PONP800107 | -0.878 |
| WERD780101 | -0.906 | NISK860101 | -0.913 | MEIH800103 | -0.918 |
| BIOV880102 | -0.932 | BIOV880101 | -0.937 | ROSG850102 | -0.940 |
| RADA880108 | -0.942 | MIYS850101 | -0.943 |            |        |

I  A/L    R/K    N/M    D/F    C/P    Q/S    E/T    G/W    H/Y    I/V
   0.941  1.112  1.038  1.071  0.866  1.150  1.100  1.055  0.911  0.742
   0.798  1.232  0.781  0.723  1.093  1.082  1.043  0.867  1.050  0.817
//
H RACS770103
D Side chain orientational preference (Rackovsky-Scheraga, 1977)
R 2004126b
A Rackovsky, S. and Scheraga, H.A.
T Hydrophobicity, hydrophilicity, and the radial and orientational
  distributions of residues in native proteins
J Proc. Natl. Acad. Sci. USA 74, 5248-5251 (1977)
* (Gly !)
* (Ratio of the numbers of occurrences in two orientations)

|            |        |            |        |            |        |
|------------|--------|------------|--------|------------|--------|
| C MEIH800102 | 0.903 | RACS770102 | 0.889  | KRIW790102 | 0.889  |
| OOBM770101 | 0.871  | JANJ780103 | 0.847  | MEIH800101 | 0.837  |
| OOBM770103 | 0.823  | GUYH850101 | 0.816  | RACS770101 | 0.801  |
| PONP800102 | -0.809 | MIYS850101 | -0.818 | PONP800103 | -0.819 |
| JANJ780102 | -0.828 | JANJ790102 | -0.834 | DESM900101 | -0.837 |
| NISK860101 | -0.837 | WERD780101 | -0.846 | WARP780101 | -0.848 |
| BIOV880101 | -0.856 | RADA880108 | -0.863 | DESM900102 | -0.868 |
| ROSG850102 | -0.901 | BIOV880102 | -0.906 | MEIH800103 | -0.919 |

I  A/L    R/K    N/M    D/F    C/P    Q/S    E/T    G/W    H/Y    I/V
   1.16   1.72   1.97   2.66   0.50   3.87   2.40   1.63   0.86   0.57
   0.51   3.90   0.40   0.43   2.04   1.61   1.48   0.75   1.72   0.59
//
H RACS820101
D Average relative fractional occurrence in A0(i) (Rackovsky-Scheraga, 1982)
R 0903736
A Rackovsky, S. and Scheraga, H.A.

T Differential geometry and polymer conformation. 4. Conformational and
  nucleation properties of individual amino acids
J Macromolecules 15, 1340-1346 (1982)
C
I   A/L    R/K    N/M    D/F    C/P    Q/S    E/T    G/W    H/Y    I/V
    0.85   2.02   0.88   1.50   0.90   1.71   1.79   1.54   1.59   0.67
    1.03   0.88   1.17   0.85   1.47   1.50   1.96   0.83   1.34   0.89
//
H RACS820102
D Average relative fractional occurrence in AR(i) (Rackovsky-Scheraga, 1982)
R 0903736
A Rackovsky, S. and Scheraga, H.A.
T Differential geometry and polymer conformation. 4. Conformational and
  nucleation properties of individual amino acids
J Macromolecules 15, 1340-1346 (1982)
C
I   A/L    R/K    N/M    D/F    C/P    Q/S    E/T    G/W    H/Y    I/V
    1.58   1.14   0.77   0.98   1.04   1.24   1.49   0.66   0.99   1.09
    1.21   1.27   1.41   1.00   1.46   1.05   0.87   1.23   0.68   0.88
//
H RACS820103
D Average relative fractional occurrence in AL(i) (Rackovsky-Scheraga, 1982)
R 0903736
A Rackovsky, S. and Scheraga, H.A.
T Differential geometry and polymer conformation. 4. Conformational and
  nucleation properties of individual amino acids
J Macromolecules 15, 1340-1346 (1982)
C
I   A/L    R/K    N/M    D/F    C/P    Q/S    E/T    G/W    H/Y    I/V
    0.82   2.60   2.07   2.64   0.00   0.00   2.62   1.63   0.00   2.32
    0.00   2.86   0.00   0.00   0.00   1.23   2.48   0.00   1.90   1.62
//
H RACS820104
D Average relative fractional occurrence in EL(i) (Rackovsky-Scheraga, 1982)
R 0903736
A Rackovsky, S. and Scheraga, H.A.
T Differential geometry and polymer conformation. 4. Conformational and
  nucleation properties of individual amino acids
J Macromolecules 15, 1340-1346 (1982)
C
I   A/L    R/K    N/M    D/F    C/P    Q/S    E/T    G/W    H/Y    I/V
    0.78   1.75   1.32   1.25   3.14   0.93   0.94   1.13   1.03   1.26
    0.91   0.85   0.41   1.07   1.73   1.31   1.57   0.98   1.31   1.11
//
H RACS820105
D Average relative fractional occurrence in E0(i) (Rackovsky-Scheraga, 1982)
R 0903736
A Rackovsky, S. and Scheraga, H.A.
T Differential geometry and polymer conformation. 4. Conformational and
  nucleation properties of individual amino acids
J Macromolecules 15, 1340-1346 (1982)
C NAKH900102   -0.839
I   A/L    R/K    N/M    D/F    C/P    Q/S    E/T    G/W    H/Y    I/V
    0.88   0.99   1.02   1.16   1.14   0.93   1.01   0.70   1.87   1.61
    1.09   0.83   1.71   1.52   0.87   1.14   0.96   1.96   1.68   1.56
//
H RACS820106
D Average relative fractional occurrence in ER(i) (Rackovsky-Scheraga, 1982)
R 0903736
A Rackovsky, S. and Scheraga, H.A.
T Differential geometry and polymer conformation. 4. Conformational and
  nucleation properties of individual amino acids
J Macromolecules 15, 1340-1346 (1982)

```
C ISOY800108    0.831
I  A/L     R/K    N/M    D/F    C/P    Q/S    E/T    G/W    H/Y    I/V
   0.30    0.90   2.73   1.26   0.72   0.97   1.33   3.09   1.33   0.45
   0.96    0.71   1.89   1.20   0.83   1.16   0.97   1.58   0.86   0.64
//
H RACS820107
D Average relative fractional occurrence in A0(i-1) (Rackovsky-Scheraga,
1982)
R 0903736
A Rackovsky, S. and Scheraga, H.A.
T Differential geometry and polymer conformation. 4.  Conformational and
  nucleation properties of individual amino acids
J Macromolecules 15, 1340-1346 (1982)
C
I  A/L     R/K    N/M    D/F    C/P    Q/S    E/T    G/W    H/Y    I/V
   0.40    1.20   1.24   1.59   2.98   0.50   1.26   1.89   2.71   1.31
   0.57    0.87   0.00   1.27   0.38   0.92   1.38   1.53   1.79   0.95
//
H RACS820108
D Average relative fractional occurrence in AR(i-1) (Rackovsky-Scheraga,
1982)
R 0903736
A Rackovsky, S. and Scheraga, H.A.
T Differential geometry and polymer conformation. 4.  Conformational and
  nucleation properties of individual amino acids
J Macromolecules 15, 1340-1346 (1982)
C KANM800101    0.914    PRAM900102    0.904    LEVM780101    0.904
  ISOY800101    0.904    ROBB760101    0.889    LEVM780104    0.889
  PALJ810102    0.881    GEIM800101    0.880    PALJ810101    0.872
  CHOP780201    0.868    QIAN880106    0.866    MAXF760101    0.860
  KANM800103    0.858    ROBB760103    0.851    GEIM800104    0.851
  TANS770101    0.845    CRAJ730101    0.839    QIAN880107    0.831
  QIAN880108    0.820    QIAN880105    0.820    NAGK730101    0.820
  BURA740101    0.809
I  A/L     R/K    N/M    D/F    C/P    Q/S    E/T    G/W    H/Y    I/V
   1.48    1.02   0.99   1.19   0.86   1.42   1.43   0.46   1.27   1.12
   1.33    1.36   1.41   1.30   0.25   0.89   0.81   1.27   0.91   0.93
//
H RACS820109
D Average relative fractional occurrence in AL(i-1) (Rackovsky-Scheraga,
1982)
R 0903736
A Rackovsky, S. and Scheraga, H.A.
T Differential geometry and polymer conformation. 4.  Conformational and
  nucleation properties of individual amino acids
J Macromolecules 15, 1340-1346 (1982)
C ISOY800108    0.848    MAXF760104    0.844
I  A/L     R/K    N/M    D/F    C/P    Q/S    E/T    G/W    H/Y    I/V
   0.00    0.00   4.14   2.15   0.00   0.00   0.00   6.49   0.00   0.00
   0.00    0.00   0.00   2.11   1.99   0.00   1.24   0.00   1.90   0.00
//
H RACS820110
D Average relative fractional occurrence in EL(i-1) (Rackovsky-Scheraga,
1982)
R 0903736
A Rackovsky, S. and Scheraga, H.A.
T Differential geometry and polymer conformation. 4.  Conformational and
  nucleation properties of individual amino acids
J Macromolecules 15, 1340-1346 (1982)
C ROBB760104    -0.818
I  A/L     R/K    N/M    D/F    C/P    Q/S    E/T    G/W    H/Y    I/V
   1.02    1.00   1.31   1.76   1.05   1.05   0.83   2.39   0.40   0.83
   1.06    0.94   1.33   0.41   2.73   1.18   0.77   1.22   1.09   0.88
//
H RACS820111
D Average relative fractional occurrence in E0(i-1) (Rackovsky-Scheraga,
1982)
R 0903736
```

A Rackovsky, S. and Scheraga, H.A.
T Differential geometry and polymer conformation. 4. Conformational and nucleation properties of individual amino acids
J Macromolecules 15, 1340-1346 (1982)
C TANS770103    0.841   MAXF760102    0.815   ROBB760105    0.803
I    A/L     R/K     N/M     D/F     C/P     Q/S     E/T     G/W     H/Y     I/V
    0.93    1.52    0.92    0.60    1.08    0.94    0.73    0.78    1.08    1.74
    1.03    1.00    1.31    1.51    1.37    0.97    1.38    1.12    1.65    1.70
//
H RACS820112
D Average relative fractional occurrence in ER(i-1) (Rackovsky-Scheraga, 1982)
R 0903736
A Rackovsky, S. and Scheraga, H.A.
T Differential geometry and polymer conformation. 4. Conformational and nucleation properties of individual amino acids
J Macromolecules 15, 1340-1346 (1982)
C
I    A/L     R/K     N/M     D/F     C/P     Q/S     E/T     G/W     H/Y     I/V
    0.99    1.19    1.15    1.18    2.32    1.52    1.36    1.40    1.06    0.81
    1.26    0.91    1.00    1.25    0.00    1.50    1.18    1.33    1.09    1.01
//
H RACS820113
D Value of theta(i) (Rackovsky-Scheraga, 1982)
R 0903736
A Rackovsky, S. and Scheraga, H.A.
T Differential geometry and polymer conformation. 4. Conformational and nucleation properties of individual amino acids
J Macromolecules 15, 1340-1346 (1982)
C
I    A/L     R/K     N/M     D/F     C/P     Q/S     E/T     G/W     H/Y     I/V
   17.05   21.25   34.81   19.27   28.84   15.42   20.12   38.14   23.07   16.66
   10.89   16.46   20.61   16.26   23.94   19.95   18.92   23.36   26.49   17.06
//
H RACS820114
D Value of theta(i-1) (Rackovsky-Scheraga, 1982)
R 0903736
A Rackovsky, S. and Scheraga, H.A.
T Differential geometry and polymer conformation. 4. Conformational and nucleation properties of individual amino acids
J Macromolecules 15, 1340-1346 (1982)
C ROBB760103   -0.806
I    A/L     R/K     N/M     D/F     C/P     Q/S     E/T     G/W     H/Y     I/V
   14.53   17.82   13.59   19.78   30.57   22.18   18.19   37.16   22.63   20.28
   14.30   14.07   20.61   19.61   52.63   18.56   21.09   19.78   26.36   21.87
//
H RADA880101
D Transfer free energy from chx to wat (Radzicka-Wolfenden, 1988)
R 1405051b
A Radzicka, A. and Wolfenden, R.
T Comparing the polarities of the amino acids: Side-chain distribution coefficients between the vapor phase, cyclohexane, 1-octanol, and neutral aqueous solution
J Biochemistry 27, 1664-1670 (1988)
* (Pro missing)
C EISD840101    0.968   WOLR810101    0.939   RADA880104    0.901
  EISD860101    0.891   KYTJ820101    0.884   RADA880107    0.881
  FAUJ830101    0.873   JANJ780102    0.855   CHOC760103    0.853
  EISD860103    0.850   JANJ790102    0.839   DESM900102    0.828
  RADA880108    0.807   YUTK870101    0.803   WOEC730101   -0.812
  CHOC760102   -0.814   GUYH850101   -0.815   JANJ780103   -0.817
  WOLS870101   -0.823   HOPT810101   -0.829   FAUJ880110   -0.838
  LEVM760101   -0.838   JANJ780101   -0.844   GRAR740102   -0.861
  OOBM770101   -0.863   FAUJ880109   -0.873   ROSM880102   -0.917
  VHEG790101   -0.925   PRAM900101   -0.932   ROSM880101   -0.978
I    A/L     R/K     N/M     D/F     C/P     Q/S     E/T     G/W     H/Y     I/V
    1.81  -14.92   -6.64   -8.72    1.28   -5.54   -6.81    0.94   -4.66    4.92
    4.92   -5.55    2.35    2.98    0.    -3.40   -2.57    2.33   -0.14    4.04

```
//
H RADA880102
D Transfer free energy from oct to wat (Radzicka-Wolfenden, 1988)
R 1405051b
A Radzicka, A. and Wolfenden, R.
T Comparing the polarities of the amino acids: Side-chain distribution
    coefficients between the vapor phase, cyclohexane, 1-octanol, and
    neutral aqueous solution
J Biochemistry 27, 1664-1670 (1988)
* (Pro Cys Asp missing)
C NOZY710101    0.917   EISD860101    0.912   MEEJ800102    0.900
  CIDH920102    0.862   CIDH920105    0.861   ZIMJ680105    0.851
  FAUJ830101    0.846   PLIV810101    0.845   VENT840101    0.826
  MIYS850101    0.824   SWER830101    0.820   CIDH920103    0.819
  CIDH920104    0.817   MEEJ810102    0.813   BROC820101    0.811
  MEIH800101   -0.816   VHEG790101   -0.818   LEVM760101   -0.838
  BULH740101   -0.856   HOPT810101   -0.859   WOLS870101   -0.873
  PARJ860101   -0.883
I    A/L      R/K      N/M      D/F     C/P      Q/S      E/T      G/W      H/Y      I/V
     0.52    -1.32    -0.01    0.      0.      -0.07    -0.79    0.       0.95     2.04
     1.76     0.08     1.32    2.09    0.       0.04     0.27    2.51     1.63     1.18
//
H RADA880103
D Transfer free energy from vap to chx (Radzicka-Wolfenden, 1988)
R 1405051b
A Radzicka, A. and Wolfenden, R.
T Comparing the polarities of the amino acids: Side-chain distribution
    coefficients between the vapor phase, cyclohexane, 1-octanol, and
    neutral aqueous solution
J Biochemistry 27, 1664-1670 (1988)
* (Pro missing)
C OOBM770105    0.912   OOBM770104    0.873   FAUJ880104   -0.806
  CHAM830105   -0.808   HUTJ700102   -0.812   ROSG850101   -0.814
  FAUJ880106   -0.823   MCMT640101   -0.833   GOLD730102   -0.864
  BIGC670101   -0.865   KRIW790103   -0.871   GRAR740103   -0.881
  CHOC750101   -0.892   LEVM760105   -0.893   RADA880106   -0.895
  CHAM830106   -0.901   CHAM820101   -0.912   LEVM760102   -0.913
  FAUJ880103   -0.923   CHOC760101   -0.924   FASG760101   -0.954
I    A/L      R/K      N/M      D/F     C/P      Q/S      E/T      G/W      H/Y      I/V
     0.13    -5.      -3.04   -2.23   -2.52   -3.84   -3.43    1.45    -5.61   -2.77
    -2.64   -3.97    -3.83   -3.74    0.     -1.66   -2.31   -8.21    -5.97   -2.05
//
H RADA880104
D Transfer free energy from chx to oct (Radzicka-Wolfenden, 1988)
R 1405051b
A Radzicka, A. and Wolfenden, R.
T Comparing the polarities of the amino acids: Side-chain distribution
    coefficients between the vapor phase, cyclohexane, 1-octanol, and
    neutral aqueous solution
J Biochemistry 27, 1664-1670 (1988)
* (Pro Cys Asp missing)
C RADA880105    0.918   WOLR810101    0.910   EISD840101    0.908
  RADA880101    0.901   RADA880107    0.897   CHOC760103    0.821
  KYTJ820101    0.819   PRAM900101   -0.803   JANJ780101   -0.825
  CHOC760102   -0.830   ROSM880102   -0.855   ROSM880101   -0.863
  FAUJ880109   -0.926
I    A/L      R/K      N/M      D/F     C/P      Q/S      E/T      G/W      H/Y      I/V
     1.29   -13.60   -6.63    0.      0.     -5.47   -6.02    0.94    -5.61    2.88
     3.16   -5.63     1.03    0.89    0.     -3.44   -2.84   -0.18    -1.77    2.86
//
H RADA880105
D Transfer free energy from vap to oct (Radzicka-Wolfenden, 1988)
R 1405051b
A Radzicka, A. and Wolfenden, R.
T Comparing the polarities of the amino acids: Side-chain distribution
    coefficients between the vapor phase, cyclohexane, 1-octanol, and
    neutral aqueous solution
J Biochemistry 27, 1664-1670 (1988)
```

```
* (Pro Cys Asp missing)
C RADA880104    0.918  WOLR810101    0.875  RADA880107    0.846
  FAUJ880109   -0.889
I    A/L     R/K     N/M     D/F     C/P     Q/S     E/T     G/W     H/Y     I/V
    1.42  -18.60   -9.67    0.      0.     -9.31   -9.45    2.39  -11.22    0.11
    0.52   -9.60   -2.80   -2.85    0.     -5.10   -5.15   -8.39   -7.74    0.81
//
H RADA880106
D Accessible surface area (Radzicka-Wolfenden, 1988)
R 1405051b
A Radzicka, A. and Wolfenden, R.
T Comparing the polarities of the amino acids: Side-chain distribution
  coefficients between the vapor phase, cyclohexane, 1-octanol, and
  neutral aqueous solution
J Biochemistry 27, 1664-1670 (1988)
* (Pro missing)
C CHAM830106    0.922  GRAR740103    0.920  KRIW790103    0.883
  CHOC760101    0.875  LEVM760105    0.871  LEVM760102    0.871
  FASG760101    0.870  FAUJ880103    0.869  CHOC750101    0.867
  BIGC670101    0.856  GOLD730102    0.854  CHAM820101    0.847
  ROSG850101    0.814  RADA880103   -0.895
I    A/L     R/K     N/M     D/F     C/P     Q/S     E/T     G/W     H/Y     I/V
    93.7   250.4   146.3   142.6   135.2   177.7   182.9    52.6   188.1   182.2
   173.7   215.2   197.6   228.6    0.     109.5   142.1   271.6   239.9   157.2
//
H RADA880107
D Energy transfer from out to in(95%buried) (Radzicka-Wolfenden, 1988)
R 1405051b
A Radzicka, A. and Wolfenden, R.
T Comparing the polarities of the amino acids: Side-chain distribution
  coefficients between the vapor phase, cyclohexane, 1-octanol, and
  neutral aqueous solution
J Biochemistry 27, 1664-1670 (1988)
* (Pro missing)
C EISD840101    0.927  JANJ790102    0.906  RADA880104    0.897
  WOLR810101    0.890  RADA880101    0.881  CHOC760103    0.870
  JANJ780102    0.856  RADA880105    0.846  KYTJ820101    0.828
  EISD860103    0.812  EISD860102   -0.837  OOBM770101   -0.854
  JANJ780103   -0.856  PRAM900101   -0.865  ROSM880101   -0.867
  ROSM880102   -0.894  JANJ780101   -0.917  CHOC760102   -0.925
  FAUJ880109   -0.957
I    A/L     R/K     N/M     D/F     C/P     Q/S     E/T     G/W     H/Y     I/V
   -0.29   -2.71   -1.18   -1.02    0.     -1.53   -0.90   -0.34   -0.94    0.24
   -0.12   -2.05   -0.24    0.      0.     -0.75   -0.71   -0.59   -1.02    0.09
//
H RADA880108
D Mean polarity (Radzicka-Wolfenden, 1988)
R 1405051b
A Radzicka, A. and Wolfenden, R.
T Comparing the polarities of the amino acids: Side-chain distribution
  coefficients between the vapor phase, cyclohexane, 1-octanol, and
  neutral aqueous solution
J Biochemistry 27, 1664-1670 (1988)
* (Pro missing)
C BIOV880101    0.981  ROSG850102    0.967  NISK860101    0.950
  MIYS850101    0.950  BIOV880102    0.942  PONP800102    0.938
  PONP800103    0.934  PONP800101    0.934  FAUJ830101    0.932
  WERD780101    0.930  MEIH800103    0.916  CIDH920104    0.914
  PLIV810101    0.906  NISK800101    0.902  MANP780101    0.900
  CIDH920105    0.898  CIDH920103    0.891  PONP800108    0.889
  DESM900102    0.881  EISD860103    0.873  JANJ780102    0.869
  ROBB790101    0.867  CIDH920101    0.858  JANJ790102    0.853
  EISD860101    0.844  KYTJ820101    0.842  PONP800106    0.835
  CIDH920102    0.833  CHOC760103    0.830  SWER830101    0.826
  JANJ790101    0.824  EISD840101    0.817  DESM900101    0.812
  RADA880101    0.807  MEEJ810101    0.804  PONP800107    0.800
  KARP850101   -0.804  JANJ780103   -0.805  LEVM760101   -0.824
  WOEC730101   -0.825  HOPT810101   -0.831  ROSM880101   -0.831
```

```
      WOLS870101    -0.840    KRIW710101    -0.847    KRIW790102    -0.856
      ROSM880102    -0.861    RACS770103    -0.863    KRIW790102    -0.864
      PALAU860101   -0.865    OOBM770103    -0.878    KARP850102    -0.879
      RACS770101    -0.887    KRIW790101    -0.897    GRAR740102    -0.899
      MEIH800101    -0.940    RACS770102    -0.942    GUYH850101    -0.948
      MEIH800102    -0.953
I     A/L    R/K    N/M    D/F    C/P    Q/S    E/T    G/W    H/Y    I/V
     -0.06  -0.84  -0.48  -0.80   1.36  -0.73  -0.77  -0.41   0.49   1.31
      1.21  -1.18   1.27   1.27   0.   -0.50  -0.27   0.88   0.33   1.09
//
H RICJ880101
D Relative preference value at N" (Richardson-Richardson, 1988)
R 1408116
A Richardson, J.S. and Richardson, D.C.
T Amino acid preferences for specific locations at the ends of alpha
  helices
J Science 240, 1648-1652 (1988)
C RICJ880102    1.000
I     A/L    R/K    N/M    D/F    C/P    Q/S    E/T    G/W    H/Y    I/V
      0.7    0.4    1.2    1.4    0.6    1.     1.     1.6    1.2    0.9
      0.9    1.     0.3    1.2    0.7    1.6    0.3    1.1    1.9    0.7
//
H RICJ880102
D Relative preference value at N' (Richardson-Richardson, 1988)
R 1408116
A Richardson, J.S. and Richardson, D.C.
T Amino acid preferences for specific locations at the ends of alpha
  helices
J Science 240, 1648-1652 (1988)
C RICJ880101    1.000
I     A/L    R/K    N/M    D/F    C/P    Q/S    E/T    G/W    H/Y    I/V
      0.7    0.4    1.2    1.4    0.6    1.     1.     1.6    1.2    0.9
      0.9    1.     0.3    1.2    0.7    1.6    0.3    1.1    1.9    0.7
//
H RICJ880103
D Relative preference value at N-cap (Richardson-Richardson, 1988)
R 1408116
A Richardson, J.S. and Richardson, D.C.
T Amino acid preferences for specific locations at the ends of alpha
  helices
J Science 240, 1648-1652 (1988)
C
I     A/L    R/K    N/M    D/F    C/P    Q/S    E/T    G/W    H/Y    I/V
      0.5    0.4    3.5    2.1    0.6    0.4    0.4    1.8    1.1    0.2
      0.2    0.7    0.8    0.2    0.8    2.3    1.6    0.3    0.8    0.1
//
H RICJ880104
D Relative preference value at N1 (Richardson-Richardson, 1988)
R 1408116
A Richardson, J.S. and Richardson, D.C.
T Amino acid preferences for specific locations at the ends of alpha
  helices
J Science 240, 1648-1652 (1988)
C
I     A/L    R/K    N/M    D/F    C/P    Q/S    E/T    G/W    H/Y    I/V
      1.2    0.7    0.7    0.8    0.8    0.7    2.2    0.3    0.7    0.9
      0.9    0.6    0.3    0.5    2.6    0.7    0.8    2.1    1.8    1.1
//
H RICJ880105
D Relative preference value at N2 (Richardson-Richardson, 1988)
R 1408116
A Richardson, J.S. and Richardson, D.C.
T Amino acid preferences for specific locations at the ends of alpha
  helices
J Science 240, 1648-1652 (1988)
C
I     A/L    R/K    N/M    D/F    C/P    Q/S    E/T    G/W    H/Y    I/V
      1.6    0.9    0.7    2.6    1.2    0.8    2.     0.9    0.7    0.7
```

```
      0.3     1.     1.    0.9    0.5    0.8    0.7    1.7    0.4    0.6
//
H RICJ880106
D Relative preference value at N3 (Richardson-Richardson, 1988)
R 1408116
A Richardson, J.S. and Richardson, D.C.
T Amino acid preferences for specific locations at the ends of alpha
  helices
J Science 240, 1648-1652 (1988)
C FAUJ880112    0.849
I    A/L    R/K    N/M    D/F    C/P    Q/S    E/T    G/W    H/Y    I/V
     1.     0.4    0.7    2.2    0.6    1.5    3.3    0.6    0.7    0.4
     0.6    0.8    1.     0.6    0.4    0.4    1.     1.4    1.2    1.1
//
H RICJ880107
D Relative preference value at N4 (Richardson-Richardson, 1988)
R 1408116
A Richardson, J.S. and Richardson, D.C.
T Amino acid preferences for specific locations at the ends of alpha
  helices
J Science 240, 1648-1652 (1988)
C CHOP780210   -0.818
I    A/L    R/K    N/M    D/F    C/P    Q/S    E/T    G/W    H/Y    I/V
     1.1    1.5    0.     0.3    1.1    1.3    0.5    0.4    1.5    1.1
     2.6    0.8    1.7    1.9    0.1    0.4    0.5    3.1    0.6    1.5
//
H RICJ880108
D Relative preference value at N5 (Richardson-Richardson, 1988)
R 1408116
A Richardson, J.S. and Richardson, D.C.
T Amino acid preferences for specific locations at the ends of alpha
  helices
J Science 240, 1648-1652 (1988)
C
I    A/L    R/K    N/M    D/F    C/P    Q/S    E/T    G/W    H/Y    I/V
     1.4    1.2    1.2    0.6    1.6    1.4    0.9    0.6    0.9    0.9
     1.1    1.9    1.7    1.     0.3    1.1    0.6    1.4    0.2    0.8
//
H RICJ880109
D Relative preference value at Mid (Richardson-Richardson, 1988)
R 1408116
A Richardson, J.S. and Richardson, D.C.
T Amino acid preferences for specific locations at the ends of alpha
  helices
J Science 240, 1648-1652 (1988)
C QIAN880106    0.834   ROBB760103    0.831   KANM800103    0.829
  CHAM830101   -0.826
I    A/L    R/K    N/M    D/F    C/P    Q/S    E/T    G/W    H/Y    I/V
     1.8    1.3    0.9    1.     0.7    1.3    0.8    0.5    1.     1.2
     1.2    1.1    1.5    1.3    0.3    0.6    1.     1.5    0.8    1.2
//
H RICJ880110
D Relative preference value at C5 (Richardson-Richardson, 1988)
R 1408116
A Richardson, J.S. and Richardson, D.C.
T Amino acid preferences for specific locations at the ends of alpha
  helices
J Science 240, 1648-1652 (1988)
C
I    A/L    R/K    N/M    D/F    C/P    Q/S    E/T    G/W    H/Y    I/V
     1.8    1.     0.6    0.7    0.     1.     1.1    0.5    2.4    1.3
     1.2    1.4    2.7    1.9    0.3    0.5    0.5    1.1    1.3    0.4
//
H RICJ880111
D Relative preference value at C4 (Richardson-Richardson, 1988)
R 1408116
A Richardson, J.S. and Richardson, D.C.
T Amino acid preferences for specific locations at the ends of alpha
```

```
        helices
      J Science 240, 1648-1652 (1988)
      C MEIH800101  -0.802   CHOP780210  -0.804   BHAR880101  -0.813
        RACS770101  -0.846
      I  A/L    R/K    N/M    D/F    C/P    Q/S    E/T    G/W    H/Y    I/V
         1.3    0.8    0.6    0.5    0.7    0.2    0.7    0.5    1.9    1.6
         1.4    1.     2.8    2.9    0.     0.5    0.6    2.1    0.8    1.4
      //
      H RICJ880112
      D Relative preference value at C3 (Richardson-Richardson, 1988)
      R 1408116
      A Richardson, J.S. and Richardson, D.C.
      T Amino acid preferences for specific locations at the ends of alpha
        helices
      J Science 240, 1648-1652 (1988)
      C
      I  A/L    R/K    N/M    D/F    C/P    Q/S    E/T    G/W    H/Y    I/V
         0.7    0.8    0.8    0.6    0.2    1.3    1.6    0.1    1.1    1.4
         1.9    2.2    1.     1.8    0.     0.6    0.7    0.4    1.1    1.3
      //
      H RICJ880113
      D Relative preference value at C2 (Richardson-Richardson, 1988)
      R 1408116
      A Richardson, J.S. and Richardson, D.C.
      T Amino acid preferences for specific locations at the ends of alpha
        helices
      J Science 240, 1648-1652 (1988)
      C
      I  A/L    R/K    N/M    D/F    C/P    Q/S    E/T    G/W    H/Y    I/V
         1.4    2.1    0.9    0.7    1.2    1.6    1.7    0.2    1.8    0.4
         0.8    1.9    1.3    0.3    0.2    1.6    0.9    0.4    0.3    0.7
      //
      H RICJ880114
      D Relative preference value at C1 (Richardson-Richardson, 1988)
      R 1408116
      A Richardson, J.S. and Richardson, D.C.
      T Amino acid preferences for specific locations at the ends of alpha
        helices
      J Science 240, 1648-1652 (1988)
      C
      I  A/L    R/K    N/M    D/F    C/P    Q/S    E/T    G/W    H/Y    I/V
         1.1    1.     1.2    0.4    1.6    2.1    0.8    0.2    3.4    0.7
         0.7    2.     1.     0.7    0.     1.7    1.     0.     1.2    0.7
      //
      H RICJ880115
      D Relative preference value at C-cap (Richardson-Richardson, 1988)
      R 1408116
      A Richardson, J.S. and Richardson, D.C.
      T Amino acid preferences for specific locations at the ends of alpha
        helices
      J Science 240, 1648-1652 (1988)
      C MAXF760104   0.919   ISOY800108   0.889   TANS770107   0.807
        MAXF760105   0.802   LEVM760103  -0.829
      I  A/L    R/K    N/M    D/F    C/P    Q/S    E/T    G/W    H/Y    I/V
         0.8    0.9    1.6    0.7    0.4    0.9    0.3    3.9    1.3    0.7
         0.7    1.3    0.8    0.5    0.7    0.8    0.3    0.     0.8    0.2
      //
      H RICJ880116
      D Relative preference value at C' (Richardson-Richardson, 1988)
      R 1408116
      A Richardson, J.S. and Richardson, D.C.
      T Amino acid preferences for specific locations at the ends of alpha
        helices
      J Science 240, 1648-1652 (1988)
      C
      I  A/L    -R/K   N/M    D/F    C/P    Q/S    E/T    G/W    H/Y    I/V
         1.     1.4    0.9    1.4    0.8    1.4    0.8    1.2    1.2    1.1
         0.9    1.2    0.8    0.1    1.9    0.7    0.8    0.4    0.9    0.6
```

```
//
H RICJ880117
D Relative preference value at C" (Richardson-Richardson, 1988)
R 1408116
A Richardson, J.S. and Richardson, D.C.
T Amino acid preferences for specific locations at the ends of alpha
  helices
J Science 240, 1648-1652 (1988)
C
I   A/L     R/K     N/M     D/F     C/P     Q/S     E/T     G/W     H/Y     I/V
    0.7     1.1     1.5     1.4     0.4     1.1     0.7     0.6     1.      0.7
    0.5     1.3     0.      1.2     1.5     0.9     2.1     2.7     0.5     1.
//
H ROBB760101
D Information measure for alpha-helix (Robson-Suzuki, 1976)
R
A Robson, B. and Suzuki, E.
T Conformational properties of amino acid residues in globular proteins
J J. Mol. Biol. 107, 327-356 (1976)
C CHOP780201    0.969   ISOY800101    0.957   MAXF760101    0.956
  TANS770101    0.948   PALJ810102    0.946   KANM800101    0.945
  PRAM900102    0.916   LEVM780101    0.916   PALJ810101    0.914
  BURA740101    0.912   LEVM780104    0.911   NAGK730101    0.910
  QIAN880106    0.904   GEIM800101    0.897   RACS820108    0.889
  KANM800103    0.886   CRAJ730101    0.875   QIAN880105    0.874
  QIAN880107    0.867   GEIM800104    0.855   ROBB760103    0.807
  PALJ810109    0.805   CHAM830101   -0.828   NAGK730103   -0.861
I   A/L     R/K     N/M     D/F     C/P     Q/S     E/T     G/W     H/Y     I/V
    6.5    -0.9    -5.1     0.5    -1.3     1.0     7.8    -8.6     1.2     0.6
    3.2     2.3     5.3     1.6    -7.7    -3.9    -2.6     1.2    -4.5     1.4
//
H ROBB760102
D Information measure for N-terminal helix (Robson-Suzuki, 1976)
R
A Robson, B. and Suzuki, E.
T Conformational properties of amino acid residues in globular proteins
J J. Mol. Biol. 107, 327-356 (1976)
C CHOP780204    0.911
I   A/L     R/K     N/M     D/F     C/P     Q/S     E/T     G/W     H/Y     I/V
    2.3    -5.2     0.3     7.4     0.8    -0.7    10.3    -5.2    -2.8    -4.0
   -2.1    -4.1    -3.5    -1.1     8.1    -3.5     2.3    -0.9    -3.7    -4.4
//
H ROBB760103
D Information measure for middle helix (Robson-Suzuki, 1976)
R
A Robson, B. and Suzuki, E.
T Conformational properties of amino acid residues in globular proteins
J J. Mol. Biol. 107, 327-356 (1976)
C QIAN880108    0.914   PTIO830101    0.903   QIAN880107    0.889
  KANM800103    0.887   QIAN880109    0.868   QIAN880106    0.854
  BEGF750101    0.852   RACS820108    0.851   ISOY800101    0.841
  RICJ880109    0.831   QIAN880105    0.811   ROBB760101    0.807
  QIAN880110    0.807   CHOP780201    0.806   FAUJ880113    0.802
  GEIM800108   -0.802   RACS820114   -0.806   QIAN880133   -0.807
  QIAN880132   -0.827   ISOY800104   -0.830   QIAN880135   -0.834
  PRAM900104   -0.840   CHOP780216   -0.841   GEIM800111   -0.843
  LEVM780103   -0.843   QIAN880134   -0.855   CHAM830101   -0.878
I   A/L     R/K     N/M     D/F     C/P     Q/S     E/T     G/W     H/Y     I/V
    6.7     0.3    -6.1    -3.1    -4.9     0.6     2.2    -6.8    -1.0     3.2
    5.5     0.5     7.2     2.8   -22.8    -3.0    -4.0     4.0    -4.6     2.5
//
H ROBB760104
D Information measure for C-terminal helix (Robson-Suzuki, 1976)
R
A Robson, B. and Suzuki, E.
T Conformational properties of amino acid residues in globular proteins
J J. Mol. Biol. 107, 327-356 (1976)
C QIAN880108    0.879   QIAN880109    0.871   CHOP780205    0.841
```

```
    BUNA790101     0.823   PTIO830101     0.817   QIAN880110     0.806
    QIAN880134    -0.802   ISOY800104    -0.817   RACS820110    -0.818
    FINA910102    -0.844
I     A/L     R/K     N/M     D/F     C/P     Q/S     E/T     G/W     H/Y     I/V
      2.3     1.4    -3.3    -4.4     6.1     2.7     2.5    -8.3     5.9    -0.5
      0.1     7.3     3.5     1.6   -24.4    -1.9    -3.7    -0.9    -0.6     2.3
//
H ROBB760105
D Information measure for extended (Robson-Suzuki, 1976)
R
A Robson, B. and Suzuki, E.
T Conformational properties of amino acid residues in globular proteins
J J. Mol. Biol. 107, 327-356 (1976)
C ROBB760106     0.949   KANM800102     0.898   KANM800104     0.885
  CHOP780202     0.885   PTIO830102     0.878   GEIM800105     0.877
  TANS770103     0.871   PALJ810103     0.869   LIFS790101     0.867
  QIAN880120     0.860   QIAN880119     0.859   ISOY800102     0.847
  LEVM780105     0.842   GEIM800107     0.836   PALJ810104     0.835
  QIAN880121     0.834   PONP800102     0.828   PONP800103     0.823
  PONP800101     0.823   BURA740102     0.821   PONP800108     0.820
  NAGK730102     0.815   MANP780101     0.805   PALJ810110     0.804
  RACS820111     0.803
I     A/L     R/K     N/M     D/F     C/P     Q/S     E/T     G/W     H/Y     I/V
     -2.3     0.4    -4.1    -4.4     4.4     1.2    -5.0    -4.2    -2.5     6.7
      2.3    -3.3     2.3     2.6    -1.8    -1.7     1.3    -1.0     4.0     6.8
//
H ROBB760106
D Information measure for pleated-sheet (Robson-Suzuki, 1976)
R
A Robson, B. and Suzuki, E.
T Conformational properties of amino acid residues in globular proteins
J J. Mol. Biol. 107, 327-356 (1976)
C ROBB760105     0.949   KANM800102     0.938   CHOP780202     0.931
  QIAN880120     0.908   QIAN880121     0.907   LIFS790101     0.906
  GEIM800107     0.899   QIAN880119     0.897   PALJ810104     0.894
  NAGK730102     0.887   PALJ810103     0.886   PTIO830102     0.882
  KANM800104     0.877   LEVM780105     0.869   CRAJ730102     0.865
  GEIM800105     0.856   CHOP780208     0.846   GEIM800106     0.838
  PALJ810110     0.836   PONP800101     0.829   LIFS790103     0.827
  MANP780101     0.824   PONP800102     0.822   PONP800103     0.812
  NISK860101     0.810   BEGF750102     0.809   PONP800108     0.808
  GEIM800110    -0.819
I     A/L     R/K     N/M     D/F     C/P     Q/S     E/T     G/W     H/Y     I/V
     -2.7     0.4    -4.2    -4.4     3.7     0.8    -8.1    -3.9    -3.0     7.7
      3.7    -2.9     3.7     3.0    -6.6    -2.4     1.7     0.3     3.3     7.1
//
H ROBB760107
D Information measure for extended without H-bond (Robson-Suzuki, 1976)
R
A Robson, B. and Suzuki, E.
T Conformational properties of amino acid residues in globular proteins
J J. Mol. Biol. 107, 327-356 (1976)
C
I     A/L     R/K     N/M     D/F     C/P     Q/S     E/T     G/W     H/Y     I/V
      0.0     1.1    -2.0    -2.6     5.4     2.4     3.1    -3.4     0.8    -0.1
     -3.7    -3.1    -2.1     0.7     7.4     1.3     0.0    -3.4     4.8     2.7
//
H ROBB760108
D Information measure for turn (Robson-Suzuki, 1976)
R
A Robson, B. and Suzuki, E.
T Conformational properties of amino acid residues in globular proteins
J J. Mol. Biol. 107, 327-356 (1976)
C ROBB760113     0.994   ROBB760110     0.960   BEGF750103     0.922
  CRAJ730103     0.912   CHOP780101     0.887   PALJ810106     0.882
  TANS770110     0.839   CHAM830101     0.812   BEGF750101    -0.819
I     A/L     R/K     N/M     D/F     C/P     Q/S     E/T     G/W     H/Y     I/V
     -5.0     2.1     4.2     3.1     4.4     0.4    -4.7     5.7    -0.3    -4.6
```

```
     -5.6      1.0    -4.8    -1.8     2.6     2.6     0.3     3.4     2.9    -6.0
//
H ROBB760109
D Information measure for N-terminal turn (Robson-Suzuki, 1976)
R
A Robson, B. and Suzuki, E.
T Conformational properties of amino acid residues in globular proteins
J J. Mol. Biol. 107, 327-356 (1976)
C
I    A/L      R/K     N/M     D/F     C/P     Q/S     E/T     G/W     H/Y     I/V
    -3.3      0.0     5.4     3.9    -0.3    -0.4    -1.8    -1.2     3.0    -0.5
    -2.3     -1.2    -4.3     0.8     6.5     1.8    -0.7    -0.8     3.1    -3.5
//
H ROBB760110
D Information measure for middle turn (Robson-Suzuki, 1976)
R
A Robson, B. and Suzuki, E.
T Conformational properties of amino acid residues in globular proteins
J J. Mol. Biol. 107, 327-356 (1976)
C ROBB760108    0.960   ROBB760113   0.957   BEGF750103   0.903
  CRAJ730103    0.887   PALJ810106   0.864   CHOP780101   0.863
  TANS770110    0.805   CHAM830101   0.804
I    A/L      R/K     N/M     D/F     C/P     Q/S     E/T     G/W     H/Y     I/V
    -4.7      2.0     3.9     1.9     6.2    -2.0    -4.2     5.7    -2.6    -7.0
    -6.2      2.8    -4.8    -3.7     3.6     2.1     0.6     3.3     3.8    -6.2
//
H ROBB760111
D Information measure for C-terminal turn (Robson-Suzuki, 1976)
R
A Robson, B. and Suzuki, E.
T Conformational properties of amino acid residues in globular proteins
J J. Mol. Biol. 107, 327-356 (1976)
C CHOP780215    0.825
I    A/L      R/K     N/M     D/F     C/P     Q/S     E/T     G/W     H/Y     I/V
    -3.7      1.0    -0.6    -0.6     4.0     3.4    -4.3     5.9    -0.8    -0.5
    -2.8      1.3    -1.6     1.6    -6.0     1.5     1.2     6.5     1.3    -4.6
//
H ROBB760112
D Information measure for coil (Robson-Suzuki, 1976)
R
A Robson, B. and Suzuki, E.
T Conformational properties of amino acid residues in globular proteins
J J. Mol. Biol. 107, 327-356 (1976)
C PALJ810115    0.885   CHOP780211   0.841   QIAN880133   0.814
  ISOY800103    0.807   QIAN880132   0.800
I    A/L      R/K     N/M     D/F     C/P     Q/S     E/T     G/W     H/Y     I/V
    -2.5     -1.2     4.6     0.0    -4.7    -0.5    -4.4     4.9     1.6    -3.3
    -2.0     -0.8    -4.1    -4.1     5.8     2.5     1.7     1.2    -0.6    -3.5
//
H ROBB760113
D Information measure for loop (Robson-Suzuki, 1976)
R
A Robson, B. and Suzuki, E.
T Conformational properties of amino acid residues in globular proteins
J J. Mol. Biol. 107, 327-356 (1976)
C ROBB760108   0.994   ROBB760110   0.957   BEGF750103   0.924
  CRAJ730103   0.916   CHOP780101   0.907   PALJ810106   0.895
  TANS770110   0.853   CHAM830101   0.841   NAGK730103   0.811
  CHOP780201  -0.811   BEGF750101  -0.826
I    A/L      R/K     N/M     D/F     C/P     Q/S     E/T     G/W     H/Y     I/V
    -5.1      2.6     4.7     3.1     3.8     0.2    -5.2     5.6    -0.9    -4.5
    -5.4      1.0    -5.3    -2.4     3.5     3.2     0.0     2.9     3.2    -6.3
//
H ROBB790101
D Hydration free energy (Robson-Osguthorpe, 1979)
R 0511124
A Robson, B. and Osguthorpe, D.J.
T Refined models for computer simulation of protein folding:
```

Applications to the study of conserved secondary structure and flexible hinge points during the folding of pancreatic trypsin inhibitor
J J. Mol. Biol. 132, 19-51 (1979)
* (Gly 0.67)

| C | | | | | | |
|---|---|---|---|---|---|---|
| CIDH920105 | 0.921 | NISK860101 | 0.912 | CIDH920104 | 0.903 | |
| CIDH920102 | 0.896 | MIYS850101 | 0.895 | BIOV880101 | 0.890 | |
| CIDH920103 | 0.884 | PLIV810101 | 0.875 | WERD780101 | 0.872 | |
| FAUJ830101 | 0.868 | RADA880108 | 0.867 | MEEJ810101 | 0.861 | |
| ROSG850102 | 0.846 | CIDH920101 | 0.846 | SWER830101 | 0.835 | |
| MANP780101 | 0.834 | PONP800108 | 0.831 | NISK800101 | 0.830 | |
| PONP800101 | 0.822 | MEEJ810102 | 0.821 | BIOV880102 | 0.821 | |
| PONP800102 | 0.807 | MEEJ800102 | 0.807 | LEVM760106 | 0.804 | |
| MEIH800103 | 0.801 | BULH740101 | -0.813 | WOLS870101 | -0.831 | |
| GRAR740102 | -0.832 | RACS770101 | -0.839 | MEIH800101 | -0.868 | |
| PARJ860101 | -0.893 | OOBM770103 | -0.909 | | | |

| I | A/L | R/K | N/M | D/F | C/P | Q/S | E/T | G/W | H/Y | I/V |
|---|---|---|---|---|---|---|---|---|---|---|
| | -1.0 | 0.3 | -0.7 | -1.2 | 2.1 | -0.1 | -0.7 | 0.3 | 1.1 | 4.0 |
| | 2.0 | -0.9 | 1.8 | 2.8 | 0.4 | -1.2 | -0.5 | 3.0 | 2.1 | 1.4 |
//
H ROSG850101
D Mean area buried on transfer (Rose et al., 1985)
R 1109092
A Rose, G.D., Geselowitz, A.R., Lesser, G.J., Lee, R.H., and Zehfus, M.H.
T Hydrophobicity of amino acid residues in globular proteins
J Science 229, 834-838 (1985)

| C | | | | | | |
|---|---|---|---|---|---|---|
| GRAR740103 | 0.922 | KRIW790103 | 0.920 | CHAM820101 | 0.917 | |
| BIGC670101 | 0.910 | GOLD730102 | 0.909 | CHOC750101 | 0.908 | |
| LEVM760106 | 0.896 | FAUJ880103 | 0.892 | CIDH920102 | 0.866 | |
| MCMT640101 | 0.857 | LEVM760107 | 0.852 | CHOC760101 | 0.842 | |
| FASG760101 | 0.838 | NOZY710101 | 0.834 | CIDH920101 | 0.831 | |
| RADA880106 | 0.814 | KARP850101 | -0.807 | RADA880103 | -0.814 | |
| WEBA780101 | -0.817 | OOBM770105 | -0.871 | OOBM770104 | -0.945 | |

| I | A/L | R/K | N/M | D/F | C/P | Q/S | E/T | G/W | H/Y | I/V |
|---|---|---|---|---|---|---|---|---|---|---|
| | 86.6 | 162.2 | 103.3 | 97.8 | 132.3 | 119.2 | 113.9 | 62.9 | 155.8 | 158.0 |
| | 164.1 | 115.5 | 172.9 | 194.1 | 92.9 | 85.6 | 106.5 | 224.6 | 177.7 | 141.0 |
//
H ROSG850102
D Mean fractional area loss (Rose et al., 1985)
R 1109092
A Rose, G.D., Geselowitz, A.R., Lesser, G.J., Lee, R.H., and Zehfus, M.H.
T Hydrophobicity of amino acid residues in globular proteins
J Science 229, 834-838 (1985)

| C | | | | | | |
|---|---|---|---|---|---|---|
| BIOV880101 | 0.981 | RADA880108 | 0.967 | NISK860101 | 0.962 | |
| BIOV880102 | 0.960 | PONP800102 | 0.949 | MEIH800103 | 0.948 | |
| PONP800103 | 0.947 | WERD780101 | 0.943 | NISK800101 | 0.942 | |
| PONP800101 | 0.938 | MIYS850101 | 0.937 | PONP800108 | 0.919 | |
| DESM900102 | 0.914 | JANJ780102 | 0.909 | FAUJ830101 | 0.904 | |
| MANP780101 | 0.903 | CIDH920104 | 0.896 | JANJ790102 | 0.892 | |
| DESM900101 | 0.866 | CIDH920105 | 0.858 | JANJ790101 | 0.857 | |
| CHOC760103 | 0.851 | ROBB790101 | 0.846 | EISD860103 | 0.846 | |
| CIDH920103 | 0.846 | PLIV810101 | 0.841 | KYTJ820101 | 0.841 | |
| WARP780101 | 0.823 | PONP800106 | 0.807 | EISD840101 | 0.806 | |
| PONP800107 | 0.803 | WOEC730101 | -0.804 | CHOC760102 | -0.819 | |
| ROSM880102 | -0.822 | PARJ860101 | -0.823 | HOPT810101 | -0.825 | |
| JANJ780101 | -0.836 | KRIW710101 | -0.852 | JANJ780103 | -0.879 | |
| GRAR740102 | -0.880 | RACS770101 | -0.880 | KARP850101 | -0.897 | |
| RACS770103 | -0.901 | OOBM770101 | -0.903 | OOBM770103 | -0.916 | |
| KRIW790102 | -0.922 | GUYH850101 | -0.929 | MEIH800101 | -0.930 | |
| KRIW790101 | -0.935 | RACS770102 | -0.940 | MEIH800102 | -0.959 | |

| I | A/L | R/K | N/M | D/F | C/P | Q/S | E/T | G/W | H/Y | I/V |
|---|---|---|---|---|---|---|---|---|---|---|
| | 0.74 | 0.64 | 0.63 | 0.62 | 0.91 | 0.62 | 0.62 | 0.72 | 0.78 | 0.88 |
| | 0.85 | 0.52 | 0.85 | 0.88 | 0.64 | 0.66 | 0.70 | 0.85 | 0.76 | 0.86 |
//
H ROSM880101
D Side chain hydropathy, uncorrected for solvation (Roseman, 1988)

```
R 1405111b
A Roseman, M.A.
T Hydrophilicity of polar amino acid side-chains is markedly reduced by
  flanking peptide bonds
J J. Mol. Biol. 200, 513-522 (1988)
C ROSM880102      0.938   PRAM900101   0.917   FAUJ880110    0.888
  GRAR740102      0.887   VHEG790101   0.883   LEVM760101    0.876
  WOLS870101      0.866   OOBM770101   0.854   HOPT810101    0.848
  FAUJ880109      0.846   WOEC730101   0.844   JANJ780101    0.822
  JANJ780103      0.810   PARJ860101   0.803   GUYH850101    0.803
  DESM900102     -0.812   NAKH900110  -0.812   WARP780101   -0.816
  CHOC760103     -0.819   BIOV880102  -0.824   JANJ790102   -0.824
  CIDH920104     -0.828   BIOV880101  -0.830   RADA880108   -0.831
  PLIV810101     -0.834   JANJ780102  -0.835   KYTJ820101   -0.845
  RADA880104     -0.863   RADA880107  -0.867   EISD860103   -0.871
  WOLR810101     -0.884   FAUJ830101  -0.907   EISD860101   -0.917
  EISD840101     -0.947   RADA880101  -0.978
I   A/L     R/K      N/M     D/F     C/P     Q/S     E/T     G/W     H/Y     I/V
   -0.67   12.1     7.23    8.72   -0.34    6.39    7.35    0.00    3.82   -3.02
   -3.02    6.13   -1.30   -3.24   -1.75    4.35    3.86   -2.86    0.98   -2.18
//
H ROSM880102
D Side chain hydropathy, corrected for solvation (Roseman, 1988)
R 1405111b
A Roseman, M.A.
T Hydrophilicity of polar amino acid side-chains is markedly reduced by
  flanking peptide bonds
J J. Mol. Biol. 200, 513-522 (1988)
C ROSM880101      0.938   PRAM900101   0.892   WOLS870101    0.877
  GRAR740102      0.870   OOBM770101   0.867   MEIH800102    0.859
  JANJ780101      0.853   CHOC760102   0.845   JANJ780103    0.838
  GUYH850101      0.837   VHEG790101   0.828   RACS770102    0.824
  FAUJ880109      0.824   LEVM760101   0.823   WOEC730101    0.801
  PARJ860101      0.801   WARP780101  -0.801   DESM900102   -0.816
  ROSG850102     -0.822   MIYS850101  -0.825   MEIH800103   -0.829
  WOLR810101     -0.829   CIDH920104  -0.831   BIOV880102   -0.837
  BIOV880101     -0.854   RADA880104  -0.855   RADA880108   -0.861
  PLIV810101     -0.864   JANJ790102  -0.866   EISD860101   -0.868
  CHOC760103     -0.869   JANJ780102  -0.870   KYTJ820101   -0.878
  RADA880107     -0.894   RADA880101  -0.917   EISD840101   -0.925
  FAUJ830101     -0.927   EISD860103  -0.943
I   A/L     R/K      N/M     D/F     C/P     Q/S     E/T     G/W     H/Y     I/V
   -0.67    3.89    2.27    1.57   -2.00    2.12    1.78    0.00    1.09   -3.02
   -3.02    2.46   -1.67   -3.24   -1.75    0.10   -0.42   -2.86    0.98   -2.18
//
H ROSM880103
D Loss of Side chain hydropathy by helix formation (Roseman, 1988)
R 1405111b
A Roseman, M.A.
T Hydrophilicity of polar amino acid side-chains is markedly reduced by
  flanking peptide bonds
J J. Mol. Biol. 200, 513-522 (1988)
C
I   A/L     R/K      N/M     D/F     C/P     Q/S     E/T     G/W     H/Y     I/V
    0.4     0.3      0.9     0.8     0.5     0.7     1.3     0.0     1.0     0.4
    0.6     0.4      0.3     0.7     0.9     0.4     0.4     0.6     1.2     0.4
//
H SIMZ760101
D Transfer free energy (Simon, 1976), Cited by Charton-Charton (1982)
R
A Simon, Z.
T
J Quantum Biochemistry and Specific Interactions, Abacus Press,
  Tunbridge Wells, Kent, England (1976)
* Cited by Charton-Charton (1982)
C ARGP820101      0.967   JOND750101   0.966   GOLD730101    0.939
  MEEJ800102      0.861   LEVM760106   0.848   CIDH920105    0.837
  MEEJ810101      0.836   CIDH920102   0.832   ZIMJ680101    0.821
```

```
        LAWE840101      0.815   BULH740102      0.815   ZIMJ680102      0.810
        MEEJ810102      0.808   NOZY710101      0.807   VENT840101      0.806
        ZIMJ680105      0.805   PLIV810101      0.805   PARJ860101     -0.825
        WOLS870101     -0.830   BULH740101     -0.894
I    A/L    R/K    N/M    D/F    C/P    Q/S    E/T    G/W    H/Y    I/V
     0.73   0.73  -0.01   0.54   0.70  -0.10   0.55   0.00   1.10   2.97
     2.49   1.50   1.30   2.65   2.60   0.04   0.44   3.00   2.97   1.69
//
H SNEP660101
D Principal component I (Sneath, 1966)
R
A Sneath, P.H.A.
T Relations between chemical structure and biological activity in
  peptides
J J. Theor. Biol. 12, 157-195 (1966)
C
I    A/L    R/K    N/M    D/F    C/P    Q/S    E/T    G/W    H/Y    I/V
     0.239  0.211  0.249  0.171  0.220  0.260  0.187  0.160  0.205  0.273
     0.281  0.228  0.253  0.234  0.165  0.236  0.213  0.183  0.193  0.255
//
H SNEP660102
D Principal component II (Sneath, 1966)
R
A Sneath, P.H.A.
T Relations between chemical structure and biological activity in
  peptides
J J. Theor. Biol. 12, 157-195 (1966)
C FAUJ880110   -0.804
I    A/L    R/K    N/M    D/F    C/P    Q/S    E/T    G/W    H/Y    I/V
     0.330 -0.176 -0.233 -0.371  0.074 -0.254 -0.409  0.370 -0.078  0.149
     0.129 -0.075 -0.092 -0.011  0.370  0.022  0.136 -0.011 -0.138  0.245
//
H SNEP660103
D Principal component III (Sneath, 1966)
R
A Sneath, P.H.A.
T Relations between chemical structure and biological activity in
  peptides
J J. Theor. Biol. 12, 157-195 (1966)
C LEVM760107   0.818   CHAM820101   0.808   ZASB820101   0.804
  OOBM770104  -0.830
I    A/L    R/K    N/M    D/F    C/P    Q/S    E/T    G/W    H/Y    I/V
    -0.110  0.079 -0.136 -0.285 -0.184 -0.067 -0.246 -0.073  0.320  0.001
    -0.008  0.049 -0.041  0.438 -0.016 -0.153 -0.208  0.493  0.381 -0.155
//
H SNEP660104
D Principal component IV (Sneath, 1966)
R
A Sneath, P.H.A.
T Relations between chemical structure and biological activity in
  peptides
J J. Theor. Biol. 12, 157-195 (1966)
C
I    A/L    R/K    N/M    D/F    C/P    Q/S    E/T    G/W    H/Y    I/V
    -0.062 -0.167  0.166 -0.079  0.380 -0.025 -0.184 -0.017  0.056 -0.309
    -0.264 -0.371  0.077  0.074 -0.036  0.470  0.348  0.050  0.220 -0.212
//
H SUEM840101
D Zimm-Bragg parameter s at 20 C (Sueki et al., 1984)
R 1004141
A Sueki, M., Lee, S., Powers, S.P., Denton, J.B., Konishi, Y., and
  Scheraga, H.A.
T Helix-coil stability constants for the naturally occurring amino acids
  in water. 22. Histidine parameters from random
  poly(hydroxybutyl)glutamine-co-L-histidine
J Macromolecules 17, 148-155 (1984)
* Charged state for Arg, His, Asp, and Glu
* (Cys Pro 0.100)
```

```
C FINA770101      0.883  PTIO830101   0.877  KANM800103   0.820
  QIAN880107      0.803  QIAN880131  -0.823  PALJ810106  -0.832
  CHOP780101     -0.845  ISOY800103  -0.850  LEVM780103  -0.864
  TANS770110     -0.864  PRAM900104  -0.865  CHOP780216  -0.874
  GEIM800108     -0.875  LEVM780106  -0.878  QIAN880133  -0.879
  QIAN880132     -0.880  GEIM800111  -0.885  CHAM830101  -0.891
  CHOP780203     -0.892
I    A/L     R/K     N/M     D/F     C/P     Q/S     E/T     G/W     H/Y     I/V
    1.071   1.033   0.784   0.680   0.922   0.977   0.970   0.591   0.850   1.140
    1.140   0.939   1.200   1.086   0.659   0.760   0.817   1.107   1.020   0.950
//
H SUEM840102
D Zimm-Bragg parameter sigma x 1.0E4 (Sueki et al., 1984)
R 1004141
A Sueki, M., Lee, S., Powers, S.P., Denton, J.B., Konishi, Y., and
  Scheraga, H.A.
T Helix-coil stability constants for the naturally occurring amino acids
  in water. 22. Histidine parameters from random
  poly(hydroxybutyl)glutamine-co-L-histidine
J Macromolecules 17, 148-155 (1984)
* Charged state for Arg, His, Asp, and Glu
* (Cys Pro !)
C
I    A/L     R/K     N/M     D/F     C/P     Q/S     E/T     G/W     H/Y     I/V
     8.0     0.1     0.1    70.0    26.0    33.0     6.0     0.1     0.1    55.0
    33.0     1.0    54.0    18.0    42.0     0.1     0.1    77.0    66.0     0.1
//
H SWER830101
D Optimal matching hydrophobicity (Sweet-Eisenberg, 1983)
R 2004095b
A Sweet, R.M. and Eisenberg, D.
T Correlation of sequence hydrophobicities measures similarity in
  three-dimensional protein structure
J J. Mol. Biol. 171, 479-488 (1983)
C CIDH920105      0.890  MIYS850101   0.889  PLIV810101   0.875
  CIDH920102      0.870  NISK860101   0.865  CIDH920103   0.865
  CIDH920104      0.862  PTIO830102   0.856  CIDH920101   0.853
  BIOV880101      0.839  VENT840101   0.836  NOZY710101   0.836
  ROBB790101      0.835  FAUJ830101   0.833  ZIMJ680105   0.829
  RADA880108      0.826  QIAN880120   0.825  EISD860101   0.824
  CHOP780202      0.823  MANP780101   0.821  RADA880102   0.820
  LIFS790101      0.815  PALJ810104   0.809  MEEJ810101   0.806
  WERD780101      0.804  RACS770101  -0.803  MEIH800101  -0.830
  WOEC730101     -0.832  OOBM770103  -0.833  WOLS870101  -0.887
  PARJ860101     -0.893  GRAR740102  -0.896  BULH740101  -0.923
I    A/L     R/K     N/M     D/F     C/P     Q/S     E/T     G/W     H/Y     I/V
   -0.40   -0.59   -0.92   -1.31    0.17   -0.91   -1.22   -0.67   -0.64    1.25
    1.22   -0.67    1.02    1.92   -0.49   -0.55   -0.28    0.50    1.67    0.91
//
H TANS770101
D Normalized frequency of alpha-helix (Tanaka-Scheraga, 1977)
R
A Tanaka, S. and Scheraga, H.A.
T Statistical mechanical treatment of protein conformation. 5. A
  multiphasic model for specific-sequence copolymers of amino acids
J Macromolecules 10, 9-20 (1977)
* Recalculated by Kidera as normalized frequencies
C ROBB760101      0.948  CHOP780201   0.947  MAXF760101   0.930
  KANM800101      0.927  NAGK730101   0.925  PALJ810102   0.923
  PALJ810101      0.918  GEIM800101   0.918  BURA740101   0.917
  LEVM780104      0.908  ISOY800101   0.906  PRAM900102   0.854
  LEVM780101      0.854  RACS820108   0.845  KANM800103   0.843
  CRAJ730101      0.843  GEIM800104   0.841  QIAN880106   0.819
  QIAN880107      0.804  NAGK730103  -0.800
I    A/L     R/K     N/M     D/F     C/P     Q/S     E/T     G/W     H/Y     I/V
    1.42   -1.06    0.71    1.01    0.73    1.02    1.63    0.50    1.20    1.12
    1.29    1.24    1.21    1.16    0.65    0.71    0.78    1.05    0.67    0.99
//
```

```
H TANS770102
D Normalized frequency of isolated helix (Tanaka-Scheraga, 1977)
R
A Tanaka, S. and Scheraga, H.A.
T Statistical mechanical treatment of protein conformation. 5.  A
  multiphasic model for specific-sequence copolymers of amino acids
J Macromolecules 10, 9-20 (1977)
* Recalculated by Kidera as normalized frequencies
C
I    A/L     R/K     N/M     D/F     C/P     Q/S     E/T     G/W     H/Y     I/V
   0.946   1.128   0.432   1.311   0.481   1.615   0.698   0.360   2.168   1.283
   1.192   1.203   0.000   0.963   2.093   0.523   1.961   1.925   0.802   0.409
//
H TANS770103
D Normalized frequency of extended structure (Tanaka-Scheraga, 1977)
R
A Tanaka, S. and Scheraga, H.A.
T Statistical mechanical treatment of protein conformation. 5.  A
  multiphasic model for specific-sequence copolymers of amino acids
J Macromolecules 10, 9-20 (1977)
* Recalculated by Kidera as normalized frequencies
C ISOY800102     0.929  MAXF760102     0.891  ROBB760105     0.871
  GEIM800105     0.850  RACS820111     0.841  PALJ810103     0.824
  WOEC730101    -0.806
I    A/L     R/K     N/M     D/F     C/P     Q/S     E/T     G/W     H/Y     I/V
   0.790   1.087   0.832   0.530   1.268   1.038   0.643   0.725   0.864   1.361
   1.111   0.735   1.092   1.052   1.249   1.093   1.214   1.114   1.340   1.428
//
H TANS770104
D Normalized frequency of chain reversal R (Tanaka-Scheraga, 1977)
R
A Tanaka, S. and Scheraga, H.A.
T Statistical mechanical treatment of protein conformation. 5.  A
  multiphasic model for specific-sequence copolymers of amino acids
J Macromolecules 10, 9-20 (1977)
* Recalculated by Kidera as normalized frequencies
C CHOP780213     0.954  ISOY800104     0.918  FINA910102     0.876
  QIAN880134     0.837  BUNA790101    -0.867
I    A/L     R/K     N/M     D/F     C/P     Q/S     E/T     G/W     H/Y     I/V
   1.194   0.795   0.659   1.056   0.678   1.290   0.928   1.015   0.611   0.603
   0.595   1.060   0.831   0.377   3.159   1.444   1.172   0.452   0.816   0.640
//
H TANS770105
D Normalized frequency of chain reversal S (Tanaka-Scheraga, 1977)
R
A Tanaka, S. and Scheraga, H.A.
T Statistical mechanical treatment of protein conformation. 5.  A
  multiphasic model for specific-sequence copolymers of amino acids
J Macromolecules 10, 9-20 (1977)
* Recalculated by Kidera as normalized frequencies
C CHOP780214     0.862  ISOY800105     0.836
I    A/L     R/K     N/M     D/F     C/P     Q/S     E/T     G/W     H/Y     I/V
   0.497   0.677   2.072   1.498   1.348   0.711   0.651   1.848   1.474   0.471
   0.656   0.932   0.425   1.348   0.179   1.151   0.749   1.283   1.283   0.654
//
H TANS770106
D Normalized frequency of chain reversal D (Tanaka-Scheraga, 1977)
R
A Tanaka, S. and Scheraga, H.A.
T Statistical mechanical treatment of protein conformation. 5.  A
  multiphasic model for specific-sequence copolymers of amino acids
J Macromolecules 10, 9-20 (1977)
* Recalculated by Kidera as normalized frequencies
C
I    A/L     R/K     N/M     D/F     C/P     Q/S     E/T     G/W     H/Y     I/V
   0.937  -1.725   1.080   1.640   1.004   1.078   0.679   0.901   1.085   0.178
   0.808   1.254   0.886   0.803   0.748   1.145   1.487   0.803   1.227   0.625
//
```

```
H TANS770107
D Normalized frequency of left-handed helix (Tanaka-Scheraga, 1977)
R
A Tanaka, S. and Scheraga, H.A.
T Statistical mechanical treatment of protein conformation. 5. A
  multiphasic model for specific-sequence copolymers of amino acids
J Macromolecules 10, 9-20 (1977)
* Recalculated by Kidera as normalized frequencies
C MAXF760104    0.913  ISOY800108    0.827  RICJ880115    0.807
I   A/L    R/K    N/M    D/F    C/P    Q/S    E/T    G/W    H/Y    I/V
   0.289  1.380  3.169  0.917  1.767  2.372  0.285  4.259  1.061  0.262
   0.000  1.288  0.000  0.393  0.000  0.160  0.218  0.000  0.654  0.167
//
H TANS770108
D Normalized frequency of zeta R (Tanaka-Scheraga, 1977)
R
A Tanaka, S. and Scheraga, H.A.
T Statistical mechanical treatment of protein conformation. 5. A
  multiphasic model for specific-sequence copolymers of amino acids
J Macromolecules 10, 9-20 (1977)
* Recalculated by Kidera as normalized frequencies
C
I   A/L    R/K    N/M    D/F    C/P    Q/S    E/T    G/W    H/Y    I/V
   0.328  2.088  1.498  3.379  0.000  0.000  0.000  0.500  1.204  2.078
   0.414  0.835  0.982  1.336  0.415  1.089  1.732  1.781  0.000  0.946
//
H TANS770109
D Normalized frequency of coil (Tanaka-Scheraga, 1977)
R
A Tanaka, S. and Scheraga, H.A.
T Statistical mechanical treatment of protein conformation. 5. A
  multiphasic model for specific-sequence copolymers of amino acids
J Macromolecules 10, 9-20 (1977)
* Recalculated by Kidera as normalized frequencies
C MAXF760105    0.878  MAXF760104    0.821  ISOY800108    0.816
I   A/L    R/K    N/M    D/F    C/P    Q/S    E/T    G/W    H/Y    I/V
   0.945  0.364  1.202  1.315  0.932  0.704  1.014  2.355  0.525  0.673
   0.758  0.947  1.028  0.622  0.579  1.140  0.863  0.777  0.907  0.561
//
H TANS770110
D Normalized frequency of chain reversal (Tanaka-Scheraga, 1977)
R
A Tanaka, S. and Scheraga, H.A.
T Statistical mechanical treatment of protein conformation. 5. A
  multiphasic model for specific-sequence copolymers of amino acids
J Macromolecules 10, 9-20 (1977)
* Recalculated by Kidera as normalized frequencies
C CHOP780101    0.956  CHOP780203    0.940  CHOP780216    0.930
  PALJ810106    0.925  QIAN880133    0.920  CHAM830101    0.917
  QIAN880132    0.903  ISOY800103    0.897  LEVM780106    0.892
  GEIM800108    0.886  GEIM800111    0.883  LEVM780103    0.875
  QIAN880131    0.873  PRAM900104    0.873  PALJ810105    0.860
  CRAJ730103    0.859  CHOP780210    0.858  ROBB760113    0.853
  ROBB760108    0.839  BEGF750103    0.834  ROBB760110    0.805
  SUEM840101   -0.864
I   A/L    R/K    N/M    D/F    C/P    Q/S    E/T    G/W    H/Y    I/V
   0.842  0.936  1.352  1.366  1.032  0.998  0.758  1.349  1.079  0.459
   0.665  1.045  0.668  0.881  1.385  1.257  1.055  0.881  1.101  0.643
//
H VASM830101
D Relative population of conformational state A (Vasquez et al., 1983)
R 0908110
A Vasquez, M., Nemethy, G., and Scheraga, H.A.
T Computed conformational states of the 20 naturally occurring amino
  acid residues and of the prototype residue alpha-aminobutyric acid
J Macromolecules 16, 1043-1049 (1983)
C
I   A/L    R/K    N/M    D/F    C/P    Q/S    E/T    G/W    H/Y    I/V
```

```
           0.135  0.296  0.196  0.289  0.159  0.236  0.184  0.051  0.223  0.173
           0.215  0.170  0.239  0.087  0.151  0.010  0.100  0.166  0.066  0.285,
//
H VASM830102
D Relative population of conformational state C (Vasquez et al., 1983)
R 0908110
A Vasquez, M., Nemethy, G., and Scheraga, H.A.
T Computed conformational states of the 20 naturally occurring amino
  acid residues and of the prototype residue alpha-aminobutyric acid
J Macromolecules 16, 1043-1049 (1983)
C
I    A/L    R/K    N/M    D/F    C/P    Q/S    E/T    G/W    H/Y    I/V
     0.507  0.459  0.287  0.223  0.592  0.383  0.445  0.390  0.310  0.111
     0.619  0.559  0.431  0.077  0.739  0.689  0.785  0.160  0.060  0.356
//
H VASM830103
D Relative population of conformational state E (Vasquez et al., 1983)
R 0908110
A Vasquez, M., Nemethy, G., and Scheraga, H.A.
T Computed conformational states of the 20 naturally occurring amino
  acid residues and of the prototype residue alpha-aminobutyric acid
J Macromolecules 16, 1043-1049 (1983)
* (Pro !)
C
I    A/L    R/K    N/M    D/F    C/P    Q/S    E/T    G/W    H/Y    I/V
     0.159  0.194  0.385  0.283  0.187  0.236  0.206  0.049  0.233  0.581
     0.083  0.159  0.198  0.682  0.366  0.150  0.074  0.463  0.737  0.301
//
H VELV850101
D Electron-ion interaction potential (Veljkovic et al., 1985)
R 2004067b
A Veljkovic, V., Cosic, I., Dimitrijevic, B., and Lalovic, D.
T Is it possible to analyze DNA and protein sequences by the method of
  digital signal processing?
J IEEE Trans. Biomed. Eng. 32, 337-341 (1985)
C
I    A/L     R/K     N/M     D/F     C/P     Q/S     E/T     G/W     H/Y     I/V
    .03731  .09593  .00359  .12630  .08292  .07606  .00580  .00499  .02415  .00000
    .00000  .03710  .08226  .09460  .01979  .08292  .09408  .05481  .05159  .00569
//
H VENT840101
D Bitterness (Venanzi, 1984)
R 1103107b
A Venanzi, T.J.
T Hydrophobicity parameters and the bitter taste of L-amino acids
J J. Theor. Biol. 111, 447-450 (1984)
C NOZY710101    0.897   PTIO830102   0.842   SWER830101    0.836
  PALJ810104    0.831   MEEJ810102   0.831   RADA880102    0.826
  CHOP780209    0.817   LIFS790101   0.814   MEEJ810101    0.813
  CIDH920105    0.813   SIMZ760101   0.806   PONP800107    0.805
  CHOP780202    0.805   GOLD730101   0.802   WOLS870101   -0.835
  PARJ860101   -0.846   BULH740101  -0.907
I    A/L    R/K    N/M    D/F    C/P    Q/S    E/T    G/W    H/Y    I/V
     0.     0.     0.     0.     0.     0.     0.     0.     0.     1.
     1.     0.     0.     1.     0.     0.     0.     1.     1.     1.
//
H VHEG790101
D Transfer free energy to lipophilic phase (von Heijne-Blomberg, 1979)
R 0509382
A von Heijne, G. and Blomberg, C.
T Trans-membrane translocation of proteins: The direct transfer model
J Eur. J. Biochem. 97, 175-181 (1979)
C PRAM900101    0.909   ROSM880101   0.883   HOPT810101    0.849
  ROSM880102    0.828   LEVM760101   0.825   RADA880102   -0.818
  NAKH900110   -0.848   EISD860101  -0.862   WOLR810101   -0.867
  EISD840101   -0.924   RADA880101  -0.925
I    A/L    R/K    N/M    D/F    C/P    Q/S    E/T    G/W    H/Y    I/V
    -12.04  39.23   4.25  23.22   3.95   2.16  16.81  -7.85   6.28 -18.32
```

```
         -17.79    9.71  -8.86 -21.98   5.82  -1.54  -4.15 -16.19  -1.51 -16.22
//
H WARP780101
D Average interactions per side chain atom (Warme-Morgan, 1978)
R 0405099
A Warme, P.K. and Morgan, R.S.
T A survey of amino acid side-chain interactions in 21 proteins
J J. Mol. Biol. 118, 289-304 (1978)
* (Gly 0.81)
C DESM900102    0.882   JANJ780102    0.878   JANJ790102    0.877
  DESM900101    0.864   BIOV880102    0.853   KYTJ820101    0.845
  MEIH800103    0.835   CHOC760103    0.824   ROSG850102    0.823
  EISD860103    0.820   CHOC760104    0.815   ROSM880102   -0.801
  ROSM880101   -0.816   MEIH800102   -0.826   PRAM900101   -0.827
  RACS770103   -0.848   CHOC760102   -0.849   JANJ780101   -0.869
  JANJ780103   -0.890   OOBM770101   -0.937
I   A/L    R/K    N/M    D/F    C/P    Q/S    E/T    G/W    H/Y    I/V
   10.04   6.18   5.63   5.76   8.89   5.41   5.37   7.99   7.49   8.72
    8.79   4.40   9.15   7.98   7.79   7.08   7.00   8.07   6.90   8.88
//
H WEBA780101
D RF value in high salt chromatography (Weber-Lacey, 1978)
R 2004106b
A Weber, A.L. and Lacey, J.C.,Jr.
T Genetic code correlations: Amino acids and their anticodon nucleotides
J J. Mol. Evol. 11, 199-210 (1978)
C OOBM770104    0.901   MEEJ800102   -0.808   ROSG850101   -0.817
  MEEJ810101   -0.831   MEEJ810102   -0.854   NOZY710101   -0.890
  LEVM760107   -0.923   GARJ730101   -0.924
I   A/L    R/K    N/M    D/F    C/P    Q/S    E/T    G/W    H/Y    I/V
    0.89   0.88   0.89   0.87   0.85   0.82   0.84   0.92   0.83   0.76
    0.73   0.97   0.74   0.52   0.82   0.96   0.92   0.20   0.49   0.85
//
H WERD780101
D Propensity to be buried inside (Wertz-Scheraga, 1978)
R 0405105
A Wertz, D.H. and Scheraga, H.A.
T Influence of water on protein structure. An analysis of the
  preferences of amino acid residues for the inside or outside and for
  specific conformations in a protein molecule
J Macromolecules 11, 9-15 (1978)
* Adjusted values
C NISK860101    0.966   BIOV880101    0.951   ROSG850102    0.943
  MIYS850101    0.934   RADA880108    0.930   BIOV880102    0.929
  CIDH920105    0.905   CIDH920104    0.896   MEIH800103    0.895
  NISK800101    0.891   PONP800102    0.883   CIDH920103    0.881
  PONP800101    0.880   CIDH920101    0.878   PONP800103    0.876
  ROBB790101    0.872   CIDH920102    0.871   FAUJ830101    0.862
  MANP780101    0.853   PONP800108    0.843   PLIV810101    0.841
  MEEJ810101    0.825   DESM900102    0.814   SWER830101    0.804
  BHAR880101   -0.803   KRIW710101   -0.819   GRAR740102   -0.826
  KARP850101   -0.842   RACS770103   -0.846   PARJ860101   -0.869
  GUYH850101   -0.871   KRIW790102   -0.875   KRIW790101   -0.899
  MEIH800102   -0.903   OOBM770103   -0.906   RACS770102   -0.906
  KARP850102   -0.909   RACS770101   -0.912   MEIH800101   -0.943
I   A/L    R/K    N/M    D/F    C/P    Q/S    E/T    G/W    H/Y    I/V
    0.52   0.49   0.42   0.37   0.83   0.35   0.38   0.41   0.70   0.79
    0.77   0.31   0.76   0.87   0.35   0.49   0.38   0.86   0.64   0.72
//
H WERD780102
D Free energy change of epsilon(i) to epsilon(ex) (Wertz-Scheraga, 1978)
R 0405105
A Wertz, D.H. and Scheraga, H.A.
T Influence of water on protein structure. An analysis of the
  preferences of amino acid residues for the inside or outside and for
  specific conformations in a protein molecule
J Macromolecules 11, 9-15 (1978)
* Adjusted values
```

```
C
I    A/L     R/K     N/M     D/F     C/P     Q/S     E/T     G/W     H/Y     I/V
     0.16   -0.20    1.03   -0.24   -0.12   -0.55   -0.45   -0.16   -0.18   -0.19
    -0.44   -0.12   -0.79   -0.25   -0.59   -0.01    0.05   -0.33   -0.42   -0.46
//
H WERD780103
D Free energy change of alpha(Ri) to alpha(Rh) (Wertz-Scheraga, 1978)
R 0405105
A Wertz, D.H. and Scheraga, H.A.
T Influence of water on protein structure. An analysis of the
  preferences of amino acid residues for the inside or outside and for
  specific conformations in a protein molecule
J Macromolecules 11, 9-15 (1978)
* Adjusted values
* (Met !)
C
I    A/L     R/K     N/M     D/F     C/P     Q/S     E/T     G/W     H/Y     I/V
     0.15   -0.37    0.69   -0.22   -0.19   -0.06    0.14    0.36   -0.25    0.02
     0.06   -0.16    0.11    1.18    0.11    0.13    0.28   -0.12    0.19   -0.08
//
H WERD780104
D Free energy change of epsilon(i) to alpha(Rh) (Wertz-Scheraga, 1978)
R 0405105
A Wertz, D.H. and Scheraga, H.A.
T Influence of water on protein structure. An analysis of the
  preferences of amino acid residues for the inside or outside and for
  specific conformations in a protein molecule
J Macromolecules 11, 9-15 (1978)
* Adjusted values
C
I    A/L     R/K     N/M     D/F     C/P     Q/S     E/T     G/W     H/Y     I/V
    -0.07   -0.40   -0.57   -0.80    0.17   -0.26   -0.63    0.27   -0.49    0.06
    -0.17   -0.45    0.03    0.40   -0.47   -0.11    0.09   -0.61   -0.61   -0.11
//
H WOEC730101
D Polar requirement (Woese, 1973)
R
A Woese, C.R.
T Evolution of genetic code
J Naturwiss. 60, 447-459 (1973)
C GRAR740102     0.960    HOPT810101    0.886    HOPA770101    0.876
  LEVM760101     0.872    PRAM900101    0.871    ROSM880101    0.844
  WOLS870101     0.841    OOBM770103    0.835    PARJ860101    0.821
  FAUJ880110     0.812    OOBM770101    0.804    ROSM880102    0.801
  CIDH920105    -0.800    MEIH800103   -0.802    EISD860103   -0.803
  ISOY800102    -0.803    ROSG850102   -0.804    TANS770103   -0.806
  RADA880101    -0.812    BIOV880102   -0.819    NISK860101   -0.822
  CIDH920104    -0.823    PONP800103   -0.823    RADA880108   -0.825
  BIOV880101    -0.829    PONP800108   -0.831    SWER830101   -0.832
  EISD860101    -0.838    MAXF760102   -0.842    DESM900102   -0.847
  FAUJ830101    -0.880
I    A/L     R/K     N/M     D/F     C/P     Q/S     E/T     G/W     H/Y     I/V
     7.0     9.1    10.0    13.0     5.5     8.6    12.5     7.9     8.4     4.9
     4.9    10.1     5.3     5.0     6.6     7.5     6.6     5.3     5.7     5.6
//
H WOLR810101
D Hydration potential (Wolfenden et al., 1981)
R 0704095
A Wolfenden, R., Andersson, L., Cullis, P.M., and Southgate, C.C.B.
T Affinties of amino acid side chains for solvent water
J Biochemistry 20, 849-855 (1981)
* (Pro 2.9)
C RADA880101     0.939    EISD840101    0.914    RADA880104    0.910
  RADA880107     0.890    KYTJ820101    0.885    RADA880105    0.875
  CHOC760103     0.873    CHOC760104    0.868    JANJ780102    0.851
  JANJ790102     0.828    JANJ780103   -0.822    ROSM880102   -0.829
  CHOC760102    -0.840    OOBM770101   -0.847    JANJ780101   -0.864
  VHEG790101    -0.867    ROSM880101   -0.884    PRAM900101   -0.887
```

```
FAUJ880109   -0.904
I    A/L    R/K    N/M    D/F    C/P    Q/S    E/T    G/W    H/Y    I/V
     1.94 -19.92  -9.68 -10.95  -1.24  -9.38 -10.20   2.39 -10.27   2.15
     2.28  -9.52  -1.48  -0.76  -3.68  -5.06  -4.88  -5.88  -6.11   1.99
//
H WOLS870101
D Principal property value z1 (Wold et al., 1987)
R 1312098b
A Wold, S., Eriksson, L., Hellberg, S., Jonsson, J., Sjostrom, M.,
  Skagerberg, B. and Wikstrom, C.
T Principal property values for six non-natural amino acids and their
  application to a structure-activity relationship for oxytocin peptide
  analogues
J Can. J. Chem. 65, 1814-1820 (1987)
C PARJ860101    0.964  BULH740101    0.929  GRAR740102    0.910
  ROSM880102    0.877  ROSM880101    0.866  OOBM770103    0.852
  MEIH800101    0.852  LEVM760101    0.845  WOEC730101    0.841
  HOPT810101    0.830  MEIH800102    0.813  RACS770102    0.802
  MANP780101   -0.809  EISD840101   -0.820  MEEJ800101   -0.823
  RADA880101   -0.823  SIMZ760101   -0.830  ROBB790101   -0.831
  NAKH900110   -0.832  VENT840101   -0.835  JOND750101   -0.837
  ARGP820101   -0.838  RADA880108   -0.840  EISD860101   -0.841
  BIOV880102   -0.842  NISK860101   -0.848  PONP800107   -0.852
  BIOV880101   -0.854  GOLD730101   -0.854  CIDH920102   -0.869
  BROC820101   -0.871  RADA880102   -0.873  NOZY710101   -0.874
  CIDH920103   -0.879  SWER830101   -0.887  CIDH920104   -0.891
  CIDH920105   -0.899  MIYS850101   -0.899  MEEJ810102   -0.905
  MEEJ810101   -0.906  EISD860101   -0.918  MEEJ800102   -0.925
  FAUJ830101   -0.928  ZIMJ680105   -0.937  PLIV810101   -0.963
I    A/L    R/K    N/M    D/F    C/P    Q/S    E/T    G/W    H/Y    I/V
     0.07   2.88   3.22   3.64   0.71   2.18   3.08   2.23   2.41  -4.44
    -4.19   2.84  -2.49  -4.92  -1.22   1.96   0.92  -4.75  -1.39  -2.69
//
H WOLS870102
D Principal property value z2 (Wold et al., 1987)
R 1312098b
A Wold, S., Eriksson, L., Hellberg, S., Jonsson, J., Sjostrom, M.,
  Skagerberg, B. and Wikstrom, C.
T Principal property values for six non-natural amino acids and their
  application to a structure-activity relationship for oxytocin peptide
  analogues
J Can. J. Chem. 65, 1814-1820 (1987)
C LEVM760102    0.881  FAUJ880106    0.866  FASG760101    0.866
  CHOC760101    0.845  LEVM760105    0.836  FAUJ880103    0.814
  OOBM770105   -0.804
I    A/L    R/K    N/M    D/F    C/P    Q/S    E/T    G/W    H/Y    I/V
    -1.73   2.52   1.45   1.13  -0.97   0.53   0.39  -5.36   1.74  -1.68
    -1.03   1.41  -0.27   1.30   0.88  -1.63  -2.09   3.65   2.32  -2.53
//
H WOLS870103
D Principal property value z3 (Wold et al., 1987)
R 1312098b
A Wold, S., Eriksson, L., Hellberg, S., Jonsson, J., Sjostrom, M.,
  Skagerberg, B. and Wikstrom, C.
T Principal property values for six non-natural amino acids and their
  application to a structure-activity relationship for oxytocin peptide
  analogues
J Can. J. Chem. 65, 1814-1820 (1987)
C
I    A/L    R/K    N/M    D/F    C/P    Q/S    E/T    G/W    H/Y    I/V
     0.09  -3.44   0.84   2.36   4.13  -1.14  -0.07   0.30   1.11  -1.03
    -0.98  -3.14  -0.41   0.45   2.23   0.57  -1.40   0.85   0.01  -1.29
//
H YUTK870101
D Unfolding Gibbs energy in water, pH7.0 (Yutani et al., 1987)
R 2004127b
A Yutani, K., Ogasahara, K., Tsujita, T., and Sugino, Y.
T Dependence of conformational stability on hydrophobicity of the amino
```

```
  acid residue in a series of variant proteins substituted at a unique
  position of tryptophan synthase alpha subunit
J Proc. Natl. Acad. Sci. USA 84, 4441-4444 (1987)
* (Arg missing)
C YUTK870102    0.827    EISD840101    0.809    RADA880101    0.803
  GUYH850101   -0.813
I A/L     R/K     N/M     D/F     C/P     Q/S     E/T     G/W     H/Y     I/V
  8.5     0.      8.2     8.5    11.0     6.3     8.8     7.1    10.1    16.8
 15.0     7.9    13.3    11.2     8.2     7.4     8.8     9.9     8.8    12.0
//
H YUTK870102
D Unfolding Gibbs energy in water, pH9.0 (Yutani et al., 1987)
R 2004127b
A Yutani, K., Ogasahara, K., Tsujita, T., and Sugino, Y.
T Dependence of conformational stability on hydrophobicity of the amino
  acid residue in a series of variant proteins substituted at a unique
  position of tryptophan synthase alpha subunit
J Proc. Natl. Acad. Sci. USA 84, 4441-4444 (1987)
* (Arg missing)
C YUTK870101    0.827
I A/L     R/K     N/M     D/F     C/P     Q/S     E/T     G/W     H/Y     I/V
  6.8     0.      6.2     7.0     8.3     8.5     4.9     6.4     9.2    10.0
 12.2     7.5     8.4     8.3     6.9     8.0     7.0     5.7     6.8     9.4
//
H YUTK870103
D Activation Gibbs energy of unfolding, pH7.0 (Yutani et al., 1987)
R 2004127b
A Yutani, K., Ogasahara, K., Tsujita, T., and Sugino, Y.
T Dependence of conformational stability on hydrophobicity of the amino
  acid residue in a series of variant proteins substituted at a unique
  position of tryptophan synthase alpha subunit
J Proc. Natl. Acad. Sci. USA 84, 4441-4444 (1987)
* (Arg missing)
C YUTK870104    0.997    EISD860102   -0.839
I A/L     R/K     N/M     D/F     C/P     Q/S     E/T     G/W     H/Y     I/V
 18.08    0.    17.47   17.36   18.17   17.93   18.16   18.24   18.49   18.62
 18.60   17.96  18.11   17.30   18.16   17.57   17.54   17.19   17.99   18.30
//
H YUTK870104
D Activation Gibbs energy of unfolding, pH9.0 (Yutani et al., 1987)
R 2004127b
A Yutani, K., Ogasahara, K., Tsujita, T., and Sugino, Y.
T Dependence of conformational stability on hydrophobicity of the amino
  acid residue in a series of variant proteins substituted at a unique
  position of tryptophan synthase alpha subunit
J Proc. Natl. Acad. Sci. USA 84, 4441-4444 (1987)
* (Arg missing)
C YUTK870103    0.997    EISD860102   -0.840
I A/L     R/K     N/M     D/F     C/P     Q/S     E/T     G/W     H/Y     I/V
 18.56    0.    18.24   17.94   17.84   18.51   17.97   18.57   18.64   19.21
 19.01   18.36  18.49   17.95   18.77   18.06   17.71   16.87   18.23   18.98
//
H ZASB820101
D Dependence of partition coefficient on ionic strength (Zaslavsky et al.,
  1982)
R 0806206
A Zaslavsky, B.Yu, Mestechkina, N.M., Miheeva, L.M., and Rogozhin, S.V.
T Measurement of relative hydrophobicity of amino acid side-chains by
  partition in an aqueous two-phase polymeric system: Hydrophobicity
  scale for non-polar and ionogenic side-chains
J J. Chromatogr. 240, 21-28 (1982)
C CIDH920102    0.809    SNEP660103    0.804    OOBM850102   -0.853
I A/L     R/K     N/M     D/F     C/P     Q/S     E/T     G/W     H/Y     I/V
 -0.152  -0.089 -0.203  -0.355          -0.181  -0.411  -0.190          -0.086
 -0.102  -0.062 -0.107   0.001  -0.181  -0.203  -0.170   0.275          -0.125
//
H ZIMJ680101
D Hydrophobicity (Zimmerman et al., 1968)
```

```
R 2004109b
A Zimmerman, J.M., Eliezer, N., and Simha, R.
T The characterization of amino acid sequences in proteins by
  statistical methods
J J. Theor. Biol. 21, 170-201 (1968)
C SIMZ760101    0.821
I A/L      R/K      N/M      D/F      C/P      Q/S      E/T      G/W      H/Y      I/V
  0.83     0.83     0.09     0.64     1.48     0.00     0.65     0.10     1.10     3.07
  2.52     1.60     1.40     2.75     2.70     0.14     0.54     0.31     2.97     1.79
//
H ZIMJ680102
D Bulkiness (Zimmerman et al., 1968)
R 2004109b
A Zimmerman, J.M., Eliezer, N., and Simha, R.
T The characterization of amino acid sequences in proteins by
  statistical methods
J J. Theor. Biol. 21, 170-201 (1968)
C FAUJ880101    0.888   LEVM760106    0.873   BULH740102    0.825
  GOLD730101    0.818   SIMZ760101    0.810
I A/L      R/K      N/M      D/F      C/P      Q/S      E/T      G/W      H/Y      I/V
  11.50    14.28    12.82    11.68    13.46    14.45    13.57    3.40     13.69    21.40
  21.40    15.71    16.25    19.80    17.43    9.47     15.77    21.67    18.03    21.57
//
H ZIMJ680103
D Polarity (Zimmerman et al., 1968)
R 2004109b
A Zimmerman, J.M., Eliezer, N., and Simha, R.
T The characterization of amino acid sequences in proteins by
  statistical methods
J J. Theor. Biol. 21, 170-201 (1968)
C PRAM900101    0.854   HOPA770101    0.815
I A/L      R/K      N/M      D/F      C/P      Q/S      E/T      G/W      H/Y      I/V
  0.00     52.00    3.38     49.70    1.48     3.53     49.90    0.00     51.60    0.13
  0.13     49.50    1.43     0.35     1.58     1.67     1.66     2.10     1.61     0.13
//
H ZIMJ680104
D Isoelectric point (Zimmerman et al., 1968)
R 2004109b
A Zimmerman, J.M., Eliezer, N., and Simha, R.
T The characterization of amino acid sequences in proteins by
  statistical methods
J J. Theor. Biol. 21, 170-201 (1968)
C KLEP840101    0.941   FAUJ880111    0.813   FINA910103    0.805
I A/L      R/K      N/M      D/F      C/P      Q/S      E/T      G/W      H/Y      I/V
  6.00     10.76    5.41     2.77     5.05     5.65     3.22     5.97     7.59     6.02
  5.98     9.74     5.74     5.48     6.30     5.68     5.66     5.89     5.66     5.96
//
H ZIMJ680105
D RF rank (Zimmerman et al., 1968)
R 2004109b
A Zimmerman, J.M., Eliezer, N., and Simha, R.
T The characterization of amino acid sequences in proteins by
  statistical methods
J J. Theor. Biol. 21, 170-201 (1968)
C MEEJ800102    0.921   EISD860101    0.900   BROC820101    0.896
  PLIV810101    0.875   BROC820102    0.865   RADA880102    0.851
  MEEJ800101    0.842   NOZY710101    0.837   SWER830101    0.829
  GOLD730101    0.820   FAUJ830101    0.816   LAWE840101    0.809
  SIMZ760101    0.805   HOPT810101   -0.816   LEVM760101   -0.844
  BULH740101   -0.879   PARJ860101   -0.886   WOLS870101   -0.937
I A/L      R/K      N/M      D/F      C/P      Q/S      E/T      G/W      H/Y      I/V
  9.9      4.6      5.4      2.8      2.8      9.0      3.2      5.6      8.2      17.1
  17.6     3.5      14.9     18.8     14.8     6.9      9.5      17.1     15.0     14.3
//
```